(12) United States Patent
Strieker et al.

(10) Patent No.: US 10,253,099 B2
(45) Date of Patent: Apr. 9, 2019

(54) CONJUGATES OF PROTEINS AND MULTIVALENT CELL-PENETRATING PEPTIDES AND THEIR USES

(71) Applicant: Ruprecht-Karls-Universitaet Heidelberg, Heidelberg (DE)

(72) Inventors: Matthias Strieker, Santa Fe, NM (US); Walter Mier, Bensheim (DE); Uwe Haberkorn, Schwetzingen (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 299 days.

(21) Appl. No.: 14/648,537

(22) PCT Filed: Dec. 4, 2013

(86) PCT No.: PCT/EP2013/075494
§ 371 (c)(1),
(2) Date: May 29, 2015

(87) PCT Pub. No.: WO2014/086835
PCT Pub. Date: Jun. 12, 2014

(65) Prior Publication Data
US 2015/0297742 A1    Oct. 22, 2015

Related U.S. Application Data

(60) Provisional application No. 61/733,619, filed on Dec. 5, 2012.

(51) Int. Cl.
| | |
|---|---|
| A61K 47/56 | (2017.01) |
| A61K 47/64 | (2017.01) |
| A61K 51/08 | (2006.01) |
| A61K 51/10 | (2006.01) |
| C07K 16/28 | (2006.01) |

(52) U.S. Cl.
CPC .......... *C07K 16/2863* (2013.01); *A61K 47/56* (2017.08); *A61K 47/641* (2017.08); *A61K 47/645* (2017.08); *A61K 51/088* (2013.01); *A61K 51/103* (2013.01); *C07K 2317/24* (2013.01)

(58) Field of Classification Search
CPC ................... A61K 47/48253; A61K 47/48315
See application file for complete search history.

(56) References Cited

FOREIGN PATENT DOCUMENTS

| | | |
|---|---|---|
| WO | WO 95/33766 | 12/1995 |
| WO | WO 03/103718 A2 | 12/2003 |
| WO | WO 2006/056227 A1 | 6/2006 |
| WO | WO 2010/129033 A2 | 11/2010 |

OTHER PUBLICATIONS

Olson et al. ("Activatable cell penetrating peptides linked to nanoparticles as dual probes for in vivo fluorescence and MR imaging of proteases," PNAS, 2010, vol. 107, 4311-4316) (Year: 2010).*
Marschall, Andrea L.J. et al., "Targeting antibodies to the cytoplasm," *mAbs*, 2011, 3(1):3-16.
Bonduelle, Colin V. et al., "Dendritic Guanidines as Efficient Analogues of Cell Penetrating Peptides," *Pharmaceuticals*, 2010, 3(3): 636-666.

* cited by examiner

*Primary Examiner* — Christina Bradley
(74) *Attorney, Agent, or Firm* — Saliwanchik, Lloyd & Eisenschenk

(57) ABSTRACT

The present invention relates to conjugates comprising a protein and multivalent cell-penetrating peptide(s), each multivalent cell-penetrating peptide comprising at least two cell-penetrating peptides, wherein the multivalent cell-penetrating peptide(s) is/are covalently attached to the protein. The present invention furthermore relates to a method of generating the conjugates and to their medical uses, in particular their use in the diagnosis, prevention and/or treatment of diseases. The present invention relates to methods of diagnosis, prevention and/or treatment of diseases, comprising administering the conjugates of the invention to a patient.

20 Claims, 11 Drawing Sheets
Specification includes a Sequence Listing.

CONJUGATES OF PROTEINS AND MULTIVALENT CELL-PENETRATING PEPTIDES AND THEIR USES

CROSS REFERENCE TO A RELATED APPLICATION

This application is a National Stage Application of International Application Number PCT/EP2013/075494, filed Dec. 4, 2013; which claims the benefit of U.S. Provisional Application Ser. No. 61/733,619, filed Dec. 5, 2012; both of which are incorporated herein by reference in their entirety.

The Sequence Listing for this application is labeled "SeqList-23Mar16-ST25.txt", which was created on Mar. 23, 2016, and is 184 KB. The entire content is incorporated herein by reference in its entirety.

The present invention relates to conjugates comprising a protein and multivalent cell-penetrating peptide(s), each multivalent cell-penetrating peptide comprising at least two cell-penetrating peptides, wherein the multivalent cell-penetrating peptide(s) is/are covalently attached to the protein. The present invention furthermore relates to a method of generating the conjugates and to their medical uses, in particular their use in the diagnosis, prevention and/or treatment of diseases. The present invention relates to methods of diagnosis, prevention and/or treatment of diseases, comprising administering the conjugates of the invention to a patient.

BACKGROUND OF THE INVENTION

The application of novel biological therapeutics based on molecular medicine knowledge is often complicated by the large size of these compounds. Most biological therapeutics with a pronounced specificity, such as antibodies, possess a high molecular weight, but which results in unfavourable pharmacokinetic qualities setting hurdles for their clinical applications. The successful clinical application of many high molecular weight drugs is hampered by their inability to efficiently bind to their target cell surfaces and/or traverse the cellular membrane (Sarko et al., 2010).

For example, antibodies and immunoglobulin-based agents are widely used in therapies for an increasing number of human malignancies (Waldmann 2003), especially cancer (Oldham & Dillman, 2008). Besides immunotherapeutic regimens based on antibody-dependent cellular cytotoxicity (ADCC) and/or complement-dependent cytotoxicity (CDC), immunoconjugates charged with toxins or radionuclides have been developed to enhance the antitumor potency (Carter 2001). The latter mode of treatment is known as radioimmunotherapy (RAIT), a concept which was proposed in the early 1950s. Now, almost 60 years later, there are only two radiolabeled antibodies, $^{90}$Y-ibritumomab tiuxetan (Zevalin®, Spectrum Pharmaceuticals) and $^{131}$I-tositumab (Bexxar®, GlaxoSmithKline), approved for clinical use (Witzig et al., 2002; Kaminski et al., 2001). Application of these two is indicated for patients with relapsed or refractory, low grade, follicular or transformed, non-Hodgkin's lymphoma (NHL). NHLs are good targets for RAIT, because they often are highly sensitive to radiation. Solid tumors are usually slow in growth and thus successful treatment remains a challenge. Especially, as full size antibodies have poor pharmacokinetic properties, i.e. slow binding kinetics and poor clearance, which results in collateral radiation-based damage (Song & Sgouros, 2011; Pouget et al., 2011), their usage in radioimmunodetection (RAID) and RAIT of cancer is limited. A plethora of antibody-based fragments and pretargeting approaches have been developed.

Cell-penetrating peptides are a relatively new class of short peptide sequences that cross the cytoplasmic membrane efficiently. Notably, when coupled to a cargo payload, they facilitate cellular uptake of the cargo. They have a broad range of possible applications in drug delivery and molecular biology (Fonseca at al., 2009; Howl et al., 2007; Kersemans et al., 2008). Antibody modifications with single CPPs have been reported in literature but mainly for molecular imaging (Hu et al., 2007; Cornelissen et al., 2007; Hu et al. 2006) and not for tumor therapy or detection. The only example for a successful application of CPPs in radioimmunoscintigraphy, is the modification of a divalent single-chain fragment of the anti-tumor-associated glycoprotein 72 monoclonal antibody CC49. When co-administered with a CPP, the tumor uptake and tumor-to-normal tissue ratio of the fragment increased significantly in tumor xenografts at 24 h (Jain et al., 2005). In contrast to single chain fragments, full-size monoclonal, tumor-targeting antibodies are readily available and clinically tested. Therefore, means and methods to improve their tumor-retention and pharmacokinetic properties are desired.

Small branched synthetic peptide conjugates were developed as vehicles for the delivery of diagnostic probes and cytotoxic agents into the cytoplasm and the nucleus (Sheldon et al., 1995; WO 95/33766 A1), which are particularly suitable as transfection agents (Singh et al., 1999).

Furthermore, means and methods to improve further clinically relevant proteins, such as coagulation factors, that improve their pharmacokinetic properties are desired.

There is a need in the art for providing means and methods for improving the pharmacokinetics and/or internalization of biologically or clinically relevant and/or therapeutic proteins, in particular to improve their use for the diagnosis and treatment of diseases.

SUMMARY OF THE INVENTION

According to the present invention this object is solved by providing a conjugate comprising a protein, and
one or several multivalent cell-penetrating peptide(s) (multivalent CPP(s)) each multivalent CPP comprising at least two cell-penetrating peptides (CPPs),
wherein the multivalent CPP(s) is/are covalently attached to the protein.

According to the present invention this object is solved by a method for generating a conjugate according to the invention, comprising the steps of
(a) providing multivalent cell-penetrating peptide(s) comprising anchoring group(s),
(b) generating a chemically activated protein, such as a chemically activated antibody, by using a linker, or providing a protein comprising coupling site(s),
(c) coupling the multivalent CPP(s) of step (a) to the protein of step (b),
(d) obtaining the conjugate,
(e) purifying the conjugate.

According to the present invention this object is solved by providing the conjugate according to the invention for use in medicine.

According to the present invention this object is solved by providing the conjugate according to the invention for use in the diagnosis, prevention and/or treatment of diseases.

According to the present invention this object is solved by using the conjugate according to the invention as a diagnostic agent.

According to the present invention this object is solved by a method for the diagnosis, prevention and/or treatment of a disease, comprising the step of administering a conjugate of the invention to a patient.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "5 to 40 amino acids" should be interpreted to include not only the explicitly recited values of 5 to 40, but also include individual values and sub-ranges within the indicated range. Thus, included in this numerical range are individual values such as 5, 6, 7, 8, 9, 10, 11, 12, 13, 14, 15, 16, 17, 18, 19, 20, . . . 38, 39, 40 and sub-ranges such as from 5 to 25, from 5 to 20, from 10 to 25, from 10 to 20 and from 15 to 25, etc. As an illustration, a numerical range of "at least 2 branching points, preferably 2 to 10" should be interpreted to include not only the explicitly recited values of 2 to 10, but also include individual values and sub-ranges within the indicated range. Thus, included in this numerical range are individual values such as 2, 3, 4, 5, 6, 7, 8, 9, 10 and sub-ranges such as from 2 to 8, from 2 to 7, from 3 to 8, 4 etc. This same principle applies to ranges reciting only one numerical value. Furthermore, such an interpretation should apply regardless of the breadth of the range or the characteristics being described.

Conjugates of a Protein with Multivalent Cell-Penetrating Peptide(s)

As described above, the present invention provides conjugates of a protein and multivalent CPP(s).

A conjugate of the invention comprises:
a protein, and
one or several multivalent cell-penetrating peptide(s) (multivalent CPP(s)) each multivalent CPP comprising at least two cell-penetrating peptides (CPPs),
wherein the multivalent CPP(s) is/are covalently attached to the protein.

Preferably, the conjugate of the invention comprises one to 100 multivalent CPPs, preferably 1 to 25, more preferably 1 to 10 CPPs.

Preferably, the multivalent cell-penetrating peptide (multivalent CPP) comprises 2 to 200 CPPs, preferably 2 to 50, more preferably 2 to 20 or 4 to 20 CPPs.

In one embodiment, the multivalent CPP comprises or consists of a dendrimer of cell-penetrating peptides.

Preferably, the multivalent CPP comprises or consists of a dendrimer of cell-penetrating peptides (cell-penetrating peptide dendrimer, dCPP) comprising a dendrimer core or scaffold and at least two cell-penetrating peptides (CPPs), which are coupled to the dendrimer core.

Dendrimers are known in the art.

"Dendrimers" or "dendrons" as used herein refer to repetitively branched (macro)molecules comprising a core, which are preferably wedge-like branched (macro)molecules. A dendrimer as used herein contains a single chemically addressable group called the focal point in the art and is called an "anchoring group" herein. A dendrimer as used herein can be not symmetric around the core.

Preferably, the dendrimer core or scaffold comprises
anchoring group(s) for coupling to the protein or linker,
branching point(s), and
optionally, spacer between the anchoring group(s) and the branching point(s).

The anchoring group of focal point serves for coupling to the protein or linker.

Preferably, the dendrimer core or scaffold comprises one anchoring group.

In some embodiments, the dendrimer core or scaffold can comprise more than one anchoring groups, such as 1 to 25 or 1 to 4.

The branching point(s) are for branching the dendrimer core and/or for coupling to the CPPs.

In one embodiment, the dendrimer core or scaffold is a peptide dendrimer core or peptidyl dendrimer core or peptidic dendrimer core. A peptide/peptidic/peptidyl dendrimer core is a dendrimer core comprising amino acids which comprise the anchoring group(s) and which form the branching points.

Peptide dendrimer cores or scaffolds are known in the art.

Peptide dendrimer core or scaffolds can comprise natural amino acids, amino acid derivatives, L- and/or D-amino acids, modified amino acids, such as β-amino acid derivatives, α,α-disubstituted amino acid derivatives, N-substituted α-amino acid derivatives, aliphatic or cyclic amines, amino- and carboxy-substituted cycloalkyl derivatives, amino- and carboxy-substituted aromatic derivatives, γ-amino acid derivatives, aliphatic α-amino acid derivatives, diamines and polyamines.

For example, a dendrimer core or scaffold can be a polylysine.

For example, a dendrimer core or scaffold can comprise lysines as branching points and cysteine(s) as the anchoring group(s) (—SH group).

For example, a dendrimer core or scaffold can comprise lysine(s) as the anchoring group(s). In this example, the branching point(s) are preferably other amino acid residues but lysines.

Further anchoring group(s) are known in the art, see e.g. Sarko et al., 2012.

For example, a dendrimer core comprises or consists of

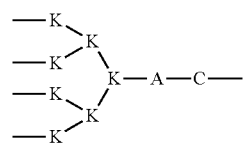

wherein K is Lys, A is Ala and Y is Cys.

For example, the dendrimer core comprises 2 to 100 branching points, preferably 2 to 20, such as 4 branching points.

Dendrimer cores or scaffolds are known in the art, see for example the review of Khandare et al. 2012.

Further dendrimer cores or scaffolds comprise or consist of a polyamidoamine (PAMAM), polypropylene imine), polyaryl ether, polyester, polyamide, polyglycerol, triazine based, poly(glycerol-succinic acid) core.

Preferably, the dCPP(s) have a size ranging from about 2 to about 100 kDa, preferably from about 2 to about 50 kDa, more preferably about 4 to 20 kDa.

In one embodiment, the multivalent CPP comprises or consists of multiple copies of CPPs, such as a linear sequence or combination of cell-penetrating peptides.

For example, the multiple copies of CPPs are linked to a linear polymer or linear scaffold.

Examples for suitable linear polymers or scaffolds are polyoxazoline copolymer (see Farkas et al., 2010) or methacrylamide polymers, such as pHPMAm (poly[N-2-hydroxypropyl]methacrylamide) (see Jay et al., 2009).

Also the linear polymer or scaffold comprises one or several anchoring groups for coupling to the protein or linker.

"Cell-penetrating peptides" (CPPs) refer to short peptides of 5 to 40 amino acids in length that facilitate cellular uptake of various cargoes, from nanosized particles to small chemical molecules and macromolecules, such as nucleic acids, peptides, proteins, drugs, liposomes etc. The "cargo" is associated with the peptides either through chemical linkage via covalent bonds or through non-covalent interactions. The attachment of one or multiple CPPs to the cargo facilitates the delivery of the cargo into cells.

CPPs typically have an amino acid composition that
(1) either contains a high relative abundance of positively charged amino acids, such as lysine or arginine,
or
(2) have sequences that contain an alternating pattern of polar/charged amino acids and non-polar, hydrophobic amino acids.

These two types of structures are referred to as
(1) polycationic or cationic
or
(2) amphipathic.

CPPs are of different sizes, amino acid sequences, and charges but all CPPs have one distinct characteristic, which is the ability to translocate the plasma membrane and facilitate the delivery of various molecular cargoes to the cytoplasm or an organelle. There has been no real consensus as to the mechanism of CPP translocation, but the theories of CPP translocation can be classified into three main entry mechanisms: direct penetration in the membrane, endocytosis-mediated entry, and translocation through the formation of a transitory structure.

Preferably, the cell-penetrating peptide comprises an amino acid sequence having 5 to 50 amino acids, preferably up to 30 amino acids, such as 5 to 30 amino acids, more preferably 5 to 25 or 8 to 25 amino acids.

Thereby, each of a CPP of a dendrimer of CPPs or each of a CPP of multiple copies of CPPs comprises such an amino acid sequence.

Preferably, the CPPs comprise natural amino acids, amino acid derivatives, D-amino acids, modified amino acids, β-amino acid derivatives, α,α-disubstituted amino acid derivatives, N-substituted α-amino acid derivatives, aliphatic or cyclic amines, amino- and carboxy-substituted cycloalkyl derivatives, amino- and carboxy-substituted aromatic derivatives, γ-amino acid derivatives, aliphatic α-amino acid derivatives, diamines and polyamines. Further modified amino acids are known to the skilled artisan.

The term "natural amino acid residue" or "natural amino acid", as used herein, denotes any of the 22 "standard" amino acids that are naturally incorporated into peptides. Of these twenty-two, twenty are directly encoded by the universal genetic code. The remaining two, selenocysteine and pyrrolysine are incorporated into proteins by unique synthetic mechanisms. Typically, the amino acid residues of a peptide according to the invention are present as L-isomers. In some embodiments, one or more, eventually all amino acid residues of a peptide according to the invention are present as D-isomers. The term "modified amino acid residue", as used herein, denotes non-standard amino acids such as modified amino acids. Examples of modifications include inter alia phosphorylation, glycosylation, acylation (e.g., acetylation, myristoylation, palmitoylation), alkylation, carboxylation, hydroxylation, glycation, biotinylation, ubiquitinylation, changes of the chemical nature (e.g., [beta]-elimination deimidation, deamidation,), and structural changes (e.g., the forming of disulfide bridges). The amino acid sequences of the peptides as defined herein are written, according to the general convention, from the amino (N)-terminus to the carboxyl (C)-terminus. However, the corresponding "reverse" peptides are also within the present invention. The term "reverse peptide", as used herein, denotes peptides having the same sequence as their "regular" counterparts but in reverse orientation, that is, from the C-terminus to the N-terminus.

Preferably, a CPP
(i) is a (carrier) peptide capable of being internalized into a cell;
and/or
(ii) comprises in its amino acid sequence at least 25% positively charged amino acid residues;
and/or
(iii) is internalized into a cell with an efficacy being at least 50% of the internalization efficacy of the TAT peptide having the amino acid sequence of SEQ ID NO: 2.

In one embodiment (ii), the CPPs have in their respective primary amino acid sequences (that is, over their entire length) at least 25%, preferably at least 30% positively charged amino acid residues. The term "positively charged amino acids" (herein also referred to as "basic amino acids"), as used herein, denotes the entirety of lysine (K), histidine (H), and arginine (R) residue present in a particular peptide. In specific embodiments, a peptide used in the present invention comprises in its primary amino acid sequence 25%, 26%, 27%, 28%, 29%, 30%, 31%, 32%, 33%, 34% or 35% positively charged amino acid residues. In other embodiments, the peptides used herein comprise in their respective primary amino acid sequences at least 35%, at least 40%, at least 45%, at least 50%, at least 55%, or at least 60% positively charged amino acid residues.
(i) Preferably, a CPP is a (carrier) peptide capable of being internalized into a cell.

The term "capable of being internalized into a cell", as used herein, refers to the ability of the peptides to pass cellular membranes (including inter alia the outer "limiting" cell membrane (also commonly referred to as "plasma membrane"), endosomal membranes, and membranes of the endoplasmatic reticulum) and/or to direct the passage of a given agent or cargo through these cellular membranes. Such passage through cellular membranes is herein also referred to as "cell penetration". Accordingly, peptides having said ability to pass through cellular membranes are herein referred to as "cell-penetrating peptides". In the context of the present invention, any possible mechanism of internalization is envisaged including both energy-dependent (i.e. active) transport mechanisms (e.g., endocytosis) and energy-independent (i.e. passive) transport mechanism (e.g., diffusion). As used herein, the term "internalization" is to be understood as involving the localization of at least a part of the peptides that passed through the plasma cellular membrane into the cytoplasma (in contrast to localization in different cellular compartments such as vesicles, endosomes or in the nucleus). In specific embodiments, a given transport mechanism that is employed ensures that at least 0.01%, at least 0.05%, at least 0.1%, at least 0.5%, at least 1%, at least 2%, at least 5% or at least 10% of the peptides or compositions internalized localize into the cytoplasm.

(iii) Preferably, a CPP is internalized into a cell with an efficacy being at least 50% of the internalization efficacy of the TAT peptide having the amino acid sequence of SEQ ID NO: 2.

Hereby, the internalization efficacy of a single CPP is referred to and not the internalization efficacy of a multivalent CPP.

According to the invention, the internalization efficacy of the multivalent CPP is preferably higher compared to the internalization efficacy of a single CPP. This allows the use of CPPs which show a rather low internalization efficacy compared to TAT and when used as single copy.

The peptides used in the present invention are internalized into a cell with an efficacy being at least 50%, such as 60% of the internalization efficacy of the TAT peptide (preferably having the amino acid sequence of SEQ ID NO. 2) (see Vives; E. et al. 1997). In other words, the functional activity of the peptides is characterized in comparison to a reference peptide (TAT represents the "gold standard" with regard to cell-penetrating peptides). In specific embodiments, the peptides used herein are internalized with an efficacy being 80%, 85%, 90% or 95% of the internalization efficacy of the TAT peptide. In specific preferred embodiments, the peptides used herein are internalized with at least the same efficacy (i.e. 100%) as the TAT peptide. Particularly preferably, the peptides used herein are internalized with a higher efficacy (i.e. more than 100% or at least 101%) as the TAT peptide, e.g., with 105%, 110%, 115%, 120%, 125%, 130%, 140%, 150%, 160%, 170%, 180%, 190%, or 200% of the internalization efficacy of the TAT peptide.

The term "internalization efficacy", as used herein, is to be understood in a broad sense. The term does not only refer to the extent to which a peptide used in the invention passes through the plasma membrane of cells (i.e. the internalization behavior per se) but also to the efficiency by which the peptide directs the passage of a given agent or cargo through the cell plasma membrane (i.e. its transfection capability; herein also referred to as "transfectivity"). Numerous methods of determining the internalization behavior and/or transfection capability of a given peptide are established in the art, for example, by attaching a detectable label (e.g. a fluorescent dye) to the peptide (and/or to the cargo to be transfected) or by fusing the peptide with a reporter molecule, thus enabling detection once cellular uptake of the peptide occurred, e.g., by means of FACS analysis or via specific antibodies (see, e.g., Ausubel, et al., 2001). The skilled person is also well aware how to select the respective concentration ranges of the peptide and, if applicable, of the cargo to be employed in such methods, which may depend on the nature of the peptide, the size of the cargo, the cell type used, and the like. In further embodiments, the peptides used in the present invention do not exert significant cytotoxic and/or immunogenic effects to their respective target cells after having been internalized, that is, they do not interfere with cell viability (at least at concentrations that are sufficient to mediate cellular transfection and/or penetration). The term "not significant", as used herein, is to be understood that less than 50%, preferably less than 40% or 30%, and particularly less than 20% or 10% of the target cells are killed after internalization of a peptide of the invention. In other embodiments, the cytotoxic (and/or immunogenic) effects exerted by the peptides upon internalization into a cell are the same or less than the corresponding effects exerted by the TAT peptide having the amino acid sequence of SEQ ID NO. 2. In specific embodiments, the cytotoxic (and/or immunogenic) effects exerted by the peptides upon internalization into a cell are less than 95%, less than 90%, less than 85%, less than 80%, less than 75%, less than 70%, less than 60%, less than 50%, less than 40%, less than 30%, less than 20%, or less than 10% of the effects exerted by the TAT peptide. The skilled person is well aware of methods of determining the cytotoxicity of a given compound and/or the viability of a given target cell to which such a compound is applied (see also, e.g., Ausubel, F. M. et al. (2001), supra). Corresponding assay kits are commercially available from various suppliers.

There exists a database of experimentally validated CPPs (CPPsite, Gautam et al., 2012). The CPP of a conjugate of the invention can be any known CPP, such as a CPP shown in that database.

In one embodiment, the multivalent CPP of the invention comprises several of the same CPP (having an identical amino acid sequence) or comprises different CPPs, i.e. CPPs with different amino acid sequences, such as 2, 3, 4 or more different CPPs.

Preferably, the cell-penetrating peptide(s) comprise or consist of the amino acid sequence selected from the group of SEQ ID NOs. 1 to 760,
or amino acid sequences having at least 90% sequence identity to the amino acid sequences of SEQ ID NOs. 1 to 760, preferably at least 95% sequence identity or 99% sequence identity.

In the embodiment, where the multivalent CPP comprises different CPPs, the CPP(s) comprise or consist of the amino acid sequence selected from the group of SEQ ID NOs. 1 to 760 or from combinations of SEQ ID NOs. 1 to 760 and/or from any subset of amino acid sequences with SEQ ID NOs. 1 to 760.

Preferably, the cell-penetrating peptide(s) comprise or consist of the amino acid sequence of
   penetratin (SEQ ID NO. 1),
   TAT (47-60) (human immunodeficiency virus-derived trans-activator of transcription, SEQ ID NO. 2),
   PreS2-TLM (hepatitis B virus-preS2-domain-derived translocation motif, SEQ ID NO. 3),
   R9 (SEQ ID NO. 4),
   MTS (membrane translocation signal, SEQ ID NO. 5),
   SynB1 (synthetic porcine protegrin 1-derived CPP, SEQ ID NO. 6),
   pVEC (vascular endothelial cadherin-derived CPP, SEQ ID NO. 7),
   NLS (nuclear localization signal, SEQ ID NO. 8),
   or combinations thereof.

For example, the cell-penetrating peptide(s) comprise the amino acid sequence of penetratin (SEQ ID NO. 1) and/or R9 (SEQ ID NO. 4).

Preferably, the cell-penetrating peptide(s) comprise or consist of the amino acid sequence of SEQ ID NOs. 9 to 77 or combinations thereof.

| Name | Sequence | SEQ ID NO. |
|---|---|---|
| TAT peptide (49-57) | RKKRRQRRR | 9 |
| TAT (48-60) | GRKKRRQRRRPPQ | 10 |
| calcitonin-derived CPP | LGTYTQDFNKFHTFPQTAIGVGAP | 11 |
| NLS | VQRKRQKLMP | 12 |
| NLS | SKKKKTKV | 13 |
| NLS | GRKRKKRT | 14 |
| polybasic CPP | RRRERRAEK | 15 |
| polybasic CPP | KCPSRRPKR | 16 |
| N-terminal repetitive domain of maize gamma-zein | (VRLPPP)n | 17 |
| | (VHLPPP)n | 18 |
| | (VKLPPP)n | 19 |
| Peptide from gp41 fusion sequence | AVGAIGALFLGFLGAAG | 20 |
| SSHR | VTVLALGALAGVGVG | 21 |
| pVEC | IAARIKLRSRQHIKLRHL | 22 |
| Vpr | DTWPGVEALIRILQQLLFIHFRIGCQH | 23 |
| VP22 | DAATATRGRSAASRPTERPRAPARSASRPRRPVD | 24 |
| gp41 fusion sequence | GALFLGWLGAAGSTMGA | 25 |
| Caiman crocodylus Ig(v) light chain | MGLGLHLLVLAAALQGA | 26 |
| CPP from pestivirus env glycoprotein | RQGAARVTSWLGRQLRIAGKRLEGRSK | 27 |
| CPP from the prion protein | MANLGYWLLALFVTMWTDVGLCKKRPKP | 28 |
| Yeast PRP6 (129-144) | TRRNKRNRIQEQLNRK | 29 |
| Phi21 N (12-29) | TAKTRYKARRAELIAERR | 30 |
| Delta N (1-22) | MDAQTRRRERRAEKQAQWKAAN | 31 |
| FHV coat (35-49) | RRRRNRTRRNRRRVR | 32 |
| BMV Gag (7-25) | KMTRAQRRAAARRNRWTAR | 33 |
| HTLV-II Rex (4-16) | TRRQRTRRARRNR | 34 |
| HIV-1 Rev (9-20) | RQARRNRRRRWR | 35 |
| RSG-1.2 | DRRRRGSRPSGAERRRRRAAAA | 36 |
| Lambda-N (48-62) | QTRRRERRAEKQAQW | 37 |
| Bipartite, Nucleoplasmin (155-170), NLS | KRPAAIKKAGQAKKKK | 38 |
| Herpesvirus, 8 k8 protein (124-135) | TRRSKRRSHRKF | 39 |
| Buforin-II (20-36) | RAGLQFPVGRVHRLLRK | 40 |
| Magainin | TRSSRAGLQFPVGRVHRLLRK | 41 |
| PDX-1-PTD | RHIKIWFQNRRMKWKK | 42 |
| crotamine | YKQCHKKGGHCFPKEKICLPPSSDEGKMDCRWRWKCCKKGSG | 43 |

-continued

| Name | Sequence | SEQ ID NO. |
|---|---|---|
| pIsI | RVIRVWFQNKRCKDKK | 44 |
| Fushi-tarazu (254-313) | SKRTRQTYTRYQTLELEKEFHENRYITRRRRIDIANALSLSERQIKIWFQNRRMKSKKDR | 45 |
| Engrailed (454-513) | EKRPRTAFSSEQLARLKREFNENRYLTERRRQQLSSELGLNEAQIKIWFQNKRAKIKKST | 46 |
| transportan | GWTLNSAGYLLGKINLKALAALAKKIL | 47 |
| Polyarginine CPP (R8) | RRRRRRRR | 48 |
| Poly-D-arginine | rrrrrrrrr | 49 |
| KLAL peptide/ model amphiphatic peptide (MAP) | KLALKLALKALKAALKLA | 50 |
| KALA model amphiphatic peptide | WEAKLAKALAKALAKHLAKALAKALKACEA | 51 |
| modeled TAT peptide | YARAAARQARA | 52 |
| b-sheet-forming peptide | DPKGDPPKGVTVTVTVTVTGKGDPKPD | 53 |
| retro-inverso forms of established CPPs | KKWKMRRNQFWVRVQR | 54 |
| W/R penetratin | RRWRRWWWRRWWRRWRR | 55 |
| MPG | GALFLGFLGAAGSTMGAWSQPKSKRKVC | 56 |
| Pep-1 | KETWWETWWTEWSQPKKKRKV | 57 |
| Signal-sequence peptides (I) | GALFLGWLGAAGSTMGAWSQPKKKRKV | 58 |
| PTD-5 | RRQRRTSKLMKR | 59 |
| RSV-A9 | RRIPNRRPRR | 60 |
| CTP-512 | YGRRARRRRRR | 61 |
| U2AF | SQMTRQARRLYV | 62 |
| 105Y | SIPPEVKFNKPFVYLI | 63 |
| Antennapedia Leader Peptide | KKWKMRRNQFWVKVQRG | 64 |
| Anti-BetaGamma | AAVALLPAVLLALLAVTDQLGEDFFAVDLEAFLQEFGLLPEKE | 65 |
| Lipid Membrane Translocating | KKAAAVLLPVLLAAP | 66 |
| Mastoparan | INLKALAALAKKIL | 67 |
| MEK1 Nterm | MPKKKPTPIQLNP | 68 |
| MPS | AAVALLPAVLLALLAK | 69 |
| RV-MAT | MNLLRKIVKNRRDEDTQKSSPASAPLDDG | 70 |
| Transdermal peptide | ACSSSPSKHCG | 71 |
| SynB3 | RRLSYSRRRF | 72 |
| PTD-4 | PIRRRKKLRRLK | 73 |
| SBP | MGLGLHLLVLAAALQGAWSQPKKKRKV | 74 |
| Pep-2 | KETWFETWFTEWSQPKKKRKV | 75 |

-continued

| Name | Sequence | SEQ ID NO. |
|---|---|---|
| Polyarginines | (R)n wherein n is at least 3, preferably 3 to 50, more preferably 3 to 15 | 76 |
| Polylysines | (K)n wherein n is at least 3, preferably 3 to 50, more preferably 3 to 15 | 77 |

Preferably, the cell-penetrating peptide(s) comprise or consist of the amino acid sequence of SEQ ID NOs. 78 to 760 or combinations thereof.

For the amino acid sequences of SEQ ID NOs. 1 to 760, see Table 1.

In an embodiment, the CPP does not consist of the amino acid sequence TPPKKKRKVEDP (SEQ ID NO:761) or of the amino acid sequence TPPKKKRKVEDP (SEQ ID NO:761) in combination with the amino acid sequence KKKKK (SEQ ID NO:762) ((Lys)$_5$). For example, the CPP does not consist of the amino acid sequence TPPKKKRK-VEDPKKKKK (SEQ ID NO:763) or KKKKKTPPKK-KRKVEDP (SEQ ID NO:764).

In an embodiment, the multivalent CPP does not consist of the amino acid sequence (TPPKKKRKVEDPKKKKK)$_n$ (SEQ ID NO:763) Or (TPPKKKRKVEDP)$_n$ (SEQ ID NO:761) with n≥2, such as 2 to 8, such as 8.

Preferably, the protein is a biological or clinically active or therapeutic protein.

Such biological or clinically active or therapeutic proteins are known in the art. See, for example, http://www.genomicglossaries.com/content/Protein_categories.asp.

Preferred examples are:
an antibody or an antibody fragment,
a coagulation factor or cofactor,
a receptor or receptor ligand(s),
insulin or insulin analogues,
interferon(s), such as IFN-α2a, IFN-β1a,
enzyme(s), such as arginine deiminase methioninase superoxide dismutase uricase
cytokine(s), such as granulocyte colony stimulating factor (G-CSF),
erythropoietin(s),
interleukin(s), such as interleukin-6, PEG-interleukin-2,
hormone(s), such as calcitonin, human growth hormone (HGF),
a vaccine,
or combinations thereof.

The antibody can be a full-size antibody, such as a monoclonal antibody, or a recombinant antibody, or engineered antibodies/antibody fragments, such as a single chain variable fragment (scFv), the fragment antigen-binding (Fab) or the Fab-Dimer (F(ab')$_2$ fragment.

In a preferred embodiment, the antibody of the conjugate of the invention is a "full-size" antibody, such as a monoclonal antibody.

Depending on the protein and/or type of multivalent CPP used in the conjugate of the invention, there are different possibilities for covalently attaching the multivalent CPP to the protein.

For example, the multivalent CPP(s) can be coupled to cysteine, glutamine or lysine residue(s) of the protein.

For example, the multivalent CPP(s) can be coupled to a chemically activated protein, wherein the protein can be chemically activated by using a suitable linker.

For example, the multivalent CPP(s) can be coupled to a protein comprising a functional group of an unnatural amino acid, which has been incorporated into the protein either by chemically modification or by recombinant expression using an expanded genetic code (see e.g. Xie & Schultz, 2006).

In one embodiment, the conjugates of the invention furthermore comprise linker connecting the protein and the multivalent CPP(s).

Preferably, the linker is a bifunctional (cross)linker covalently coupling the protein with the multivalent cell-penetrating peptide(s).

For example, the linker is a bifunctional (cross)linker, such as succinimidyl-4-(N-maleimidomethyl)cyclohexane-1-carboxylate (SMCC).

Further linker are known in the art, see e.g. the review Sarko et al., 2012.

In a preferred embodiment, the conjugate of the invention comprises
an antibody,
one or several cell-penetrating peptide dendrimer(s) (dCPP),
one or several linker, preferably bifunctional (cross)linker(s), each covalently coupling the antibody with a dCPP.

For example, the conjugate of the invention comprises
an antibody,
one cell-penetrating peptide dendrimer (dCPP),
a linker, preferably one bifunctional (cross)linker.

Preferably, the conjugates of the invention comprise further component(s), such as
labels
such as radioisotope(s), fluorescent dye(s), quantum dots, contrast agent(s)
drugs or prodrugs,
further biologically active component(s),
or combinations thereof.

Depending on the further component(s) and/or the protein, such as the specificity of the antibody, the conjugates of the invention can be used for the diagnosis, prevention and/or treatment of diseases.

For example, a conjugate comprising a cell-specific antibody and a radioisotope is suitable for radioimaging, radioimmunodetection but also for radioimmunotherapy.

For example, a conjugate comprising a cell-specific antibody and drug(s) is suitable for cell-specific drug delivery.

For example, a conjugate comprising a tumor-specific antibody is suitable for the diagnosis, prevention and/or treatment of that tumor/cancer.

Method of Generating the Multivalent CPP Protein Conjugates

As described above, the present invention provides a method for generating the conjugates of a protein and a multivalent cell-penetrating peptide of the invention.

Depending on the protein and/or type of multivalent CPP used in the conjugate of the invention, there are different possibilities for covalently attaching the multivalent CPP to the protein.

For example, the multivalent CPP(s) can be coupled to coupling site(s) comprised in the protein.

The coupling site(s) can be the sides chains of cysteine(s), glutamine and/or lysine(s) and/or unnatural amino acids.

The coupling site(s) can be the side chains of cysteine(s), glutamine or lysine(s), which are within the amino acid sequence of the protein, such as naturally occurring and/or added.

For coupling to glutamine, see e.g. Jeger at al., 2010, describing the site-specific modification of proteins at glutamine residues using transglutaminase.

The coupling site(s) can be unnatural amino acids, preferably incorporated into the amino acid sequence of the protein by recombinant expression of the protein by using an expanded genetic code, as described in Xie & Schultz, 2006.

For example, the multivalent CPP(s) can be coupled to a chemically activated protein, wherein the protein can be chemically activated by using a suitable linker.

The method of the invention comprises the steps of
(a) providing multivalent cell-penetrating peptide(s) (multivalent CPP(s)) comprising one or several anchoring group(s),
(b) generating a chemically activated protein, such as a chemically activated antibody, by using a linker, or providing a protein comprising coupling site(s),
(c) coupling the multivalent CPP(s) of step (a) to the protein of step (b),
(d) obtaining the conjugate,
(e) purifying the conjugate.

In one embodiment, the method of the invention comprises the steps of
(a) providing cell-penetrating peptide dendrimer(s) (dCPPs) comprising one or several anchoring group(s),
(b) generating a chemically activated protein by using a linker, or providing a protein comprising coupling site(s),
(c) coupling the cell-penetrating peptide dendrimer(s) of step (a) to the protein of step (b), namely the chemically activated protein or the protein comprising coupling site(s),
(d) obtaining the conjugate,
(e) purifying the conjugate.

For example, the anchoring group(s) of the dCPP(s) provided in step (a) can be sulfhydryl group(s) (such as comprised in a cysteine) or amino group(s) (such as comprised in lysine(s).

For example, in step (b) a chemically activated protein, such as a chemically activated antibody, can be provided, such as a maleimide-activated protein/antibody.

For example, the linker is a bifunctional (cross)linker, such as succinimidyl-4-(N-maleimidomethyl)cyclohexane-1-carboxylate (SMCC).

Further linker are known in the art, see e.g. the review Sarko et al., 2012.

The method preferably comprises using in step (b) excess of the linker, preferably to generate a protein (such as an antibody) having one or several maleimide molecules on the surface.

For example, in step (b) the coupling site(s) of the protein can be
the side chains of cysteine(s), glutamine(s) or lysine(s), which are within the amino acid sequence of the protein, such as naturally occurring and/or added, and/or
unnatural amino acids, preferably incorporated into the amino acid sequence of the protein by recombinant expression of the protein by using an expanded genetic code, as described in Xie & Schultz, 2006.

The method preferably comprises using in step (c) excess of the cell-penetrating peptide dendrimer(s).

Uses of the Conjugates of a Protein and Multivalent CPP(s)

As described above, the present invention provides the conjugates of the invention for use in medicine.

As described above, the present invention provides the conjugates of the invention for use in the diagnosis, prevention and/or treatment of diseases.

Preferably, the diagnosis comprises radioimmunodetection, radioimmunoscintigraphy, radioimmunotomography, radioimmunotomography.

Preferably, the prevention and/or treatment of a disease comprises immunotherapy and radioimmunotherapy.

The disease can be cancer, a coagulation disorder, a cardiovascular disease, an immune disease, an infectious disease, a neuronal disease, an inflammatory disease, a heritable disease or a rheumatic disease.

Preferably, the diagnosis, prevention and/or treatment comprises cell-specific targeting.

More preferably, the cell-specific targeting of diseased cells, tissues and organs; cell-specific labelling of diseased cells, tissues and organs; and/or cell-specific drug delivery to diseased cells, tissues and organs, wherein the diseased cells, tissues and organs are preferably tumor related.

As described above, the present invention provides the use of the conjugates of the invention as diagnostic or a diagnostic agent.

The conjugates of the present invention can also be used in vitro, such as for cell-specific targeting.

Methods of Diagnosis and Therapy

As described above, the present invention provides a method for the diagnosis, prevention and/or treatment of a disease.

The method of the invention comprises the step of administering a conjugate of the invention to a patient.

Preferably, the diagnosis comprises radioimmunodetection, radioimmunoscintigraphy, radioimmunotomography.

Preferably, the prevention and/or treatment of a disease comprises immunotherapy and radioimmunotherapy.

Preferably, the disease is cancer, a coagulation disorder, a cardiovascular disease, an immune disease, an infectious disease, a neuronal disease, an inflammatory disease, a heritable disease or a rheumatic disease.

Preferably, the diagnosis, prevention and/or treatment comprises cell-specific targeting.

More preferably, comprising the cell-specific targeting of diseased cells, tissues and organs; cell-specific labelling of diseased cells, tissues and organs; and/or cell-specific drug delivery to diseased cells, tissues and organs, wherein the diseased cells, tissues and organs are preferably tumor related.

Further Description of the Invention and of a Preferred Embodiment

The inventors have developed a novel modification route employing cell-penetrating peptide dendrimers (dCPPs) for the generation of antibody conjugates, in particular conjugates with highly specific, full-size monoclonoal antibodies (mAbs) for application in immunotherapy, radioimmunotherapy and imaging.

In the present invention, the development of a general modification strategy for antibodies, such as mAbs, by employing a commercially available, heterobifunctional crosslinker and tetravalent cell-penetrating peptide dendrimers, is described. The crosslinker reacts with a random lysine side chain of the antibody and allows in a second step the attachment of the dCPP. A tetravalent CPP dendrimer was used, as the attachment of a single CPP reportedly did not significantly increase the tumor-to-blood ratio (Hu et al., 2007) and therefore will not result in improved pharmacokinetics as compared to the unmodified antibody.

In the present invention, the syntheses of eight different CPP dendrimers and their conjugation to a tumor-targeting antibody is described. In addition, the impact of the dCPP attachment to the antibody (mAb) in terms of target cell binding is lined out. Finally, the improvement of the pharmacokinetic properties of the antibody, resulting from the coupling to the dCPPs, is shown by biodistribution studies as well as small animal scintigraphic and PET imaging.

The use of radiolabeled antibodies in imaging and therapy of solid tumors is limited due to their size, resulting in poor pharmacokinetics and clearance. To overcome these problems cell-penetrating peptide dendrimers (dCPPs) were conjugated to an EGFR-specific antibody and evaluated in vitro and in vivo.

Results: In contrast to the unmodified antibody, the immunoconjugates showed up to four-fold higher EGFR-positive cell binding in vitro and were internalized. Organ distribution studies of the mAb-dCPP conjugates with highest target affinity showed better tumor-to-blood ratios compared to the unmodified antibody. Small animal imaging revealed faster clearance of the conjugates.

Conclusions: The conjugation of antibodies with dCPPs leads to improved target cell binding and to favorable pharmacokinetics. These results demonstrate that dCPPs serve as a powerful tool for improving antibody performance in radioimmunoscintigraphy and therapy.

Discussion

Cell Penetrating Peptides Dendrimer Syntheses and Conjugation to the Antibody.

The challenging syntheses of the dendrimers worked in general quite satisfactory taken into account that tetramers with a total number of up to 77 amino acid residues (dSynB1 and dpVEC) were synthesized. Two dendrimers—dpVEC and dMTS—had only moderate yields (4 µmol, 6.7%), whereas the majority of the dendrimers were obtained in good yields (≥15 µmol or 30%), even the dR9 with its 36 arginine residues.

The purified dCPPs were then used in crosslinking reactions employing the heterobifunctional crosslinker SMCC. It has been previously shown that not the size of the molecule, which is attached to the antibody does impact its antigen binding capacity, but the number of molecules (Wangler et al., 2008). The fewer molecules are attached to the mAB the less likely is an inflicted damage to the antigen binding capability; i.e. a single dCPP, which is up to 10 kDa in size can be attached to an antibody without disturbing the antibody performance, whereas coupling of four significantly smaller, non-dendritic CPPs, with 2.5 kDa each, to the mAb are more likely to have a negative effect on the antigen binding capability. Therefore, in the first reaction—the attack of the activated N-hydroxyl succinimidyl (NHS) ester by side chain amines of the antibody—different equivalents of the crosslinker SMCC were used to generate a maleimide-activated antibody (FIG. 2A). The excess of crosslinker is necessary, as most of the NHS ester will hydrolyze in the aqueous conjugation buffer. An excess between 7- and 30-fold of SMCC was used to determine optimal reaction conditions to yield in average one maleimide molecule on the surface of the antibody. This was done to ensure in the second reaction a single sulfhydryl-mediated dCPP attachment to the maleimide and hence to the antibody. The dCPP concentration was kept constant in the second reaction (15-fold excess) in order to keep the reaction conditions simple and to facilitate complete modification of all maleimide molecules present on the antibody. As demonstrated in FIG. 2B, 15 equivalents of SMCC in the first reaction generated mAb-dCPP conjugates with an approximate ratio of 1:1, leaving a small portion of the antibody unmodified. Although a 30-fold excess of the crosslinker yielded almost complete modification of the mAb, it also resulted in more than one dCPP attachment. As outlined before, a single attachment of a large molecule will most likely not affect antigen binding, but multiple crosslinked molecules will. Therefore, the incomplete outcome of the modification reaction with 15-fold excess of SMCC was accepted to prevail antigen binding of the mAB-dCPP conjugates. Excess dCPPs were removed and the conjugate was purified by size exclusion chromatography.

Cell Binding and Internalization Studies.

In these studies, the conjugates and the unmodified antibody were incubated with tumor cell lines in vitro to examine the influence of the dCPPs on cell binding and internalization. Prior to the assays it was proven that the two cell lines were definitely suitable as model cell lines for the antibody's target—EGFR—expression (A431) and the lack of the antigen (DU-145) by western blot (FIG. 8). The cells were then incubated with radioactively labeled mAb and the conjugates thereof. In general a higher binding percentage of the applied dose per one million A431 cells was observed for the conjugates compared to the unmodified mAb. Notably the absolute values were at least twice the mAb binding percentage. For most of the conjugates—dTAT, dPenetratin, dMTS—these values were threefold higher and for dR9 even 4.2-fold. Another interesting finding was that the dCPP-conjugates were internalized but to very different extent. Whereas for some dCPPs high accumulation inside the cells of up to 40% of the applied dose was observed, for other dCPPs this value was barely 10%. The difference between the internalization rates might be due to tetrameric structure of dCPP. As a single CPP together with its cargo is usually capable to translocate into the cell, this uptake might be disturbed by the dendritic structure. Although CPP cell membrane transduction is still not fully understood and an ongoing area of research three mechanisms are proposed, dependent on the CPP these are: direct membrane penetration; uptake via endocytosis; and translocation by transitory structure formation (Madani et al., 2011; Trabulo et al., 2010). The latter was proposed to be the main mechanism of internalization for amphipathic CPPs, such as pVEC and SynB1 (Deshayes et al., 2006). Thus, it is likely that this transitory structure formation cannot occur or it as least disturbed in the dendritic structure, which might explain the low internalization rates for these conjugates. Nevertheless, even those amphipathic dCPPs showed high overall binding rates, which might be explained by a dock and lock mechanism, i.e. the immunoconjugate binds to the antigen present on the target cell and the dCPP locks onto the cell surface (FIG. 6A) but the transitory structure formation necessary for membrane translocation is disturbed or slowed down. However, the interactions between the membrane and the dCPP facilitate strong binding interaction between the immunoconjugate and the membrane. For most of the mAb-dCPP the following binding mode can be hypothesized: first, the antibody part binds to the antigen; second, the dCPP subunit binds to the cell membrane; and third facilitates endocytosis or other modes of membrane translocation and subsequent internalization (FIG. 6B). The hypothesis that antigen binding occurs prior to and might be crucial for cell penetration is supported by the fact that binding to the control cell line was low for most of the conjugates.

Biodistribution Studies.

In order to keep the number of laboratory animals low, only for the two most promising mAb-dCPPs and the unmodified antibody organ distribution studies were conducted. In general it was found that the conjugates were enriched in the tumor tissue at approximately the same level as the unmodified mAb. However, all other organs contained very little radioactivity for the conjugates, whereas all well blood perfused organs—kidneys, heart, and lung—contained relatively high radioactivity amounts for the mAb (FIG. 4A). The most notable difference between the immunoconjugates and matuzumab was the tumor-to-blood ratio. Within the first 4 h after injection, this ratio was approximately the same for all examined radiopharmaceuticals. But already after 24 h this ratio developed into different directions. For the conjugates mAb-dPenetratin and mAb-dCPP the tumor-to-blood ratio showed a 23 and 81% improvement, and 47 and 112% after 48 h, respectively. Thus, it became obvious that the conjugates bound faster to the tumor lesion compared to unmodified matuzumab. Taking into account that the conjugates still contained a small amount of unmodified mAb, one could hypothesize that the residual activity found in the blood might result from the unconjugated mAb impurity. Anyway, the overall clearance from the blood circuit is definitely improved compared to the unmodified antibody.

Imaging.

The recorded planar scintigraphic images of the $^{125}$I-labeled mAb-conjugates are of remarkable quality. In most cases a good contrast, i.e. a good tumor-blood-ratio, for full size antibodies in radioimmunoscintigraphy is not observed until three to four days post injection (Smith-Jones et al., 2003). However, with the here described immunoconjugates 24 hours were more than sufficient to distinguish clearly between the tumor lesion stored activity and the little still circulating activity (FIG. 9), which to date, has been achieved only with smaller antibody fragments co-administered with penetratin, but not with full-size mAbs (Jain et al., 2005). The observed differences between the immoconjugates and the unmodified antibody became even more obvious after 48 hours: a significant amount of the unmodified antibody was still not cleared from the blood flow (FIG. 5A). This observance is in good agreement with the biodistribution studies and further proves that the conjugates bind more efficiently to the target cells. Consequently the radioimmunoconjugates a faster clearance compared to the unmodified antibody was seen.

The PET images of $^{124}$I-matuzumab and its conjugates further validates that the unmodified antibody is longer in circulation than its dCPP-modified derivatives. In addition, bladder visualization for mAb and mAb-dPenetratin indicates renal clearance for both, the antibody and the conjugates.

Conclusions

The conjugation of the EGFR targeting antibody matuzumab to dCPPs improved the antibody performance. This was demonstrated by in vitro cell binding experiments in which the immunoconjugates bound up to fourfold stronger to the target cells and for some dCPP-conjugates a large portion was internalized into the target cells. Depending on the intended therapeutic use of the conjugates the dCPP can be chosen. If internalization is desired, e.g. for radioimmunotherapy, as the radiation damage will be more efficient by trapping of the tracer inside the cells, dR9 is a good choice, where one third of the activity was taken up by the cells. For the use in normal immunotherapy a CPP dendrimer, like dpVEC or dSynB1, which increases binding of the antibody to the target cells, but only slightly mediates internalization, is a good candidate to increase antibody-dependent cell-mediated cytotoxicity. The biodistribution studies demonstrated that the conjugates, if compared with the unmodified antibody bind faster and more specific to the target cells, as very little activity was observed in other organs. In addition the radioimmunoconjugates developed favorable tumor-to-blood ratios as they are faster cleared from the blood stream. This was further validated by radioimmunoscintigraphy and PET imaging: the conjugates showed almost no background of circulating activity, whereas a significant amount was visualized for the unmodified antibody.

Slow binding and clearance are the major drawbacks of full size antibodies in radioimmunotherapy and imaging often resulting in radiation damage. This can now be improved by conjugation to cell-penetrating peptide dendrimers. Herein a valuable example is presented for how a full size antibody can be modified with large molecules without reducing the antigen binding capability.

More generally, the method described increases the specificity of tumor uptake of antibodies and thus provides the basis to reduce the side effects.

Notably, the modification strategy works without the necessity to use smaller antibody-based entities, such as single chain antibodies or antibody fragments. Such smaller antibody-based entities can, however, also be used in the conjugates of the invention in order to generate diagnostically and/or therapeutically valuable conjugates. Depending on the desired use of the conjugate(s), the skilled artisan can choose between using a specific full size antibody or its fragments or genetically engineered constructs which might show further clinically interesting features.

TABLE 1

CPP sequences.
One letter code used. L-amino acids are in upper case, D-amino acids in lower case. Repetitions are written in parenthesis.

| Seq ID NO | Sequence |
| --- | --- |
| 1 | RQIKIWFQNRRMKWKK |
| 2 | YGRKKRRQRRRPPQ |
| 3 | PLSSIFSRIGDP |

TABLE 1-continued

CPP sequences.
One letter code used. L-amino acids are in upper case, D-amino acids in lower case. Repetitions are written in parenthesis.

| Seq ID NO | Sequence |
|---|---|
| 4 | RRRRRRRR |
| 5 | AAVALLPAVLLALLAP |
| 6 | RGGRLSYSRRRFSTSTGR |
| 7 | LLIILRRRIRKQAHAHSK |
| 8 | PKKKRKV |
| 9 | RKKRRQRRR |
| 10 | GRKKRRQRRRPPQ |
| 11 | LGTYTQDFNKFHTFPQTAIGVGAP |
| 12 | VQRKRQKLMP |
| 13 | SKKKKTKV |
| 14 | GRKRKKRT |
| 15 | RRRERRAEK |
| 16 | KCPSRRPKR |
| 17 | (VRLPPP)$n$ |
| 18 | (VHLPPP)$n$ |
| 19 | (VKLPPP)$n$ |
| 20 | AVGAIGALFLGFLGAAG |
| 21 | VTVLALGALAGVGVG |
| 22 | IAARIKLRSRQHIKLRHL |
| 23 | DTWPGVEALIRILQQLLFIHFRIGCQH |
| 24 | DAATATRGRSAASRPTERPRAPARSASRPRRPVD |
| 25 | GALFLGWLGAAGSTMGA |
| 26 | MGLGLHLLVLAAALQGA |
| 27 | RQGAARVTSWLGRQLRIAGKRLEGRSK |
| 28 | MANLGYWLLALFVTMWTDVGLCKKRPKP |
| 29 | TRRNKRNRIQEQLNRK |
| 30 | TAKTRYKARRAELIAERR |
| 31 | MDAQTRRRERRAEKQAQWKAAN |
| 32 | RRRRNRTRRNRRRVR |
| 33 | KMTRAQRRAAARRNRWTAR |
| 34 | TRRQRTRRARRNR |
| 35 | RQARRNRRRWR |
| 36 | DRRRGSRPSGAERRRRRAAAA |
| 37 | QTRRRERRAEKQAQW |
| 38 | KRPAAIKKAGQAKKKK |
| 39 | TRRSKRRSHRKF |
| 40 | RAGLQFPVGRVHRLLRK |

TABLE 1-continued

CPP sequences.
One letter code used. L-amino acids are in upper case, D-amino acids in lower case. Repetitions are written in parenthesis.

| Seq ID NO | Sequence |
|---|---|
| 41 | TRSSRAGLQFPVGRVHRLLRK |
| 42 | RHIKIWFQNRRMKWKK |
| 43 | YKQCHKKGGHCFPKEKICLPPSSDFGKMDCRWRWKCCKKGSG |
| 44 | RVIRVWFQNKRCKDKK |
| 45 | SKRTRQTYTRYQTLELEKEFHFNRYITRRRIDIANALSLSERQIKIWFQNRRMKSKKDR |
| 46 | EKRPRTAFSSEQLARLKREFNENRYLTERRRQQLSSELGLNEAQIKIWFQNKRAKIKKST |
| 47 | GWTLNSAGYLLGKINLKALAALAKKIL |
| 48 | RRRRRRRR |
| 49 | rrrrrrrr |
| 50 | KLALKLALKALKAALKLA |
| 51 | WEAKLAKALAKALAKHLAKALAKALKACEA |
| 52 | YARLAARQARA |
| 53 | DPKGDPPKGVTVTVTVTVTGKGDPKPD |
| 54 | KKWKMRRNQFWVRVQR |
| 55 | RRWRRWWWRRWWRRWRR |
| 56 | GALFLGFLGAAGSTMGAWSQPKSKRKVC |
| 57 | KETWWETWWTEWSQPKKKRKV |
| 58 | GALFLGWLGAAGSTMGAWSQPKKKRKV |
| 59 | RRQRRTSKLMKR |
| 60 | RRIPNRRPRR |
| 61 | YGRRARRRRRR |
| 62 | SQMTRQARRLYV |
| 63 | SIPPEVKFNKPFVYLI |
| 64 | KKWKMRRNQFWVKVQRG |
| 65 | AAVALLPAVLLALLAVTDQLGEDFFAVDLEAFLQEFGLLPEKE |
| 66 | KKAAAVLLPVLLAAP |
| 67 | INLKALAALAKKIL |
| 68 | MPKKKPTPIQLNP |
| 69 | AAVALLPAVLLALLAK |
| 70 | MNLLRKIVKNRRDEDTQKSSPASAPLDDG |
| 71 | ACSSSPSKHCG |
| 72 | RRLSYSRRRF |
| 73 | PIRRRKKLRRLK |
| 74 | MGLGLHLLVLAAALQGAWSQPKKKRKV |
| 75 | KETWEETWFTEWSQPKKKRKV |
| 76 | (R)n (n ≥ 3) |
| 77 | (K)n (n ≥ 3) |

TABLE 1-continued

CPP sequences.
One letter code used. L-amino acids are in upper case, D-amino acids in lower case. Repetitions are written in parenthesis.

| Seq ID NO | Sequence |
|---|---|
| 78 | KIAAKSIAKIWKSILKIA |
| 79 | KALAKALAKLWKALAKAA |
| 80 | KLALKLALKWAKLALKAA |
| 81 | KLLAKAAKKWLLLALKAA |
| 82 | KLLAKAALKWLLKALKAA |
| 83 | KALKKLLAKWLAAAKALL |
| 84 | KLAAALLKKWKKLAAALL |
| 85 | KALAALLKKWAKLLAALK |
| 86 | KALAALLKKLAKLLAALK |
| 87 | KLALKLALKALKAALK |
| 88 | KLAKALKAALKLA |
| 89 | KLALKLALKALKAA |
| 90 | KLGLKLGLKGLKGGLKLG |
| 91 | KLALKLALKALQAALQLA |
| 92 | KLALQLALQALQAALQLA |
| 93 | QLALQLALQALQAALQLA |
| 94 | ELALELALEALEAALELA |
| 95 | LKTLATALTKLAKTLTTL |
| 96 | LLKTTALLKTTALLKTTA |
| 97 | LKTLTETLKELTKTLTEL |
| 98 | LLKTTELLKTTELLKTTE |
| 99 | klalklalkalkaalkla |
| 100 | KALKLKLALALLAKLKLA |
| 101 | KKWKMRRNQFWIKIQR |
| 102 | rqikiwfqnrrmkwkk |
| 103 | RQIKIWFPNRRMKWKK |
| 104 | RQPKIWFPNRRKPWKK |
| 105 | RQIKIWFQNRRMKWK |
| 106 | RQIKIWFQNRRMKW |
| 107 | RQIKIWFQNRRMK |
| 108 | RQIKIWFQNRRM |
| 109 | RQIKIWFQNRR |
| 110 | RQIKIWFQNR |
| 111 | RQIKIWFQN |
| 112 | RQIKIWFQ |
| 113 | RQIKIW |
| 114 | QIKIWFQNRRMKWKK |

TABLE 1-continued

CPP sequences.
One letter code used. L-amino acids are in upper case, D-amino acids in lower case. Repetitions are written in parenthesis.

| Seq ID NO | Sequence |
|---|---|
| 115 | IKIWFQNRRMKWKK |
| 116 | KIWFQNRRMKWKK |
| 117 | IWFQNRRMKWKK |
| 118 | WFQNRRMKWKK |
| 119 | FQNRRMKWKK |
| 120 | QNRRMKWKK |
| 121 | NRRMKWKK |
| 122 | RRMKWKK |
| 123 | RMKWKK |
| 124 | AQIKIWFQNRRMKWKK |
| 125 | RAIKIWFQNRRMKWKK |
| 126 | RQAKIWFQNRRMKWKK |
| 127 | RQIAIWFQNRRMKWKK |
| 128 | RQIKAWFQNRRMKWKK |
| 129 | RQIKIAFQNRRMKWKK |
| 130 | RQIKIWAQNRRMKWKK |
| 131 | RQIKIWFANRRMKWKK |
| 132 | RQIKIWFQARRMKWKK |
| 133 | RQIKIWFQNARMKWKK |
| 134 | RQIKIWFQNRAMKWKK |
| 135 | RQIKIWFQNRRAKWKK |
| 136 | RQIKIWFQNRRMAWKK |
| 137 | RQIKIWFQNRRMKAKK |
| 138 | RQIKIWFQNRRMKWAK |
| 139 | RQIKIWFQNRRMKWKA |
| 140 | CRQIKIWFPNRRMKWKKC |
| 141 | RQIKIWFPNRRMKWKK |
| 142 | RQIKIFFQNRRMKFKK |
| 143 | RQIRIWFQNRRMRWRR |
| 144 | RRRRRRRW |
| 145 | GRKKRRQRRRPWQ |
| 146 | GRKKRRQRRRPWQ |
| 147 | RQIRIWFQNRRMRWRR |
| 148 | RRWRRWWRRWWRRWRR |
| 149 | RQIKIWFQNMRRKWKK |
| 150 | KMDCRWRWKCCKK |
| 151 | MDCRWRWKCCKK |

TABLE 1-continued

CPP sequences.
One letter code used. L-amino acids are in upper case, D-amino acids in lower case. Repetitions are written in parenthesis.

| Seq ID NO | Sequence |
|---|---|
| 152 | DCRWRWKCCKK |
| 153 | CRWRWKCCKK |
| 154 | RWRWKCCKK |
| 155 | KMDCRWRWKCKK |
| 156 | KMDCRWRWKKK |
| 157 | KMDRWRWKKK |
| 158 | KDCRWRWKCCKK |
| 159 | KCRWRWKCCKK |
| 160 | KRWRWKCCKK |
| 161 | MDCRWRWKXCKK |
| 162 | DCRWRWKXCKK |
| 163 | DCRWRWKCXKK |
| 164 | CRWRWKXCKK |
| 165 | CRWRWKCXKK |
| 166 | RWRWKXCKK |
| 167 | MDCRWRWKXXKK |
| 168 | DCRWRWKXXKK |
| 169 | CRWRWKXXKK |
| 170 | RWRWKXXKK |
| 171 | CRWRWKCSKK |
| 172 | SRWRWKCCKK |
| 173 | SRWRWKCSKK |
| 174 | SRWRWKSCKK |
| 175 | CRWRWKSSKK |
| 176 | SRWRWKSSKK |
| 177 | CRFRWKCCKK |
| 178 | CRWRFKCCKK |
| 179 | CRFRFKCCKK |
| 180 | crwrwkcckk |
| 181 | KCCKWRWRCK |
| 182 | kcckwrwrck |
| 183 | CrWRWKCCKK |
| 184 | CRwRWKCCKK |
| 185 | CRWrWKCCKK |
| 186 | CRWRwKCCKK |
| 187 | CrwrwKCCKK |
| 188 | CRWRWKCGCKK |

TABLE 1-continued

CPP sequences.
One letter code used. L-amino acids are in upper case, D-amino acids in lower case. Repetitions are written in parenthesis.

| Seq ID NO | Sequence |
| --- | --- |
| 189 | KCGCRWRWKCGCKK |
| 190 | CRWRWKCG |
| 191 | KMDXRWRWKCCKK |
| 192 | KMDXRWRWKXCKK |
| 193 | KMDXRWRWKXXKK |
| 194 | KMDXRWRWKCXKK |
| 195 | MDCRWRWKCXKK |
| 196 | KMDCRWRWKCSKK |
| 197 | KMDCRWRWKSCKK |
| 198 | KMDSRWRWKCCKK |
| 199 | KMDCRWRWKSSKK |
| 200 | KMDSRWRWKSSKK |
| 201 | KMDSRWRWKSCKK |
| 202 | KMDSRWRWKCSKK |
| 203 | KMDCRWRPKCCKK |
| 204 | KMDCRPRPKCCKK |
| 205 | KMDXRPRPKCCKK |
| 206 | KMDXRPRPKXCKK |
| 207 | KMDXRPRPKCXKK |
| 208 | KMDCRPRPKXCKK |
| 209 | KMDCRPRPKCXKK |
| 210 | rkkrrqrrr |
| 211 | rrrqrrkkr |
| 212 | RKKRRRESRKKRRRES |
| 213 | GRPRESGKKRKRKRLKP |
| 214 | GKRKKKGKLGKKRDP |
| 215 | GKRKKKGKLGKKRPRSR |
| 216 | RKKRRRESRRARRSPRHL |
| 217 | SRRARRSPRESGKKRKRKR |
| 218 | VKRGLKLRHVRPRVTRMDV |
| 219 | SRRPARRSPRHLGSG |
| 220 | LRRERQSRLRRERQSR |
| 221 | GAYDLRRRERQSRLRRRERQSR |
| 222 | VPMLK |
| 223 | VPTLK |
| 224 | VPALR |
| 225 | VSALK |

TABLE 1-continued

CPP sequences.
One letter code used. L-amino acids are in upper case, D-amino acids in lower case. Repetitions are written in parenthesis.

| Seq ID NO | Sequence |
|---|---|
| 226 | PMLKE |
| 227 | VPALK |
| 228 | VSLKK |
| 229 | VSGKK |
| 230 | KLPVM |
| 231 | IPMIK |
| 232 | KLGVM |
| 233 | KLPVT |
| 234 | VPMIK |
| 235 | IPALK |
| 236 | IPMLK |
| 237 | VPTLQ |
| 238 | QLPVM |
| 239 | ELPVM |
| 240 | VPTLE |
| 241 | vptlk |
| 242 | AYRIKPTFRRLKWKYKGKFW |
| 243 | HARIKPTFRRLKWKYKGKFW |
| 244 | HYRIKPTARRLKWKYKGKFW |
| 245 | HYRIKPTFRRLAWKYKGKFW |
| 246 | HYRIKPTFRRLKWKYKGKFA |
| 247 | VNADIKATTVFGGKYVSLTTP |
| 248 | GKYVSLTTPKNPTKRRITPKDV |
| 249 | TKRRITPKDVIDVRSVTTEINT |
| 250 | RSVTTEINTLFQTLTSIAEKVDP |
| 251 | AEKVDPVKLNLTLSAAAEALTGLGDK |
| 252 | GLGDKFGESIVNANTVLDDLNSRMPQSRHDIQQL |
| 253 | GDVYADAAPDLFDFLDSSVTTARTINA |
| 254 | ARTINAQQAELDSALLAAAGFGNTTADVFDRG |
| 255 | ADVFDRGGPYLQRGVADLVPTATLLDTYSP |
| 256 | LDTYSPELFCTIRNFYDADRPDRGAAA |
| 257 | TKRRITPKDVIDVRSVTTEINT |
| 258 | TKRRITPDDVIDVRSVTTEINT |
| 259 | TKRRITPKKVIDVRSVTTEINT |
| 260 | TKRRITPKDVIDVRSVTTKINT |
| 261 | TKRRITPKDVIDV |
| 262 | TKRRITPKDVIDVESVTTEINT |

TABLE 1-continued

CPP sequences.
One letter code used. L-amino acids are in upper case, D-amino acids in lower case. Repetitions are written in parenthesis.

| Seq ID NO | Sequence |
|---|---|
| 263 | TARRITPKDVIDVRSVTTEINT |
| 264 | TKAARITPKDVIDVRSVTTEINT |
| 265 | HHHHHHTKRRITPKDVIDVRSVTTEINT |
| 266 | KLWMRWYSPTTRRYG |
| 267 | DSLKSYWYLQKFSWR |
| 268 | RTLVNEYKNTLKFSK |
| 269 | IPSRWKDQFWKRWHY |
| 270 | GYGNCRHFKQKPRRD |
| 271 | KNAWKHSSCHHRHQI |
| 272 | RVREWWYTITLKQES |
| 273 | QQHLLIAINGYPRYN |
| 274 | WKCRRQCFRVLHHWN |
| 275 | RLWMRWYSPTTRRYG |
| 276 | KLWMRWYSATTRRYG |
| 277 | KLWMRWYSPWTRRYG |
| 278 | RLWMRWYSPWTRRYG |
| 279 | RLWMRWYSPWTRRWG |
| 280 | ALWMRWYSPTTRRYG |
| 281 | RAWMRWYSPTTRRYG |
| 282 | RLWMRWYSPTTRRYG |
| 283 | RLWMRWYSPTTRRYG |
| 284 | RLWMAWYSPTTRRYG |
| 285 | RLWMRAYSPTTRRYG |
| 286 | RLWMRWASPTTRRYG |
| 287 | RLWMRWYAPTTRRYG |
| 288 | RLWMRWYSPATRRYG |
| 289 | RLWMRWYSPTARRYG |
| 290 | RLWMRWYSPTARRYG |
| 291 | RLWMRWYSPTTRAYG |
| 292 | RLWMRWYSPTTRRAG |
| 293 | RLWMRWYSPTTRRYA |
| 294 | RLLMRLYSPTTRRYG |
| 295 | RLFMRFYSPTTRRYG |
| 296 | RLIMRIYSPTTRRYG |
| 297 | RLVMRVYSPTTRRYG |
| 298 | RLYMRYYSPTTRRYG |
| 299 | YGRKKKRRQRRR |

TABLE 1-continued

CPP sequences.
One letter code used. L-amino acids are in upper case, D-amino acids in lower case. Repetitions are written in parenthesis.

| Seq ID NO | Sequence |
|---|---|
| 300 | ALIILRRRIRKQAHAHSK |
| 301 | LAIILRRRIRKQAHAHSK |
| 302 | LLAILRRRIRKQAHAHSK |
| 303 | LLIALRRRIRKQAHAHSK |
| 304 | LLIIARRRIRKQAHAHSK |
| 305 | LLIILARRIRKQAHAHSK |
| 306 | LLIILRARIRKQAHAHSK |
| 307 | LLIILRRAIRKQAHAHSK |
| 308 | LLIILRRRARKQAHAHSK |
| 309 | LLIILRRRIARKQAHAHSK |
| 310 | LLIILRRRIRAQAHAHSK |
| 311 | LLIILRRRIRKAAHAHSK |
| 312 | LLIILRRRIRKQaHAHSK |
| 313 | LLIILRRRIRKQAAAHSK |
| 314 | LLIILRRRIRKQAHaHSK |
| 315 | LLIILRRRIRKQAHAASK |
| 316 | LLIILRRRIRKQAHAHAK |
| 317 | LLIILRRRIRKQAHAHSA |
| 318 | KSHAHAQKRIRRRLIILL |
| 319 | lliilrrrirkqahahsk |
| 320 | RRIRPRP |
| 321 | RRIRPRPPRLPRPRP |
| 322 | RRIRPRPPRLPRPRPRPLPFPRPG |
| 323 | RRIRPRPPRLPRPRPRP |
| 324 | PRPPRLPRPRPRPLPFPRPG |
| 325 | PPRLPRPRPRPLPFPRPG |
| 326 | RLPRPRPRPLPFPRPG |
| 327 | PRPRPRPLPFPRPG |
| 328 | PRPRPLPFPRPG |
| 329 | PRPLPFPRPG |
| 330 | RVTSWLGRQLRIAGKRLEGRSK |
| 331 | GRQLRIAGKRLEGRSK |
| 332 | RRVTSWLGRQLRIAGKRLEGRSK |
| 333 | RVRSWLGRQLRIAGKRLEGRSK |
| 334 | GRQLRIAGKRLRGRSK |
| 335 | GRQLRIAGRRLRGRSR |
| 336 | GRQLRRAGRRLRGRSR |

TABLE 1-continued

CPP sequences.
One letter code used. L-amino acids are in upper case, D-amino acids in lower case. Repetitions are written in parenthesis.

| Seq ID NO | Sequence |
|---|---|
| 337 | GRQLRIAGRRLRRRSR |
| 338 | GRQLRRAGRRLRRRSR |
| 339 | RQLRIAGRRLRGRSR |
| 340 | rsrgrlrrgairlqrg |
| 341 | KLIKGRIPIKFGKADCDRPPKHSQNGMGK |
| 342 | KLIKGRTPIKFGKADCDRPPKHSQNGM |
| 343 | KLIKGRIPIKFGKADCDRPPKHSQNGK |
| 344 | KGRTPIKFGKADCDRPPKHSQNGMGK |
| 345 | KLIKGRTPIKFGKADCDRPPKHSGK |
| 346 | KLIKGRTPIKFGKARCRRPPKHSGK |
| 347 | KLIKGRTPIKEGK |
| 348 | KRIPNKKPGKKTTTKPTKKPTIKTTKKDLKPQTTKPK |
| 349 | KRIPNKKPGKKTTTKPTKKPTIKTTKKDLK |
| 350 | KRIPNKKPGKKTTTKPTKKPTIKTTKK |
| 351 | KRIPNKKPGKKTTTKPTKKPTIK |
| 352 | KRIPNKKPGKKTTTKPTKK |
| 353 | KRIPNKKPGKKT |
| 354 | KRIPNKKPGKK |
| 355 | KRIPNKKPKK |
| 356 | KKPGKKTTTKPTKKPTIKTTKK |
| 357 | KKPGKKTTTKPTKK |
| 358 | KKPTIKTTKK |
| 359 | KKTTTKPTKK |
| 360 | KSICKTIPSNKPKKK |
| 361 | KTIPSNKPKKK |
| 362 | KPRSKNPPKKPK |
| 363 | DRDDRDDRDDRDDRDDR |
| 364 | ERERERERERERER |
| 365 | WRWRWRWRWRWR |
| 366 | DRDRDRDRDR |
| 367 | GALFLGFLGAAGSTMGAWSQPKKKRKV |
| 368 | DRRRRGSRPSGAERRRR |
| 369 | NRARRNRRRVR |
| 370 | RTRRNRRRVR |
| 371 | RNRSRHRR |
| 372 | MVRRFLVTLRIRRACGPPRVRV |
| 373 | FVTRGCPRRLVARLIRVMVPRR |

TABLE 1-continued

CPP sequences.
One letter code used. L-amino acids are in upper case, D-amino acids in lower case. Repetitions are written in parenthesis.

| Seq ID NO | Sequence |
|---|---|
| 374 | VRRFLVTLRIRRA |
| 375 | RVRILARFLRTRV |
| 376 | RVRVFVVHIPRLT |
| 377 | VIRVHFRLPVRTV |
| 378 | MVRRFLVTLRIRRACGPPRVRVFVVHIPRLTGEWAAP |
| 379 | FRVPLRIRPCVVAPRLVMVRHTFGRIARWVAGPLETR |
| 380 | AGYLLGKINLKALAALAKKIL |
| 381 | GTKMIFVGIKKKEERADLIAYLKKA |
| 382 | KKKEERADLIAYLKKA |
| 383 | KMIFVGIKKKEERA |
| 384 | KMIFVGIKKK |
| 385 | EKGKKIFIMK |
| 386 | KGKKIFIMK |
| 387 | RRRRNRTRRNRRRVRGC |
| 388 | TRRQRTRRARRNRGC |
| 389 | KMTRAQRRAAARRNRWTARGC |
| 390 | KLTRAQRRAAARKNKRNTRGC |
| 391 | NAKTRRHERRRKLAIERGC |
| 392 | MDAQTRRRERRAEKQAQWKAANGC |
| 393 | TAKTRYKARRAELIAERRGC |
| 394 | SQMTRQARRLYBGC |
| 395 | KRRIRRERNKMAAAKSRNRRRELTDTGC |
| 396 | RIKAERKRMRNRIAASKSRKRKLERIARGC |
| 397 | KRARNTEAARRSRARKLQRMKQGC |
| 398 | KCFQWQRNMRKVRGPPVSCIKR |
| 399 | KCFQWQRNMRKVRGPPVSC |
| 400 | KCFQWQRNMRKVRGPPVSSIKR |
| 401 | KCFQWQRNMRKVR |
| 402 | FQWQRNMRKVRGPPVS |
| 403 | QWQRNMRKVRGPPVSCIKR |
| 404 | QWQRNMRKVR |
| 405 | KCFMWQEMLNKAGVPKLRCARK |
| 406 | KWFETWFTEWPKKRK |
| 407 | GLWRALWRLLRSLWRLLWRA |
| 408 | GLWWRLWWRLRSWFRLWFRA |
| 409 | DAATATRGRSAASRPTQRPRAPARSASRPRRPVE |
| 410 | GALFLGFLGAAGSTMGAWSQPKKKRKV |

TABLE 1-continued

CPP sequences.
One letter code used. L-amino acids are in upper case, D-amino acids in lower case. Repetitions are written in parenthesis.

| Seq ID NO | Sequence |
|---|---|
| 411 | GALFLGFLGAAGSTMGAWSQPKSKRKV |
| 412 | AKVKDEPQRRSARLSAKPAPPKPEPKPKKAPAKK |
| 413 | akykdepqrrsarlsakpappkpepkpkkapakk |
| 414 | PSSSSSSRIGDP |
| 415 | vrlpppvrlpppvrlppp |
| 416 | VELPPPVELPPPVELPPP |
| 417 | ALWMTLLKKVLKAAAKAALNAVLVGANA |
| 418 | ALWKTLLKKVLKA |
| 419 | ALWKTLLKKVLKAPKKKRKV |
| 420 | PKKKRKVALWKTLLKKVLKA |
| 421 | VKRKKKPALWKTLLKKVLKA |
| 422 | RQARRNRRRALWKTLLKKVLKA |
| 423 | RQARRNRRRC |
| 424 | EEEAAGRKRKKRT |
| 425 | EEE |
| 426 | EEEAA |
| 427 | EEEAAKKK |
| 428 | FFFAAGRKRKKRT |
| 429 | AAGRKRKKRT |
| 430 | YYYAAGRKRKKRT |
| 431 | MVTVLFRRLRIRRACGPPRVRV |
| 432 | AGYLLGKINLKALAALAKKIL |
| 433 | GKKKKRKREKL |
| 434 | ERKKRRRE |
| 435 | FKKFRKF |
| 436 | YTQDFNKFHTFPQTAIGVGAP |
| 437 | DFNKFHTFPQTAIGVGAP |
| 438 | KFHTFPQTAIGVGAP |
| 439 | TFPQTAIGVGAP |
| 440 | GYGRKKRRQRRRG |
| 441 | FLGKKFKKYFLQLLK |
| 442 | FLIFIRVICIVIAKLKANLMCKT |
| 443 | KKAAQIRSQVMTHLRVI |
| 444 | YIVLRRRRKRVNTKRS |
| 445 | RRKLSQQKEKK |
| 446 | VQAILRRNWNQYKIQ |
| 447 | KTVLLRKLLKLLVRKI |

TABLE 1-continued

CPP sequences.
One letter code used. L-amino acids are in upper case, D-amino acids in lower case. Repetitions are written in parenthesis.

| Seq ID NO | Sequence |
|---|---|
| 448 | LLKKRKVVRLIKFLLK |
| 449 | KLPCRSNTFLNIFRRKKPG |
| 450 | KKICTRKPRFMSAWAQ |
| 451 | rggrlsysrrrfststgr |
| 452 | rrlsysrrrf |
| 453 | RGGRLAYLRRRWAVLGR |
| 454 | MANLGCWMLVLEVATWSDLGLCKKRPHP |
| 455 | MVKSKIGSWILVLFVAMWSDVGLCKKRPKP |
| 456 | LLGDFFRKSKEKIGKEFKRIVQRIKDFLRNLVPRTESC |
| 457 | GIGKFLHSAKKWGKAFVGQIMNC |
| 458 | TRSSRAGLQWPVGRVHRLLRKGGC |
| 459 | YGRKKRRQRRR |
| 460 | EKRPRTAFSSEQLARLKREFNENRYLTTERRRQQLSSELGLNEAQIKIWFQNKRAKIKKST |
| 461 | GRRRRRRRRRPPQ |
| 462 | GALFLGFLGAAGSTMGAWSQPKKKRKV |
| 463 | GALFLAFLAAALSLMGLWSQPKKKRRV |
| 464 | MLLLTRRRST |
| 465 | CGNKRTRGC |
| 466 | TSPLNIHNGQKL |
| 467 | GLRKRLRKFRNKIKEK |
| 468 | GLLEALAELLEGLRKRLRKFRNKIKEK |
| 469 | CVQWSLLRGYQPC |
| 470 | RQIKIFFQNRRMKWKK |
| 471 | ASMWERVKSIIKSSLAAASNI |
| 472 | ASMWERVKSIIKSSLAAASNI |
| 473 | DPKGDPKGVTVTVTVTVTGKGDPKPD |
| 474 | CSIPPEVKFNPFVYLI |
| 475 | csippevkfnpfvyli |
| 476 | PFVYLI |
| 477 | NKPILVFY |
| 478 | YKQCHKKGGKKGSG |
| 479 | YKQCHKKGGXKKGSG |
| 480 | GSGKKGGKKHCQKY |
| 481 | GSGKKGGKKICQKY |
| 482 | YTAIAWVKAFIRKLRK |
| 483 | IAWVKAFIRKLRKGPLG |
| 484 | LIRLWSHLIHIWFQNRRLKWKKK |

TABLE 1-continued

CPP sequences.
One letter code used. L-amino acids are in upper case, D-amino acids in lower case. Repetitions are written in parenthesis.

| Seq ID NO | Sequence |
|---|---|
| 485 | KKKKKKGGFLGFWRGENGRKTRSAYERMCILKGK |
| 486 | RLSGMNEVLSFRWL |
| 487 | GPFHEYQFLEPPV |
| 488 | GSPWGLQHHPPRT |
| 489 | AAVALLPAVLLALLAPEILLPNNYNAYESYKYPGMFIALSK |
| 490 | AAVALLPAVLLALLAPVQRKRQKLMP |
| 491 | MGLGLHLLVLAAALQGAKKKRKV |
| 492 | WEAALAEALAEALAEHLAEALAEALEALAA |
| 493 | GLFEALLELLESLWELLLEA |
| 494 | GLFKALLKLLKSLWKLLLKA |
| 495 | GLFRALLRLLRSLWRLLLRA |
| 496 | CGAYDLRRRERQSRLRRRERQSR |
| 497 | RKKRRRESRKKRRRESC |
| 498 | CVKRGLKLRHVRPRVTRDV |
| 499 | CRQIKIWFQNRRMKWKK |
| 500 | PPKKSAQCLRYKKPE |
| 501 | DPVDTPNPTRRKPGK |
| 502 | KRVSRNKSEKKRR |
| 503 | GRRHHCRSKAKRSRHH |
| 504 | SARHHCRSKAKRSRHH |
| 505 | SRAHHCRSKAKRSRHH |
| 506 | SRRAHCRSKAKRSRHH |
| 507 | SRRHACRSKAKRSRHH |
| 508 | SRRHHARSKAKRSRHH |
| 509 | SRRHHCRAKAKRSRHH |
| 510 | SRRHHCRSAAKRSRHH |
| 511 | SRRHHCRSKAKRSRHH |
| 512 | SRRHHCRSKAKRSRHH |
| 513 | SRRHHCRSKAKRARHH |
| 514 | SRRHHCRSKAKRSAHH |
| 515 | RRHHCRSKAKRSR |
| 516 | GRKGKHKRKKLP |
| 517 | GKKKKKKKK |
| 518 | GKRVAKRKLIEQNRERRR |
| 519 | GRKLKKKKNEKEDKRPRT |
| 520 | GKKTNLFSALIKKKKTA |
| 521 | GRRERNKMAAAKCRNRRR |

TABLE 1-continued

CPP sequences.
One letter code used. L-amino acids are in upper case, D-amino acids in lower case. Repetitions are written in parenthesis.

| Seq ID NO | Sequence |
| --- | --- |
| 522 | GKRARNTEAARRSRARKL |
| 523 | GRRRRATAKYRTAH |
| 524 | GKRRRATAKYRSAH |
| 525 | GRRRRKRLSHRT |
| 526 | GRRRRRERNK |
| 527 | GKHRHERGHHRDRRER |
| 528 | GKKKRKLSNRESAKRSR |
| 529 | MIIYRDLISH |
| 530 | MIIYRDLIS |
| 531 | MIIYRDLI |
| 532 | IIYRDLISH |
| 533 | MIIYRDL |
| 534 | MIIYRD |
| 535 | IYRDLISH |
| 536 | AIIYRDLIS |
| 537 | MAIYRDLIS |
| 538 | MIAYRDLIS |
| 539 | MIIARDLIS |
| 540 | MIIYADLIS |
| 541 | MITYRALIS |
| 542 | MIIYRDAIS |
| 543 | MIIYRDLAS |
| 544 | MIIYRDLIA |
| 545 | MIIYRDLISKK |
| 546 | MIIYRDKKSH |
| 547 | MIIFRDLISH |
| 548 | MIISRDLISH |
| 549 | QIISRDLISH |
| 550 | CIISRDLISH |
| 551 | MIIYRALISHKK |
| 552 | MIIYRIAASHKK |
| 553 | MIIRRDLISE |
| 554 | MIIYRAEISH |
| 555 | MIIYARRAEE |
| 556 | MIIFRIAASHKK |
| 557 | MIIFRALISHKK |
| 558 | MIIFRAAASHKK |

TABLE 1-continued

CPP sequences.
One letter code used. L-amino acids are in upper case, D-amino acids in lower case. Repetitions are written in parenthesis.

| Seq ID NO | Sequence |
| --- | --- |
| 559 | FIIFRIAASHKK |
| 560 | LIIFRIAASHKK |
| 561 | WIIFRIAASHKK |
| 562 | WIIFRAAASHKK |
| 563 | WIIFRALISHKK |
| 564 | MIIFRIAAYHKK |
| 565 | WIIFRIAAYHKK |
| 566 | MIIFRIAATHKK |
| 567 | WIIFRIAATHKK |
| 568 | MIIFKIAASHKK |
| 569 | WIIFKIAASHKK |
| 570 | MIIFAIAASHKK |
| 571 | LIIFRILISHKK |
| 572 | MIIFRALISHKK |
| 573 | LIIFRILISHRR |
| 574 | LIIFRILISHHH |
| 575 | LIIFRILISHK |
| 576 | LIIFRILISHR |
| 577 | LIIFRILISH |
| 578 | LIIFAIAASHKK |
| 579 | LIIFAILISHKK |
| 580 | RILQQLLFIHFRIGCRHSRI |
| 581 | RILQQLLFIHFRIGCRH |
| 582 | RILQQLLFIHFRIGC |
| 583 | RIFIHFRIGC |
| 584 | RIFIRIGC |
| 585 | RILQQLLFIHF |
| 586 | RIFIGC |
| 587 | FIRIGC |
| 588 | DTWAGVEAIIRILQQLLFIHFR |
| 589 | IGCRH |
| 590 | GYGRKKRRGRRRTHRLPRRRRRR |
| 591 | KRIIQRILSRNS |
| 592 | KRIHPRLTRSIR |
| 593 | PPRLRKRRQLNM |
| 594 | MHKRPTTPSRKM |
| 595 | RQRSRRRPLNIR |

TABLE 1-continued

CPP sequences.
One letter code used. L-amino acids are in upper case, D-amino acids in lower case. Repetitions are written in parenthesis.

| Seq ID NO | Sequence |
|---|---|
| 596 | RIRMIQNLIKKT |
| 597 | SRRKRQRSNMRI |
| 598 | QRIRKSKISRTL |
| 599 | PSKRLLHNNLRR |
| 600 | HRHIRRQSLIML |
| 601 | PQNRLQIRRHSK |
| 602 | PPHNRIQRRLNM |
| 603 | SMLKRNHSTSNR |
| 604 | GSRHPSLIIPRQ |
| 605 | SPMQKTMNLPPM |
| 606 | NKRILIRIMTRP |
| 607 | HGWZIHGLLHRA |
| 608 | AVPAKKRZKSV |
| 609 | PNTRVRPDVSF |
| 610 | LTRNYEAWVPTP |
| 611 | SAETVESCLAKSH |
| 612 | YSHIATLPFTPT |
| 613 | SYIQRTPSTTLP |
| 614 | AVPAENALNNPF |
| 615 | SFHQFARATLAS |
| 616 | QSPTDFTFPNPL |
| 617 | HFAAWGGWSLVH |
| 618 | HIQLSPFSQSWR |
| 619 | LTMPSDLQPVLW |
| 620 | FQPYDHPAEVSY |
| 621 | FDPFFWKYSPRD |
| 622 | FAPWDTASFMLG |
| 623 | FTYKNFFWLPEL |
| 624 | SATGAPWKMWVR |
| 625 | SLGWMLPFSPPF |
| 626 | SHAFTWPTYLQL |
| 627 | SHNWLPLWPLRP |
| 628 | SWLPYPWHVPSS |
| 629 | SWWTPWHVHSES |
| 630 | SWAQHLSLPPVL |
| 631 | SSSIFPPWLSFF |
| 632 | LNVPPSWFLSQR |

TABLE 1-continued

CPP sequences.
One letter code used. L-amino acids are in upper case, D-amino acids in lower case. Repetitions are written in parenthesis.

| Seq ID NO | Sequence |
| --- | --- |
| 633 | LDITPFLSLTLP |
| 634 | LPHPVLHMGPLR |
| 635 | VSKQPYYMWNGN |
| 636 | NYTTYKSHFQDR |
| 637 | AIPNNQLGFPFK |
| 638 | NIENSTLATPLS |
| 639 | YPYDANHTRSPT |
| 640 | DPATNPGPHFPR |
| 641 | TLPSPLALLTVH |
| 642 | HPGSPFPPEHRP |
| 643 | TSHTDAPPARSP |
| 644 | MTPSSLSTLPWP |
| 645 | VLGQSGYLMPMR |
| 646 | QPIIITSPYLPS |
| 647 | TPKTMTQTYDFS |
| 648 | NSGTMQSASRAT |
| 649 | QAASRVENYMHR |
| 650 | HQHKPPPLTNNW |
| 651 | SNPWDSLLSVST |
| 652 | KTIEAHPPYYAS |
| 653 | EPDNWSLDFPRR |
| 654 | HQHKPPPLTNNW |
| 655 | GLWRALWRLLRSLWRLLWKA |
| 656 | GLWRALWRALWRSLWKLKRKV |
| 657 | GLWRALWRALRSLWKLKRKV |
| 658 | GLWRALWRGLRSLWKLKRKV |
| 659 | GLWRALWRGLRSLWKKKRKV |
| 660 | GLWRALWRALWRSLWKLKWKV |
| 661 | GLWRALWRALWRSLWKSKRKV |
| 662 | GLWRALWRALWRSLWKKKRKV |
| 663 | GLWRALWRALWRSLWKLKRKV |
| 664 | GLWRALWRLLRSLWRLLWSQPKKKRKV |
| 665 | YARAARRAARR |
| 666 | PARAARRAARR |
| 667 | YPRAARRAARR |
| 668 | YRRAARRAARA |
| 669 | YGRRARRAARR |

TABLE 1-continued

CPP sequences.
One letter code used. L-amino acids are in upper case, D-amino acids in lower case. Repetitions are written in parenthesis.

| Seq ID NO | Sequence |
|---|---|
| 670 | YAREARRAARR |
| 671 | YGRRARRAARR |
| 672 | YKRAARRAARR |
| 673 | YARKARRAARR |
| 674 | YKRKARRAARR |
| 675 | YGRRARRAARR |
| 676 | YGRRARRRARR |
| 677 | YGRRRRRRRRR |
| 678 | YRRRRRRRRRR |
| 679 | GKINLKALAALAKKIL |
| 680 | GRKKRRQRRRPPQGRKKRRQRRRPPQGRKKRRQRRRPPQ |
| 681 | GEQIAQLIAGYIDIILKKKKSK |
| 682 | AAVALLPAVLLALLAPRKKRRQRRRPPQ |
| 683 | AAVALLPAVLLALLAPRKKRRQRRRPPQC |
| 684 | RKKRRQRRRPPQCAAVALLPAVLLALLAP |
| 685 | RRRQRRKRGGDIMGEWGNEIFGAIAGFLG |
| 686 | RRRQRRKRGGDIMGEWGNEIFGAIAGFLG |
| 687 | YGRKKRRQRRRGCYGRKKRRQRRRG |
| 688 | AAVALLPAVLLALLAPRRRRRRR |
| 689 | RLWRALPRVLRRLLRP |
| 690 | AAVALLPAVLLALLAPSGASGLDKRDYV |
| 691 | LLETLLKPFQCRICMRNFSTRQARRNHRRRHRR |
| 692 | AAVACRICMRNFSTRQARRNHRRRHRR |
| 693 | RQIKIWFQNRRMKWKKDIMGEWGNEIFGAIAGFLG |
| 694 | SGRGKQGGKARAKAKTRSSRAGLQFPVGRVHRLLRKG |
| 695 | SGRGKQGGKARAKAKTRSSRAGLQFPVGRVHRLLRKGC |
| 696 | KKDGKKRKRSRKESYSVYVYKVLKQ |
| 697 | KGSKKAVTKAQKKDGKKRKRSRKESYSVYVYKVLKQ |
| 698 | KETWWETWWTEWSQPGRKKRRQRRRPPQ |
| 699 | RVIRWFQNKRCKDKK |
| 700 | LGLLLRHLRHHSNLLANI |
| 701 | KLWSAWPSLWSSLWKP |
| 702 | GLGSLLKKAGKKLKQPKSKRKV |
| 703 | FKQqQqQqQqQq |
| 704 | YRFK |
| 705 | YRFKYRFKYRLFK |
| 706 | WRFKKSKRKV |

TABLE 1-continued

CPP sequences.
One letter code used. L-amino acids are in upper case, D-amino acids in lower case. Repetitions are written in parenthesis.

| Seq ID NO | Sequence |
|---|---|
| 707 | WRFKAAVALLPAVLLALLAP |
| 708 | WRFKWRFK |
| 709 | WRFKWRFKWRFK |
| 710 | KGSKKAVTKAQKKDGKKRKRSRKESYSVYVYKVLKQ |
| 711 | RGSRRAVTRAQRRDGRRRRRSRRESYSVYVYRVLRQ |
| 712 | RVIRWFQNKRSKDKK |
| 713 | AAVALLPAVLLALLAPRKKRRQRRRPPQ |
| 714 | CWKKK |
| 715 | CWKKKKKKKK |
| 716 | CWKKKKKKKKKKKKK |
| 717 | CWKKKKKKKKKKKKKKKKKK |
| 718 | KKKKKKKKKKKKKKKKKK |
| 719 | kkwkmrrGaGrrrrrrrrr |
| 720 | APWHLSSQYSRT |
| 721 | AAVALLPAVLLALLAKKNNLKDCGLF |
| 722 | AAVALLPAVLLALLAKKNNLKECGLY |
| 723 | AHALCLTERQIKIWFQNRRMKWKKEN |
| 724 | AHALCPPERQIKIWFQNRRMKWKKEN |
| 725 | AYALCLTERQIKIWFANRRMKWKKEN |
| 726 | GGVCPKILKKCRRDSDCPGACICRGNGYCGSGSD |
| 727 | GGVCPKILAACRRDSDCPGACICRGNGYCGSGSD |
| 728 | GGVCPAILKKCRRDSDCPGACICRGNGYCGSGSD |
| 729 | GGVCPKILAKCRRDSDCPGACICRGNGYCGSGSD |
| 730 | GGVCPKILKACRRDSDCPGACICRGNGYCGSGSD |
| 731 | GLPVCGETCVGGTCNTPGCKCSWPVCTRN |
| 732 | GLPVCGETCVGGTCNTPGCTCSWPKCTRN |
| 733 | GRCTKSIPPICFPD |
| 734 | RQIKIWFQNRRMKWKKTYADFIASGRTGRRNAI |
| 735 | GRKKRRQRRRPPQTYADFIASGRTGRRNAI |
| 736 | AGYLLGKINLKALAALAKKIL |
| 737 | AGYLLGKINLKALAALAKKILTYADFIASGRTGRRNAI |
| 738 | RRRRRRRRRR |
| 739 | RRRRRRRRRRTYADFIASGRTGRRNAI |
| 740 | rrrrrrrrk |
| 741 | rRRRRRRRr |
| 742 | rRrRrRrRr |
| 743 | KCFQWQRNMRKVRGPPVSCIKR |

TABLE 1-continued

CPP sequences.
One letter code used. L-amino acids are in upper case, D-amino acids
in lower case. Repetitions are written in parenthesis.

| Seq ID NO | Sequence |
|---|---|
| 744 | kcfqwqrnmrkvrgppvscikr |
| 745 | KLALKLALKALKAALKLAGC |
| 746 | KLULKLULKULKAULKLUGC<br>Wherein U is Aib (α-aminoisobutyric acid) |
| 747 | GGGARKKAAKAARKKAAKAARKKAAKAARKKAAKA |
| 748 | GRKKRRQRRRPPQC |
| 749 | TRQARRNRRRRWRERQRGC |
| 750 | RRRRNRTRRNRRRVRGC |
| 751 | KMTRAQRRAAARRNRWTARGC |
| 752 | TRRQRTRRARRNRGC |
| 753 | RIKAERKRMRNRIAASKSRKRKLERIARGC |
| 754 | KRRIRRERNKMAAAKSRNRRRELTDTGC |
| 755 | WLRRIKAWLRRIKALNRQLGVAA |
| 756 | crkkrrqrrr |
| 757 | crrrrrrrr |
| 758 | ckkkkkkkk |
| 759 | GRKKRRQRRRPP |
| 760 | rrrrrrrr |

The following examples and drawings illustrate the present invention without, however, limiting the same thereto.

A) Schematic presentation of the dendrimer showing branching (lysine) and focal (cysteine) points.

B) Chemical structure of the dendrimer core. Lysine branching points are shown in dark orange and the cross-linking-referring sulfhydryl group of cysteine in red.

C) Schematic dCPP structure in one letter code exemplified by penetratin.

Figure 2:
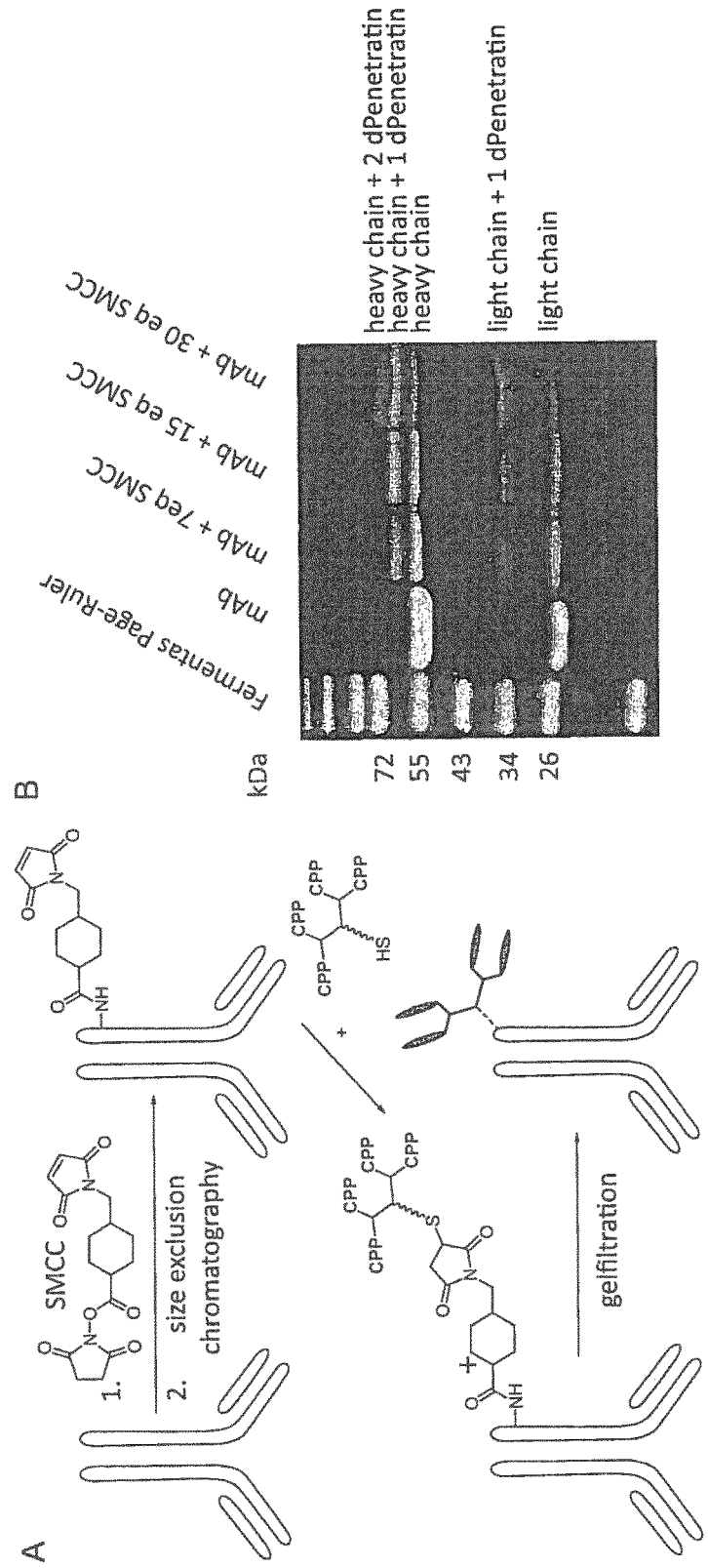

FIG. 2: Conjugation of the mAb with dCPPs.

A) Schematic overview of antibody activation by SMCC and subsequent coupling to the dCPP. In the first step, the mAb is activated as maleimide, which is attacked by the free sulfhydryl-group of the dCPP in the second step. Excess dCPP is removed by gelfiltration.

B) Influence of SMCC excesses in the conjugation reaction analyzed by SDS-PAGE. The image is shown in reverse grayscale to improve contrast.

Figure 3:
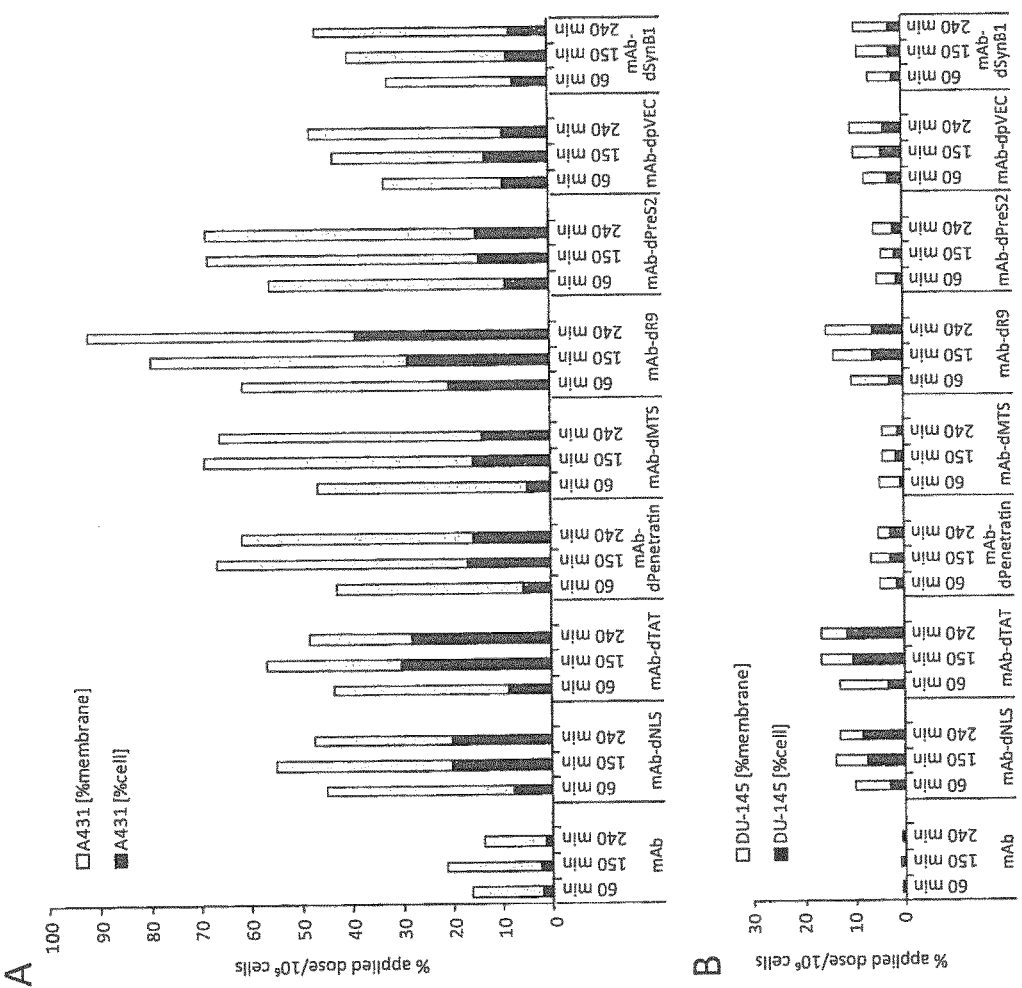

FIG. 3: Binding of matuzumab and of the mAb-dCPP conjugates
to A) A431 cells and B) to the control cell line DU-145. The internalized portion of the activity is illustrated in the lower part of the bars in black, the membrane bound activity by the upper part shown in gray. For clarity reasons the error bars are omitted.

Figure 4:
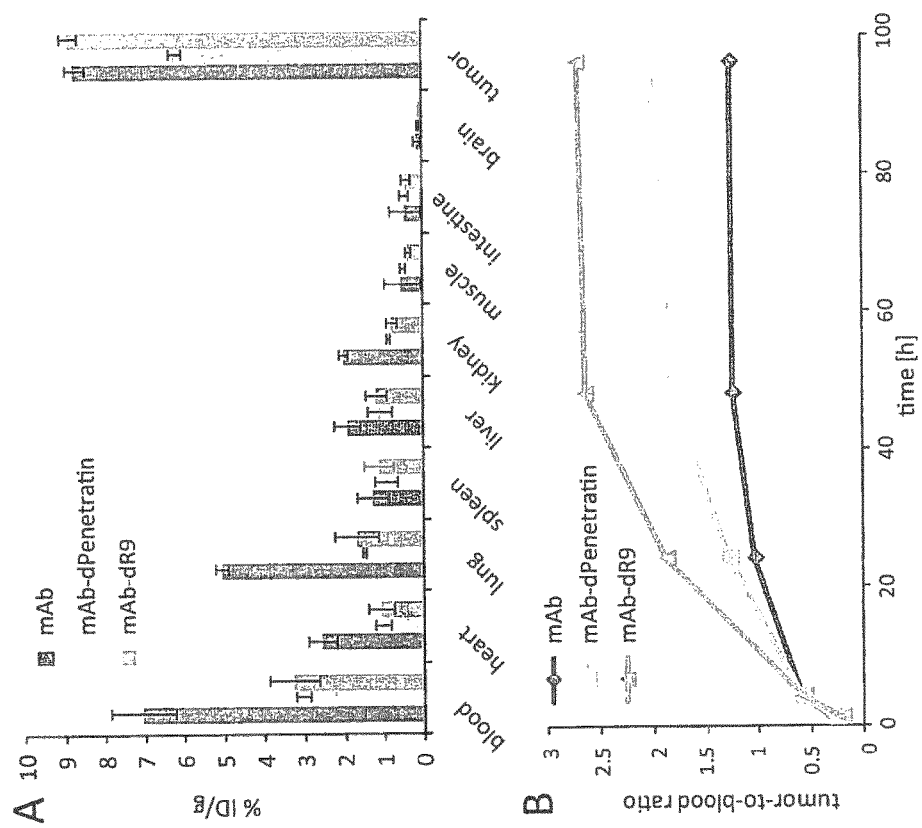

FIG. 4:
A) Organ and tissue distribution of the $^{131}$I-labeled antibody, mAb-dPenetratin and mAb-dR9 96 hours after injection into A431 xenografts.

B) Time-dependent development of the tumor-to-blood ratio of the naked antibody and the immunoconjugates.

Figure 5:
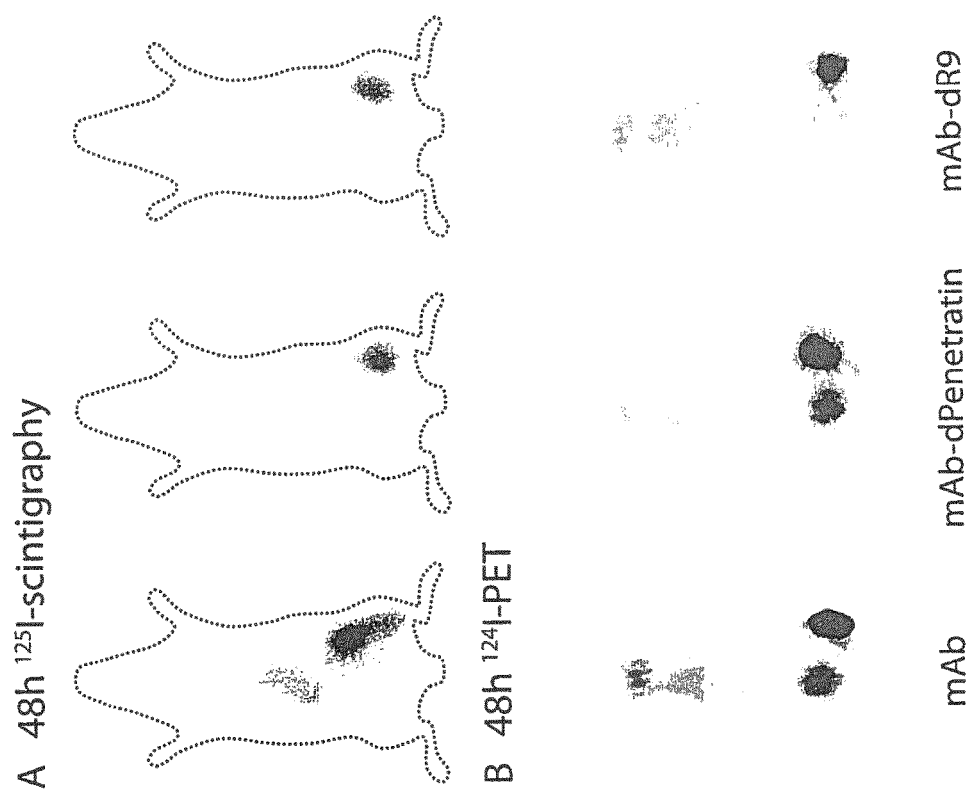

FIG. 5:
A) Planar scintigraphic images of A431 tumor-bearing nude mice 48 hours after injection of $^{125}$I-labeled mAb, mAb-dPenetratin and mAb-dR9. B) As FIG. 5A, except that the radioiodination was carried out with iodine-124 and that static PET images were recorded.

Figure 6:
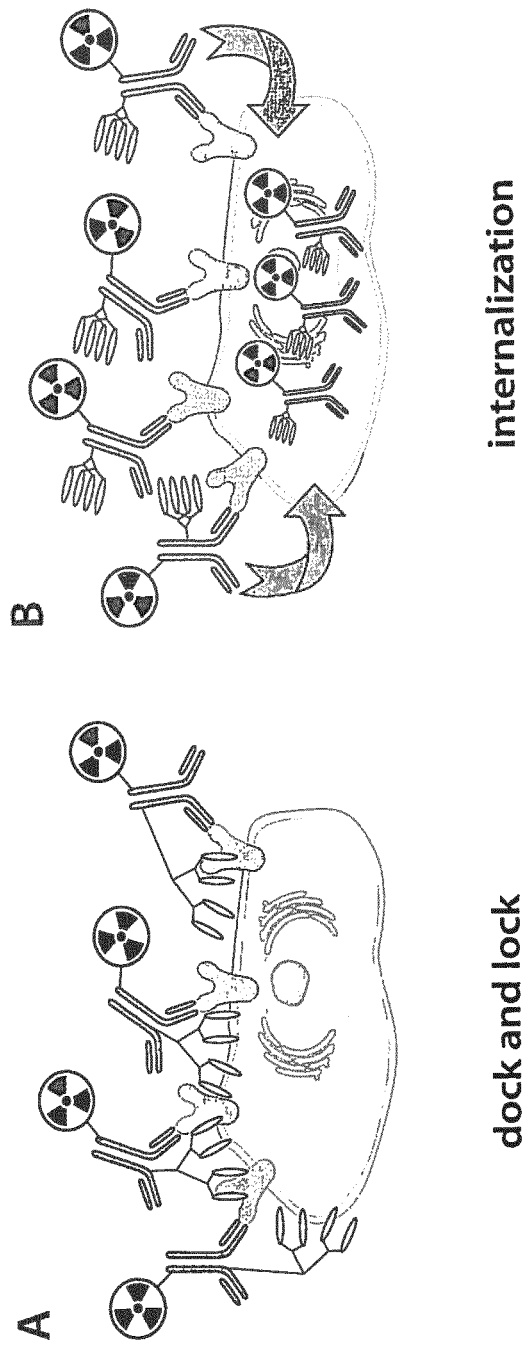

FIG. 6: Possible mechanisms for target cell binding by the mAb-dCPPs.

A) For little internalized conjugates, mainly with amphipathic dCPPs, a dock and lock mechanism is hypothesized. The antibody binds to its antigen, but the internalization is disturbed, as a transitory structure necessary for uptake, is not formed by the CPP dendrimer, but the dCPP still locks onto the cell surface.

B) Internalization mechanism: The antibody binds to the target structure on the cell surface and then the dCPP promotes cell uptake either by direct translocation or endocytosis.

Figure 7:
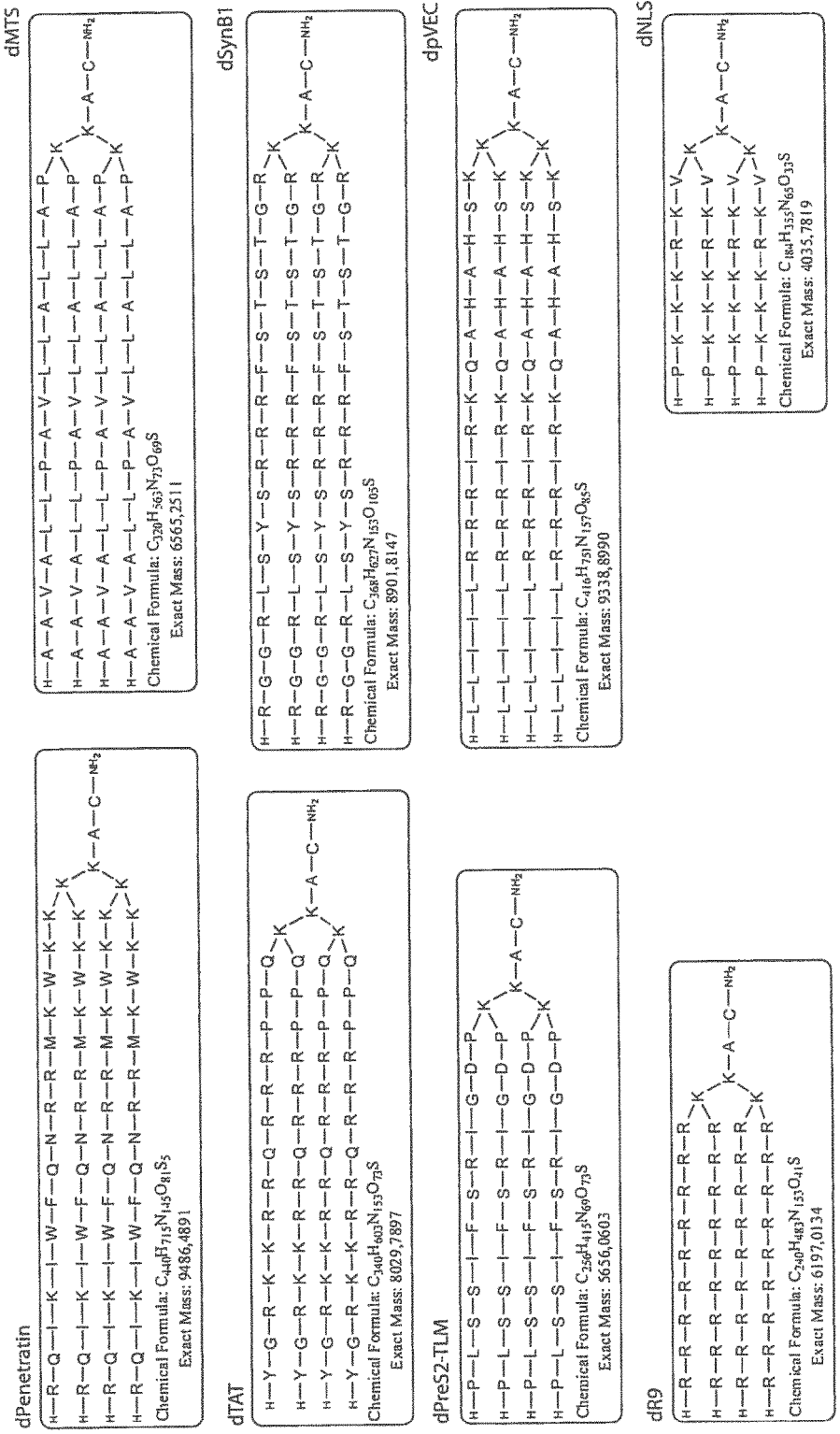

FIG. 7: Schematic overview of the structures of the synthesized dCPPs.

Figure 8:
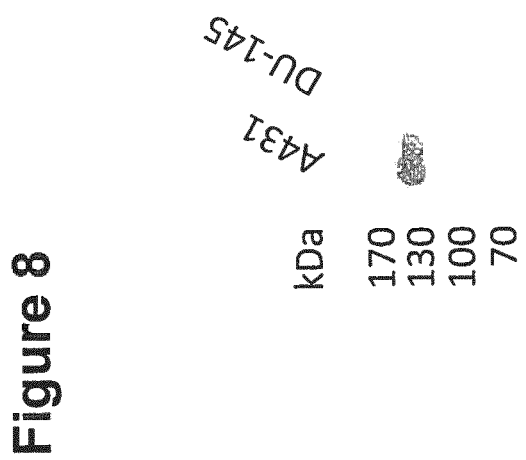

FIG. 8: Western blot analysis of EGFR-expression by A431 and DU-145 cells.

Matuzuinab was used as primary antibody. Horseradish peroxidase conjugated goat anti-human IgG served as secondary antibody.

FIG. 9:

Planar scintigraphic images of A431 xenografts injected with $^{125}$I-labeled matuzumab, mAb-dPenetratin and mAb-dR9. The images were recorded at 1, 4, 24, and 48 hours p.i.

Figure 10:
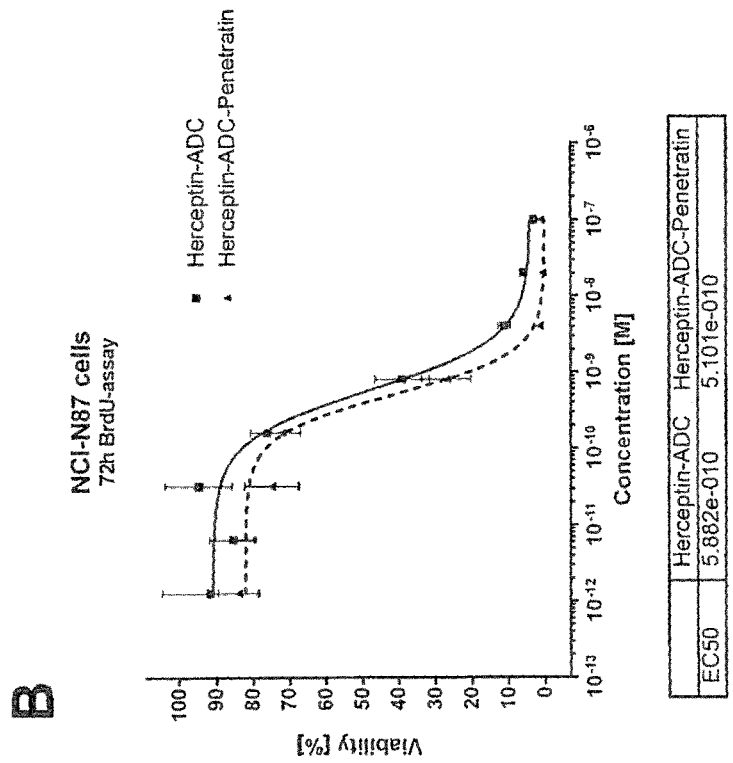
Figure 10:
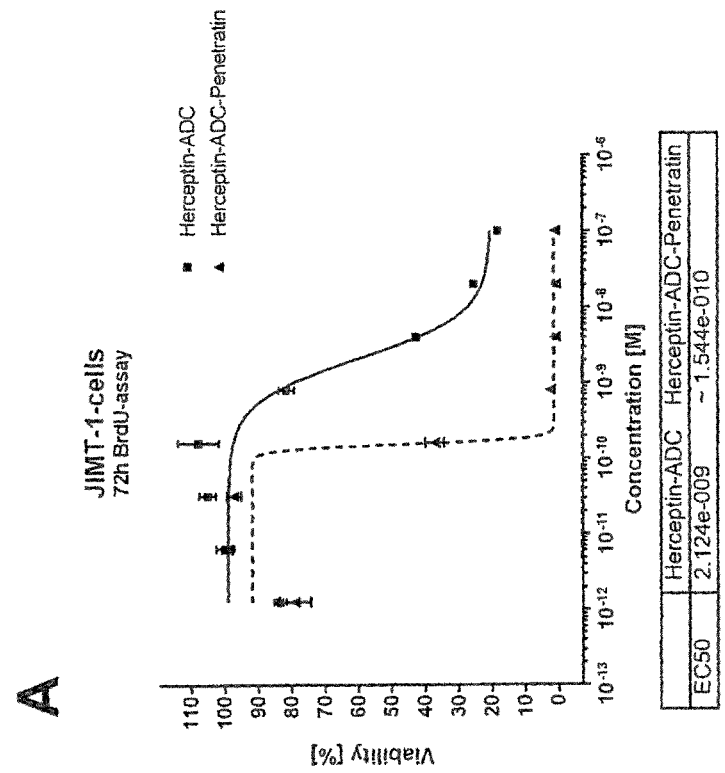

FIG. 10: Cytotoxicity assays with Penetratin antibody conjugates

A) Cytotoxicity assay with EGFR-positive cells
B) Cytotoxicity assay with EGFR-negative cells The cells were treated for 72 hours with different concentrations of a toxin-antibody-Penetratin (4-mer) conjugate (Herceptin-ADC-Penetratin) or a toxin-antibody-conjugate without Penetratin (Herceptin-ADC), respectively. Then, the cell viability was tested via BrdU incorporation. The tables show the molar EC50 concentrations.

Figure 11:
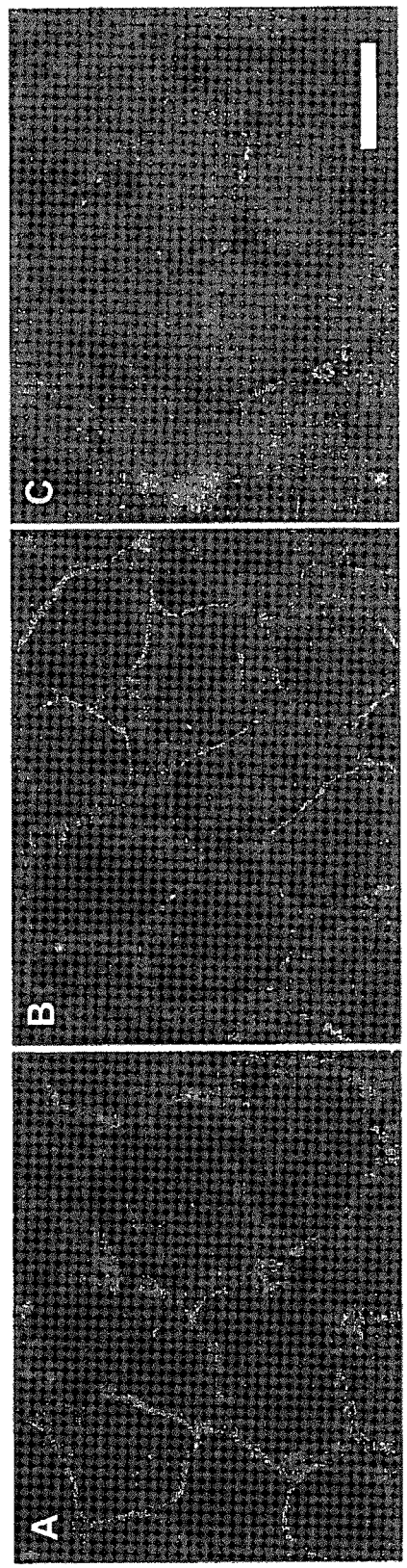

FIG. 11: Cellular uptake of Penetratin antibody conjugates

Incubation of A431 cells (EGFR positive cells) with
A) Native EGFR antibody
B) EGFR antibody Pen10-conjugate (4-mer) (Pen-10=10-mer-Penetratin partial structure, a control peptide causing reduced internalization)
C) EGFR antibody Penetratin-conjugate (4-mer)

Experimental conditions: Incubation for 1 hour with a concentration of 1 µg/ml of all 3 antibodies, fixation of the cells with PFA after incubation, staining with fluorescence-labelled secondary anti-huIgG antibody (AlexaFluor-488), image acquisition with 100× objective lens, fluorescence microscope Keyence BioRevo BZ-9000

Bar: 20 µm

EXAMPLES

1. Materials and Methods 1.1 General.

All chemicals were purchased from Sigma-Aldrich (Schnelldorf, Germany) at the highest available purity unless otherwise stated. Fmoc-protect amino acid building blocks were purchased from Bachem (Bubendorf, Switzerland). Anti-EGFR antibody Matuzumab (EMD72000) was provided by Merck KGaA (Darmstadt, Germany) (see also EP 0 531 472 B1, U.S. Pat. No. 5,558,864, WO 2009/043490 A1). Radioactive iodine I-125 and I-131 isotopes were purchased from Perkin-Elmer (Rodgau, Germany) and Eckert & Ziegler (Berlin, Germany) for I-124.

1.2 Synthesis of Dendritic Cell-Penetrating Peptides (dCPPs).

Branched structures of the CPPs were obtained by manual generation of a solid phase peptide synthesis (SPPS) resin, presenting four amino groups—α- and ε-amines of lysines—as branching points, one alanine residue as spacer and a cysteine as focal group for crosslinking with the antibody using 9-fluorenylmethoxycarbonyl (Fmoc)-protected L-α-amino acids. The desired sequence—K$_2$KAC—was yielded on resin by subsequent incubation of 1.5 g Amphisphere 40 RAM (0.4 mmol/g), swollen in dichloromethane (DCM) and washed four times using dimethyl formamide (DMF), with 4 eq of Fmoc-Cys(Trt)-OH, 4 eq Fmoc-Ala-OH, 3 eq Fmoc-Lys(Fmoc)-OH and 6 eq Fmoc-Lys(Fmoc)-OH respectively. For the coupling steps (75 min) equal amounts of O-(Benzotriazol-1-yl)-N,N,N',N'-tetramethyluronium hexafluoro-phosphate (HBTU) and 500 µL N,N-Diisopropylethylamine (DIPEA) were added. After each coupling the resin was washed five times with DMF and Fmoc was cleaved by consecutive incubation with 10 mL (1 min) and 7 mL (10 min) of 25% (v/v) piperidine solution in DMF followed by DMF washing steps (5×).

This dried resin (150 mg, for each dCPP), containing the four-branch core molecule, was then used in a fully automated peptide synthesizer (Applied Biosystems 433 A, Carlsbad, Calif., USA) with 10 eq (Fmoc)-protected amino acid building blocks. HBTU/DIPEA in NMP was used as a coupling reagent. Fmoc deprotection efficiency was monitored at 301 nm. Cleavage from solid support was performed with TFA/H$_2$O/triisopropylsilane (95:2.5:2.5) for 2 h at ambient temperature. The peptide was precipitated with cold diethyl ether and pelletized (4000 rpm, 4° C., 5 min), washed with diethyl ether, dried in vacuo, and subject to preparative HPLC purification (Waters, Eschbom, Germany; XBridge BEH 130 PREP; C18 column, 5 µm pore size, 150×19 mm). Fractions containing the product were identified by using HPLC-ESI-MS with Orbitrap technology (Exactive, Thermo Fisher Scientific, Waltham, Mass., USA) equipped with an Agilent 1200 HPLC system and a Hypersil Gold C18 column (Thermo Fisher Scientific, Bonn, Germany; 1.9 µm, 200×2.1 mm), pooled and freeze-dried.

1.3 Conjugation of dCPPs with the Monoclonal Antibody.

Conjugation was carried out using the commercially available, hetero-bifunctional crosslinker SMCC (Thermo Fisher Scientific, Bonn, Germany). Crosslinking was carried out according to the manufacturer's protocol. In brief, 7, 15 and 30 equivalents of the crosslinker (15 mg/mL in DMF) were added to the monoclonal antibody (mAb) solution (1.5 mg/mL in PBS) and incubated at room temperature for 30 min. Excess crosslinker was removed by using pre-equilibrated (PBS, pH 7.4) NAP-10 columns (GE Healthcare, Freiburg, Germany). The maleimide-activated mAb solutions were concentrated to 1 mg/mL (concentration determination using Bradford test (Bradford, 1976)) using 100 k Amicon Ultra-0.5 mL centrifugal filters (Merck Millipore, Darmstadt, Germany). Then the maleimide-activated mAb was incubated with 15 eq of the eight different dCPPs (20 mg/mL) at room temperature for 45 min. Reactions with 15 eq SMCC in the first coupling yielded the best results, i.e. predominantly a single attachment of a dCPP to the mAb. Excess dCPP and in part unmodified mAb were removed by size exclusion chromatography using a FPLC manifold equipped with a Superdex 200, 10/300 GL (GE Healthcare) column and PBS as the mobile phase. Fractions containing the antibody-dCPP conjugates were identified by UV-monitoring (λ=280 nm), pooled and concentrated to approximately 0.1 mg/mL using 30 k Amicon Ultra-15 centrifugal filters (Merck Millipore).

1.4 Western Blot.

A431 and DU-145 cells were grown to 80% confluency. Cells were washed twice with 10 mL ice-cold PBS pH 7.4, scraped off and centrifuged (3 min, 1000 rpm). The pellet was washed with 5 mL PBS (3 min, 1000 rpm) and lysed by addition of 2 mL 1% Triton X-100 followed by centrifugation (10 min, 2700 rpm). The supernatant was loaded onto a polyacrylamide gel and SDS-PAGE was performed. Proteins were transferred from the gel to a nitrocellulose membrane using a Mini Trans-Blotter (100 V for 90 min) Non-specific binding sites were blocked by 5% non-fat milk powder in TBST buffer (1 h, RT). Matuzumab (anti-EGFR-antibody; 1:1000 dilution) was used as primary antibody and incubated with the membrane overnight at 4° C. After washing in TBST, the nitrocellulose membrane was incubated with horseradish peroxidase conjugated goat polyclonal anti-human IgG antibody (Thermo Fisher Scientific, Bonn, Germany; 1:1000 dilution) in blocking buffer at room temperature for 60 min. Antibody binding was determined using an enhanced chemiluminescence detection system (Western Lightening Plus ECL, Perkin-Elmer) according to the manufacturer's protocol and exposures were recorded on hyperfilms (10 s to 3 min).

1.5 Radiolabeling.

A modified version of the established chloramine-T method (Hunter & Greenwood, 1962) employing [$^{125}$I]—NaI or [$^{131}$I]—NaI was used to introduce the radioactive iodine at random tyrosine side-chains of the mAb-dCPP conjugate. In brief, 30 µL of the conjugates (0.1 mg/mL) was mixed with 20 µL of phosphate buffer (0.25 M, pH 7.5). A solution containing 1-30 MBq [$^{125}$I]—NaI or [$^{131}$I]—NaI in 10 µM NaOH was added and the labeling reaction was started by addition of an aqueous chloramine-T solution (10 mM, 5 µL). After 30 s, the labeling reaction was quenched by adding a saturated aqueous solution of methionine (10 µL). The labeling reaction mixture was passed over a PBS equilibrated buffer exchange column (NAP-10, GE Healthcare) and 300 µL fractions were collected. 5 µL of each fraction was transferred to a new vial and analyzed for γ-radiation using a γ-counter (LB 2111, Berthold Technologies, Bad Wildbad, Germany). Fractions 4-6 usually contained the radioactively labeled immunoreagent and were pooled. For in vivo experiments, the volume was reduced to 100 µL in vacuo, and for cell binding experiments the solution was used as was.

1.6 Cell Binding and Uptake Assays.

For binding experiments approximately 5×10$^5$ cells of the EGFR-positive cell line A431 or the EGFR-negative, control cell line DU-145 cells were seeded into six-well plates and cultivated in 3 mL/well of RPMI-1640 (with 10% fetal calf serum—FCS) at 37° C. in a 5% $CO_2$ incubator. After 24 h the medium was replaced with 1 mL fresh medium (without FCS) containing 0.8-1.2×10$^6$ cpm of $^{125}$I-labeled mAb-dCPP conjugate and incubated for 60, 150 or 240 min at 37° C. After incubation the medium was removed and cells were washed three times with 1 mL ice cold PBS in order to remove unbound radiolabeled mAb-dCPP conjugates. To determine membrane bound activity, each well was incubated with 1 mL glycine buffer (50 mm glycine-HCl, pH 2.2) for 10 min at room temperature. The cells were washed again with PBS and subsequently lysed using 0.5 mL 0.3 mm sodium hydroxide solution. Radioactivity of the membrane bound fraction (glycine wash) and the internalized fraction (sodium hydroxide lysis) was measured using a γ-counter (LB 951 G, Berthold Technologies). The radioactivity was calculated as percentage applied dose per 10$^6$ cells.

1.7 In Vivo Experiments.

All animal experiments were carried out in conformity with German and European animal protection laws.

1.8 Biodistribution Studies.

Radioactivity amounts of approximately 1 MBq of $^{131}$I-labeled mAb-dCPPs in PBS were administered intravenously into female six-week old, immunodeficient, A431 tumor-bearing BALB/c nude mice (Charles River, Sulzfeld, Germany). After 1, 4, 24 and 48 h the mice (n=3; 18-22 g) were sacrificed, and selected tissue/blood samples (heart, lung, spleen, liver, kidney, muscle, intestine, brain and tumor) were removed, drained of blood, weighed, and the radioactivity determined using a γ-counter (LB 951G, Berthold Technologies). The percentage of injected dose per gram of tissue (% ID/g) was calculated.

1.9 Small Animal Imaging.

Planar scintigraphy studies were performed using female BALB/c nude mice (Charles River, Sulzfeld, Germany), carrying subcutaneously transplanted A431 tumors. A cell suspension of 5×10$^6$ cells in 100 µL OPTI-MEM (Life Technologies, Darmstadt, Germany) was injected subcutaneously into the hind leg of the animals and the tumors were grown to a size of 1.0 cm$^3$ in 10-12 days. Selected $^{125}$I-labeled mAb-dCPP conjugates (7-10 MBq) were injected into the tail vein of the animals and planar scintigraphic images were recorded, while mice were anesthetized by 3-4% sevoflurane (Abbott, Wiesbaden, Germany), at defined time points using a γ-imager (Biospace Lab, Paris, France).

Small-animal PET imaging was carried out using female BALB/c nude mice (Charles River) with xenografted A431 tumors. A suspension of 5×10$^6$ A431 cells in 100 µL OPTI-MEM (Life Technologies) was injected subcutaneously into the hind leg of the mice. Tumors were grown to a size of 0.5-0.7 cm$^3$ in 11 days. PET scans, of anesthetized mice (3-4% sevoflurane, Abbott) in prone position, were performed using a Inveon microPET system (Siemens, Knoxville, Tenn., USA). $^{124}$I-labeled mAb-CPP conjugates (10-12 MBq in 100 µL PBS) were injected intravenously, and static images were acquired after 4, 24 and 48 h. Image data reconstructions and analyses were carried out using Inveon Research Workplace software (Siemens, Knoxville, Tenn., USA).

2. Results 2.1 Syntheses of Cell-Penetrating Peptides Dendrimers.

Figure 1:
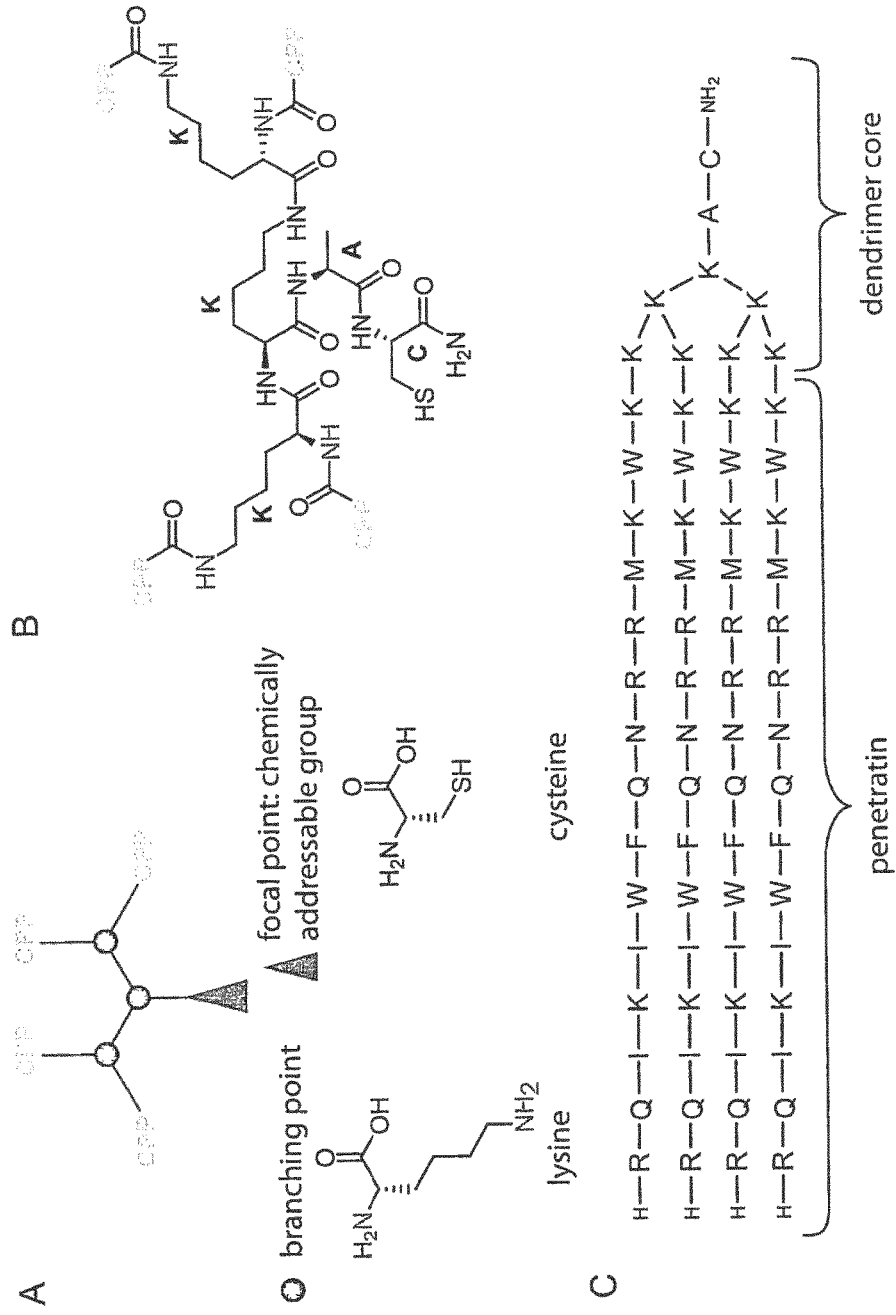
FIG. 1: Overview of cell-penetrating dendrimer syntheses.

In the first step the core of the dendrimer was synthesized using Fmoc-based solid phase peptide synthesis (SPPS). A cysteine residue as orthogonal, chemically addressable sulfhydryl group for crosslinking was coupled via its carboxyl-group onto the solid support (FIG. 1A), followed by an alanine residue, which served as a linker. In the next step the branching points were coupled to the resin. Due to their α- and ε-amino groups, lysine qualifies to fulfill this task (Tam, 1988). By simultaneous deprotection of both amino groups two coupling positions are generated for the next amino acid during SPPS. In the final step of the core peptide synthesis, an additional lysine residue is coupled, and a tetravalent resin was gained, i.e. dendrimers with four branches will be obtained (FIG. 1B). This core peptide containing resin was used as a scaffold in SPPS for the generation of eight different tetravalent, dendritic cell-penetrating peptides (Table 2). After cleavage from solid support and side chain deprotection, the dendrimers were obtained as C-terminally amides for enhanced stability and their identities were proven by high-resolution mass spectrometry (Table 2). The structures of the generated dCPPs are exemplified by the dendritic tetravalent penetratin (FIG. 1C). An overview on the schematic structures of the synthesized dCPPs can be found in FIG. 7.

TABLE 2

Synthesized dCPPs, sequences, molecular weight and references.

| dCPP | Sequence of the Monomer | Calc. Mw of dCPP [Da] | Observed (M + H)+ [Da] | Reference |
|---|---|---|---|---|
| dPenetratin | RQIKIWFQNRRMKWKK (SEQ ID NO: 1) | 9486 | 9487 | Dupont et al., 2011 |
| dTAT (47-60) | YGRKKRRQRRRPPQ (SEQ ID NO: 2) | 8029 | 8030 | Vives et al., 1997 |
| dPreS2-TLM | PLSSIFSRIGDP (SEQ ID NO: 3) | 5656 | 5657 | Oess et al., 2000 |
| dR9 | RRRRRRRRR (SEQ ID NO: 4) | 6197 | 6198 | Mitchell et al., 2000 |
| dMTS | AAVALLPAVLLALLAP (SEQ ID NO: 5) | 6565 | 6566 | Kersemans et al., 2008 |
| dSynB1 | RGGRLSYSRRRFSTSTGR (SEQ ID NO: 6) | 8901 | 8902 | Rousselle et al., 2000 |
| dpVEC | LLIILRRRIRKQAHAHSK (SEQ ID NO: 7) | 9338 | 9340 | Elmquist et al., 2001 |
| dNLS | PKKKRKV (SEQ ID NO: 8) | 4035 | 4036 | Kalderon et al., 1984 |

Abbreviations:
Prefix d: dendritic;
CPP: cell-penetrating peptide;
TAT: human immunodeficiency virus-derived trans-activator of transcription;
preS2-TLM: hepatitis B virus-preS2-domain-derived translocation motif;
MTS: membrane translocation signal;
SynB1: synthetic porcine protegrin 1-derived CPP;
pVEC: vascular endothelial cadherin-derived CPP;
NLS: nuclear localization signal.

2.2 Conjugation of the dCPPs with a Monoclonal Antibody.

The epidermal growth factor receptor (EGFR) specific, humanized, monoclonal antibody Matuzumab (EMD72000, Merck, see also EP 0 531 472 B1, U.S. Pat. No. 5,558,864, WO 2009/043490 A1) was used in conjugation experiments. Crosslinking of the individual dCPPs was carried out employing the heterobifunctional crosslinker SMCC (FIG. 2A). To determine, the optimal crosslinker-to-antibody ratio the mAb was incubated with 7, 15 or 30 equivalents of SMCC. Amine groups of the mAb attacked the activated ester of SMCC, resulting in maleimide-activated antibody. Excess crosslinker was then removed by size exclusion chromatography using buffer exchange columns. Subsequently, the conjugation experiment was carried out using the maleimide-activated mAb and a 15-fold excess of the corresponding dCPP to allow efficient coupling between the mAb-maleimide and the sulfhydryl group of the dCPP. Exemplary, the reaction is shown for dendritic, tetravalent penetratin (dPenetratin, FIG. 2B). 15 equivalents of SMCC in the first reaction turned out to be ideal for the desired 1:1 or less coupling of the mAb to the dCPP.

2.3 Western Blot.

To test the binding of the immunoconjugates to EGFR-expressing cells, the expression of the target antigen was validated by western blot. Therefore, the whole cell lysates of the EGFR-positive human epidermoid carcinoma cell line A431 and the EGFR-negative human prostate carcinoma cell line DU-145 were prepared and used in western blot analysis. The binding of the EGFR-targeting antibody matuzumab was visualized by a HRP-conjugated goat anti-human IgG antibody. The western blot (FIG. 8) revealed that matuzumab exclusively binds to A431, where a clear band at approximately 130 kDa is visible, which is in good agreement with the molecular weight of EGFR (132 kDa). No binding of the mAb to the control cell line DU-145 was observed.

2.4 Cell Binding and Internalization Experiments.

The antibody and the conjugates were labeled with iodine-125 at a random tyrosine side chain using chlorarnine-T and [$^{125}$I]—NaI, as outlined in the methods section. The labeled antibody and the eight immunoconjugates respectively were added to the cell culture medium and incubated with the EGFR-positive cell line A431 for 60, 150 or 240 min. Control experiments were carried out accordingly with the EGFR-negative cell line DU-145. To be able to distinguish between membrane bound activity and internalized activity, the cells were washed with glycine buffer (pH 2.2) first to remove membrane-bound activity. In the second step the cells were lysed and internalized activity was measured. The measurement revealed that 22±0.2% of the applied dose of the radiolabeled, unmodified matuzumab bound to the EGFR-positive cells A431 (FIG. 3A), whereas no binding was observed for the control cell line DU-145. In addition only a small portion of the activity was internalized into the EGFR-positive cells (3%, FIG. 3A, black part of column). For the antibody, if modified with cell-penetrating peptide dendrimers, these values were in general higher and binding of the applied dose to the cells ranged from 47±0.5% (mAb-dSynB1) to 92±1.2% (mAb-dR9). Internalization rates were also higher, with a maximum of 38±0.9% (mAb-dR9) and a minimum of 9±0.7% (mAb-dSynB1). Binding of the immunoconjugates to the control cell line (FIG. 3B) was low (<10%) to moderate (16±1.1% for mAb-dTAT, 14±0.6% for mAb-dR9 and 13±0.6% for mAb-dNLS). The detailed results are visualized in FIG. 3.

Furthermore, FIG. 10 shows that a toxin-conjugated antibody furthermore conjugated with Penetratin (4-mer) exhibits increased cell toxicity compared to the toxin-conjugated antibody without Penetratin (FIG. 10A).

In addition, FIG. 11 shows fluorescence imaging results showing the cellular uptake of Penetratin antibody conjugates into A431 cells. As can be seen, EGFR antibody Penetratin-conjugate (4-mer) is internalized in A431 cells (FIG. 11C), whereas native EGFR antibody is not internalized (FIG. 11A) and the conjugate with Pen10 (4-mer), the control peptide, known to cause lower internalization rates, shows only reduced internalization (FIG. 11B).

2.5 Biodistribution Studies.

The two most promising immunoconjugates, based on the cell binding and internalization experiments, were chosen for biodistribution studies. These two were mAb-dPenetratin and mAb-dR9. Although mAb-R9 was more unspecific—14±0.6% binding to the control cell line—than other conjugates, it had the highest binding value of the eight different conjugates (92±1.2% binding). The immunoconjugate of matuzumab and dendritic penetratin showed good binding to A431 cells (68±0.9% binding) and low affinity for the control cell line (maximum 5±0.2%). As control, the unmodified antibody was used. All three compounds were labeled with iodine-131 and injected into A431 tumor-bearing mice. At different time points the mice were sacrificed, dissected and organs were examined for radioactivity uptake. This is exemplified by FIG. 4A, where the biodistribution after 96 hours is shown. At this time point the differences between the dCPP-modified antibody and the wildtype became most obvious. Tumor binding was high for all three compounds (8.9±0.2% for mAb-dR9, 8.7±0.3% for mAb and 6.2±0.2% for mAb-dPenetratin), whereas binding to other organs is less than 1.7%, except for the unmodified mAb. There, high values of 2.0±0.1%, 2.6±0.4% and 5.1±0.2% were observed for the kidneys, the heart and the lung, respectively. Most significantly, the blood contained 7.1±0.8% of the injected dose for the unmodified mAb; for mAb-dPenetratin and mAb-dR9 the blood contained 3.1±0.2% and 3.3±0.6% respectively, resulting in favorable tumor-to-blood ratios for the conjugates. As depicted in FIG. 4B, within the first four hours after administration of the antibody and the immunoconjugates, similar values for the tumor-to-blood ratios were observed. However, after 24 h there was a significant difference between the conjugates and the unmodified antibody for this ratio, which was even higher after 48 h. Over the full course of the 96 h examination period, the tumor-to-blood ratio reached a value of 2.7 for mAb-dR9 and 2.0 for mAb-dPenetratin, whereas the unmodified antibody did not exceed 1.3.

2.6 Small Animal Imaging Experiments.

Figure 9:
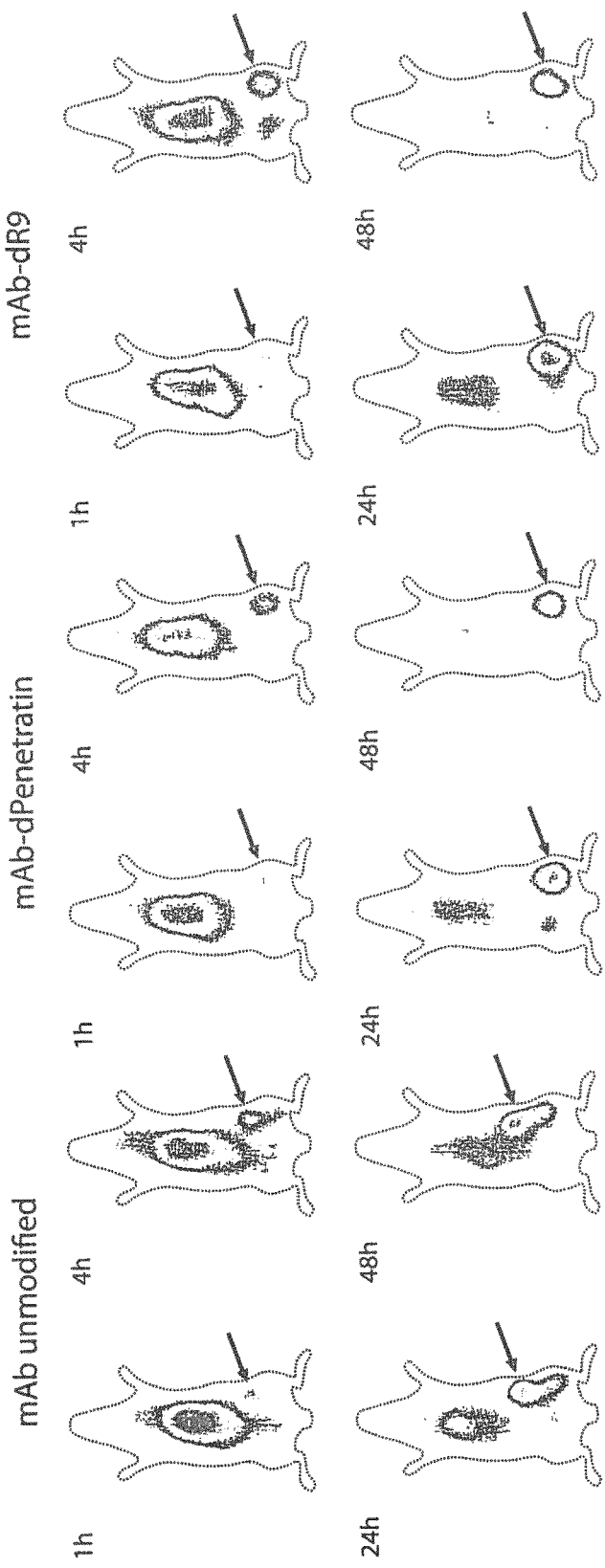

In the first set of experiments, planar scintigraphic images were recorded of athymic nude mice, with A431 tumors xenografted into the upper hind limb. The antibody and the immunoconjugates mAb-dR9 and mAb-dPenetratin were labeled with iodine-125. Then the radioactive compounds were administered intravenously into individual rodents, in order to record planar images after 1, 4, 24 and 48 h (FIG. 9). After 48 h (FIG. 5A) the differences between the unmodified and the conjugated antibody became obvious. In all mice high accumulation of the different radiopharmaceuticals was observed at the upper hind limb tumor site. A significant amount of the applied dose was still in circulation for the unmodified antibody, whereas almost no background was observed for the conjugates mAB-dPenetratin and mAb-dR9.

In the second experimental setup, the antibody and its conjugates were radiolabeled with the positron emitter iodine-124 as outlined in the material and methods section. Again, these radiopharmaceuticals were administered intravenously into individual A431 nude mice xenografts and static PET images were recorded. As observed for the planar $^{125}$I-images, the PET images showed that the conjugates had a faster clearance from the blood than the unmodified antibody. In addition, accumulation of radioactivity in the urinary tract was observed for mAb and mAb-dPenetratin. For all three examined radiopharmaceuticals a significant amount of the applied dose was found in the thyroid with the unconjugated antibody showing the highest value.

The features disclosed in the foregoing description, in the claims and/or in the accompanying drawings may, both separately and in any combination thereof, be material for realizing the invention in diverse forms thereof.

REFERENCES

Ausubel, F. M. et al. (2001) Current Protocols in Molecular Biology, Wiley & Sons, Hoboken, N.J., USA.

Bradford M M. A rapid and sensitive method for the quantitation of microgram quantities of protein utilizing the principle of protein-dye binding. *Anal Biochem*. May 7, 1976; 72:248-254.

Carter P. Improving the efficacy of antibody-based cancer therapies. *Nat Rev Cancer*. November 2001; 1(2):118-129.

Cornelissen B, Hu M, McLarty K, Costantini D, Reilly R M. Cellular penetration and nuclear importation properties of 111In-labeled and 123I-labeled HIV-1 tat peptide immunoconjugates in BT-474 human breast cancer cells. *Nucl Med Biol*. January 2007; 34(1):37-46.

Deshayes S, Plenat T, Chamet P, Divita G, Molle G, Heitz F. Formation of transmembrane ionic channels of primary amphipathic cell-penetrating peptides. Consequences on the mechanism of cell penetration. *Biochim Biophys Acta*. November 2006; 1758(11): 1846-1851.

Dupont E, Prochiantz A, Joliot A. Penetratin story: an overview. *Methods Mol Biol*. 2011; 683:21-29.

Elmquist A, Lindgren M, Bartfai T, Langel U. VE-cadherin-derived cell-penetrating peptide, pVEC, with carrier functions. *Exp Cell Res*. Oct. 1, 2001; 269(2):237-244.

Farkas P, Korcová. J, Kronek J, Bystrický S. Preparation of synthetic polyoxazoline based carrier and *Vibrio cholerae* O-specific polysaccharide conjugate vaccine. *Eur J Med Chem*. 2010 February; 45(2):795-9.

Fonseca S B, Pereira M P, Kelley S O. Recent advances in the use of cell-penetrating peptides for medical and biological applications. *Adv Drug Deliv Rev*. Sep. 30, 2009; 61(11):953-964.

Gautam A, Singh H, Tyagi A, Chaudhary K, Kumar R, Kapoor P, Raghava G P. CPPsite: a curated database of cell penetrating peptides. Database (Oxford). 2012 Mar. 7; 2012:bas015. Print 2012.

Howl J, Nicholl I D, Jones S. The many futures for cell-penetrating peptides: how soon is now? *Biochem Soc Trans*. August 2007; 35(Pt 4):767-769.

Hu M, Chen P, Wang J, Chan C, Scollard D A, Reilly R M. Site-specific conjugation of HIV-1 tat peptides to IgG: a potential route to construct radioimmunoconjugates for targeting intracellular and nuclear epitopes in cancer. *Eur J Nucl Med Mol Imaging*. March 2006; 33(3):301-310.

Hu M, Chen P, Wang J, Scollard D A, Vallis K A, Reilly R M. 123I-labeled HIV-1 tat peptide radioimmunoconjugates are imported into the nucleus of human breast cancer cells and functionally interact in vitro and in vivo with the cyclin-dependent kinase inhibitor, p21(WAF-1/Cip-1). *Eur J Nucl Med Mol Imaging*. March 2007; 34(3):368-377.

Hunter W M, Greenwood F C. Preparation of iodine-131 labelled human growth hormone of high specific activity. *Nature*. May 5, 1962; 194:495-496.

Jain M, Chauhan S C, Singh A P, Venkatraman G, Colcher D, Batra S K. Penetratin improves tumor retention of single-chain antibodies: a novel step toward optimization of radioimmunotherapy of solid tumors. *Cancer Res*. Sep. 1, 2005; 65(17):7840-7846.

Jay J I, Lai B E, Myszka D G, Mahalingam A, Langheinrich K, Katz D F, Kiser P F. Multivalent benzoboroxole functionalized polymers as gp120 glycan targeted microbicide entry inhibitors. *Mol Pharm*. 2010 Feb. 1; 7(1):116-29.

Jeger S, Zimmermann K, Blanc A, Grünberg J, Honer M, Hunziker P, Struthers H, Schibli R. Site-specific and stoichiometric modification of antibodies by bacterial transglutaminase. *Angew Chem Int Ed Engl*. 2010 Dec. 17; 49(51):9995-7.

Kalderon D, Roberts B L, Richardson W D, Smith A E. A short amino acid sequence able to specify nuclear location. *Cell*. December 1984; 39(3 Pt 2):499-509.

Kaminski M S, Zelenetz A D, Press O W, et al. Pivotal study of iodine I 131 tositumomab for chemotherapy-refractory low-grade or transformed low-grade B-cell non-Hodgkin's lymphomas. *J Clin Oncol*. Oct. 1, 2001; 19(19):3918-3928.

Kersemans V, Kersemans K, Cornelissen B. Cell penetrating peptides for in vivo molecular imaging applications. *Curr Pharm Des*. 2008; 14(24):2415-2447.

Khandare J, Calderon M, Dagia N M, Haag R. Multifunctional dendritic polymers in nanomedicine: opportunities and challenges. *Chem Soc Rev*. 2012; 41(7):2824-48. Review.

Madani F, Lindberg S, Langel U, Futaki S, Graslund A. Mechanisms of cellular uptake of cell-penetrating peptides. *J Biophys*. 2011; 2011:414729.

Mammen M, Choi S-K, Whitesides G M. Polyvalent interactions in biological systems: Implications for design and use of multivalent ligands and inhibitors. *Angew. Chem. Int. Ed*. 1998; 37: 2754-2794. Review.

Mitchell D J, Kim D T, Steinman L, Fathman C G, Rothbard J B. Polyarginine enters cells more efficiently than other polycationic homopolymers. *J Pept Res*. November 2000; 56(5):318-325.

Oess S, Hildt E. Novel cell permeable motif derived from the PreS2-domain of hepatitis-B virus surface antigens. *Gene Ther*. May 2000; 7(9):750-758.

Oldham R K, Dillman R O. Monoclonal antibodies in cancer therapy: 25 years of progress. *J Clin Oncol*. Apr. 10, 2008; 26(11):1774-1777.

Pouget J P, Navarro-Teulon I, Bardies M, et al. Clinical radioimmunotherapy—the role of radiobiology. *Nat Rev Clin Oncol*. December 2011; 8(12):720-734.

Rousselle C, Clair P, Lefauconnier J M, Kaczorek M, Scherrmann J M, Temsamani J. New advances in the transport of doxorubicin through the blood-brain barrier by a peptide vector-mediated strategy. *Mol Pharmacol*. April 2000; 57(4):679-686.

Sarko D, Beijer B, Garcia Boy R, Nothelfer E M, Leotta K, Eisenhut M, Altmann. A, Haberkom U, Mier W. The pharmacokinetics of cell-penetrating peptides. *Mol Pharm*. 2010 Dec. 6; 7(6):2224-31.

Sarko D, Eisenhut M, Haberkorn U, Mier W. Bifunctional chelators in the design and application of radiopharmaceuticals for oncological diseases. *Curr Med Chem*. 2012; 19(17):2667-88. Review.

Singh D, Bisland S K, Kawamura K, Gariepy J. Peptide-based intracellular shuttle able to facilitate gene transfer in mammalian cells. *Bioconj Chem* 1999; 10(5):745-54.

Smith-Jones P M, Vallabhajosula S, Navarro V, Bastidas D, Goldsmith S J, Bander N H. Radiolabeled monoclonal antibodies specific to the extracellular domain of prostate-specific membrane antigen: preclinical studies in nude mice bearing LNCaP human prostate tumor. *J Nucl Med*. April 2003; 44(4):610-617.

Song H, Sgouros G. Radioimmunotherapy of solid tumors: searching for the right target. *Curr Drug Deliv*. January 2011; 8(1):26-44.

Tam J P. Synthetic peptide vaccine design: synthesis and properties of a high-density multiple antigenic peptide system. *Proc Natl Acad Sci USA*. August 1988; 85(15):5409-5413.

Trabulo S, Cardoso A L, Mano M, De Lima M C P. Cell-Penetrating Peptides—Mechanisms of Cellular Uptake and Generation of Delivery Systems. *Pharmaceuticals*. 2010; 3(4):961-993.

Vives E, Brodin P, Lebleu. B. A truncated HIV-1 Tat protein basic domain rapidly translocates through the plasma membrane and accumulates in the cell nucleus. *J Biol Chem*. Jun. 20, 1997; 272(25):16010-16017.

Waldmann T A. Immunotherapy: past, present and future. *Nat Med*. March 2003; 9(3):269-277.

Wangler C, Moldenhauer G, Eisenhut M, Haberkorn U, Mier W. Antibody-dendrimer conjugates: the number, not the size of the dendrimers, determines the immunoreactivity. *Bioconjug Chem*. April 2008; 19(4):813-820.

Witzig T E, Gordon L I, Cabanillas F, et al. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma. *J Clin Oncol*. May 15, 2002; 20(10):2453-2463.

Xie J, Schultz P G. A chemical toolkit for proteins—an expanded genetic code. *Nat Rev Mol Cell Biol*. 2006 October; 7(10):775-82.

The invention claimed is:

1. A conjugate comprising:
   a protein, and
   one or more multivalent cell-penetrating peptide(s) (multivalent CPP(s)) each multivalent CPP comprising at least two cell-penetrating peptides (CPPs),
   wherein the multivalent CPP(s) is/are covalently attached to the protein,
   wherein the one or more multivalent CPP is a dendrimer of cell-penetrating peptides (cell-penetrating peptide dendrimer, dCPP) comprising a dendrimer core and at least two cell-penetrating peptides (CPPs), which are coupled to the dendrimer core,
   said dendrimer core being a peptidyl dendrimer core comprising lysines as branching points and cysteine(s) as the anchoring group(s), and comprises:

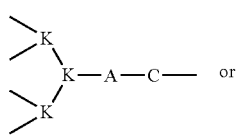 or

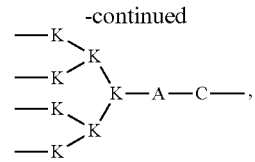

wherein K is Lys, A is Ala and C is Cys,
wherein the CPPs each comprises the amino acid sequence of
   penetratin (SEQ ID NO: 1),
   TAT (47-60) (human immunodeficiency virus-derived trans-activator of transcription, SEQ ID NO: 2),
   PreS2-TLM (hepatitis B virus-preS2-domain-derived translocation motif, SEQ ID NO: 3), R9 (SEQ ID NO: 4),
   MTS (membrane translocation signal, SEQ ID NO: 5),
   SynB1 (synthetic porcine protegrin 1-derived CPP, SEQ ID NO: 6),
   pVEC (vascular endothelial cadherin-derived CPP, SEQ ID NO: 7), or
   NLS (nuclear localization signal, SEQ ID NO: 8),
   or a combination thereof,
and/or the wherein the CPPs each comprises an amino acid sequence of SEQ ID NOs: 9 to 77 or a combination thereof, and/or wherein the CPPs each comprises an amino acid sequence of SEQ ID NOs: 78 to 760 or a combination thereof.

2. The conjugate of claim 1, wherein the one or more multivalent CPPs comprise 2 to 50 CPPs.

3. The conjugate of claim 1, wherein the one or more multivalent CPPs comprise a dendrimer of cell-penetrating peptides or multiple copies of CPPs.

4. The conjugate of claim 1, wherein the dendrimer core comprises anchoring group(s), branching point(s), and, optionally, a spacer between the anchoring group(s) and the branching point(s).

5. The conjugate of claim 1, wherein the one or more multivalent CPPs each comprises an amino acid sequence having 5 to 30 amino acids.

6. The conjugate of claim 1, wherein the one or more multivalent CPPs comprise one or more of natural amino acids, amino acid derivatives, D-amino acids, modified amino acids, β-amino acid derivatives, α,α-disubstituted amino acid derivatives, N-substituted α-amino acid derivatives, aliphatic or cyclic amines, amino- and carboxy-substituted cycloalkyl derivatives, amino- and carboxy-substituted aromatic derivatives, γ-amino acid derivatives, aliphatic α-amino acid derivatives, diamines and polyamines.

7. The conjugate of claim 1, wherein the CPPs each is a peptide capable of being internalized into a cell
and/or wherein the CPPs each comprises in its amino acid sequence at least 25% positively charged amino acid residues,
and/or wherein the CPPs each is internalized into a cell with an efficacy being at least 50% of the internalization efficacy of the TAT peptide having the amino acid sequence of SEQ ID NO: 2.

8. The conjugate of claim 1, wherein the CPPs each comprise the amino acid sequence of
penetratin (SEQ ID NO: 1), and/or
R9 (SEQ ID NO: 4).

9. The conjugate of claim 1, wherein the one or more cell-penetrating peptide(s) each comprise an amino acid sequence selected from SEQ ID NOs. 1 to 760 or amino acid sequences having at least 90% sequence identity to an amino acid sequence of SEQ ID NOs. 1 to 760.

10. The conjugate of claim 1, wherein the one or more multivalent CPPs each comprises 2 more different CPPs.

11. The conjugate of claim 1, wherein the protein is a biological or clinically active or therapeutic protein.

12. The conjugate of claim 1, furthermore comprising a linker connecting the protein and the one or more multivalent CPP(s).

13. The conjugate of claim 12, wherein the linker is a bifunctional (cross)linker covalently coupling the protein with the one or more multivalent CPPs.

14. The conjugate of claim 1, comprising
an antibody,
one or more cell-penetrating peptide dendrimer(s) (dCPP), and
one or more linkers each covalently coupling the antibody with a dCPP.

15. The conjugate of claim 1, further comprising
a label,
a drug or prodrug, and/or
a further biologically active component.

16. A method for generating a conjugate according to claim 1, comprising the steps of
(a) providing multivalent cell-penetrating peptide(s) (multivalent CPP(s)) comprising anchoring group(s),
(b) generating a chemically activated protein by using a linker, or providing a protein comprising coupling site(s),
(c) coupling the multivalent CPP(s) of step (a) to the protein of step (b),
(d) obtaining the conjugate,
(e) purifying the conjugate.

17. The method of claim 16, wherein in step (a) cell-penetrating peptide dendrimer(s) (dCPPs) comprising one or more anchoring group(s) are provided.

18. The method of claim 16, wherein the linker is a bifunctional (cross) linker and/or comprising using in step (b) excess of the linker to generate a chemically activated protein having one or more maleimide molecule(s) on the surface.

19. The method of claim 17, comprising using in step (c) excess of the cell-penetrating peptide dendrimer(s).

20. The method of claim 16, wherein the coupling site(s) of the protein are the side chains of cysteine(s), glutamine(s) and/or lysine(s) and/or unnatural amino acids.

* * * * *

UNITED STATES PATENT AND TRADEMARK OFFICE
CERTIFICATE OF CORRECTION

PATENT NO. : 10,253,099 B2
APPLICATION NO. : 14/648537
DATED : April 9, 2019
INVENTOR(S) : Matthias Strieker, Walter Mier and Uwe Haberkorn It is certified that error appears in the above-identified patent and that said Letters Patent is hereby corrected as shown below:

In the Specification

Column 11,
Line 8, "EFHEN" should read --EFHFN--.

Column 23,
Line 25, "YARL" should read --YARA--.

Column 25,
Line 24, "KLAK" should read --KLAL--.

Column 35,
Line 38, "RLW" should read --RLA--.
Line 39, "RLWM" should read --RLWA--.
Line 51, "SPTARRYG" should read --SPTTARYG--.

Column 39,
Line 15, "GRIP" should read --GRTP--.
Line 19, "GRIP" should read --GRTP--.
Line 26, "KEGK" should read --KFGK--.

Column 43,
Line 12, "aky" should read --akv--.

Column 45,
Line 18, "LEVA" should read --LFVA--.

Column 51,
Line 28, "FRAL" should read --FRIL--.

Signed and Sealed this
Twenty-second Day of October, 2019

Andrei Iancu
*Director of the United States Patent and Trademark Office*

Column 55,
Line 64, "GRRARR" should read --GRAARR--.

Column 57,
Line 11, "YGRRA" should read --YEREA--.

SEQUENCE LISTING

```
<160> NUMBER OF SEQ ID NOS: 764

<210> SEQ ID NO 1
<211> LENGTH: 16
<212> TYPE: PRT
<213> ORGANISM: Artificial Sequence
```

```
<220> FEATURE:
<223> OTHER INFORMATION: Penetratin

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: CPP

<400> SEQUENCE: 2

Tyr Gly Arg Lys Lys Arg Arg Gln Arg Arg Pro Pro Gln
1               5                   10

<210> SEQ ID NO 3
<211> LENGTH: 12
<212> TYPE: PRT
<213> ORGANISM: Artificial Sequence
<220> FEATURE:
<223> OTHER INFORMATION: CPP

<400> SEQUENCE: 3

Pro Leu Ser Ser Ile Phe Ser Arg Ile Gly Asp Pro
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Polyarginine CPP (R9)

<400> SEQUENCE: 4

Arg Arg Arg Arg Arg Arg Arg Arg Arg
1               5

<210> SEQ ID NO 5
<211> LENGTH: 16
<212> TYPE: PRT
<213> ORGANISM: Artificial Sequence
<220> FEATURE:
<223> OTHER INFORMATION: MTS membran translocation signal

<400> SEQUENCE: 5

Ala Ala Val Ala Leu Leu Pro Ala Val Leu Leu Ala Leu Leu Ala Pro
1               5                   10                  15

<210> SEQ ID NO 6
<211> LENGTH: 18
<212> TYPE: PRT
<213> ORGANISM: Artificial Sequence
<220> FEATURE:
<223> OTHER INFORMATION: synthetic porcine protegrin 1-derived CPP

<400> SEQUENCE: 6

Arg Gly Gly Arg Leu Ser Tyr Ser Arg Arg Arg Phe Ser Thr Ser Thr
1               5                   10                  15

Gly Arg

<210> SEQ ID NO 7
<211> LENGTH: 18
<212> TYPE: PRT
```

```
<213> ORGANISM: Artificial Sequence
<220> FEATURE:
<223> OTHER INFORMATION: vascular endothelial cadherin-derived CPP

<400> SEQUENCE: 7

Leu Leu Ile Ile Leu Arg Arg Arg Ile Arg Lys Gln Ala His Ala His
1               5                   10                  15

Ser Lys

<210> SEQ ID NO 8
<211> LENGTH: 7
<212> TYPE: PRT
<213> ORGANISM: Artificial Sequence
<220> FEATURE:
<223> OTHER INFORMATION: NLS nuclear localization signal

<400> SEQUENCE: 8

Pro Lys Lys Lys Arg Lys Val
1               5

<210> SEQ ID NO 9
<211> LENGTH: 9
<212> TYPE: PRT
<213> ORGANISM: Artificial Sequence
<220> FEATURE:
<223> OTHER INFORMATION: CPP

<400> SEQUENCE: 9

Arg Lys Lys Arg Arg Gln Arg Arg Arg
1               5

<210> SEQ ID NO 10
<211> LENGTH: 13
<212> TYPE: PRT
<213> ORGANISM: Artificial Sequence
<220> FEATURE:
<223> OTHER INFORMATION: CPP

<400> SEQUENCE: 10

Gly Arg Lys Lys Arg Arg Gln Arg Arg Arg Pro Pro Gln
1               5                   10

<210> SEQ ID NO 11
<211> LENGTH: 24
<212> TYPE: PRT
<213> ORGANISM: Artificial Sequence
<220> FEATURE:
<223> OTHER INFORMATION: calcitonin-derived CPP

<400> SEQUENCE: 11

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 12
<211> LENGTH: 10
<212> TYPE: PRT
<213> ORGANISM: Artificial Sequence
<220> FEATURE:
<223> OTHER INFORMATION: NLS

<400> SEQUENCE: 12

Val Gln Arg Lys Arg Gln Lys Leu Met Pro
1               5                   10
```

```
<210> SEQ ID NO 13
<211> LENGTH: 8
<212> TYPE: PRT
<213> ORGANISM: Artificial Sequence
<220> FEATURE:
<223> OTHER INFORMATION: NLS

<400> SEQUENCE: 13

Ser Lys Lys Lys Lys Thr Lys Val
1               5

<210> SEQ ID NO 14
<211> LENGTH: 8
<212> TYPE: PRT
<213> ORGANISM: Artificial Sequence
<220> FEATURE:
<223> OTHER INFORMATION: NLS

<400> SEQUENCE: 14

Gly Arg Lys Arg Lys Lys Arg Thr
1               5

<210> SEQ ID NO 15
<211> LENGTH: 9
<212> TYPE: PRT
<213> ORGANISM: Artificial Sequence
<220> FEATURE:
<223> OTHER INFORMATION: polybasic CPP

<400> SEQUENCE: 15

Arg Arg Arg Glu Arg Arg Ala Glu Lys
1               5

<210> SEQ ID NO 16
<211> LENGTH: 9
<212> TYPE: PRT
<213> ORGANISM: Artificial Sequence
<220> FEATURE:
<223> OTHER INFORMATION: polybasic CPP

<400> SEQUENCE: 16

Lys Cys Pro Ser Arg Arg Pro Lys Arg
1               5

<210> SEQ ID NO 17
<211> LENGTH: 6
<212> TYPE: PRT
<213> ORGANISM: Artificial Sequence
<220> FEATURE:
<223> OTHER INFORMATION: N-terminal repetitive domain of maize gamma-
      zein

<400> SEQUENCE: 17

Val Arg Leu Pro Pro Pro
1               5

<210> SEQ ID NO 18
<211> LENGTH: 6
<212> TYPE: PRT
<213> ORGANISM: Artificial Sequence
<220> FEATURE:
<223> OTHER INFORMATION: N-terminal repetitive domain of maize gamma-
      zein

<400> SEQUENCE: 18

Val His Leu Pro Pro Pro
1               5
```

<210> SEQ ID NO 19
<211> LENGTH: 6
<212> TYPE: PRT
<213> ORGANISM: Artificial Sequence
<220> FEATURE:
<223> OTHER INFORMATION: N-terminal repetitive domain of maize gamma-
      zein

<400> SEQUENCE: 19

Val Lys Leu Pro Pro Pro
1               5

<210> SEQ ID NO 20
<211> LENGTH: 17
<212> TYPE: PRT
<213> ORGANISM: Artificial Sequence
<220> FEATURE:
<223> OTHER INFORMATION: Peptide from gp41 fusion sequence

<400> SEQUENCE: 20

Ala Val Gly Ala Ile Gly Ala Leu Phe Leu Gly Phe Leu Gly Ala Ala
1               5                   10                  15

Gly

<210> SEQ ID NO 21
<211> LENGTH: 15
<212> TYPE: PRT
<213> ORGANISM: Artificial Sequence
<220> FEATURE:
<223> OTHER INFORMATION: SSHR

<400> SEQUENCE: 21

Val Thr Val Leu Ala Leu Gly Ala Leu Ala Gly Val Gly Val Gly
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: pVEC

<400> SEQUENCE: 22

Ile Ala Ala Arg Ile Lys Leu Arg Ser Arg Gln His Ile Lys Leu Arg
1               5                   10                  15

His Leu

<210> SEQ ID NO 23
<211> LENGTH: 27
<212> TYPE: PRT
<213> ORGANISM: Artificial Sequence
<220> FEATURE:
<223> OTHER INFORMATION: Vpr

<400> SEQUENCE: 23

Asp Thr Trp Pro Gly Val Glu Ala Leu Ile Arg Ile Leu Gln Gln Leu
1               5                   10                  15

Leu Phe Ile His Phe Arg Ile Gly Cys Gln His
                20                  25

<210> SEQ ID NO 24
<211> LENGTH: 34
<212> TYPE: PRT
<213> ORGANISM: Artificial Sequence

<220> FEATURE:
<223> OTHER INFORMATION: VP22

<400> SEQUENCE: 24

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 25
<211> LENGTH: 17
<212> TYPE: PRT
<213> ORGANISM: Artificial Sequence
<220> FEATURE:
<223> OTHER INFORMATION: gp41 fusion sequence

<400> SEQUENCE: 25

Gly Ala Leu Phe Leu Gly Trp Leu Gly Ala Ala Gly Ser Thr Met Gly
1               5                   10                  15

Ala

<210> SEQ ID NO 26
<211> LENGTH: 17
<212> TYPE: PRT
<213> ORGANISM: Artificial Sequence
<220> FEATURE:
<223> OTHER INFORMATION: Caiman crocodylus Ig(v) light chain

<400> SEQUENCE: 26

Met Gly Leu Gly Leu His Leu Leu Val Leu Ala Ala Ala Leu Gln Gly
1               5                   10                  15

Ala

<210> SEQ ID NO 27
<211> LENGTH: 27
<212> TYPE: PRT
<213> ORGANISM: Artificial Sequence
<220> FEATURE:
<223> OTHER INFORMATION: CPP from pestivirus env glycoprotein

<400> SEQUENCE: 27

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25

<210> SEQ ID NO 28
<211> LENGTH: 28
<212> TYPE: PRT
<213> ORGANISM: Artificial Sequence
<220> FEATURE:
<223> OTHER INFORMATION: CPP from the prion protein

<400> SEQUENCE: 28

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 29
<211> LENGTH: 16
<212> TYPE: PRT

<213> ORGANISM: Artificial Sequence
<220> FEATURE:
<223> OTHER INFORMATION: Yeast PRP6 (129-144)

<400> SEQUENCE: 29

Thr Arg Arg Asn Lys Arg Asn Arg Ile Gln Glu Gln Leu Asn Arg Lys
1               5                   10                  15

<210> SEQ ID NO 30
<211> LENGTH: 18
<212> TYPE: PRT
<213> ORGANISM: Artificial Sequence
<220> FEATURE:
<223> OTHER INFORMATION: Phi21 N (12-29)

<400> SEQUENCE: 30

Thr Ala Lys Thr Arg Tyr Lys Ala Arg Arg Ala Glu Leu Ile Ala Glu
1               5                   10                  15

Arg Arg

<210> SEQ ID NO 31
<211> LENGTH: 22
<212> TYPE: PRT
<213> ORGANISM: Artificial Sequence
<220> FEATURE:
<223> OTHER INFORMATION: Delta N (1-22)

<400> SEQUENCE: 31

Met Asp Ala Gln Thr Arg Arg Glu Arg Arg Ala Glu Lys Gln Ala
1               5                   10                  15

Gln Trp Lys Ala Ala Asn
            20

<210> SEQ ID NO 32
<211> LENGTH: 15
<212> TYPE: PRT
<213> ORGANISM: Artificial Sequence
<220> FEATURE:
<223> OTHER INFORMATION: FHV coat (35-49)

<400> SEQUENCE: 32

Arg Arg Arg Arg Asn Arg Thr Arg Arg Asn Arg Arg Arg Val Arg
1               5                   10                  15

<210> SEQ ID NO 33
<211> LENGTH: 19
<212> TYPE: PRT
<213> ORGANISM: Artificial Sequence
<220> FEATURE:
<223> OTHER INFORMATION: BMV Gag (7-25)

<400> SEQUENCE: 33

Lys Met Thr Arg Ala Gln Arg Arg Ala Ala Ala Arg Arg Asn Arg Trp
1               5                   10                  15

Thr Ala Arg

<210> SEQ ID NO 34
<211> LENGTH: 13
<212> TYPE: PRT
<213> ORGANISM: Artificial Sequence
<220> FEATURE:
<223> OTHER INFORMATION: HTLV-II Rex (4-16)

<400> SEQUENCE: 34

Thr Arg Arg Gln Arg Thr Arg Arg Ala Arg Arg Asn Arg

```
                           1               5                  10

<210> SEQ ID NO 35
<211> LENGTH: 12
<212> TYPE: PRT
<213> ORGANISM: Artificial Sequence
<220> FEATURE:
<223> OTHER INFORMATION: HIV-1 Rev (9-20)

<400> SEQUENCE: 35

Arg Gln Ala Arg Arg Asn Arg Arg Arg Arg Trp Arg
1               5                   10

<210> SEQ ID NO 36
<211> LENGTH: 22
<212> TYPE: PRT
<213> ORGANISM: Artificial Sequence
<220> FEATURE:
<223> OTHER INFORMATION: RSG-1.2

<400> SEQUENCE: 36

Asp Arg Arg Arg Arg Gly Ser Arg Pro Ser Gly Ala Glu Arg Arg
1               5                   10                  15

Arg Arg Ala Ala Ala Ala
            20

<210> SEQ ID NO 37
<211> LENGTH: 15
<212> TYPE: PRT
<213> ORGANISM: Artificial Sequence
<220> FEATURE:
<223> OTHER INFORMATION: Lambda-N (48-62)

<400> SEQUENCE: 37

Gln Thr Arg Arg Arg Glu Arg Arg Ala Glu Lys Gln Ala Gln Trp
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Bipartite, Nucleoplasmin (155-170), NLS

<400> SEQUENCE: 38

Lys Arg Pro Ala Ala Ile Lys Lys Ala Gly Gln Ala Lys Lys Lys Lys
1               5                   10                  15

<210> SEQ ID NO 39
<211> LENGTH: 12
<212> TYPE: PRT
<213> ORGANISM: Artificial Sequence
<220> FEATURE:
<223> OTHER INFORMATION: Herpesvirus, 8 k8 protein (124-135)

<400> SEQUENCE: 39

Thr Arg Arg Ser Lys Arg Arg Ser His Arg Lys Phe
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Buforin-II (20-36)

<400> SEQUENCE: 40
```

```
Arg Ala Gly Leu Gln Phe Pro Val Gly Arg Val His Arg Leu Leu Arg
1               5                   10                  15

Lys

<210> SEQ ID NO 41
<211> LENGTH: 21
<212> TYPE: PRT
<213> ORGANISM: Artificial Sequence
<220> FEATURE:
<223> OTHER INFORMATION: Magainin

<400> SEQUENCE: 41

Thr Arg Ser Ser Arg Ala Gly Leu Gln Phe Pro Val Gly Arg Val His
1               5                   10                  15

Arg Leu Leu Arg Lys
            20

<210> SEQ ID NO 42
<211> LENGTH: 16
<212> TYPE: PRT
<213> ORGANISM: Artificial Sequence
<220> FEATURE:
<223> OTHER INFORMATION: PDX-1-PTD

<400> SEQUENCE: 42

Arg His Ile Lys Ile Trp Phe Gln Asn Arg Arg Met Lys Trp Lys Lys
1               5                   10                  15

<210> SEQ ID NO 43
<211> LENGTH: 42
<212> TYPE: PRT
<213> ORGANISM: Artificial Sequence
<220> FEATURE:
<223> OTHER INFORMATION: crotamine

<400> SEQUENCE: 43

Tyr Lys Gln Cys His Lys Lys Gly Gly His Cys Phe Pro Lys Glu Lys
1               5                   10                  15

Ile Cys Leu Pro Pro Ser Ser Asp Phe Gly Lys Met Asp Cys Arg Trp
            20                  25                  30

Arg Trp Lys Cys Cys Lys Lys Gly Ser Gly
        35                  40

<210> SEQ ID NO 44
<211> LENGTH: 16
<212> TYPE: PRT
<213> ORGANISM: Artificial Sequence
<220> FEATURE:
<223> OTHER INFORMATION: pIsI

<400> SEQUENCE: 44

Arg Val Ile Arg Val Trp Phe Gln Asn Lys Arg Cys Lys Asp Lys Lys
1               5                   10                  15

<210> SEQ ID NO 45
<211> LENGTH: 60
<212> TYPE: PRT
<213> ORGANISM: Artificial Sequence
<220> FEATURE:
<223> OTHER INFORMATION: Fushi-tarazu (254-313)

<400> SEQUENCE: 45

Ser Lys Arg Thr Arg Gln Thr Tyr Thr Arg Tyr Gln Thr Leu Glu Leu
1               5                   10                  15
```

Glu Lys Glu Phe His Phe Asn Arg Tyr Ile Thr Arg Arg Arg Ile
            20                  25                  30

Asp Ile Ala Asn Ala Leu Ser Leu Ser Glu Arg Gln Ile Lys Ile Trp
        35                  40                  45

Phe Gln Asn Arg Arg Met Lys Ser Lys Lys Asp Arg
    50                  55                  60

<210> SEQ ID NO 46
<211> LENGTH: 60
<212> TYPE: PRT
<213> ORGANISM: Artificial Sequence
<220> FEATURE:
<223> OTHER INFORMATION: Engrailed (454-513)

<400> SEQUENCE: 46

Glu Lys Arg Pro Arg Thr Ala Phe Ser Ser Glu Gln Leu Ala Arg Leu
1               5                   10                  15

Lys Arg Glu Phe Asn Glu Asn Arg Tyr Leu Thr Glu Arg Arg Arg Gln
            20                  25                  30

Gln Leu Ser Ser Glu Leu Gly Leu Asn Glu Ala Gln Ile Lys Ile Trp
        35                  40                  45

Phe Gln Asn Lys Arg Ala Lys Ile Lys Lys Ser Thr
    50                  55                  60

<210> SEQ ID NO 47
<211> LENGTH: 27
<212> TYPE: PRT
<213> ORGANISM: Artificial Sequence
<220> FEATURE:
<223> OTHER INFORMATION: transportan

<400> SEQUENCE: 47

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 48
<211> LENGTH: 8
<212> TYPE: PRT
<213> ORGANISM: Artificial Sequence
<220> FEATURE:
<223> OTHER INFORMATION: Polyarginine CPP (R8)

<400> SEQUENCE: 48

Arg Arg Arg Arg Arg Arg Arg Arg
1               5

<210> SEQ ID NO 49
<211> LENGTH: 9
<212> TYPE: PRT
<213> ORGANISM: Artificial Sequence
<220> FEATURE:
<223> OTHER INFORMATION: Poly-D-arginine

<400> SEQUENCE: 49

Arg Arg Arg Arg Arg Arg Arg Arg Arg
1               5

<210> SEQ ID NO 50
<211> LENGTH: 18
<212> TYPE: PRT
<213> ORGANISM: Artificial Sequence

```
<220> FEATURE:
<223> OTHER INFORMATION: KLAL peptide/model amphiphatic peptide (MAP)

<400> SEQUENCE: 50

Lys Leu Ala Leu Lys Leu Ala Leu Lys Ala Leu Lys Ala Ala Leu Lys
1               5                   10                  15

Leu Ala

<210> SEQ ID NO 51
<211> LENGTH: 30
<212> TYPE: PRT
<213> ORGANISM: Artificial Sequence
<220> FEATURE:
<223> OTHER INFORMATION: KALA model amphiphatic peptide

<400> SEQUENCE: 51

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 52
<211> LENGTH: 11
<212> TYPE: PRT
<213> ORGANISM: Artificial Sequence
<220> FEATURE:
<223> OTHER INFORMATION: modeled TAT peptide

<400> SEQUENCE: 52

Tyr Ala Arg Ala Ala Ala Arg Gln Ala Arg Ala
1               5                   10

<210> SEQ ID NO 53
<211> LENGTH: 27
<212> TYPE: PRT
<213> ORGANISM: Artificial Sequence
<220> FEATURE:
<223> OTHER INFORMATION: b-sheet-forming peptide

<400> SEQUENCE: 53

Asp Pro Lys Gly Asp Pro Pro Lys Gly Val Thr Val Thr Val Thr Val
1               5                   10                  15

Thr Val Thr Gly Lys Gly Asp Pro Lys Pro Asp
            20                  25

<210> SEQ ID NO 54
<211> LENGTH: 16
<212> TYPE: PRT
<213> ORGANISM: Artificial Sequence
<220> FEATURE:
<223> OTHER INFORMATION: retro-inverso forms of established CPPs

<400> SEQUENCE: 54

Lys Lys Trp Lys Met Arg Arg Asn Gln Phe Trp Val Arg Val Gln Arg
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: W/R penetratin

<400> SEQUENCE: 55

Arg Arg Trp Arg Arg Trp Trp Trp Arg Arg Trp Trp Arg Arg Trp Arg
```

```
1               5                   10                  15
Arg

<210> SEQ ID NO 56
<211> LENGTH: 28
<212> TYPE: PRT
<213> ORGANISM: Artificial Sequence
<220> FEATURE:
<223> OTHER INFORMATION: MPG

<400> SEQUENCE: 56

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val Cys
            20                  25

<210> SEQ ID NO 57
<211> LENGTH: 21
<212> TYPE: PRT
<213> ORGANISM: Artificial Sequence
<220> FEATURE:
<223> OTHER INFORMATION: Pep-1

<400> SEQUENCE: 57

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 58
<211> LENGTH: 27
<212> TYPE: PRT
<213> ORGANISM: Artificial Sequence
<220> FEATURE:
<223> OTHER INFORMATION: Signal-sequence peptides (I)

<400> SEQUENCE: 58

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 59
<211> LENGTH: 12
<212> TYPE: PRT
<213> ORGANISM: Artificial Sequence
<220> FEATURE:
<223> OTHER INFORMATION: PTD-5

<400> SEQUENCE: 59

Arg Arg Gln Arg Arg Thr Ser Lys Leu Met Lys Arg
1               5                   10

<210> SEQ ID NO 60
<211> LENGTH: 10
<212> TYPE: PRT
<213> ORGANISM: Artificial Sequence
<220> FEATURE:
<223> OTHER INFORMATION: RSV-A9

<400> SEQUENCE: 60

Arg Arg Ile Pro Asn Arg Arg Pro Arg Arg
1               5                   10
```

```
<210> SEQ ID NO 61
<211> LENGTH: 11
<212> TYPE: PRT
<213> ORGANISM: Artificial Sequence
<220> FEATURE:
<223> OTHER INFORMATION: CTP-512

<400> SEQUENCE: 61

Tyr Gly Arg Arg Ala Arg Arg Arg Arg Arg
1               5                   10

<210> SEQ ID NO 62
<211> LENGTH: 12
<212> TYPE: PRT
<213> ORGANISM: Artificial Sequence
<220> FEATURE:
<223> OTHER INFORMATION: U2AF

<400> SEQUENCE: 62

Ser Gln Met Thr Arg Gln Ala Arg Arg Leu Tyr Val
1               5                   10

<210> SEQ ID NO 63
<211> LENGTH: 16
<212> TYPE: PRT
<213> ORGANISM: Artificial Sequence
<220> FEATURE:
<223> OTHER INFORMATION: 105Y

<400> SEQUENCE: 63

Ser Ile Pro Pro Glu Val Lys Phe Asn Lys Pro Phe Val Tyr Leu Ile
1               5                   10                  15

<210> SEQ ID NO 64
<211> LENGTH: 17
<212> TYPE: PRT
<213> ORGANISM: Artificial Sequence
<220> FEATURE:
<223> OTHER INFORMATION: Antennapedia Leader Peptide

<400> SEQUENCE: 64

Lys Lys Trp Lys Met Arg Arg Asn Gln Phe Trp Val Lys Val Gln Arg
1               5                   10                  15

Gly

<210> SEQ ID NO 65
<211> LENGTH: 43
<212> TYPE: PRT
<213> ORGANISM: Artificial Sequence
<220> FEATURE:
<223> OTHER INFORMATION: Anti-BetaGamma

<400> SEQUENCE: 65

Ala Ala Val Ala Leu Leu Pro Ala Val Leu Leu Ala Leu Leu Ala Val
1               5                   10                  15

Thr Asp Gln Leu Gly Glu Asp Phe Phe Ala Val Asp Leu Glu Ala Phe
            20                  25                  30

Leu Gln Glu Phe Gly Leu Leu Pro Glu Lys Glu
        35                  40

<210> SEQ ID NO 66
<211> LENGTH: 15
<212> TYPE: PRT
<213> ORGANISM: Artificial Sequence
<220> FEATURE:
<223> OTHER INFORMATION: Lipid Membrane Translocating
```

```
<400> SEQUENCE: 66

Lys Lys Ala Ala Ala Val Leu Leu Pro Val Leu Leu Ala Ala Pro
1               5                   10                  15

<210> SEQ ID NO 67
<211> LENGTH: 14
<212> TYPE: PRT
<213> ORGANISM: Artificial Sequence
<220> FEATURE:
<223> OTHER INFORMATION: Mastoparan

<400> SEQUENCE: 67

Ile Asn Leu Lys Ala Leu Ala Ala Leu Ala Lys Lys Ile Leu
1               5                   10

<210> SEQ ID NO 68
<211> LENGTH: 13
<212> TYPE: PRT
<213> ORGANISM: Artificial Sequence
<220> FEATURE:
<223> OTHER INFORMATION: MEK1 Nterm

<400> SEQUENCE: 68

Met Pro Lys Lys Lys Pro Thr Pro Ile Gln Leu Asn Pro
1               5                   10

<210> SEQ ID NO 69
<211> LENGTH: 16
<212> TYPE: PRT
<213> ORGANISM: Artificial Sequence
<220> FEATURE:
<223> OTHER INFORMATION: MPS

<400> SEQUENCE: 69

Ala Ala Val Ala Leu Leu Pro Ala Val Leu Leu Ala Leu Leu Ala Lys
1               5                   10                  15

<210> SEQ ID NO 70
<211> LENGTH: 29
<212> TYPE: PRT
<213> ORGANISM: Artificial Sequence
<220> FEATURE:
<223> OTHER INFORMATION: RV-MAT

<400> SEQUENCE: 70

Met Asn Leu Leu Arg Lys Ile Val Lys Asn Arg Arg Asp Glu Asp Thr
1               5                   10                  15

Gln Lys Ser Ser Pro Ala Ser Ala Pro Leu Asp Asp Gly
            20                  25

<210> SEQ ID NO 71
<211> LENGTH: 11
<212> TYPE: PRT
<213> ORGANISM: Artificial Sequence
<220> FEATURE:
<223> OTHER INFORMATION: Transdermal peptide

<400> SEQUENCE: 71

Ala Cys Ser Ser Ser Pro Ser Lys His Cys Gly
1               5                   10

<210> SEQ ID NO 72
<211> LENGTH: 10
<212> TYPE: PRT
<213> ORGANISM: Artificial Sequence
```

```
<220> FEATURE:
<223> OTHER INFORMATION: SynB3

<400> SEQUENCE: 72

Arg Arg Leu Ser Tyr Ser Arg Arg Arg Phe
1               5                   10

<210> SEQ ID NO 73
<211> LENGTH: 12
<212> TYPE: PRT
<213> ORGANISM: Artificial Sequence
<220> FEATURE:
<223> OTHER INFORMATION: PTD-4

<400> SEQUENCE: 73

Pro Ile Arg Arg Arg Lys Lys Leu Arg Arg Leu Lys
1               5                   10

<210> SEQ ID NO 74
<211> LENGTH: 27
<212> TYPE: PRT
<213> ORGANISM: Artificial Sequence
<220> FEATURE:
<223> OTHER INFORMATION: SBP

<400> SEQUENCE: 74

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 75
<211> LENGTH: 21
<212> TYPE: PRT
<213> ORGANISM: Artificial Sequence
<220> FEATURE:
<223> OTHER INFORMATION: Pep-2

<400> SEQUENCE: 75

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 76
<211> LENGTH: 4
<212> TYPE: PRT
<213> ORGANISM: Artificial Sequence
<220> FEATURE:
<223> OTHER INFORMATION: Polyarginines (R)n wherein n is at least 3,
      preferably 3 to 50, more preferably 3 to 15

<400> SEQUENCE: 76

Arg Arg Arg Arg
1

<210> SEQ ID NO 77
<211> LENGTH: 4
<212> TYPE: PRT
<213> ORGANISM: Artificial Sequence
<220> FEATURE:
<223> OTHER INFORMATION: Polylysines (K)n wherein n is at least 3,
      preferably 3 to 50, more preferably 3 to 15

<400> SEQUENCE: 77

Lys Lys Lys Lys
```

<210> SEQ ID NO 78
<211> LENGTH: 18
<212> TYPE: PRT
<213> ORGANISM: Artificial Sequence
<220> FEATURE:
<223> OTHER INFORMATION: CPP

<400> SEQUENCE: 78

Lys Ile Ala Ala Lys Ser Ile Ala Lys Ile Trp Lys Ser Ile Leu Lys
1               5                   10                  15

Ile Ala

<210> SEQ ID NO 79
<211> LENGTH: 18
<212> TYPE: PRT
<213> ORGANISM: Artificial Sequence
<220> FEATURE:
<223> OTHER INFORMATION: CPP

<400> SEQUENCE: 79

Lys Ala Leu Ala Lys Ala Leu Ala Lys Leu Trp Lys Ala Leu Ala Lys
1               5                   10                  15

Ala Ala

<210> SEQ ID NO 80
<211> LENGTH: 18
<212> TYPE: PRT
<213> ORGANISM: Artificial Sequence
<220> FEATURE:
<223> OTHER INFORMATION: CPP

<400> SEQUENCE: 80

Lys Leu Ala Leu Lys Leu Ala Leu Lys Trp Ala Lys Leu Ala Leu Lys
1               5                   10                  15

Ala Ala

<210> SEQ ID NO 81
<211> LENGTH: 18
<212> TYPE: PRT
<213> ORGANISM: Artificial Sequence
<220> FEATURE:
<223> OTHER INFORMATION: CPP

<400> SEQUENCE: 81

Lys Leu Leu Ala Lys Ala Ala Lys Lys Trp Leu Leu Leu Ala Leu Lys
1               5                   10                  15

Ala Ala

<210> SEQ ID NO 82
<211> LENGTH: 18
<212> TYPE: PRT
<213> ORGANISM: Artificial Sequence
<220> FEATURE:
<223> OTHER INFORMATION: CPP

<400> SEQUENCE: 82

Lys Leu Leu Ala Lys Ala Ala Leu Lys Trp Leu Leu Lys Ala Leu Lys
1               5                   10                  15

Ala Ala

<210> SEQ ID NO 83

```
<211> LENGTH: 18
<212> TYPE: PRT
<213> ORGANISM: Artificial Sequence
<220> FEATURE:
<223> OTHER INFORMATION: CPP

<400> SEQUENCE: 83

Lys Ala Leu Lys Lys Leu Leu Ala Lys Trp Leu Ala Ala Ala Lys Ala
1               5                   10                  15

Leu Leu

<210> SEQ ID NO 84
<211> LENGTH: 18
<212> TYPE: PRT
<213> ORGANISM: Artificial Sequence
<220> FEATURE:
<223> OTHER INFORMATION: CPP

<400> SEQUENCE: 84

Lys Leu Ala Ala Ala Leu Leu Lys Lys Trp Lys Lys Leu Ala Ala Ala
1               5                   10                  15

Leu Leu

<210> SEQ ID NO 85
<211> LENGTH: 18
<212> TYPE: PRT
<213> ORGANISM: Artificial Sequence
<220> FEATURE:
<223> OTHER INFORMATION: CPP

<400> SEQUENCE: 85

Lys Ala Leu Ala Ala Leu Leu Lys Lys Trp Ala Lys Leu Leu Ala Ala
1               5                   10                  15

Leu Lys

<210> SEQ ID NO 86
<211> LENGTH: 18
<212> TYPE: PRT
<213> ORGANISM: Artificial Sequence
<220> FEATURE:
<223> OTHER INFORMATION: CPP

<400> SEQUENCE: 86

Lys Ala Leu Ala Ala Leu Leu Lys Lys Leu Ala Lys Leu Leu Ala Ala
1               5                   10                  15

Leu Lys

<210> SEQ ID NO 87
<211> LENGTH: 16
<212> TYPE: PRT
<213> ORGANISM: Artificial Sequence
<220> FEATURE:
<223> OTHER INFORMATION: CPP

<400> SEQUENCE: 87

Lys Leu Ala Leu Lys Leu Ala Leu Lys Ala Leu Lys Ala Ala Leu Lys
1               5                   10                  15

<210> SEQ ID NO 88
<211> LENGTH: 14
<212> TYPE: PRT
<213> ORGANISM: Artificial Sequence
<220> FEATURE:
<223> OTHER INFORMATION: CPP
```

```
<400> SEQUENCE: 88

Lys Leu Ala Leu Lys Ala Leu Lys Ala Ala Leu Lys Leu Ala
1               5                   10

<210> SEQ ID NO 89
<211> LENGTH: 14
<212> TYPE: PRT
<213> ORGANISM: Artificial Sequence
<220> FEATURE:
<223> OTHER INFORMATION: CPP

<400> SEQUENCE: 89

Lys Leu Ala Leu Lys Leu Ala Leu Lys Ala Leu Lys Ala Ala
1               5                   10

<210> SEQ ID NO 90
<211> LENGTH: 18
<212> TYPE: PRT
<213> ORGANISM: Artificial Sequence
<220> FEATURE:
<223> OTHER INFORMATION: CPP

<400> SEQUENCE: 90

Lys Leu Gly Leu Lys Leu Gly Leu Lys Gly Leu Lys Gly Gly Leu Lys
1               5                   10                  15

Leu Gly

<210> SEQ ID NO 91
<211> LENGTH: 18
<212> TYPE: PRT
<213> ORGANISM: Artificial Sequence
<220> FEATURE:
<223> OTHER INFORMATION: CPP

<400> SEQUENCE: 91

Lys Leu Ala Leu Lys Leu Ala Leu Lys Ala Leu Gln Ala Ala Leu Gln
1               5                   10                  15

Leu Ala

<210> SEQ ID NO 92
<211> LENGTH: 18
<212> TYPE: PRT
<213> ORGANISM: Artificial Sequence
<220> FEATURE:
<223> OTHER INFORMATION: CPP

<400> SEQUENCE: 92

Lys Leu Ala Leu Gln Leu Ala Leu Gln Ala Leu Gln Ala Ala Leu Gln
1               5                   10                  15

Leu Ala

<210> SEQ ID NO 93
<211> LENGTH: 18
<212> TYPE: PRT
<213> ORGANISM: Artificial Sequence
<220> FEATURE:
<223> OTHER INFORMATION: CPP

<400> SEQUENCE: 93

Gln Leu Ala Leu Gln Leu Ala Leu Gln Ala Leu Gln Ala Ala Leu Gln
1               5                   10                  15

Leu Ala
```

```
<210> SEQ ID NO 94
<211> LENGTH: 18
<212> TYPE: PRT
<213> ORGANISM: Artificial Sequence
<220> FEATURE:
<223> OTHER INFORMATION: CPP

<400> SEQUENCE: 94

Glu Leu Ala Leu Glu Leu Ala Leu Glu Ala Leu Glu Ala Ala Leu Glu
1               5                   10                  15

Leu Ala

<210> SEQ ID NO 95
<211> LENGTH: 18
<212> TYPE: PRT
<213> ORGANISM: Artificial Sequence
<220> FEATURE:
<223> OTHER INFORMATION: CPP

<400> SEQUENCE: 95

Leu Lys Thr Leu Ala Thr Ala Leu Thr Lys Leu Ala Lys Thr Leu Thr
1               5                   10                  15

Thr Leu

<210> SEQ ID NO 96
<211> LENGTH: 18
<212> TYPE: PRT
<213> ORGANISM: Artificial Sequence
<220> FEATURE:
<223> OTHER INFORMATION: CPP

<400> SEQUENCE: 96

Leu Leu Lys Thr Thr Ala Leu Leu Lys Thr Thr Ala Leu Leu Lys Thr
1               5                   10                  15

Thr Ala

<210> SEQ ID NO 97
<211> LENGTH: 18
<212> TYPE: PRT
<213> ORGANISM: Artificial Sequence
<220> FEATURE:
<223> OTHER INFORMATION: CPP

<400> SEQUENCE: 97

Leu Lys Thr Leu Thr Glu Thr Leu Lys Glu Leu Thr Lys Thr Leu Thr
1               5                   10                  15

Glu Leu

<210> SEQ ID NO 98
<211> LENGTH: 18
<212> TYPE: PRT
<213> ORGANISM: Artificial Sequence
<220> FEATURE:
<223> OTHER INFORMATION: CPP

<400> SEQUENCE: 98

Leu Leu Lys Thr Thr Glu Leu Leu Lys Thr Thr Glu Leu Leu Lys Thr
1               5                   10                  15

Thr Glu

<210> SEQ ID NO 99
<211> LENGTH: 18
<212> TYPE: PRT
<213> ORGANISM: Artificial Sequence
```

```
<220> FEATURE:
<223> OTHER INFORMATION: CPP with all D-amino acids

<400> SEQUENCE: 99

Lys Leu Ala Leu Lys Leu Ala Leu Lys Ala Leu Lys Ala Ala Leu Lys
1               5                   10                  15

Leu Ala

<210> SEQ ID NO 100
<211> LENGTH: 18
<212> TYPE: PRT
<213> ORGANISM: Artificial Sequence
<220> FEATURE:
<223> OTHER INFORMATION: CPP

<400> SEQUENCE: 100

Lys Ala Leu Lys Leu Lys Leu Ala Leu Ala Leu Leu Ala Lys Leu Lys
1               5                   10                  15

Leu Ala

<210> SEQ ID NO 101
<211> LENGTH: 16
<212> TYPE: PRT
<213> ORGANISM: Artificial Sequence
<220> FEATURE:
<223> OTHER INFORMATION: CPP

<400> SEQUENCE: 101

Lys Lys Trp Lys Met Arg Arg Asn Gln Phe Trp Ile Lys Ile Gln Arg
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: CPP with all D-amino acids

<400> SEQUENCE: 102

Arg Gln Ile Lys Ile Trp Phe Gln Asn Arg Arg Met Lys Trp Lys Lys
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: CPP

<400> SEQUENCE: 103

Arg Gln Ile Lys Ile Trp Phe Pro Asn Arg Arg Met Lys Trp Lys Lys
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: CPP

<400> SEQUENCE: 104

Arg Gln Pro Lys Ile Trp Phe Pro Asn Arg Arg Lys Pro Trp Lys Lys
1               5                   10                  15

<210> SEQ ID NO 105
```

<211> LENGTH: 15
<212> TYPE: PRT
<213> ORGANISM: Artificial Sequence
<220> FEATURE:
<223> OTHER INFORMATION: CPP

<400> SEQUENCE: 105

Arg Gln Ile Lys Ile Trp Phe Gln Asn Arg Arg Met Lys Trp Lys
1               5                   10                  15

<210> SEQ ID NO 106
<211> LENGTH: 14
<212> TYPE: PRT
<213> ORGANISM: Artificial Sequence
<220> FEATURE:
<223> OTHER INFORMATION: CPP

<400> SEQUENCE: 106

Arg Gln Ile Lys Ile Trp Phe Gln Asn Arg Arg Met Lys Trp
1               5                   10

<210> SEQ ID NO 107
<211> LENGTH: 13
<212> TYPE: PRT
<213> ORGANISM: Artificial Sequence
<220> FEATURE:
<223> OTHER INFORMATION: CPP

<400> SEQUENCE: 107

Arg Gln Ile Lys Ile Trp Phe Gln Asn Arg Arg Met Lys
1               5                   10

<210> SEQ ID NO 108
<211> LENGTH: 12
<212> TYPE: PRT
<213> ORGANISM: Artificial Sequence
<220> FEATURE:
<223> OTHER INFORMATION: CPP

<400> SEQUENCE: 108

Arg Gln Ile Lys Ile Trp Phe Gln Asn Arg Arg Met
1               5                   10

<210> SEQ ID NO 109
<211> LENGTH: 11
<212> TYPE: PRT
<213> ORGANISM: Artificial Sequence
<220> FEATURE:
<223> OTHER INFORMATION: CPP

<400> SEQUENCE: 109

Arg Gln Ile Lys Ile Trp Phe Gln Asn Arg Arg
1               5                   10

<210> SEQ ID NO 110
<211> LENGTH: 10
<212> TYPE: PRT
<213> ORGANISM: Artificial Sequence
<220> FEATURE:
<223> OTHER INFORMATION: CPP

<400> SEQUENCE: 110

Arg Gln Ile Lys Ile Trp Phe Gln Asn Arg
1               5                   10

<210> SEQ ID NO 111
<211> LENGTH: 9

```
<212> TYPE: PRT
<213> ORGANISM: Artificial Sequence
<220> FEATURE:
<223> OTHER INFORMATION: CPP

<400> SEQUENCE: 111

Arg Gln Ile Lys Ile Trp Phe Gln Asn
1               5

<210> SEQ ID NO 112
<211> LENGTH: 8
<212> TYPE: PRT
<213> ORGANISM: Artificial Sequence
<220> FEATURE:
<223> OTHER INFORMATION: CPP

<400> SEQUENCE: 112

Arg Gln Ile Lys Ile Trp Phe Gln
1               5

<210> SEQ ID NO 113
<211> LENGTH: 6
<212> TYPE: PRT
<213> ORGANISM: Artificial Sequence
<220> FEATURE:
<223> OTHER INFORMATION: CPP

<400> SEQUENCE: 113

Arg Gln Ile Lys Ile Trp
1               5

<210> SEQ ID NO 114
<211> LENGTH: 15
<212> TYPE: PRT
<213> ORGANISM: Artificial Sequence
<220> FEATURE:
<223> OTHER INFORMATION: CPP

<400> SEQUENCE: 114

Gln Ile Lys Ile Trp Phe Gln Asn Arg Arg Met Lys Trp Lys Lys
1               5                   10                  15

<210> SEQ ID NO 115
<211> LENGTH: 14
<212> TYPE: PRT
<213> ORGANISM: Artificial Sequence
<220> FEATURE:
<223> OTHER INFORMATION: CPP

<400> SEQUENCE: 115

Ile Lys Ile Trp Phe Gln Asn Arg Arg Met Lys Trp Lys Lys
1               5                   10

<210> SEQ ID NO 116
<211> LENGTH: 13
<212> TYPE: PRT
<213> ORGANISM: Artificial Sequence
<220> FEATURE:
<223> OTHER INFORMATION: CPP

<400> SEQUENCE: 116

Lys Ile Trp Phe Gln Asn Arg Arg Met Lys Trp Lys Lys
1               5                   10

<210> SEQ ID NO 117
<211> LENGTH: 12
<212> TYPE: PRT
```

```
<213> ORGANISM: Artificial Sequence
<220> FEATURE:
<223> OTHER INFORMATION: CPP

<400> SEQUENCE: 117

Ile Trp Phe Gln Asn Arg Arg Met Lys Trp Lys Lys
1               5                   10

<210> SEQ ID NO 118
<211> LENGTH: 11
<212> TYPE: PRT
<213> ORGANISM: Artificial Sequence
<220> FEATURE:
<223> OTHER INFORMATION: CPP

<400> SEQUENCE: 118

Trp Phe Gln Asn Arg Arg Met Lys Trp Lys Lys
1               5                   10

<210> SEQ ID NO 119
<211> LENGTH: 10
<212> TYPE: PRT
<213> ORGANISM: Artificial Sequence
<220> FEATURE:
<223> OTHER INFORMATION: CPP

<400> SEQUENCE: 119

Phe Gln Asn Arg Arg Met Lys Trp Lys Lys
1               5                   10

<210> SEQ ID NO 120
<211> LENGTH: 9
<212> TYPE: PRT
<213> ORGANISM: Artificial Sequence
<220> FEATURE:
<223> OTHER INFORMATION: CPP

<400> SEQUENCE: 120

Gln Asn Arg Arg Met Lys Trp Lys Lys
1               5

<210> SEQ ID NO 121
<211> LENGTH: 8
<212> TYPE: PRT
<213> ORGANISM: Artificial Sequence
<220> FEATURE:
<223> OTHER INFORMATION: CPP

<400> SEQUENCE: 121

Asn Arg Arg Met Lys Trp Lys Lys
1               5

<210> SEQ ID NO 122
<211> LENGTH: 7
<212> TYPE: PRT
<213> ORGANISM: Artificial Sequence
<220> FEATURE:
<223> OTHER INFORMATION: CPP

<400> SEQUENCE: 122

Arg Arg Met Lys Trp Lys Lys
1               5

<210> SEQ ID NO 123
<211> LENGTH: 6
<212> TYPE: PRT
<213> ORGANISM: Artificial Sequence
```

```
<220> FEATURE:
<223> OTHER INFORMATION: CPP

<400> SEQUENCE: 123

Arg Met Lys Trp Lys Lys
1               5

<210> SEQ ID NO 124
<211> LENGTH: 16
<212> TYPE: PRT
<213> ORGANISM: Artificial Sequence
<220> FEATURE:
<223> OTHER INFORMATION: CPP

<400> SEQUENCE: 124

Ala Gln Ile Lys Ile Trp Phe Gln Asn Arg Arg Met Lys Trp Lys Lys
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: CPP

<400> SEQUENCE: 125

Arg Ala Ile Lys Ile Trp Phe Gln Asn Arg Arg Met Lys Trp Lys Lys
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: CPP

<400> SEQUENCE: 126

Arg Gln Ala Lys Ile Trp Phe Gln Asn Arg Arg Met Lys Trp Lys Lys
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: CPP

<400> SEQUENCE: 127

Arg Gln Ile Ala Ile Trp Phe Gln Asn Arg Arg Met Lys Trp Lys Lys
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: CPP

<400> SEQUENCE: 128

Arg Gln Ile Lys Ala Trp Phe Gln Asn Arg Arg Met Lys Trp Lys Lys
1               5                   10                  15

<210> SEQ ID NO 129
<211> LENGTH: 16
<212> TYPE: PRT
<213> ORGANISM: Artificial Sequence
<220> FEATURE:
```

```
<223> OTHER INFORMATION: CPP

<400> SEQUENCE: 129

Arg Gln Ile Lys Ile Ala Phe Gln Asn Arg Arg Met Lys Trp Lys Lys
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: CPP

<400> SEQUENCE: 130

Arg Gln Ile Lys Ile Trp Ala Gln Asn Arg Arg Met Lys Trp Lys Lys
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: CPP

<400> SEQUENCE: 131

Arg Gln Ile Lys Ile Trp Phe Ala Asn Arg Arg Met Lys Trp Lys Lys
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: CPP

<400> SEQUENCE: 132

Arg Gln Ile Lys Ile Trp Phe Gln Ala Arg Arg Met Lys Trp Lys Lys
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: CPP

<400> SEQUENCE: 133

Arg Gln Ile Lys Ile Trp Phe Gln Asn Ala Arg Met Lys Trp Lys Lys
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: CPP

<400> SEQUENCE: 134

Arg Gln Ile Lys Ile Trp Phe Gln Asn Arg Ala Met Lys Trp Lys Lys
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: CPP
```

```
<400> SEQUENCE: 135

Arg Gln Ile Lys Ile Trp Phe Gln Asn Arg Arg Ala Lys Trp Lys Lys
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: CPP

<400> SEQUENCE: 136

Arg Gln Ile Lys Ile Trp Phe Gln Asn Arg Arg Met Ala Trp Lys Lys
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: CPP

<400> SEQUENCE: 137

Arg Gln Ile Lys Ile Trp Phe Gln Asn Arg Arg Met Lys Ala Lys Lys
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: CPP

<400> SEQUENCE: 138

Arg Gln Ile Lys Ile Trp Phe Gln Asn Arg Arg Met Lys Trp Ala Lys
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: CPP

<400> SEQUENCE: 139

Arg Gln Ile Lys Ile Trp Phe Gln Asn Arg Arg Met Lys Trp Lys Ala
1               5                   10                  15

<210> SEQ ID NO 140
<211> LENGTH: 18
<212> TYPE: PRT
<213> ORGANISM: Artificial Sequence
<220> FEATURE:
<223> OTHER INFORMATION: CPP

<400> SEQUENCE: 140

Cys Arg Gln Ile Lys Ile Trp Phe Pro Asn Arg Arg Met Lys Trp Lys
1               5                   10                  15

Lys Cys

<210> SEQ ID NO 141
<211> LENGTH: 16
<212> TYPE: PRT
<213> ORGANISM: Artificial Sequence
<220> FEATURE:
```

<223> OTHER INFORMATION: CPP

<400> SEQUENCE: 141

Arg Gln Ile Lys Ile Trp Phe Pro Asn Arg Arg Met Lys Trp Lys Lys
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: CPP

<400> SEQUENCE: 142

Arg Gln Ile Lys Ile Phe Phe Gln Asn Arg Arg Met Lys Phe Lys Lys
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: CPP

<400> SEQUENCE: 143

Arg Gln Ile Arg Ile Trp Phe Gln Asn Arg Arg Met Arg Trp Arg Arg
1               5                   10                  15

<210> SEQ ID NO 144
<211> LENGTH: 8
<212> TYPE: PRT
<213> ORGANISM: Artificial Sequence
<220> FEATURE:
<223> OTHER INFORMATION: CPP

<400> SEQUENCE: 144

Arg Arg Arg Arg Arg Arg Arg Trp
1               5

<210> SEQ ID NO 145
<211> LENGTH: 13
<212> TYPE: PRT
<213> ORGANISM: Artificial Sequence
<220> FEATURE:
<223> OTHER INFORMATION: CPP

<400> SEQUENCE: 145

Gly Arg Lys Lys Arg Arg Gln Arg Arg Arg Pro Trp Gln
1               5                   10

<210> SEQ ID NO 146
<211> LENGTH: 13
<212> TYPE: PRT
<213> ORGANISM: Artificial Sequence
<220> FEATURE:
<223> OTHER INFORMATION: CPP

<400> SEQUENCE: 146

Gly Arg Lys Lys Arg Arg Gln Arg Arg Arg Pro Trp Gln
1               5                   10

<210> SEQ ID NO 147
<211> LENGTH: 16
<212> TYPE: PRT
<213> ORGANISM: Artificial Sequence
<220> FEATURE:
<223> OTHER INFORMATION: CPP

<400> SEQUENCE: 147

Arg Gln Ile Arg Ile Trp Phe Gln Asn Arg Arg Met Arg Trp Arg Arg
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: CPP

<400> SEQUENCE: 148

Arg Arg Trp Arg Arg Trp Trp Arg Arg Trp Trp Arg Arg Trp Arg Arg
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: CPP

<400> SEQUENCE: 149

Arg Gln Ile Lys Ile Trp Phe Gln Asn Met Arg Arg Lys Trp Lys Lys
1               5                   10                  15

<210> SEQ ID NO 150
<211> LENGTH: 13
<212> TYPE: PRT
<213> ORGANISM: Artificial Sequence
<220> FEATURE:
<223> OTHER INFORMATION: CPP

<400> SEQUENCE: 150

Lys Met Asp Cys Arg Trp Arg Trp Lys Cys Cys Lys Lys
1               5                   10

<210> SEQ ID NO 151
<211> LENGTH: 12
<212> TYPE: PRT
<213> ORGANISM: Artificial Sequence
<220> FEATURE:
<223> OTHER INFORMATION: CPP

<400> SEQUENCE: 151

Met Asp Cys Arg Trp Arg Trp Lys Cys Cys Lys Lys
1               5                   10

<210> SEQ ID NO 152
<211> LENGTH: 11
<212> TYPE: PRT
<213> ORGANISM: Artificial Sequence
<220> FEATURE:
<223> OTHER INFORMATION: CPP

<400> SEQUENCE: 152

Asp Cys Arg Trp Arg Trp Lys Cys Cys Lys Lys
1               5                   10

<210> SEQ ID NO 153
<211> LENGTH: 10
<212> TYPE: PRT
<213> ORGANISM: Artificial Sequence
<220> FEATURE:
<223> OTHER INFORMATION: CPP

```
<400> SEQUENCE: 153

Cys Arg Trp Arg Trp Lys Cys Cys Lys Lys
1               5                   10

<210> SEQ ID NO 154
<211> LENGTH: 9
<212> TYPE: PRT
<213> ORGANISM: Artificial Sequence
<220> FEATURE:
<223> OTHER INFORMATION: CPP

<400> SEQUENCE: 154

Arg Trp Arg Trp Lys Cys Cys Lys Lys
1               5

<210> SEQ ID NO 155
<211> LENGTH: 12
<212> TYPE: PRT
<213> ORGANISM: Artificial Sequence
<220> FEATURE:
<223> OTHER INFORMATION: CPP

<400> SEQUENCE: 155

Lys Met Asp Cys Arg Trp Arg Trp Lys Cys Lys Lys
1               5                   10

<210> SEQ ID NO 156
<211> LENGTH: 11
<212> TYPE: PRT
<213> ORGANISM: Artificial Sequence
<220> FEATURE:
<223> OTHER INFORMATION: CPP

<400> SEQUENCE: 156

Lys Met Asp Cys Arg Trp Arg Trp Lys Lys Lys
1               5                   10

<210> SEQ ID NO 157
<211> LENGTH: 10
<212> TYPE: PRT
<213> ORGANISM: Artificial Sequence
<220> FEATURE:
<223> OTHER INFORMATION: CPP

<400> SEQUENCE: 157

Lys Met Asp Arg Trp Arg Trp Lys Lys Lys
1               5                   10

<210> SEQ ID NO 158
<211> LENGTH: 12
<212> TYPE: PRT
<213> ORGANISM: Artificial Sequence
<220> FEATURE:
<223> OTHER INFORMATION: CPP

<400> SEQUENCE: 158

Lys Asp Cys Arg Trp Arg Trp Lys Cys Cys Lys Lys
1               5                   10

<210> SEQ ID NO 159
<211> LENGTH: 11
<212> TYPE: PRT
<213> ORGANISM: Artificial Sequence
<220> FEATURE:
<223> OTHER INFORMATION: CPP

<400> SEQUENCE: 159
```

```
Lys Cys Arg Trp Arg Trp Lys Cys Cys Lys Lys
1               5                   10
```

<210> SEQ ID NO 160
<211> LENGTH: 10
<212> TYPE: PRT
<213> ORGANISM: Artificial Sequence
<220> FEATURE:
<223> OTHER INFORMATION: CPP

<400> SEQUENCE: 160

```
Lys Arg Trp Arg Trp Lys Cys Cys Lys Lys
1               5                   10
```

<210> SEQ ID NO 161
<211> LENGTH: 12
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (9)..(9)
<223> OTHER INFORMATION: Xaa can be any naturally occurring amino acid

<400> SEQUENCE: 161

```
Met Asp Cys Arg Trp Arg Trp Lys Xaa Cys Lys Lys
1               5                   10
```

<210> SEQ ID NO 162
<211> LENGTH: 11
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (8)..(8)
<223> OTHER INFORMATION: Xaa can be any naturally occurring amino acid

<400> SEQUENCE: 162

```
Asp Cys Arg Trp Arg Trp Lys Xaa Cys Lys Lys
1               5                   10
```

<210> SEQ ID NO 163
<211> LENGTH: 11
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (9)..(9)
<223> OTHER INFORMATION: Xaa can be any naturally occurring amino acid

<400> SEQUENCE: 163

```
Asp Cys Arg Trp Arg Trp Lys Cys Xaa Lys Lys
1               5                   10
```

<210> SEQ ID NO 164
<211> LENGTH: 10
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (7)..(7)
<223> OTHER INFORMATION: Xaa can be any naturally occurring amino acid

```
<400> SEQUENCE: 164

Cys Arg Trp Arg Trp Lys Xaa Cys Lys Lys
1               5                   10

<210> SEQ ID NO 165
<211> LENGTH: 10
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (8)..(8)
<223> OTHER INFORMATION: Xaa can be any naturally occurring amino acid

<400> SEQUENCE: 165

Cys Arg Trp Arg Trp Lys Cys Xaa Lys Lys
1               5                   10

<210> SEQ ID NO 166
<211> LENGTH: 9
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (6)..(6)
<223> OTHER INFORMATION: Xaa can be any naturally occurring amino acid

<400> SEQUENCE: 166

Arg Trp Arg Trp Lys Xaa Cys Lys Lys
1               5

<210> SEQ ID NO 167
<211> LENGTH: 12
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (9)..(10)
<223> OTHER INFORMATION: Xaa can be any naturally occurring amino acid

<400> SEQUENCE: 167

Met Asp Cys Arg Trp Arg Trp Lys Xaa Xaa Lys Lys
1               5                   10

<210> SEQ ID NO 168
<211> LENGTH: 11
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (8)..(9)
<223> OTHER INFORMATION: Xaa can be any naturally occurring amino acid

<400> SEQUENCE: 168

Asp Cys Arg Trp Arg Trp Lys Xaa Xaa Lys Lys
1               5                   10

<210> SEQ ID NO 169
<211> LENGTH: 10
<212> TYPE: PRT
<213> ORGANISM: Artificial Sequence
```

```
<220> FEATURE:
<223> OTHER INFORMATION: CPP
<220> FEATURE:
<221> NAME/KEY: misc_feature
<222> LOCATION: (7)..(8)
<223> OTHER INFORMATION: Xaa can be any naturally occurring amino acid

<400> SEQUENCE: 169

Cys Arg Trp Arg Trp Lys Xaa Xaa Lys Lys
1               5                   10

<210> SEQ ID NO 170
<211> LENGTH: 9
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (6)..(7)
<223> OTHER INFORMATION: Xaa can be any naturally occurring amino acid

<400> SEQUENCE: 170

Arg Trp Arg Trp Lys Xaa Xaa Lys Lys
1               5

<210> SEQ ID NO 171
<211> LENGTH: 10
<212> TYPE: PRT
<213> ORGANISM: Artificial Sequence
<220> FEATURE:
<223> OTHER INFORMATION: CPP

<400> SEQUENCE: 171

Cys Arg Trp Arg Trp Lys Cys Ser Lys Lys
1               5                   10

<210> SEQ ID NO 172
<211> LENGTH: 10
<212> TYPE: PRT
<213> ORGANISM: Artificial Sequence
<220> FEATURE:
<223> OTHER INFORMATION: CPP

<400> SEQUENCE: 172

Ser Arg Trp Arg Trp Lys Cys Cys Lys Lys
1               5                   10

<210> SEQ ID NO 173
<211> LENGTH: 10
<212> TYPE: PRT
<213> ORGANISM: Artificial Sequence
<220> FEATURE:
<223> OTHER INFORMATION: CPP

<400> SEQUENCE: 173

Ser Arg Trp Arg Trp Lys Cys Ser Lys Lys
1               5                   10

<210> SEQ ID NO 174
<211> LENGTH: 10
<212> TYPE: PRT
<213> ORGANISM: Artificial Sequence
<220> FEATURE:
<223> OTHER INFORMATION: CPP

<400> SEQUENCE: 174

Ser Arg Trp Arg Trp Lys Ser Cys Lys Lys
```

```
1               5                   10

<210> SEQ ID NO 175
<211> LENGTH: 10
<212> TYPE: PRT
<213> ORGANISM: Artificial Sequence
<220> FEATURE:
<223> OTHER INFORMATION: CPP

<400> SEQUENCE: 175

Cys Arg Trp Arg Trp Lys Ser Ser Lys Lys
1               5                   10

<210> SEQ ID NO 176
<211> LENGTH: 10
<212> TYPE: PRT
<213> ORGANISM: Artificial Sequence
<220> FEATURE:
<223> OTHER INFORMATION: CPP

<400> SEQUENCE: 176

Ser Arg Trp Arg Trp Lys Ser Ser Lys Lys
1               5                   10

<210> SEQ ID NO 177
<211> LENGTH: 10
<212> TYPE: PRT
<213> ORGANISM: Artificial Sequence
<220> FEATURE:
<223> OTHER INFORMATION: CPP

<400> SEQUENCE: 177

Cys Arg Phe Arg Trp Lys Cys Cys Lys Lys
1               5                   10

<210> SEQ ID NO 178
<211> LENGTH: 10
<212> TYPE: PRT
<213> ORGANISM: Artificial Sequence
<220> FEATURE:
<223> OTHER INFORMATION: CPP

<400> SEQUENCE: 178

Cys Arg Trp Arg Phe Lys Cys Cys Lys Lys
1               5                   10

<210> SEQ ID NO 179
<211> LENGTH: 10
<212> TYPE: PRT
<213> ORGANISM: Artificial Sequence
<220> FEATURE:
<223> OTHER INFORMATION: CPP

<400> SEQUENCE: 179

Cys Arg Phe Arg Phe Lys Cys Cys Lys Lys
1               5                   10

<210> SEQ ID NO 180
<211> LENGTH: 10
<212> TYPE: PRT
<213> ORGANISM: Artificial Sequence
<220> FEATURE:
<223> OTHER INFORMATION: CPP

<400> SEQUENCE: 180

Cys Arg Trp Arg Trp Lys Cys Cys Lys Lys
1               5                   10
```

```
<210> SEQ ID NO 181
<211> LENGTH: 10
<212> TYPE: PRT
<213> ORGANISM: Artificial Sequence
<220> FEATURE:
<223> OTHER INFORMATION: CPP

<400> SEQUENCE: 181

Lys Cys Cys Lys Trp Arg Trp Arg Cys Lys
1               5                   10

<210> SEQ ID NO 182
<211> LENGTH: 10
<212> TYPE: PRT
<213> ORGANISM: Artificial Sequence
<220> FEATURE:
<223> OTHER INFORMATION: CPP

<400> SEQUENCE: 182

Lys Cys Cys Lys Trp Arg Trp Arg Cys Lys
1               5                   10

<210> SEQ ID NO 183
<211> LENGTH: 10
<212> TYPE: PRT
<213> ORGANISM: Artificial Sequence
<220> FEATURE:
<223> OTHER INFORMATION: CPP

<400> SEQUENCE: 183

Cys Arg Trp Arg Trp Lys Cys Cys Lys Lys
1               5                   10

<210> SEQ ID NO 184
<211> LENGTH: 10
<212> TYPE: PRT
<213> ORGANISM: Artificial Sequence
<220> FEATURE:
<223> OTHER INFORMATION: CPP

<400> SEQUENCE: 184

Cys Arg Trp Arg Trp Lys Cys Cys Lys Lys
1               5                   10

<210> SEQ ID NO 185
<211> LENGTH: 10
<212> TYPE: PRT
<213> ORGANISM: Artificial Sequence
<220> FEATURE:
<223> OTHER INFORMATION: CPP

<400> SEQUENCE: 185

Cys Arg Trp Arg Trp Lys Cys Cys Lys Lys
1               5                   10

<210> SEQ ID NO 186
<211> LENGTH: 10
<212> TYPE: PRT
<213> ORGANISM: Artificial Sequence
<220> FEATURE:
<223> OTHER INFORMATION: CPP

<400> SEQUENCE: 186

Cys Arg Trp Arg Trp Lys Cys Cys Lys Lys
1               5                   10
```

<210> SEQ ID NO 187
<211> LENGTH: 10
<212> TYPE: PRT
<213> ORGANISM: Artificial Sequence
<220> FEATURE:
<223> OTHER INFORMATION: CPP

<400> SEQUENCE: 187

Cys Arg Trp Arg Trp Lys Cys Cys Lys Lys
1               5                   10

<210> SEQ ID NO 188
<211> LENGTH: 11
<212> TYPE: PRT
<213> ORGANISM: Artificial Sequence
<220> FEATURE:
<223> OTHER INFORMATION: CPP

<400> SEQUENCE: 188

Cys Arg Trp Arg Trp Lys Cys Gly Cys Lys Lys
1               5                   10

<210> SEQ ID NO 189
<211> LENGTH: 14
<212> TYPE: PRT
<213> ORGANISM: Artificial Sequence
<220> FEATURE:
<223> OTHER INFORMATION: CPP

<400> SEQUENCE: 189

Lys Cys Gly Cys Arg Trp Arg Trp Lys Cys Gly Cys Lys Lys
1               5                   10

<210> SEQ ID NO 190
<211> LENGTH: 8
<212> TYPE: PRT
<213> ORGANISM: Artificial Sequence
<220> FEATURE:
<223> OTHER INFORMATION: CPP

<400> SEQUENCE: 190

Cys Arg Trp Arg Trp Lys Cys Gly
1               5

<210> SEQ ID NO 191
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (4)..(4)
<223> OTHER INFORMATION: Xaa can be any naturally occurring amino acid

<400> SEQUENCE: 191

Lys Met Asp Xaa Arg Trp Arg Trp Lys Cys Cys Lys Lys
1               5                   10

<210> SEQ ID NO 192
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (4)..(4)

<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 192

Lys Met Asp Xaa Arg Trp Arg Trp Lys Xaa Cys Lys Lys
1               5                   10

<210> SEQ ID NO 193
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 193

Lys Met Asp Xaa Arg Trp Arg Trp Lys Xaa Xaa Lys Lys
1               5                   10

<210> SEQ ID NO 194
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 194

Lys Met Asp Xaa Arg Trp Arg Trp Lys Cys Xaa Lys Lys
1               5                   10

<210> SEQ ID NO 195
<211> LENGTH: 12
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (10)..(10)
<223> OTHER INFORMATION: Xaa can be any naturally occurring amino acid

<400> SEQUENCE: 195

Met Asp Cys Arg Trp Arg Trp Lys Cys Xaa Lys Lys
1               5                   10

<210> SEQ ID NO 196
<211> LENGTH: 13
<212> TYPE: PRT
<213> ORGANISM: Artificial Sequence
<220> FEATURE:
<223> OTHER INFORMATION: CPP

<400> SEQUENCE: 196

```
Lys Met Asp Cys Arg Trp Arg Trp Lys Cys Ser Lys Lys
1               5                   10
```

<210> SEQ ID NO 197
<211> LENGTH: 13
<212> TYPE: PRT
<213> ORGANISM: Artificial Sequence
<220> FEATURE:
<223> OTHER INFORMATION: CPP

<400> SEQUENCE: 197

```
Lys Met Asp Cys Arg Trp Arg Trp Lys Ser Cys Lys Lys
1               5                   10
```

<210> SEQ ID NO 198
<211> LENGTH: 13
<212> TYPE: PRT
<213> ORGANISM: Artificial Sequence
<220> FEATURE:
<223> OTHER INFORMATION: CPP

<400> SEQUENCE: 198

```
Lys Met Asp Ser Arg Trp Arg Trp Lys Cys Cys Lys Lys
1               5                   10
```

<210> SEQ ID NO 199
<211> LENGTH: 13
<212> TYPE: PRT
<213> ORGANISM: Artificial Sequence
<220> FEATURE:
<223> OTHER INFORMATION: CPP

<400> SEQUENCE: 199

```
Lys Met Asp Cys Arg Trp Arg Trp Lys Ser Ser Lys Lys
1               5                   10
```

<210> SEQ ID NO 200
<211> LENGTH: 13
<212> TYPE: PRT
<213> ORGANISM: Artificial Sequence
<220> FEATURE:
<223> OTHER INFORMATION: CPP

<400> SEQUENCE: 200

```
Lys Met Asp Ser Arg Trp Arg Trp Lys Ser Ser Lys Lys
1               5                   10
```

<210> SEQ ID NO 201
<211> LENGTH: 13
<212> TYPE: PRT
<213> ORGANISM: Artificial Sequence
<220> FEATURE:
<223> OTHER INFORMATION: CPP

<400> SEQUENCE: 201

```
Lys Met Asp Ser Arg Trp Arg Trp Lys Ser Cys Lys Lys
1               5                   10
```

<210> SEQ ID NO 202
<211> LENGTH: 13
<212> TYPE: PRT
<213> ORGANISM: Artificial Sequence
<220> FEATURE:
<223> OTHER INFORMATION: CPP

<400> SEQUENCE: 202

```
Lys Met Asp Ser Arg Trp Arg Trp Lys Cys Ser Lys Lys
1               5                   10
```

<210> SEQ ID NO 203
<211> LENGTH: 13
<212> TYPE: PRT
<213> ORGANISM: Artificial Sequence
<220> FEATURE:
<223> OTHER INFORMATION: CPP

<400> SEQUENCE: 203

```
Lys Met Asp Cys Arg Trp Arg Pro Lys Cys Cys Lys Lys
1               5                   10
```

<210> SEQ ID NO 204
<211> LENGTH: 13
<212> TYPE: PRT
<213> ORGANISM: Artificial Sequence
<220> FEATURE:
<223> OTHER INFORMATION: CPP

<400> SEQUENCE: 204

```
Lys Met Asp Cys Arg Pro Arg Pro Lys Cys Cys Lys Lys
1               5                   10
```

<210> SEQ ID NO 205
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (4)..(4)
<223> OTHER INFORMATION: Xaa can be any naturally occurring amino acid

<400> SEQUENCE: 205

```
Lys Met Asp Xaa Arg Pro Arg Pro Lys Cys Cys Lys Lys
1               5                   10
```

<210> SEQ ID NO 206
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 206

```
Lys Met Asp Xaa Arg Pro Arg Pro Lys Xaa Cys Lys Lys
1               5                   10
```

<210> SEQ ID NO 207
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (4)..(4)
<223> OTHER INFORMATION: Xaa can be any naturally occurring amino acid
<220> FEATURE:

```
<221> NAME/KEY: misc_feature
<222> LOCATION: (11)..(11)
<223> OTHER INFORMATION: Xaa can be any naturally occurring amino acid

<400> SEQUENCE: 207

Lys Met Asp Xaa Arg Pro Arg Pro Lys Cys Xaa Lys Lys
1               5                   10

<210> SEQ ID NO 208
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (10)..(10)
<223> OTHER INFORMATION: Xaa can be any naturally occurring amino acid

<400> SEQUENCE: 208

Lys Met Asp Cys Arg Pro Arg Pro Lys Xaa Cys Lys Lys
1               5                   10

<210> SEQ ID NO 209
<211> LENGTH: 13
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (11)..(11)
<223> OTHER INFORMATION: Xaa can be any naturally occurring amino acid

<400> SEQUENCE: 209

Lys Met Asp Cys Arg Pro Arg Pro Lys Cys Xaa Lys Lys
1               5                   10

<210> SEQ ID NO 210
<211> LENGTH: 9
<212> TYPE: PRT
<213> ORGANISM: Artificial Sequence
<220> FEATURE:
<223> OTHER INFORMATION: CPP

<400> SEQUENCE: 210

Arg Lys Lys Arg Arg Gln Arg Arg Arg
1               5

<210> SEQ ID NO 211
<211> LENGTH: 9
<212> TYPE: PRT
<213> ORGANISM: Artificial Sequence
<220> FEATURE:
<223> OTHER INFORMATION: CPP

<400> SEQUENCE: 211

Arg Arg Arg Gln Arg Arg Lys Lys Arg
1               5

<210> SEQ ID NO 212
<211> LENGTH: 16
<212> TYPE: PRT
<213> ORGANISM: Artificial Sequence
<220> FEATURE:
<223> OTHER INFORMATION: CPP

<400> SEQUENCE: 212
```

Arg Lys Lys Arg Arg Arg Glu Ser Arg Lys Arg Arg Glu Ser
1               5                   10                  15

<210> SEQ ID NO 213
<211> LENGTH: 17
<212> TYPE: PRT
<213> ORGANISM: Artificial Sequence
<220> FEATURE:
<223> OTHER INFORMATION: CPP

<400> SEQUENCE: 213

Gly Arg Pro Arg Glu Ser Gly Lys Lys Arg Lys Arg Lys Arg Leu Lys
1               5                   10                  15
Pro

<210> SEQ ID NO 214
<211> LENGTH: 15
<212> TYPE: PRT
<213> ORGANISM: Artificial Sequence
<220> FEATURE:
<223> OTHER INFORMATION: CPP

<400> SEQUENCE: 214

Gly Lys Arg Lys Lys Lys Gly Lys Leu Gly Lys Lys Arg Asp Pro
1               5                   10                  15

<210> SEQ ID NO 215
<211> LENGTH: 17
<212> TYPE: PRT
<213> ORGANISM: Artificial Sequence
<220> FEATURE:
<223> OTHER INFORMATION: CPP

<400> SEQUENCE: 215

Gly Lys Arg Lys Lys Lys Gly Lys Leu Gly Lys Lys Arg Pro Arg Ser
1               5                   10                  15
Arg

<210> SEQ ID NO 216
<211> LENGTH: 18
<212> TYPE: PRT
<213> ORGANISM: Artificial Sequence
<220> FEATURE:
<223> OTHER INFORMATION: CPP

<400> SEQUENCE: 216

Arg Lys Lys Arg Arg Arg Glu Ser Arg Ala Arg Arg Ser Pro Arg
1               5                   10                  15
His Leu

<210> SEQ ID NO 217
<211> LENGTH: 19
<212> TYPE: PRT
<213> ORGANISM: Artificial Sequence
<220> FEATURE:
<223> OTHER INFORMATION: CPP

<400> SEQUENCE: 217

Ser Arg Arg Ala Arg Arg Ser Pro Arg Glu Ser Gly Lys Lys Arg Lys
1               5                   10                  15
Arg Lys Arg

<210> SEQ ID NO 218
<211> LENGTH: 19

```
<212> TYPE: PRT
<213> ORGANISM: Artificial Sequence
<220> FEATURE:
<223> OTHER INFORMATION: CPP

<400> SEQUENCE: 218

Val Lys Arg Gly Leu Lys Leu Arg His Val Arg Pro Arg Val Thr Arg
1               5                   10                  15

Met Asp Val

<210> SEQ ID NO 219
<211> LENGTH: 14
<212> TYPE: PRT
<213> ORGANISM: Artificial Sequence
<220> FEATURE:
<223> OTHER INFORMATION: CPP

<400> SEQUENCE: 219

Ser Arg Arg Ala Arg Arg Ser Pro Arg His Leu Gly Ser Gly
1               5                   10

<210> SEQ ID NO 220
<211> LENGTH: 16
<212> TYPE: PRT
<213> ORGANISM: Artificial Sequence
<220> FEATURE:
<223> OTHER INFORMATION: CPP

<400> SEQUENCE: 220

Leu Arg Arg Glu Arg Gln Ser Arg Leu Arg Arg Glu Arg Gln Ser Arg
1               5                   10                  15

<210> SEQ ID NO 221
<211> LENGTH: 22
<212> TYPE: PRT
<213> ORGANISM: Artificial Sequence
<220> FEATURE:
<223> OTHER INFORMATION: CPP

<400> SEQUENCE: 221

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 222
<211> LENGTH: 5
<212> TYPE: PRT
<213> ORGANISM: Artificial Sequence
<220> FEATURE:
<223> OTHER INFORMATION: CPP

<400> SEQUENCE: 222

Val Pro Met Leu Lys
1               5

<210> SEQ ID NO 223
<211> LENGTH: 5
<212> TYPE: PRT
<213> ORGANISM: Artificial Sequence
<220> FEATURE:
<223> OTHER INFORMATION: CPP

<400> SEQUENCE: 223

Val Pro Thr Leu Lys
1               5
```

<210> SEQ ID NO 224
<211> LENGTH: 5
<212> TYPE: PRT
<213> ORGANISM: Artificial Sequence
<220> FEATURE:
<223> OTHER INFORMATION: CPP

<400> SEQUENCE: 224

Val Pro Ala Leu Arg
1               5

<210> SEQ ID NO 225
<211> LENGTH: 5
<212> TYPE: PRT
<213> ORGANISM: Artificial Sequence
<220> FEATURE:
<223> OTHER INFORMATION: CPP

<400> SEQUENCE: 225

Val Ser Ala Leu Lys
1               5

<210> SEQ ID NO 226
<211> LENGTH: 5
<212> TYPE: PRT
<213> ORGANISM: Artificial Sequence
<220> FEATURE:
<223> OTHER INFORMATION: CPP

<400> SEQUENCE: 226

Pro Met Leu Lys Glu
1               5

<210> SEQ ID NO 227
<211> LENGTH: 5
<212> TYPE: PRT
<213> ORGANISM: Artificial Sequence
<220> FEATURE:
<223> OTHER INFORMATION: CPP

<400> SEQUENCE: 227

Val Pro Ala Leu Lys
1               5

<210> SEQ ID NO 228
<211> LENGTH: 5
<212> TYPE: PRT
<213> ORGANISM: Artificial Sequence
<220> FEATURE:
<223> OTHER INFORMATION: CPP

<400> SEQUENCE: 228

Val Ser Leu Lys Lys
1               5

<210> SEQ ID NO 229
<211> LENGTH: 5
<212> TYPE: PRT
<213> ORGANISM: Artificial Sequence
<220> FEATURE:
<223> OTHER INFORMATION: CPP

<400> SEQUENCE: 229

Val Ser Gly Lys Lys
1               5

```
<210> SEQ ID NO 230
<211> LENGTH: 5
<212> TYPE: PRT
<213> ORGANISM: Artificial Sequence
<220> FEATURE:
<223> OTHER INFORMATION: CPP

<400> SEQUENCE: 230

Lys Leu Pro Val Met
1               5

<210> SEQ ID NO 231
<211> LENGTH: 5
<212> TYPE: PRT
<213> ORGANISM: Artificial Sequence
<220> FEATURE:
<223> OTHER INFORMATION: CPP

<400> SEQUENCE: 231

Ile Pro Met Ile Lys
1               5

<210> SEQ ID NO 232
<211> LENGTH: 5
<212> TYPE: PRT
<213> ORGANISM: Artificial Sequence
<220> FEATURE:
<223> OTHER INFORMATION: CPP

<400> SEQUENCE: 232

Lys Leu Gly Val Met
1               5

<210> SEQ ID NO 233
<211> LENGTH: 5
<212> TYPE: PRT
<213> ORGANISM: Artificial Sequence
<220> FEATURE:
<223> OTHER INFORMATION: CPP

<400> SEQUENCE: 233

Lys Leu Pro Val Thr
1               5

<210> SEQ ID NO 234
<211> LENGTH: 5
<212> TYPE: PRT
<213> ORGANISM: Artificial Sequence
<220> FEATURE:
<223> OTHER INFORMATION: CPP

<400> SEQUENCE: 234

Val Pro Met Ile Lys
1               5

<210> SEQ ID NO 235
<211> LENGTH: 5
<212> TYPE: PRT
<213> ORGANISM: Artificial Sequence
<220> FEATURE:
<223> OTHER INFORMATION: CPP

<400> SEQUENCE: 235

Ile Pro Ala Leu Lys
1               5
```

```
<210> SEQ ID NO 236
<211> LENGTH: 5
<212> TYPE: PRT
<213> ORGANISM: Artificial Sequence
<220> FEATURE:
<223> OTHER INFORMATION: CPP

<400> SEQUENCE: 236

Ile Pro Met Leu Lys
1               5

<210> SEQ ID NO 237
<211> LENGTH: 5
<212> TYPE: PRT
<213> ORGANISM: Artificial Sequence
<220> FEATURE:
<223> OTHER INFORMATION: CPP

<400> SEQUENCE: 237

Val Pro Thr Leu Gln
1               5

<210> SEQ ID NO 238
<211> LENGTH: 5
<212> TYPE: PRT
<213> ORGANISM: Artificial Sequence
<220> FEATURE:
<223> OTHER INFORMATION: CPP

<400> SEQUENCE: 238

Gln Leu Pro Val Met
1               5

<210> SEQ ID NO 239
<211> LENGTH: 5
<212> TYPE: PRT
<213> ORGANISM: Artificial Sequence
<220> FEATURE:
<223> OTHER INFORMATION: CPP

<400> SEQUENCE: 239

Glu Leu Pro Val Met
1               5

<210> SEQ ID NO 240
<211> LENGTH: 5
<212> TYPE: PRT
<213> ORGANISM: Artificial Sequence
<220> FEATURE:
<223> OTHER INFORMATION: CPP

<400> SEQUENCE: 240

Val Pro Thr Leu Glu
1               5

<210> SEQ ID NO 241
<211> LENGTH: 5
<212> TYPE: PRT
<213> ORGANISM: Artificial Sequence
<220> FEATURE:
<223> OTHER INFORMATION: CPP

<400> SEQUENCE: 241

Val Pro Thr Leu Lys
1               5

<210> SEQ ID NO 242
```

```
<211> LENGTH: 20
<212> TYPE: PRT
<213> ORGANISM: Artificial Sequence
<220> FEATURE:
<223> OTHER INFORMATION: CPP

<400> SEQUENCE: 242

Ala Tyr Arg Ile Lys Pro Thr Phe Arg Arg Leu Lys Trp Lys Tyr Lys
1               5                   10                  15

Gly Lys Phe Trp
            20

<210> SEQ ID NO 243
<211> LENGTH: 20
<212> TYPE: PRT
<213> ORGANISM: Artificial Sequence
<220> FEATURE:
<223> OTHER INFORMATION: CPP

<400> SEQUENCE: 243

His Ala Arg Ile Lys Pro Thr Phe Arg Arg Leu Lys Trp Lys Tyr Lys
1               5                   10                  15

Gly Lys Phe Trp
            20

<210> SEQ ID NO 244
<211> LENGTH: 20
<212> TYPE: PRT
<213> ORGANISM: Artificial Sequence
<220> FEATURE:
<223> OTHER INFORMATION: CPP

<400> SEQUENCE: 244

His Tyr Arg Ile Lys Pro Thr Ala Arg Arg Leu Lys Trp Lys Tyr Lys
1               5                   10                  15

Gly Lys Phe Trp
            20

<210> SEQ ID NO 245
<211> LENGTH: 20
<212> TYPE: PRT
<213> ORGANISM: Artificial Sequence
<220> FEATURE:
<223> OTHER INFORMATION: CPP

<400> SEQUENCE: 245

His Tyr Arg Ile Lys Pro Thr Phe Arg Arg Leu Ala Trp Lys Tyr Lys
1               5                   10                  15

Gly Lys Phe Trp
            20

<210> SEQ ID NO 246
<211> LENGTH: 20
<212> TYPE: PRT
<213> ORGANISM: Artificial Sequence
<220> FEATURE:
<223> OTHER INFORMATION: CPP

<400> SEQUENCE: 246

His Tyr Arg Ile Lys Pro Thr Phe Arg Arg Leu Lys Trp Lys Tyr Lys
1               5                   10                  15

Gly Lys Phe Ala
            20
```

```
<210> SEQ ID NO 247
<211> LENGTH: 21
<212> TYPE: PRT
<213> ORGANISM: Artificial Sequence
<220> FEATURE:
<223> OTHER INFORMATION: CPP

<400> SEQUENCE: 247

Val Asn Ala Asp Ile Lys Ala Thr Thr Val Phe Gly Gly Lys Tyr Val
1               5                   10                  15

Ser Leu Thr Thr Pro
            20

<210> SEQ ID NO 248
<211> LENGTH: 22
<212> TYPE: PRT
<213> ORGANISM: Artificial Sequence
<220> FEATURE:
<223> OTHER INFORMATION: CPP

<400> SEQUENCE: 248

Gly Lys Tyr Val Ser Leu Thr Thr Pro Lys Asn Pro Thr Lys Arg Arg
1               5                   10                  15

Ile Thr Pro Lys Asp Val
            20

<210> SEQ ID NO 249
<211> LENGTH: 22
<212> TYPE: PRT
<213> ORGANISM: Artificial Sequence
<220> FEATURE:
<223> OTHER INFORMATION: CPP

<400> SEQUENCE: 249

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 250
<211> LENGTH: 23
<212> TYPE: PRT
<213> ORGANISM: Artificial Sequence
<220> FEATURE:
<223> OTHER INFORMATION: CPP

<400> SEQUENCE: 250

Arg Ser Val Thr Thr Glu Ile Asn Thr Leu Phe Gln Thr Leu Thr Ser
1               5                   10                  15

Ile Ala Glu Lys Val Asp Pro
            20

<210> SEQ ID NO 251
<211> LENGTH: 26
<212> TYPE: PRT
<213> ORGANISM: Artificial Sequence
<220> FEATURE:
<223> OTHER INFORMATION: CPP

<400> SEQUENCE: 251

Ala Glu Lys Val Asp Pro Val Lys Leu Asn Leu Thr Leu Ser Ala Ala
1               5                   10                  15

Ala Glu Ala Leu Thr Gly Leu Gly Asp Lys
            20                  25
```

<210> SEQ ID NO 252
<211> LENGTH: 34
<212> TYPE: PRT
<213> ORGANISM: Artificial Sequence
<220> FEATURE:
<223> OTHER INFORMATION: CPP

<400> SEQUENCE: 252

Gly Leu Gly Asp Lys Phe Gly Glu Ser Ile Val Asn Ala Asn Thr Val
1               5                   10                  15

Leu Asp Asp Leu Asn Ser Arg Met Pro Gln Ser Arg His Asp Ile Gln
            20                  25                  30

Gln Leu

<210> SEQ ID NO 253
<211> LENGTH: 27
<212> TYPE: PRT
<213> ORGANISM: Artificial Sequence
<220> FEATURE:
<223> OTHER INFORMATION: CPP

<400> SEQUENCE: 253

Gly Asp Val Tyr Ala Asp Ala Ala Pro Asp Leu Phe Asp Phe Leu Asp
1               5                   10                  15

Ser Ser Val Thr Thr Ala Arg Thr Ile Asn Ala
            20                  25

<210> SEQ ID NO 254
<211> LENGTH: 32
<212> TYPE: PRT
<213> ORGANISM: Artificial Sequence
<220> FEATURE:
<223> OTHER INFORMATION: CPP

<400> SEQUENCE: 254

Ala Arg Thr Ile Asn Ala Gln Gln Ala Glu Leu Asp Ser Ala Leu Leu
1               5                   10                  15

Ala Ala Ala Gly Phe Gly Asn Thr Thr Ala Asp Val Phe Asp Arg Gly
            20                  25                  30

<210> SEQ ID NO 255
<211> LENGTH: 30
<212> TYPE: PRT
<213> ORGANISM: Artificial Sequence
<220> FEATURE:
<223> OTHER INFORMATION: CPP

<400> SEQUENCE: 255

Ala Asp Val Phe Asp Arg Gly Gly Pro Tyr Leu Gln Arg Gly Val Ala
1               5                   10                  15

Asp Leu Val Pro Thr Ala Thr Leu Leu Asp Thr Tyr Ser Pro
            20                  25                  30

<210> SEQ ID NO 256
<211> LENGTH: 27
<212> TYPE: PRT
<213> ORGANISM: Artificial Sequence
<220> FEATURE:
<223> OTHER INFORMATION: CPP

<400> SEQUENCE: 256

Leu Asp Thr Tyr Ser Pro Glu Leu Phe Cys Thr Ile Arg Asn Phe Tyr
1               5                   10                  15

Asp Ala Asp Arg Pro Asp Arg Gly Ala Ala Ala
            20                  25

<210> SEQ ID NO 257
<211> LENGTH: 22
<212> TYPE: PRT
<213> ORGANISM: Artificial Sequence
<220> FEATURE:
<223> OTHER INFORMATION: CPP

<400> SEQUENCE: 257

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 258
<211> LENGTH: 22
<212> TYPE: PRT
<213> ORGANISM: Artificial Sequence
<220> FEATURE:
<223> OTHER INFORMATION: CPP

<400> SEQUENCE: 258

Thr Lys Arg Arg Ile Thr Pro Asp Asp Val Ile Asp Val Arg Ser Val
1               5                   10                  15

Thr Thr Glu Ile Asn Thr
            20

<210> SEQ ID NO 259
<211> LENGTH: 22
<212> TYPE: PRT
<213> ORGANISM: Artificial Sequence
<220> FEATURE:
<223> OTHER INFORMATION: CPP

<400> SEQUENCE: 259

Thr Lys Arg Arg Ile Thr Pro Lys Lys Val Ile Asp Val Arg Ser Val
1               5                   10                  15

Thr Thr Glu Ile Asn Thr
            20

<210> SEQ ID NO 260
<211> LENGTH: 22
<212> TYPE: PRT
<213> ORGANISM: Artificial Sequence
<220> FEATURE:
<223> OTHER INFORMATION: CPP

<400> SEQUENCE: 260

Thr Lys Arg Arg Ile Thr Pro Lys Asp Val Ile Asp Val Arg Ser Val
1               5                   10                  15

Thr Thr Lys Ile Asn Thr
            20

<210> SEQ ID NO 261
<211> LENGTH: 13
<212> TYPE: PRT
<213> ORGANISM: Artificial Sequence
<220> FEATURE:
<223> OTHER INFORMATION: CPP

<400> SEQUENCE: 261

Thr Lys Arg Arg Ile Thr Pro Lys Asp Val Ile Asp Val
1               5                   10

```
<210> SEQ ID NO 262
<211> LENGTH: 22
<212> TYPE: PRT
<213> ORGANISM: Artificial Sequence
<220> FEATURE:
<223> OTHER INFORMATION: CPP

<400> SEQUENCE: 262

Thr Lys Arg Arg Ile Thr Pro Lys Asp Val Ile Asp Val Glu Ser Val
1               5                   10                  15

Thr Thr Glu Ile Asn Thr
            20

<210> SEQ ID NO 263
<211> LENGTH: 22
<212> TYPE: PRT
<213> ORGANISM: Artificial Sequence
<220> FEATURE:
<223> OTHER INFORMATION: CPP

<400> SEQUENCE: 263

Thr Ala Arg Arg Ile Thr Pro Lys Asp Val Ile Asp Val Arg Ser Val
1               5                   10                  15

Thr Thr Glu Ile Asn Thr
            20

<210> SEQ ID NO 264
<211> LENGTH: 23
<212> TYPE: PRT
<213> ORGANISM: Artificial Sequence
<220> FEATURE:
<223> OTHER INFORMATION: CPP

<400> SEQUENCE: 264

Thr Lys Ala Ala Arg Ile Thr Pro Lys Asp Val Ile Asp Val Arg Ser
1               5                   10                  15

Val Thr Thr Glu Ile Asn Thr
            20

<210> SEQ ID NO 265
<211> LENGTH: 28
<212> TYPE: PRT
<213> ORGANISM: Artificial Sequence
<220> FEATURE:
<223> OTHER INFORMATION: CPP

<400> SEQUENCE: 265

His His His His His His Thr Lys Arg Arg Ile Thr Pro Lys Asp Val
1               5                   10                  15

Ile Asp Val Arg Ser Val Thr Thr Glu Ile Asn Thr
            20                  25

<210> SEQ ID NO 266
<211> LENGTH: 15
<212> TYPE: PRT
<213> ORGANISM: Artificial Sequence
<220> FEATURE:
<223> OTHER INFORMATION: CPP

<400> SEQUENCE: 266

Lys Leu Trp Met Arg Trp Tyr Ser Pro Thr Thr Arg Arg Tyr Gly
1               5                   10                  15
```

```
<210> SEQ ID NO 267
<211> LENGTH: 15
<212> TYPE: PRT
<213> ORGANISM: Artificial Sequence
<220> FEATURE:
<223> OTHER INFORMATION: CPP

<400> SEQUENCE: 267

Asp Ser Leu Lys Ser Tyr Trp Tyr Leu Gln Lys Phe Ser Trp Arg
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: CPP

<400> SEQUENCE: 268

Arg Thr Leu Val Asn Glu Tyr Lys Asn Thr Leu Lys Phe Ser Lys
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: CPP

<400> SEQUENCE: 269

Ile Pro Ser Arg Trp Lys Asp Gln Phe Trp Lys Arg Trp His Tyr
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: CPP

<400> SEQUENCE: 270

Gly Tyr Gly Asn Cys Arg His Phe Lys Gln Lys Pro Arg Arg Asp
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: CPP

<400> SEQUENCE: 271

Lys Asn Ala Trp Lys His Ser Ser Cys His His Arg His Gln Ile
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: CPP

<400> SEQUENCE: 272

Arg Val Arg Glu Trp Trp Tyr Thr Ile Thr Leu Lys Gln Glu Ser
1               5                   10                  15

<210> SEQ ID NO 273
```

```
<211> LENGTH: 15
<212> TYPE: PRT
<213> ORGANISM: Artificial Sequence
<220> FEATURE:
<223> OTHER INFORMATION: CPP

<400> SEQUENCE: 273

Gln Gln His Leu Leu Ile Ala Ile Asn Gly Tyr Pro Arg Tyr Asn
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: CPP

<400> SEQUENCE: 274

Trp Lys Cys Arg Arg Gln Cys Phe Arg Val Leu His His Trp Asn
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: CPP

<400> SEQUENCE: 275

Arg Leu Trp Met Arg Trp Tyr Ser Pro Thr Thr Arg Arg Tyr Gly
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: CPP

<400> SEQUENCE: 276

Lys Leu Trp Met Arg Trp Tyr Ser Ala Thr Thr Arg Arg Tyr Gly
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: CPP

<400> SEQUENCE: 277

Lys Leu Trp Met Arg Trp Tyr Ser Pro Trp Thr Arg Arg Tyr Gly
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: CPP

<400> SEQUENCE: 278

Arg Leu Trp Met Arg Trp Tyr Ser Pro Trp Thr Arg Arg Tyr Gly
1               5                   10                  15

<210> SEQ ID NO 279
<211> LENGTH: 15
```

```
<212> TYPE: PRT
<213> ORGANISM: Artificial Sequence
<220> FEATURE:
<223> OTHER INFORMATION: CPP

<400> SEQUENCE: 279

Arg Leu Trp Met Arg Trp Tyr Ser Pro Trp Thr Arg Arg Trp Gly
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: CPP

<400> SEQUENCE: 280

Ala Leu Trp Met Arg Trp Tyr Ser Pro Thr Thr Arg Arg Tyr Gly
1               5                   10                  15

<210> SEQ ID NO 281
<211> LENGTH: 15
<212> TYPE: PRT
<213> ORGANISM: Artificial Sequence
<220> FEATURE:
<223> OTHER INFORMATION: CPP

<400> SEQUENCE: 281

Arg Ala Trp Met Arg Trp Tyr Ser Pro Thr Thr Arg Arg Tyr Gly
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: CPP

<400> SEQUENCE: 282

Arg Leu Ala Met Arg Trp Tyr Ser Pro Thr Thr Arg Arg Tyr Gly
1               5                   10                  15

<210> SEQ ID NO 283
<211> LENGTH: 15
<212> TYPE: PRT
<213> ORGANISM: Artificial Sequence
<220> FEATURE:
<223> OTHER INFORMATION: CPP

<400> SEQUENCE: 283

Arg Leu Trp Ala Arg Trp Tyr Ser Pro Thr Thr Arg Arg Tyr Gly
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: CPP

<400> SEQUENCE: 284

Arg Leu Trp Met Ala Trp Tyr Ser Pro Thr Thr Arg Arg Tyr Gly
1               5                   10                  15

<210> SEQ ID NO 285
<211> LENGTH: 15
<212> TYPE: PRT
```

<213> ORGANISM: Artificial Sequence
<220> FEATURE:
<223> OTHER INFORMATION: CPP

<400> SEQUENCE: 285

Arg Leu Trp Met Arg Ala Tyr Ser Pro Thr Thr Arg Arg Tyr Gly
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: CPP

<400> SEQUENCE: 286

Arg Leu Trp Met Arg Trp Ala Ser Pro Thr Thr Arg Arg Tyr Gly
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: CPP

<400> SEQUENCE: 287

Arg Leu Trp Met Arg Trp Tyr Ala Pro Thr Thr Arg Arg Tyr Gly
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: CPP

<400> SEQUENCE: 288

Arg Leu Trp Met Arg Trp Tyr Ser Pro Ala Thr Arg Arg Tyr Gly
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: CPP

<400> SEQUENCE: 289

Arg Leu Trp Met Arg Trp Tyr Ser Pro Thr Ala Arg Arg Tyr Gly
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: CPP

<400> SEQUENCE: 290

Arg Leu Trp Met Arg Trp Tyr Ser Pro Thr Thr Ala Arg Tyr Gly
1               5                   10                  15

<210> SEQ ID NO 291
<211> LENGTH: 15
<212> TYPE: PRT
<213> ORGANISM: Artificial Sequence

```
<220> FEATURE:
<223> OTHER INFORMATION: CPP

<400> SEQUENCE: 291

Arg Leu Trp Met Arg Trp Tyr Ser Pro Thr Thr Arg Ala Tyr Gly
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: CPP

<400> SEQUENCE: 292

Arg Leu Trp Met Arg Trp Tyr Ser Pro Thr Thr Arg Arg Ala Gly
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: CPP

<400> SEQUENCE: 293

Arg Leu Trp Met Arg Trp Tyr Ser Pro Thr Thr Arg Arg Tyr Ala
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: CPP

<400> SEQUENCE: 294

Arg Leu Leu Met Arg Leu Tyr Ser Pro Thr Thr Arg Arg Tyr Gly
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: CPP

<400> SEQUENCE: 295

Arg Leu Phe Met Arg Phe Tyr Ser Pro Thr Thr Arg Arg Tyr Gly
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: CPP

<400> SEQUENCE: 296

Arg Leu Ile Met Arg Ile Tyr Ser Pro Thr Thr Arg Arg Tyr Gly
1               5                   10                  15

<210> SEQ ID NO 297
<211> LENGTH: 15
<212> TYPE: PRT
<213> ORGANISM: Artificial Sequence
<220> FEATURE:
```

```
<223> OTHER INFORMATION: CPP

<400> SEQUENCE: 297

Arg Leu Val Met Arg Val Tyr Ser Pro Thr Thr Arg Arg Tyr Gly
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: CPP

<400> SEQUENCE: 298

Arg Leu Tyr Met Arg Tyr Tyr Ser Pro Thr Thr Arg Arg Tyr Gly
1               5                   10                  15

<210> SEQ ID NO 299
<211> LENGTH: 12
<212> TYPE: PRT
<213> ORGANISM: Artificial Sequence
<220> FEATURE:
<223> OTHER INFORMATION: CPP

<400> SEQUENCE: 299

Tyr Gly Arg Lys Lys Lys Arg Arg Gln Arg Arg Arg
1               5                   10

<210> SEQ ID NO 300
<211> LENGTH: 18
<212> TYPE: PRT
<213> ORGANISM: Artificial Sequence
<220> FEATURE:
<223> OTHER INFORMATION: CPP

<400> SEQUENCE: 300

Ala Leu Ile Ile Leu Arg Arg Arg Ile Arg Lys Gln Ala His Ala His
1               5                   10                  15

Ser Lys

<210> SEQ ID NO 301
<211> LENGTH: 18
<212> TYPE: PRT
<213> ORGANISM: Artificial Sequence
<220> FEATURE:
<223> OTHER INFORMATION: CPP

<400> SEQUENCE: 301

Leu Ala Ile Ile Leu Arg Arg Arg Ile Arg Lys Gln Ala His Ala His
1               5                   10                  15

Ser Lys

<210> SEQ ID NO 302
<211> LENGTH: 18
<212> TYPE: PRT
<213> ORGANISM: Artificial Sequence
<220> FEATURE:
<223> OTHER INFORMATION: CPP

<400> SEQUENCE: 302

Leu Leu Ala Ile Leu Arg Arg Arg Ile Arg Lys Gln Ala His Ala His
1               5                   10                  15

Ser Lys
```

```
<210> SEQ ID NO 303
<211> LENGTH: 18
<212> TYPE: PRT
<213> ORGANISM: Artificial Sequence
<220> FEATURE:
<223> OTHER INFORMATION: CPP

<400> SEQUENCE: 303

Leu Leu Ile Ala Leu Arg Arg Ile Arg Lys Gln Ala His Ala His
1               5                   10                  15

Ser Lys

<210> SEQ ID NO 304
<211> LENGTH: 18
<212> TYPE: PRT
<213> ORGANISM: Artificial Sequence
<220> FEATURE:
<223> OTHER INFORMATION: CPP

<400> SEQUENCE: 304

Leu Leu Ile Ile Ala Arg Arg Ile Arg Lys Gln Ala His Ala His
1               5                   10                  15

Ser Lys

<210> SEQ ID NO 305
<211> LENGTH: 18
<212> TYPE: PRT
<213> ORGANISM: Artificial Sequence
<220> FEATURE:
<223> OTHER INFORMATION: CPP

<400> SEQUENCE: 305

Leu Leu Ile Ile Leu Ala Arg Arg Ile Arg Lys Gln Ala His Ala His
1               5                   10                  15

Ser Lys

<210> SEQ ID NO 306
<211> LENGTH: 18
<212> TYPE: PRT
<213> ORGANISM: Artificial Sequence
<220> FEATURE:
<223> OTHER INFORMATION: CPP

<400> SEQUENCE: 306

Leu Leu Ile Ile Leu Arg Ala Arg Ile Arg Lys Gln Ala His Ala His
1               5                   10                  15

Ser Lys

<210> SEQ ID NO 307
<211> LENGTH: 18
<212> TYPE: PRT
<213> ORGANISM: Artificial Sequence
<220> FEATURE:
<223> OTHER INFORMATION: CPP

<400> SEQUENCE: 307

Leu Leu Ile Ile Leu Arg Arg Ala Ile Arg Lys Gln Ala His Ala His
1               5                   10                  15

Ser Lys

<210> SEQ ID NO 308
<211> LENGTH: 18
<212> TYPE: PRT
<213> ORGANISM: Artificial Sequence
```

```
<220> FEATURE:
<223> OTHER INFORMATION: CPP

<400> SEQUENCE: 308

Leu Leu Ile Ile Leu Arg Arg Arg Ala Arg Lys Gln Ala His Ala
1               5                   10                  15

Ser Lys

<210> SEQ ID NO 309
<211> LENGTH: 19
<212> TYPE: PRT
<213> ORGANISM: Artificial Sequence
<220> FEATURE:
<223> OTHER INFORMATION: CPP

<400> SEQUENCE: 309

Leu Leu Ile Ile Leu Arg Arg Arg Ile Ala Arg Lys Gln Ala His Ala
1               5                   10                  15

His Ser Lys

<210> SEQ ID NO 310
<211> LENGTH: 18
<212> TYPE: PRT
<213> ORGANISM: Artificial Sequence
<220> FEATURE:
<223> OTHER INFORMATION: CPP

<400> SEQUENCE: 310

Leu Leu Ile Ile Leu Arg Arg Arg Ile Arg Ala Gln Ala His Ala His
1               5                   10                  15

Ser Lys

<210> SEQ ID NO 311
<211> LENGTH: 18
<212> TYPE: PRT
<213> ORGANISM: Artificial Sequence
<220> FEATURE:
<223> OTHER INFORMATION: CPP

<400> SEQUENCE: 311

Leu Leu Ile Ile Leu Arg Arg Arg Ile Arg Lys Ala Ala His Ala His
1               5                   10                  15

Ser Lys

<210> SEQ ID NO 312
<211> LENGTH: 18
<212> TYPE: PRT
<213> ORGANISM: Artificial Sequence
<220> FEATURE:
<223> OTHER INFORMATION: CPP

<400> SEQUENCE: 312

Leu Leu Ile Ile Leu Arg Arg Arg Ile Arg Lys Gln Ala His Ala His
1               5                   10                  15

Ser Lys

<210> SEQ ID NO 313
<211> LENGTH: 18
<212> TYPE: PRT
<213> ORGANISM: Artificial Sequence
<220> FEATURE:
<223> OTHER INFORMATION: CPP

<400> SEQUENCE: 313
```

```
Leu Leu Ile Ile Leu Arg Arg Arg Ile Arg Lys Gln Ala Ala Ala His
1               5                   10                  15

Ser Lys

<210> SEQ ID NO 314
<211> LENGTH: 18
<212> TYPE: PRT
<213> ORGANISM: Artificial Sequence
<220> FEATURE:
<223> OTHER INFORMATION: CPP

<400> SEQUENCE: 314

Leu Leu Ile Ile Leu Arg Arg Arg Ile Arg Lys Gln Ala His Ala His
1               5                   10                  15

Ser Lys

<210> SEQ ID NO 315
<211> LENGTH: 18
<212> TYPE: PRT
<213> ORGANISM: Artificial Sequence
<220> FEATURE:
<223> OTHER INFORMATION: CPP

<400> SEQUENCE: 315

Leu Leu Ile Ile Leu Arg Arg Arg Ile Arg Lys Gln Ala His Ala Ala
1               5                   10                  15

Ser Lys

<210> SEQ ID NO 316
<211> LENGTH: 18
<212> TYPE: PRT
<213> ORGANISM: Artificial Sequence
<220> FEATURE:
<223> OTHER INFORMATION: CPP

<400> SEQUENCE: 316

Leu Leu Ile Ile Leu Arg Arg Arg Ile Arg Lys Gln Ala His Ala His
1               5                   10                  15

Ala Lys

<210> SEQ ID NO 317
<211> LENGTH: 18
<212> TYPE: PRT
<213> ORGANISM: Artificial Sequence
<220> FEATURE:
<223> OTHER INFORMATION: CPP

<400> SEQUENCE: 317

Leu Leu Ile Ile Leu Arg Arg Arg Ile Arg Lys Gln Ala His Ala His
1               5                   10                  15

Ser Ala

<210> SEQ ID NO 318
<211> LENGTH: 18
<212> TYPE: PRT
<213> ORGANISM: Artificial Sequence
<220> FEATURE:
<223> OTHER INFORMATION: CPP

<400> SEQUENCE: 318

Lys Ser His Ala His Ala Gln Lys Arg Ile Arg Arg Leu Ile Ile
1               5                   10                  15
```

Leu Leu

<210> SEQ ID NO 319
<211> LENGTH: 18
<212> TYPE: PRT
<213> ORGANISM: Artificial Sequence
<220> FEATURE:
<223> OTHER INFORMATION: CPP

<400> SEQUENCE: 319

Leu Leu Ile Ile Leu Arg Arg Arg Ile Arg Lys Gln Ala His Ala His
1               5                   10                  15

Ser Lys

<210> SEQ ID NO 320
<211> LENGTH: 7
<212> TYPE: PRT
<213> ORGANISM: Artificial Sequence
<220> FEATURE:
<223> OTHER INFORMATION: CPP

<400> SEQUENCE: 320

Arg Arg Ile Arg Pro Arg Pro
1               5

<210> SEQ ID NO 321
<211> LENGTH: 15
<212> TYPE: PRT
<213> ORGANISM: Artificial Sequence
<220> FEATURE:
<223> OTHER INFORMATION: CPP

<400> SEQUENCE: 321

Arg Arg Ile Arg Pro Arg Pro Pro Arg Leu Pro Arg Pro Arg Pro
1               5                   10                  15

<210> SEQ ID NO 322
<211> LENGTH: 24
<212> TYPE: PRT
<213> ORGANISM: Artificial Sequence
<220> FEATURE:
<223> OTHER INFORMATION: CPP

<400> SEQUENCE: 322

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 323
<211> LENGTH: 17
<212> TYPE: PRT
<213> ORGANISM: Artificial Sequence
<220> FEATURE:
<223> OTHER INFORMATION: CPP

<400> SEQUENCE: 323

Arg Arg Ile Arg Pro Arg Pro Pro Arg Leu Pro Arg Pro Arg Pro Arg
1               5                   10                  15

Pro

<210> SEQ ID NO 324
<211> LENGTH: 20
<212> TYPE: PRT
<213> ORGANISM: Artificial Sequence

```
<220> FEATURE:
<223> OTHER INFORMATION: CPP

<400> SEQUENCE: 324

Pro Arg Pro Pro Arg Leu Pro Arg Pro Arg Pro Arg Pro Leu Pro Phe
1               5                   10                  15

Pro Arg Pro Gly
            20

<210> SEQ ID NO 325
<211> LENGTH: 18
<212> TYPE: PRT
<213> ORGANISM: Artificial Sequence
<220> FEATURE:
<223> OTHER INFORMATION: CPP

<400> SEQUENCE: 325

Pro Pro Arg Leu Pro Arg Pro Arg Pro Arg Pro Leu Pro Phe Pro Arg
1               5                   10                  15

Pro Gly

<210> SEQ ID NO 326
<211> LENGTH: 16
<212> TYPE: PRT
<213> ORGANISM: Artificial Sequence
<220> FEATURE:
<223> OTHER INFORMATION: CPP

<400> SEQUENCE: 326

Arg Leu Pro Arg Pro Arg Pro Arg Pro Leu Pro Phe Pro Arg Pro Gly
1               5                   10                  15

<210> SEQ ID NO 327
<211> LENGTH: 14
<212> TYPE: PRT
<213> ORGANISM: Artificial Sequence
<220> FEATURE:
<223> OTHER INFORMATION: CPP

<400> SEQUENCE: 327

Pro Arg Pro Arg Pro Arg Pro Leu Pro Phe Pro Arg Pro Gly
1               5                   10

<210> SEQ ID NO 328
<211> LENGTH: 12
<212> TYPE: PRT
<213> ORGANISM: Artificial Sequence
<220> FEATURE:
<223> OTHER INFORMATION: CPP

<400> SEQUENCE: 328

Pro Arg Pro Arg Pro Leu Pro Phe Pro Arg Pro Gly
1               5                   10

<210> SEQ ID NO 329
<211> LENGTH: 10
<212> TYPE: PRT
<213> ORGANISM: Artificial Sequence
<220> FEATURE:
<223> OTHER INFORMATION: CPP

<400> SEQUENCE: 329

Pro Arg Pro Leu Pro Phe Pro Arg Pro Gly
1               5                   10
```

-continued

```
<210> SEQ ID NO 330
<211> LENGTH: 22
<212> TYPE: PRT
<213> ORGANISM: Artificial Sequence
<220> FEATURE:
<223> OTHER INFORMATION: CPP

<400> SEQUENCE: 330

Arg Val Thr Ser Trp Leu Gly Arg Gln Leu Arg Ile Ala Gly Lys Arg
1               5                   10                  15

Leu Glu Gly Arg Ser Lys
            20

<210> SEQ ID NO 331
<211> LENGTH: 16
<212> TYPE: PRT
<213> ORGANISM: Artificial Sequence
<220> FEATURE:
<223> OTHER INFORMATION: CPP

<400> SEQUENCE: 331

Gly Arg Gln Leu Arg Ile Ala Gly Lys Arg Leu Glu Gly Arg Ser Lys
1               5                   10                  15

<210> SEQ ID NO 332
<211> LENGTH: 23
<212> TYPE: PRT
<213> ORGANISM: Artificial Sequence
<220> FEATURE:
<223> OTHER INFORMATION: CPP

<400> SEQUENCE: 332

Arg Arg Val Thr Ser Trp Leu Gly Arg Gln Leu Arg Ile Ala Gly Lys
1               5                   10                  15

Arg Leu Glu Gly Arg Ser Lys
            20

<210> SEQ ID NO 333
<211> LENGTH: 22
<212> TYPE: PRT
<213> ORGANISM: Artificial Sequence
<220> FEATURE:
<223> OTHER INFORMATION: CPP

<400> SEQUENCE: 333

Arg Val Arg Ser Trp Leu Gly Arg Gln Leu Arg Ile Ala Gly Lys Arg
1               5                   10                  15

Leu Glu Gly Arg Ser Lys
            20

<210> SEQ ID NO 334
<211> LENGTH: 16
<212> TYPE: PRT
<213> ORGANISM: Artificial Sequence
<220> FEATURE:
<223> OTHER INFORMATION: CPP

<400> SEQUENCE: 334

Gly Arg Gln Leu Arg Ile Ala Gly Lys Arg Leu Arg Gly Arg Ser Lys
1               5                   10                  15

<210> SEQ ID NO 335
<211> LENGTH: 16
<212> TYPE: PRT
<213> ORGANISM: Artificial Sequence
<220> FEATURE:
```

<223> OTHER INFORMATION: CPP

<400> SEQUENCE: 335

Gly Arg Gln Leu Arg Ile Ala Gly Arg Arg Leu Arg Gly Arg Ser Arg
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: CPP

<400> SEQUENCE: 336

Gly Arg Gln Leu Arg Arg Ala Gly Arg Arg Leu Arg Gly Arg Ser Arg
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: CPP

<400> SEQUENCE: 337

Gly Arg Gln Leu Arg Ile Ala Gly Arg Arg Leu Arg Arg Arg Ser Arg
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: CPP

<400> SEQUENCE: 338

Gly Arg Gln Leu Arg Arg Ala Gly Arg Arg Leu Arg Arg Arg Ser Arg
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: CPP

<400> SEQUENCE: 339

Arg Gln Leu Arg Ile Ala Gly Arg Arg Leu Arg Gly Arg Ser Arg
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: CPP

<400> SEQUENCE: 340

Arg Ser Arg Gly Arg Leu Arg Arg Gly Ala Ile Arg Leu Gln Arg Gly
1               5                   10                  15

<210> SEQ ID NO 341
<211> LENGTH: 29
<212> TYPE: PRT
<213> ORGANISM: Artificial Sequence
<220> FEATURE:
<223> OTHER INFORMATION: CPP

```
<400> SEQUENCE: 341

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 342
<211> LENGTH: 27
<212> TYPE: PRT
<213> ORGANISM: Artificial Sequence
<220> FEATURE:
<223> OTHER INFORMATION: CPP

<400> SEQUENCE: 342

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met
            20                  25

<210> SEQ ID NO 343
<211> LENGTH: 27
<212> TYPE: PRT
<213> ORGANISM: Artificial Sequence
<220> FEATURE:
<223> OTHER INFORMATION: CPP

<400> SEQUENCE: 343

Lys Leu Ile Lys Gly Arg Thr Pro Ile Lys Phe Gly Lys Ala Asp Cys
1               5                   10                  15

Asp Arg Pro Pro Lys His Ser Gln Asn Gly Lys
            20                  25

<210> SEQ ID NO 344
<211> LENGTH: 26
<212> TYPE: PRT
<213> ORGANISM: Artificial Sequence
<220> FEATURE:
<223> OTHER INFORMATION: CPP

<400> SEQUENCE: 344

Lys Gly Arg Thr Pro Ile Lys Phe Gly Lys Ala Asp Cys Asp Arg Pro
1               5                   10                  15

Pro Lys His Ser Gln Asn Gly Met Gly Lys
            20                  25

<210> SEQ ID NO 345
<211> LENGTH: 25
<212> TYPE: PRT
<213> ORGANISM: Artificial Sequence
<220> FEATURE:
<223> OTHER INFORMATION: CPP

<400> SEQUENCE: 345

Lys Leu Ile Lys Gly Arg Thr Pro Ile Lys Phe Gly Lys Ala Asp Cys
1               5                   10                  15

Asp Arg Pro Pro Lys His Ser Gly Lys
            20                  25

<210> SEQ ID NO 346
<211> LENGTH: 25
<212> TYPE: PRT
<213> ORGANISM: Artificial Sequence
<220> FEATURE:
```

```
<223> OTHER INFORMATION: CPP

<400> SEQUENCE: 346

Lys Leu Ile Lys Gly Arg Thr Pro Ile Lys Phe Gly Lys Ala Arg Cys
1               5                   10                  15

Arg Arg Pro Pro Lys His Ser Gly Lys
            20                  25

<210> SEQ ID NO 347
<211> LENGTH: 13
<212> TYPE: PRT
<213> ORGANISM: Artificial Sequence
<220> FEATURE:
<223> OTHER INFORMATION: CPP

<400> SEQUENCE: 347

Lys Leu Ile Lys Gly Arg Thr Pro Ile Lys Phe Gly Lys
1               5                   10

<210> SEQ ID NO 348
<211> LENGTH: 37
<212> TYPE: PRT
<213> ORGANISM: Artificial Sequence
<220> FEATURE:
<223> OTHER INFORMATION: CPP

<400> SEQUENCE: 348

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys Pro Gln
            20                  25                  30

Thr Thr Lys Pro Lys
        35

<210> SEQ ID NO 349
<211> LENGTH: 30
<212> TYPE: PRT
<213> ORGANISM: Artificial Sequence
<220> FEATURE:
<223> OTHER INFORMATION: CPP

<400> SEQUENCE: 349

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys
            20                  25                  30

<210> SEQ ID NO 350
<211> LENGTH: 27
<212> TYPE: PRT
<213> ORGANISM: Artificial Sequence
<220> FEATURE:
<223> OTHER INFORMATION: CPP

<400> SEQUENCE: 350

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys
            20                  25

<210> SEQ ID NO 351
<211> LENGTH: 23
<212> TYPE: PRT
<213> ORGANISM: Artificial Sequence
```

<220> FEATURE:
<223> OTHER INFORMATION: CPP

<400> SEQUENCE: 351

Lys Arg Ile Pro Asn Lys Lys Pro Gly Lys Lys Thr Thr Thr Lys Pro
1               5                   10                  15

Thr Lys Lys Pro Thr Ile Lys
            20

<210> SEQ ID NO 352
<211> LENGTH: 19
<212> TYPE: PRT
<213> ORGANISM: Artificial Sequence
<220> FEATURE:
<223> OTHER INFORMATION: CPP

<400> SEQUENCE: 352

Lys Arg Ile Pro Asn Lys Lys Pro Gly Lys Lys Thr Thr Thr Lys Pro
1               5                   10                  15

Thr Lys Lys

<210> SEQ ID NO 353
<211> LENGTH: 12
<212> TYPE: PRT
<213> ORGANISM: Artificial Sequence
<220> FEATURE:
<223> OTHER INFORMATION: CPP

<400> SEQUENCE: 353

Lys Arg Ile Pro Asn Lys Lys Pro Gly Lys Lys Thr
1               5                   10

<210> SEQ ID NO 354
<211> LENGTH: 11
<212> TYPE: PRT
<213> ORGANISM: Artificial Sequence
<220> FEATURE:
<223> OTHER INFORMATION: CPP

<400> SEQUENCE: 354

Lys Arg Ile Pro Asn Lys Lys Pro Gly Lys Lys
1               5                   10

<210> SEQ ID NO 355
<211> LENGTH: 10
<212> TYPE: PRT
<213> ORGANISM: Artificial Sequence
<220> FEATURE:
<223> OTHER INFORMATION: CPP

<400> SEQUENCE: 355

Lys Arg Ile Pro Asn Lys Lys Pro Lys Lys
1               5                   10

<210> SEQ ID NO 356
<211> LENGTH: 22
<212> TYPE: PRT
<213> ORGANISM: Artificial Sequence
<220> FEATURE:
<223> OTHER INFORMATION: CPP

<400> SEQUENCE: 356

Lys Lys Pro Gly Lys Lys Thr Thr Thr Lys Pro Thr Lys Lys Pro Thr
1               5                   10                  15

Ile Lys Thr Thr Lys Lys

<210> SEQ ID NO 357
<211> LENGTH: 14
<212> TYPE: PRT
<213> ORGANISM: Artificial Sequence
<220> FEATURE:
<223> OTHER INFORMATION: CPP

<400> SEQUENCE: 357

Lys Lys Pro Gly Lys Lys Thr Thr Thr Lys Pro Thr Lys Lys
1               5                   10

<210> SEQ ID NO 358
<211> LENGTH: 10
<212> TYPE: PRT
<213> ORGANISM: Artificial Sequence
<220> FEATURE:
<223> OTHER INFORMATION: CPP

<400> SEQUENCE: 358

Lys Lys Pro Thr Ile Lys Thr Thr Lys Lys
1               5                   10

<210> SEQ ID NO 359
<211> LENGTH: 10
<212> TYPE: PRT
<213> ORGANISM: Artificial Sequence
<220> FEATURE:
<223> OTHER INFORMATION: CPP

<400> SEQUENCE: 359

Lys Lys Thr Thr Thr Lys Pro Thr Lys Lys
1               5                   10

<210> SEQ ID NO 360
<211> LENGTH: 15
<212> TYPE: PRT
<213> ORGANISM: Artificial Sequence
<220> FEATURE:
<223> OTHER INFORMATION: CPP

<400> SEQUENCE: 360

Lys Ser Ile Cys Lys Thr Ile Pro Ser Asn Lys Pro Lys Lys Lys
1               5                   10                  15

<210> SEQ ID NO 361
<211> LENGTH: 11
<212> TYPE: PRT
<213> ORGANISM: Artificial Sequence
<220> FEATURE:
<223> OTHER INFORMATION: CPP

<400> SEQUENCE: 361

Lys Thr Ile Pro Ser Asn Lys Pro Lys Lys
1               5                   10

<210> SEQ ID NO 362
<211> LENGTH: 12
<212> TYPE: PRT
<213> ORGANISM: Artificial Sequence
<220> FEATURE:
<223> OTHER INFORMATION: CPP

<400> SEQUENCE: 362

Lys Pro Arg Ser Lys Asn Pro Pro Lys Lys Pro Lys
1               5                   10

<210> SEQ ID NO 363
<211> LENGTH: 17
<212> TYPE: PRT
<213> ORGANISM: Artificial Sequence
<220> FEATURE:
<223> OTHER INFORMATION: CPP

<400> SEQUENCE: 363

Asp Arg Asp Asp Arg Asp Asp Arg Asp Asp Arg Asp Asp Arg Asp Asp
1               5                   10                  15

Arg

<210> SEQ ID NO 364
<211> LENGTH: 14
<212> TYPE: PRT
<213> ORGANISM: Artificial Sequence
<220> FEATURE:
<223> OTHER INFORMATION: CPP

<400> SEQUENCE: 364

Glu Arg Glu Arg Glu Arg Glu Arg Glu Arg Glu Arg Glu Arg
1               5                   10

<210> SEQ ID NO 365
<211> LENGTH: 14
<212> TYPE: PRT
<213> ORGANISM: Artificial Sequence
<220> FEATURE:
<223> OTHER INFORMATION: CPP

<400> SEQUENCE: 365

Trp Arg Trp Arg Trp Arg Trp Arg Trp Arg Trp Arg Trp Arg
1               5                   10

<210> SEQ ID NO 366
<211> LENGTH: 10
<212> TYPE: PRT
<213> ORGANISM: Artificial Sequence
<220> FEATURE:
<223> OTHER INFORMATION: CPP

<400> SEQUENCE: 366

Asp Arg Asp Arg Asp Arg Asp Arg Asp Arg
1               5                   10

<210> SEQ ID NO 367
<211> LENGTH: 27
<212> TYPE: PRT
<213> ORGANISM: Artificial Sequence
<220> FEATURE:
<223> OTHER INFORMATION: CPP

<400> SEQUENCE: 367

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 368
<211> LENGTH: 17
<212> TYPE: PRT
<213> ORGANISM: Artificial Sequence
<220> FEATURE:
<223> OTHER INFORMATION: CPP

```
<400> SEQUENCE: 368

Asp Arg Arg Arg Arg Gly Ser Arg Pro Ser Gly Ala Glu Arg Arg
1               5                   10                  15

Arg

<210> SEQ ID NO 369
<211> LENGTH: 11
<212> TYPE: PRT
<213> ORGANISM: Artificial Sequence
<220> FEATURE:
<223> OTHER INFORMATION: CPP

<400> SEQUENCE: 369

Asn Arg Ala Arg Arg Asn Arg Arg Arg Val Arg
1               5                   10

<210> SEQ ID NO 370
<211> LENGTH: 10
<212> TYPE: PRT
<213> ORGANISM: Artificial Sequence
<220> FEATURE:
<223> OTHER INFORMATION: CPP

<400> SEQUENCE: 370

Arg Thr Arg Arg Asn Arg Arg Arg Val Arg
1               5                   10

<210> SEQ ID NO 371
<211> LENGTH: 8
<212> TYPE: PRT
<213> ORGANISM: Artificial Sequence
<220> FEATURE:
<223> OTHER INFORMATION: CPP

<400> SEQUENCE: 371

Arg Asn Arg Ser Arg His Arg Arg
1               5

<210> SEQ ID NO 372
<211> LENGTH: 22
<212> TYPE: PRT
<213> ORGANISM: Artificial Sequence
<220> FEATURE:
<223> OTHER INFORMATION: CPP

<400> SEQUENCE: 372

Met Val Arg Arg Phe Leu Val Thr Leu Arg Ile Arg Arg Ala Cys Gly
1               5                   10                  15

Pro Pro Arg Val Arg Val
            20

<210> SEQ ID NO 373
<211> LENGTH: 22
<212> TYPE: PRT
<213> ORGANISM: Artificial Sequence
<220> FEATURE:
<223> OTHER INFORMATION: CPP

<400> SEQUENCE: 373

Phe Val Thr Arg Gly Cys Pro Arg Arg Leu Val Ala Arg Leu Ile Arg
1               5                   10                  15

Val Met Val Pro Arg Arg
            20
```

```
<210> SEQ ID NO 374
<211> LENGTH: 13
<212> TYPE: PRT
<213> ORGANISM: Artificial Sequence
<220> FEATURE:
<223> OTHER INFORMATION: CPP

<400> SEQUENCE: 374

Val Arg Arg Phe Leu Val Thr Leu Arg Ile Arg Arg Ala
1               5                   10

<210> SEQ ID NO 375
<211> LENGTH: 13
<212> TYPE: PRT
<213> ORGANISM: Artificial Sequence
<220> FEATURE:
<223> OTHER INFORMATION: CPP

<400> SEQUENCE: 375

Arg Val Arg Ile Leu Ala Arg Phe Leu Arg Thr Arg Val
1               5                   10

<210> SEQ ID NO 376
<211> LENGTH: 13
<212> TYPE: PRT
<213> ORGANISM: Artificial Sequence
<220> FEATURE:
<223> OTHER INFORMATION: CPP

<400> SEQUENCE: 376

Arg Val Arg Val Phe Val Val His Ile Pro Arg Leu Thr
1               5                   10

<210> SEQ ID NO 377
<211> LENGTH: 13
<212> TYPE: PRT
<213> ORGANISM: Artificial Sequence
<220> FEATURE:
<223> OTHER INFORMATION: CPP

<400> SEQUENCE: 377

Val Ile Arg Val His Phe Arg Leu Pro Val Arg Thr Val
1               5                   10

<210> SEQ ID NO 378
<211> LENGTH: 37
<212> TYPE: PRT
<213> ORGANISM: Artificial Sequence
<220> FEATURE:
<223> OTHER INFORMATION: CPP

<400> SEQUENCE: 378

Met Val Arg Arg Phe Leu Val Thr Leu Arg Ile Arg Arg Ala Cys Gly
1               5                   10                  15

Pro Pro Arg Val Arg Val Phe Val Val His Ile Pro Arg Leu Thr Gly
            20                  25                  30

Glu Trp Ala Ala Pro
        35

<210> SEQ ID NO 379
<211> LENGTH: 37
<212> TYPE: PRT
<213> ORGANISM: Artificial Sequence
<220> FEATURE:
<223> OTHER INFORMATION: CPP

<400> SEQUENCE: 379
```

Phe Arg Val Pro Leu Arg Ile Arg Pro Cys Val Val Ala Pro Arg Leu
1               5                   10                  15

Val Met Val Arg His Thr Phe Gly Arg Ile Ala Arg Trp Val Ala Gly
            20                  25                  30

Pro Leu Glu Thr Arg
            35

<210> SEQ ID NO 380
<211> LENGTH: 21
<212> TYPE: PRT
<213> ORGANISM: Artificial Sequence
<220> FEATURE:
<223> OTHER INFORMATION: CPP

<400> SEQUENCE: 380

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 381
<211> LENGTH: 25
<212> TYPE: PRT
<213> ORGANISM: Artificial Sequence
<220> FEATURE:
<223> OTHER INFORMATION: CPP

<400> SEQUENCE: 381

Gly Thr Lys Met Ile Phe Val Gly Ile Lys Lys Lys Glu Glu Arg Ala
1               5                   10                  15

Asp Leu Ile Ala Tyr Leu Lys Lys Ala
            20                  25

<210> SEQ ID NO 382
<211> LENGTH: 16
<212> TYPE: PRT
<213> ORGANISM: Artificial Sequence
<220> FEATURE:
<223> OTHER INFORMATION: CPP

<400> SEQUENCE: 382

Lys Lys Lys Glu Glu Arg Ala Asp Leu Ile Ala Tyr Leu Lys Lys Ala
1               5                   10                  15

<210> SEQ ID NO 383
<211> LENGTH: 14
<212> TYPE: PRT
<213> ORGANISM: Artificial Sequence
<220> FEATURE:
<223> OTHER INFORMATION: CPP

<400> SEQUENCE: 383

Lys Met Ile Phe Val Gly Ile Lys Lys Lys Glu Glu Arg Ala
1               5                   10

<210> SEQ ID NO 384
<211> LENGTH: 10
<212> TYPE: PRT
<213> ORGANISM: Artificial Sequence
<220> FEATURE:
<223> OTHER INFORMATION: CPP

<400> SEQUENCE: 384

Lys Met Ile Phe Val Gly Ile Lys Lys Lys

```
1               5              10

<210> SEQ ID NO 385
<211> LENGTH: 10
<212> TYPE: PRT
<213> ORGANISM: Artificial Sequence
<220> FEATURE:
<223> OTHER INFORMATION: CPP

<400> SEQUENCE: 385

Glu Lys Gly Lys Lys Ile Phe Ile Met Lys
1               5                   10

<210> SEQ ID NO 386
<211> LENGTH: 9
<212> TYPE: PRT
<213> ORGANISM: Artificial Sequence
<220> FEATURE:
<223> OTHER INFORMATION: CPP

<400> SEQUENCE: 386

Lys Gly Lys Lys Ile Phe Ile Met Lys
1               5

<210> SEQ ID NO 387
<211> LENGTH: 17
<212> TYPE: PRT
<213> ORGANISM: Artificial Sequence
<220> FEATURE:
<223> OTHER INFORMATION: CPP

<400> SEQUENCE: 387

Arg Arg Arg Arg Asn Arg Thr Arg Arg Asn Arg Arg Arg Val Arg Gly
1               5                   10                  15

Cys

<210> SEQ ID NO 388
<211> LENGTH: 15
<212> TYPE: PRT
<213> ORGANISM: Artificial Sequence
<220> FEATURE:
<223> OTHER INFORMATION: CPP

<400> SEQUENCE: 388

Thr Arg Arg Gln Arg Thr Arg Arg Ala Arg Arg Asn Arg Gly Cys
1               5                   10                  15

<210> SEQ ID NO 389
<211> LENGTH: 21
<212> TYPE: PRT
<213> ORGANISM: Artificial Sequence
<220> FEATURE:
<223> OTHER INFORMATION: CPP

<400> SEQUENCE: 389

Lys Met Thr Arg Ala Gln Arg Arg Ala Ala Ala Arg Arg Asn Arg Trp
1               5                   10                  15

Thr Ala Arg Gly Cys
                20

<210> SEQ ID NO 390
<211> LENGTH: 21
<212> TYPE: PRT
<213> ORGANISM: Artificial Sequence
<220> FEATURE:
<223> OTHER INFORMATION: CPP
```

<400> SEQUENCE: 390

Lys Leu Thr Arg Ala Gln Arg Arg Ala Ala Arg Lys Asn Lys Arg
1               5                   10                  15

Asn Thr Arg Gly Cys
            20

<210> SEQ ID NO 391
<211> LENGTH: 19
<212> TYPE: PRT
<213> ORGANISM: Artificial Sequence
<220> FEATURE:
<223> OTHER INFORMATION: CPP

<400> SEQUENCE: 391

Asn Ala Lys Thr Arg Arg His Glu Arg Arg Lys Leu Ala Ile Glu
1               5                   10                  15

Arg Gly Cys

<210> SEQ ID NO 392
<211> LENGTH: 24
<212> TYPE: PRT
<213> ORGANISM: Artificial Sequence
<220> FEATURE:
<223> OTHER INFORMATION: CPP

<400> SEQUENCE: 392

Met Asp Ala Gln Thr Arg Arg Arg Glu Arg Arg Ala Glu Lys Gln Ala
1               5                   10                  15

Gln Trp Lys Ala Ala Asn Gly Cys
            20

<210> SEQ ID NO 393
<211> LENGTH: 20
<212> TYPE: PRT
<213> ORGANISM: Artificial Sequence
<220> FEATURE:
<223> OTHER INFORMATION: CPP

<400> SEQUENCE: 393

Thr Ala Lys Thr Arg Tyr Lys Ala Arg Arg Ala Glu Leu Ile Ala Glu
1               5                   10                  15

Arg Arg Gly Cys
            20

<210> SEQ ID NO 394
<211> LENGTH: 14
<212> TYPE: PRT
<213> ORGANISM: Artificial Sequence
<220> FEATURE:
<223> OTHER INFORMATION: CPP

<400> SEQUENCE: 394

Ser Gln Met Thr Arg Gln Ala Arg Arg Leu Tyr Asx Gly Cys
1               5                   10

<210> SEQ ID NO 395
<211> LENGTH: 28
<212> TYPE: PRT
<213> ORGANISM: Artificial Sequence
<220> FEATURE:
<223> OTHER INFORMATION: CPP

<400> SEQUENCE: 395

-continued

```
Lys Arg Arg Ile Arg Glu Arg Asn Lys Met Ala Ala Ala Lys Ser
1               5                   10                  15

Arg Asn Arg Arg Arg Glu Leu Thr Asp Thr Gly Cys
            20                  25
```

<210> SEQ ID NO 396
<211> LENGTH: 30
<212> TYPE: PRT
<213> ORGANISM: Artificial Sequence
<220> FEATURE:
<223> OTHER INFORMATION: CPP

<400> SEQUENCE: 396

```
Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg Gly Cys
            20                  25                  30
```

<210> SEQ ID NO 397
<211> LENGTH: 24
<212> TYPE: PRT
<213> ORGANISM: Artificial Sequence
<220> FEATURE:
<223> OTHER INFORMATION: CPP

<400> SEQUENCE: 397

```
Lys Arg Ala Arg Asn Thr Glu Ala Ala Arg Arg Ser Arg Ala Arg Lys
1               5                   10                  15

Leu Gln Arg Met Lys Gln Gly Cys
            20
```

<210> SEQ ID NO 398
<211> LENGTH: 22
<212> TYPE: PRT
<213> ORGANISM: Artificial Sequence
<220> FEATURE:
<223> OTHER INFORMATION: CPP

<400> SEQUENCE: 398

```
Lys Cys Phe Gln Trp Gln Arg Asn Met Arg Lys Val Arg Gly Pro Pro
1               5                   10                  15

Val Ser Cys Ile Lys Arg
            20
```

<210> SEQ ID NO 399
<211> LENGTH: 19
<212> TYPE: PRT
<213> ORGANISM: Artificial Sequence
<220> FEATURE:
<223> OTHER INFORMATION: CPP

<400> SEQUENCE: 399

```
Lys Cys Phe Gln Trp Gln Arg Asn Met Arg Lys Val Arg Gly Pro Pro
1               5                   10                  15

Val Ser Cys
```

<210> SEQ ID NO 400
<211> LENGTH: 22
<212> TYPE: PRT
<213> ORGANISM: Artificial Sequence
<220> FEATURE:
<223> OTHER INFORMATION: CPP

<400> SEQUENCE: 400

-continued

```
Lys Cys Phe Gln Trp Gln Arg Asn Met Arg Lys Val Arg Gly Pro Pro
1               5                   10                  15

Val Ser Ser Ile Lys Arg
            20

<210> SEQ ID NO 401
<211> LENGTH: 13
<212> TYPE: PRT
<213> ORGANISM: Artificial Sequence
<220> FEATURE:
<223> OTHER INFORMATION: CPP

<400> SEQUENCE: 401

Lys Cys Phe Gln Trp Gln Arg Asn Met Arg Lys Val Arg
1               5                   10

<210> SEQ ID NO 402
<211> LENGTH: 16
<212> TYPE: PRT
<213> ORGANISM: Artificial Sequence
<220> FEATURE:
<223> OTHER INFORMATION: CPP

<400> SEQUENCE: 402

Phe Gln Trp Gln Arg Asn Met Arg Lys Val Arg Gly Pro Pro Val Ser
1               5                   10                  15

<210> SEQ ID NO 403
<211> LENGTH: 19
<212> TYPE: PRT
<213> ORGANISM: Artificial Sequence
<220> FEATURE:
<223> OTHER INFORMATION: CPP

<400> SEQUENCE: 403

Gln Trp Gln Arg Asn Met Arg Lys Val Arg Gly Pro Pro Val Ser Cys
1               5                   10                  15

Ile Lys Arg

<210> SEQ ID NO 404
<211> LENGTH: 10
<212> TYPE: PRT
<213> ORGANISM: Artificial Sequence
<220> FEATURE:
<223> OTHER INFORMATION: CPP

<400> SEQUENCE: 404

Gln Trp Gln Arg Asn Met Arg Lys Val Arg
1               5                   10

<210> SEQ ID NO 405
<211> LENGTH: 22
<212> TYPE: PRT
<213> ORGANISM: Artificial Sequence
<220> FEATURE:
<223> OTHER INFORMATION: CPP

<400> SEQUENCE: 405

Lys Cys Phe Met Trp Gln Glu Met Leu Asn Lys Ala Gly Val Pro Lys
1               5                   10                  15

Leu Arg Cys Ala Arg Lys
            20

<210> SEQ ID NO 406
<211> LENGTH: 15
```

```
<212> TYPE: PRT
<213> ORGANISM: Artificial Sequence
<220> FEATURE:
<223> OTHER INFORMATION: CPP

<400> SEQUENCE: 406

Lys Trp Phe Glu Thr Trp Phe Thr Glu Trp Pro Lys Lys Arg Lys
1               5                   10                  15

<210> SEQ ID NO 407
<211> LENGTH: 20
<212> TYPE: PRT
<213> ORGANISM: Artificial Sequence
<220> FEATURE:
<223> OTHER INFORMATION: CPP

<400> SEQUENCE: 407

Gly Leu Trp Arg Ala Leu Trp Arg Leu Leu Arg Ser Leu Trp Arg Leu
1               5                   10                  15

Leu Trp Arg Ala
            20

<210> SEQ ID NO 408
<211> LENGTH: 20
<212> TYPE: PRT
<213> ORGANISM: Artificial Sequence
<220> FEATURE:
<223> OTHER INFORMATION: CPP

<400> SEQUENCE: 408

Gly Leu Trp Trp Arg Leu Trp Trp Arg Leu Arg Ser Trp Phe Arg Leu
1               5                   10                  15

Trp Phe Arg Ala
            20

<210> SEQ ID NO 409
<211> LENGTH: 34
<212> TYPE: PRT
<213> ORGANISM: Artificial Sequence
<220> FEATURE:
<223> OTHER INFORMATION: CPP

<400> SEQUENCE: 409

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Glu

<210> SEQ ID NO 410
<211> LENGTH: 27
<212> TYPE: PRT
<213> ORGANISM: Artificial Sequence
<220> FEATURE:
<223> OTHER INFORMATION: CPP

<400> SEQUENCE: 410

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 411
<211> LENGTH: 27
```

<212> TYPE: PRT
<213> ORGANISM: Artificial Sequence
<220> FEATURE:
<223> OTHER INFORMATION: CPP

<400> SEQUENCE: 411

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 412
<211> LENGTH: 34
<212> TYPE: PRT
<213> ORGANISM: Artificial Sequence
<220> FEATURE:
<223> OTHER INFORMATION: CPP

<400> SEQUENCE: 412

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 413
<211> LENGTH: 34
<212> TYPE: PRT
<213> ORGANISM: Artificial Sequence
<220> FEATURE:
<223> OTHER INFORMATION: CPP

<400> SEQUENCE: 413

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 414
<211> LENGTH: 12
<212> TYPE: PRT
<213> ORGANISM: Artificial Sequence
<220> FEATURE:
<223> OTHER INFORMATION: CPP

<400> SEQUENCE: 414

Pro Ser Ser Ser Ser Ser Ser Arg Ile Gly Asp Pro
1               5                   10

<210> SEQ ID NO 415
<211> LENGTH: 18
<212> TYPE: PRT
<213> ORGANISM: Artificial Sequence
<220> FEATURE:
<223> OTHER INFORMATION: CPP

<400> SEQUENCE: 415

Val Arg Leu Pro Pro Pro Val Arg Leu Pro Pro Pro Val Arg Leu Pro
1               5                   10                  15

Pro Pro

<210> SEQ ID NO 416

```
<211> LENGTH: 18
<212> TYPE: PRT
<213> ORGANISM: Artificial Sequence
<220> FEATURE:
<223> OTHER INFORMATION: CPP

<400> SEQUENCE: 416

Val Glu Leu Pro Pro Pro Val Glu Leu Pro Pro Val Glu Leu Pro
1               5                   10                  15

Pro Pro

<210> SEQ ID NO 417
<211> LENGTH: 28
<212> TYPE: PRT
<213> ORGANISM: Artificial Sequence
<220> FEATURE:
<223> OTHER INFORMATION: CPP

<400> SEQUENCE: 417

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 418
<211> LENGTH: 13
<212> TYPE: PRT
<213> ORGANISM: Artificial Sequence
<220> FEATURE:
<223> OTHER INFORMATION: CPP

<400> SEQUENCE: 418

Ala Leu Trp Lys Thr Leu Leu Lys Lys Val Leu Lys Ala
1               5                   10

<210> SEQ ID NO 419
<211> LENGTH: 20
<212> TYPE: PRT
<213> ORGANISM: Artificial Sequence
<220> FEATURE:
<223> OTHER INFORMATION: CPP

<400> SEQUENCE: 419

Ala Leu Trp Lys Thr Leu Leu Lys Lys Val Leu Lys Ala Pro Lys Lys
1               5                   10                  15

Lys Arg Lys Val
            20

<210> SEQ ID NO 420
<211> LENGTH: 20
<212> TYPE: PRT
<213> ORGANISM: Artificial Sequence
<220> FEATURE:
<223> OTHER INFORMATION: CPP

<400> SEQUENCE: 420

Pro Lys Lys Lys Arg Lys Val Ala Leu Trp Lys Thr Leu Leu Lys Lys
1               5                   10                  15

Val Leu Lys Ala
            20

<210> SEQ ID NO 421
<211> LENGTH: 20
<212> TYPE: PRT
<213> ORGANISM: Artificial Sequence
```

```
<220> FEATURE:
<223> OTHER INFORMATION: CPP

<400> SEQUENCE: 421

Val Lys Arg Lys Lys Pro Ala Leu Trp Lys Thr Leu Leu Lys Lys
1               5                   10                  15

Val Leu Lys Ala
            20

<210> SEQ ID NO 422
<211> LENGTH: 22
<212> TYPE: PRT
<213> ORGANISM: Artificial Sequence
<220> FEATURE:
<223> OTHER INFORMATION: CPP

<400> SEQUENCE: 422

Arg Gln Ala Arg Arg Asn Arg Arg Arg Ala Leu Trp Lys Thr Leu Leu
1               5                   10                  15

Lys Lys Val Leu Lys Ala
            20

<210> SEQ ID NO 423
<211> LENGTH: 10
<212> TYPE: PRT
<213> ORGANISM: Artificial Sequence
<220> FEATURE:
<223> OTHER INFORMATION: CPP

<400> SEQUENCE: 423

Arg Gln Ala Arg Arg Asn Arg Arg Arg Cys
1               5                   10

<210> SEQ ID NO 424
<211> LENGTH: 13
<212> TYPE: PRT
<213> ORGANISM: Artificial Sequence
<220> FEATURE:
<223> OTHER INFORMATION: CPP

<400> SEQUENCE: 424

Glu Glu Glu Ala Ala Gly Arg Lys Arg Lys Lys Arg Thr
1               5                   10

<210> SEQ ID NO 425
<211> LENGTH: 4
<212> TYPE: PRT
<213> ORGANISM: Artificial Sequence
<220> FEATURE:
<223> OTHER INFORMATION: CPP with amino acid sequence EEE

<400> SEQUENCE: 425

Glu Glu Glu Glu
1

<210> SEQ ID NO 426
<211> LENGTH: 5
<212> TYPE: PRT
<213> ORGANISM: Artificial Sequence
<220> FEATURE:
<223> OTHER INFORMATION: CPP

<400> SEQUENCE: 426

Glu Glu Glu Ala Ala
1               5
```

<210> SEQ ID NO 427
<211> LENGTH: 8
<212> TYPE: PRT
<213> ORGANISM: Artificial Sequence
<220> FEATURE:
<223> OTHER INFORMATION: CPP

<400> SEQUENCE: 427

Glu Glu Glu Ala Ala Lys Lys Lys
1               5

<210> SEQ ID NO 428
<211> LENGTH: 13
<212> TYPE: PRT
<213> ORGANISM: Artificial Sequence
<220> FEATURE:
<223> OTHER INFORMATION: CPP

<400> SEQUENCE: 428

Phe Phe Phe Ala Ala Gly Arg Lys Arg Lys Lys Arg Thr
1               5                   10

<210> SEQ ID NO 429
<211> LENGTH: 10
<212> TYPE: PRT
<213> ORGANISM: Artificial Sequence
<220> FEATURE:
<223> OTHER INFORMATION: CPP

<400> SEQUENCE: 429

Ala Ala Gly Arg Lys Arg Lys Lys Arg Thr
1               5                   10

<210> SEQ ID NO 430
<211> LENGTH: 13
<212> TYPE: PRT
<213> ORGANISM: Artificial Sequence
<220> FEATURE:
<223> OTHER INFORMATION: CPP

<400> SEQUENCE: 430

Tyr Tyr Tyr Ala Ala Gly Arg Lys Arg Lys Lys Arg Thr
1               5                   10

<210> SEQ ID NO 431
<211> LENGTH: 22
<212> TYPE: PRT
<213> ORGANISM: Artificial Sequence
<220> FEATURE:
<223> OTHER INFORMATION: CPP

<400> SEQUENCE: 431

Met Val Thr Val Leu Phe Arg Arg Leu Arg Ile Arg Arg Ala Cys Gly
1               5                   10                  15

Pro Pro Arg Val Arg Val
            20

<210> SEQ ID NO 432
<211> LENGTH: 21
<212> TYPE: PRT
<213> ORGANISM: Artificial Sequence
<220> FEATURE:
<223> OTHER INFORMATION: CPP

<400> SEQUENCE: 432

Ala Gly Tyr Leu Leu Gly Lys Ile Asn Leu Lys Ala Leu Ala Ala Leu

```
            1               5                  10                  15

Ala Lys Lys Ile Leu
            20

<210> SEQ ID NO 433
<211> LENGTH: 11
<212> TYPE: PRT
<213> ORGANISM: Artificial Sequence
<220> FEATURE:
<223> OTHER INFORMATION: CPP

<400> SEQUENCE: 433

Gly Lys Lys Lys Lys Arg Lys Arg Glu Lys Leu
1               5                  10

<210> SEQ ID NO 434
<211> LENGTH: 8
<212> TYPE: PRT
<213> ORGANISM: Artificial Sequence
<220> FEATURE:
<223> OTHER INFORMATION: CPP

<400> SEQUENCE: 434

Glu Arg Lys Lys Arg Arg Arg Glu
1               5

<210> SEQ ID NO 435
<211> LENGTH: 7
<212> TYPE: PRT
<213> ORGANISM: Artificial Sequence
<220> FEATURE:
<223> OTHER INFORMATION: CPP

<400> SEQUENCE: 435

Phe Lys Lys Phe Arg Lys Phe
1               5

<210> SEQ ID NO 436
<211> LENGTH: 21
<212> TYPE: PRT
<213> ORGANISM: Artificial Sequence
<220> FEATURE:
<223> OTHER INFORMATION: CPP

<400> SEQUENCE: 436

Tyr Thr Gln Asp Phe Asn Lys Phe His Thr Phe Pro Gln Thr Ala Ile
1               5                  10                  15

Gly Val Gly Ala Pro
            20

<210> SEQ ID NO 437
<211> LENGTH: 18
<212> TYPE: PRT
<213> ORGANISM: Artificial Sequence
<220> FEATURE:
<223> OTHER INFORMATION: CPP

<400> SEQUENCE: 437

Asp Phe Asn Lys Phe His Thr Phe Pro Gln Thr Ala Ile Gly Val Gly
1               5                  10                  15

Ala Pro

<210> SEQ ID NO 438
<211> LENGTH: 15
<212> TYPE: PRT
```

```
<213> ORGANISM: Artificial Sequence
<220> FEATURE:
<223> OTHER INFORMATION: CPP

<400> SEQUENCE: 438

Lys Phe His Thr Phe Pro Gln Thr Ala Ile Gly Val Gly Ala Pro
1               5                   10                  15

<210> SEQ ID NO 439
<211> LENGTH: 12
<212> TYPE: PRT
<213> ORGANISM: Artificial Sequence
<220> FEATURE:
<223> OTHER INFORMATION: CPP

<400> SEQUENCE: 439

Thr Phe Pro Gln Thr Ala Ile Gly Val Gly Ala Pro
1               5                   10

<210> SEQ ID NO 440
<211> LENGTH: 13
<212> TYPE: PRT
<213> ORGANISM: Artificial Sequence
<220> FEATURE:
<223> OTHER INFORMATION: CPP

<400> SEQUENCE: 440

Gly Tyr Gly Arg Lys Lys Arg Arg Gln Arg Arg Arg Gly
1               5                   10

<210> SEQ ID NO 441
<211> LENGTH: 15
<212> TYPE: PRT
<213> ORGANISM: Artificial Sequence
<220> FEATURE:
<223> OTHER INFORMATION: CPP

<400> SEQUENCE: 441

Phe Leu Gly Lys Lys Phe Lys Lys Tyr Phe Leu Gln Leu Leu Lys
1               5                   10                  15

<210> SEQ ID NO 442
<211> LENGTH: 23
<212> TYPE: PRT
<213> ORGANISM: Artificial Sequence
<220> FEATURE:
<223> OTHER INFORMATION: CPP

<400> SEQUENCE: 442

Phe Leu Ile Phe Ile Arg Val Ile Cys Ile Val Ile Ala Lys Leu Lys
1               5                   10                  15

Ala Asn Leu Met Cys Lys Thr
            20

<210> SEQ ID NO 443
<211> LENGTH: 17
<212> TYPE: PRT
<213> ORGANISM: Artificial Sequence
<220> FEATURE:
<223> OTHER INFORMATION: CPP

<400> SEQUENCE: 443

Lys Lys Ala Ala Gln Ile Arg Ser Gln Val Met Thr His Leu Arg Val
1               5                   10                  15

Ile
```

```
<210> SEQ ID NO 444
<211> LENGTH: 16
<212> TYPE: PRT
<213> ORGANISM: Artificial Sequence
<220> FEATURE:
<223> OTHER INFORMATION: CPP

<400> SEQUENCE: 444

Tyr Ile Val Leu Arg Arg Arg Lys Arg Val Asn Thr Lys Arg Ser
1               5                   10                  15

<210> SEQ ID NO 445
<211> LENGTH: 11
<212> TYPE: PRT
<213> ORGANISM: Artificial Sequence
<220> FEATURE:
<223> OTHER INFORMATION: CPP

<400> SEQUENCE: 445

Arg Arg Lys Leu Ser Gln Gln Lys Glu Lys Lys
1               5                   10

<210> SEQ ID NO 446
<211> LENGTH: 15
<212> TYPE: PRT
<213> ORGANISM: Artificial Sequence
<220> FEATURE:
<223> OTHER INFORMATION: CPP

<400> SEQUENCE: 446

Val Gln Ala Ile Leu Arg Arg Asn Trp Asn Gln Tyr Lys Ile Gln
1               5                   10                  15

<210> SEQ ID NO 447
<211> LENGTH: 16
<212> TYPE: PRT
<213> ORGANISM: Artificial Sequence
<220> FEATURE:
<223> OTHER INFORMATION: CPP

<400> SEQUENCE: 447

Lys Thr Val Leu Leu Arg Lys Leu Leu Lys Leu Leu Val Arg Lys Ile
1               5                   10                  15

<210> SEQ ID NO 448
<211> LENGTH: 16
<212> TYPE: PRT
<213> ORGANISM: Artificial Sequence
<220> FEATURE:
<223> OTHER INFORMATION: CPP

<400> SEQUENCE: 448

Leu Leu Lys Lys Arg Lys Val Val Arg Leu Ile Lys Phe Leu Leu Lys
1               5                   10                  15

<210> SEQ ID NO 449
<211> LENGTH: 19
<212> TYPE: PRT
<213> ORGANISM: Artificial Sequence
<220> FEATURE:
<223> OTHER INFORMATION: CPP

<400> SEQUENCE: 449

Lys Leu Pro Cys Arg Ser Asn Thr Phe Leu Asn Ile Phe Arg Arg Lys
1               5                   10                  15

Lys Pro Gly
```

```
<210> SEQ ID NO 450
<211> LENGTH: 16
<212> TYPE: PRT
<213> ORGANISM: Artificial Sequence
<220> FEATURE:
<223> OTHER INFORMATION: CPP

<400> SEQUENCE: 450

Lys Lys Ile Cys Thr Arg Lys Pro Arg Phe Met Ser Ala Trp Ala Gln
1               5                   10                  15

<210> SEQ ID NO 451
<211> LENGTH: 18
<212> TYPE: PRT
<213> ORGANISM: Artificial Sequence
<220> FEATURE:
<223> OTHER INFORMATION: CPP

<400> SEQUENCE: 451

Arg Gly Gly Arg Leu Ser Tyr Ser Arg Arg Phe Ser Thr Ser Thr
1               5                   10                  15

Gly Arg

<210> SEQ ID NO 452
<211> LENGTH: 10
<212> TYPE: PRT
<213> ORGANISM: Artificial Sequence
<220> FEATURE:
<223> OTHER INFORMATION: CPP

<400> SEQUENCE: 452

Arg Arg Leu Ser Tyr Ser Arg Arg Arg Phe
1               5                   10

<210> SEQ ID NO 453
<211> LENGTH: 17
<212> TYPE: PRT
<213> ORGANISM: Artificial Sequence
<220> FEATURE:
<223> OTHER INFORMATION: CPP

<400> SEQUENCE: 453

Arg Gly Gly Arg Leu Ala Tyr Leu Arg Arg Arg Trp Ala Val Leu Gly
1               5                   10                  15

Arg

<210> SEQ ID NO 454
<211> LENGTH: 28
<212> TYPE: PRT
<213> ORGANISM: Artificial Sequence
<220> FEATURE:
<223> OTHER INFORMATION: CPP

<400> SEQUENCE: 454

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro
            20                  25

<210> SEQ ID NO 455
<211> LENGTH: 30
<212> TYPE: PRT
<213> ORGANISM: Artificial Sequence
<220> FEATURE:
```

<223> OTHER INFORMATION: CPP

<400> SEQUENCE: 455

Met Val Lys Ser Lys Ile Gly Ser Trp Ile Leu Val Leu Phe Val Ala
1               5                   10                  15
Met Trp Ser Asp Val Gly Leu Cys Lys Lys Arg Pro Lys Pro
            20                  25                  30

<210> SEQ ID NO 456
<211> LENGTH: 38
<212> TYPE: PRT
<213> ORGANISM: Artificial Sequence
<220> FEATURE:
<223> OTHER INFORMATION: CPP

<400> SEQUENCE: 456

Leu Leu Gly Asp Phe Phe Arg Lys Ser Lys Glu Lys Ile Gly Lys Glu
1               5                   10                  15
Phe Lys Arg Ile Val Gln Arg Ile Lys Asp Phe Leu Arg Asn Leu Val
            20                  25                  30
Pro Arg Thr Glu Ser Cys
        35

<210> SEQ ID NO 457
<211> LENGTH: 23
<212> TYPE: PRT
<213> ORGANISM: Artificial Sequence
<220> FEATURE:
<223> OTHER INFORMATION: CPP

<400> SEQUENCE: 457

Gly Ile Gly Lys Phe Leu His Ser Ala Lys Lys Trp Gly Lys Ala Phe
1               5                   10                  15
Val Gly Gln Ile Met Asn Cys
            20

<210> SEQ ID NO 458
<211> LENGTH: 24
<212> TYPE: PRT
<213> ORGANISM: Artificial Sequence
<220> FEATURE:
<223> OTHER INFORMATION: CPP

<400> SEQUENCE: 458

Thr Arg Ser Ser Arg Ala Gly Leu Gln Trp Pro Val Gly Arg Val His
1               5                   10                  15
Arg Leu Leu Arg Lys Gly Gly Cys
            20

<210> SEQ ID NO 459
<211> LENGTH: 11
<212> TYPE: PRT
<213> ORGANISM: Artificial Sequence
<220> FEATURE:
<223> OTHER INFORMATION: CPP

<400> SEQUENCE: 459

Tyr Gly Arg Lys Lys Arg Arg Gln Arg Arg Arg
1               5                   10

<210> SEQ ID NO 460
<211> LENGTH: 61
<212> TYPE: PRT
<213> ORGANISM: Artificial Sequence

<220> FEATURE:
<223> OTHER INFORMATION: CPP

<400> SEQUENCE: 460

Glu Lys Arg Pro Arg Thr Ala Phe Ser Ser Glu Gln Leu Ala Arg Leu
1               5                   10                  15

Lys Arg Glu Phe Asn Glu Asn Arg Tyr Leu Thr Thr Glu Arg Arg Arg
            20                  25                  30

Gln Gln Leu Ser Ser Glu Leu Gly Leu Asn Glu Ala Gln Ile Lys Ile
        35                  40                  45

Trp Phe Gln Asn Lys Arg Ala Lys Ile Lys Lys Ser Thr
    50                  55                  60

<210> SEQ ID NO 461
<211> LENGTH: 13
<212> TYPE: PRT
<213> ORGANISM: Artificial Sequence
<220> FEATURE:
<223> OTHER INFORMATION: CPP

<400> SEQUENCE: 461

Gly Arg Arg Arg Arg Arg Arg Arg Arg Pro Pro Gln
1               5                   10

<210> SEQ ID NO 462
<211> LENGTH: 27
<212> TYPE: PRT
<213> ORGANISM: Artificial Sequence
<220> FEATURE:
<223> OTHER INFORMATION: CPP

<400> SEQUENCE: 462

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 463
<211> LENGTH: 27
<212> TYPE: PRT
<213> ORGANISM: Artificial Sequence
<220> FEATURE:
<223> OTHER INFORMATION: CPP

<400> SEQUENCE: 463

Gly Ala Leu Phe Leu Ala Phe Leu Ala Ala Ala Leu Ser Leu Met Gly
1               5                   10                  15

Leu Trp Ser Gln Pro Lys Lys Lys Arg Arg Val
            20                  25

<210> SEQ ID NO 464
<211> LENGTH: 10
<212> TYPE: PRT
<213> ORGANISM: Artificial Sequence
<220> FEATURE:
<223> OTHER INFORMATION: CPP

<400> SEQUENCE: 464

Met Leu Leu Leu Thr Arg Arg Arg Ser Thr
1               5                   10

<210> SEQ ID NO 465
<211> LENGTH: 9
<212> TYPE: PRT

```
<213> ORGANISM: Artificial Sequence
<220> FEATURE:
<223> OTHER INFORMATION: CPP

<400> SEQUENCE: 465

Cys Gly Asn Lys Arg Thr Arg Gly Cys
1               5

<210> SEQ ID NO 466
<211> LENGTH: 12
<212> TYPE: PRT
<213> ORGANISM: Artificial Sequence
<220> FEATURE:
<223> OTHER INFORMATION: CPP

<400> SEQUENCE: 466

Thr Ser Pro Leu Asn Ile His Asn Gly Gln Lys Leu
1               5                   10

<210> SEQ ID NO 467
<211> LENGTH: 16
<212> TYPE: PRT
<213> ORGANISM: Artificial Sequence
<220> FEATURE:
<223> OTHER INFORMATION: CPP

<400> SEQUENCE: 467

Gly Leu Arg Lys Arg Leu Arg Lys Phe Arg Asn Lys Ile Lys Glu Lys
1               5                   10                  15

<210> SEQ ID NO 468
<211> LENGTH: 27
<212> TYPE: PRT
<213> ORGANISM: Artificial Sequence
<220> FEATURE:
<223> OTHER INFORMATION: CPP

<400> SEQUENCE: 468

Gly Leu Leu Glu Ala Leu Ala Glu Leu Leu Glu Gly Leu Arg Lys Arg
1               5                   10                  15

Leu Arg Lys Phe Arg Asn Lys Ile Lys Glu Lys
            20                  25

<210> SEQ ID NO 469
<211> LENGTH: 13
<212> TYPE: PRT
<213> ORGANISM: Artificial Sequence
<220> FEATURE:
<223> OTHER INFORMATION: CPP

<400> SEQUENCE: 469

Cys Val Gln Trp Ser Leu Leu Arg Gly Tyr Gln Pro Cys
1               5                   10

<210> SEQ ID NO 470
<211> LENGTH: 16
<212> TYPE: PRT
<213> ORGANISM: Artificial Sequence
<220> FEATURE:
<223> OTHER INFORMATION: CPP

<400> SEQUENCE: 470

Arg Gln Ile Lys Ile Phe Phe Gln Asn Arg Arg Met Lys Trp Lys Lys
1               5                   10                  15

<210> SEQ ID NO 471
```

```
<211> LENGTH: 21
<212> TYPE: PRT
<213> ORGANISM: Artificial Sequence
<220> FEATURE:
<223> OTHER INFORMATION: CPP

<400> SEQUENCE: 471

Ala Ser Met Trp Glu Arg Val Lys Ser Ile Ile Lys Ser Ser Leu Ala
1               5                   10                  15

Ala Ala Ser Asn Ile
            20

<210> SEQ ID NO 472
<211> LENGTH: 21
<212> TYPE: PRT
<213> ORGANISM: Artificial Sequence
<220> FEATURE:
<223> OTHER INFORMATION: CPP

<400> SEQUENCE: 472

Ala Ser Met Trp Glu Arg Val Lys Ser Ile Ile Lys Ser Ser Leu Ala
1               5                   10                  15

Ala Ala Ser Asn Ile
            20

<210> SEQ ID NO 473
<211> LENGTH: 26
<212> TYPE: PRT
<213> ORGANISM: Artificial Sequence
<220> FEATURE:
<223> OTHER INFORMATION: CPP

<400> SEQUENCE: 473

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 474
<211> LENGTH: 16
<212> TYPE: PRT
<213> ORGANISM: Artificial Sequence
<220> FEATURE:
<223> OTHER INFORMATION: CPP

<400> SEQUENCE: 474

Cys Ser Ile Pro Pro Glu Val Lys Phe Asn Pro Phe Val Tyr Leu Ile
1               5                   10                  15

<210> SEQ ID NO 475
<211> LENGTH: 16
<212> TYPE: PRT
<213> ORGANISM: Artificial Sequence
<220> FEATURE:
<223> OTHER INFORMATION: CPP

<400> SEQUENCE: 475

Cys Ser Ile Pro Pro Glu Val Lys Phe Asn Pro Phe Val Tyr Leu Ile
1               5                   10                  15

<210> SEQ ID NO 476
<211> LENGTH: 6
<212> TYPE: PRT
<213> ORGANISM: Artificial Sequence
<220> FEATURE:
<223> OTHER INFORMATION: CPP
```

```
<400> SEQUENCE: 476

Pro Phe Val Tyr Leu Ile
1               5

<210> SEQ ID NO 477
<211> LENGTH: 8
<212> TYPE: PRT
<213> ORGANISM: Artificial Sequence
<220> FEATURE:
<223> OTHER INFORMATION: CPP

<400> SEQUENCE: 477

Asn Lys Pro Ile Leu Val Phe Tyr
1               5

<210> SEQ ID NO 478
<211> LENGTH: 14
<212> TYPE: PRT
<213> ORGANISM: Artificial Sequence
<220> FEATURE:
<223> OTHER INFORMATION: CPP

<400> SEQUENCE: 478

Tyr Lys Gln Cys His Lys Lys Gly Gly Lys Lys Gly Ser Gly
1               5                   10

<210> SEQ ID NO 479
<211> LENGTH: 15
<212> TYPE: PRT
<213> ORGANISM: Artificial Sequence
<220> FEATURE:
<223> OTHER INFORMATION: CPP
<220> FEATURE:
<221> NAME/KEY: misc_feature
<222> LOCATION: (10)..(10)
<223> OTHER INFORMATION: Xaa can be any naturally occurring amino acid

<400> SEQUENCE: 479

Tyr Lys Gln Cys His Lys Lys Gly Gly Xaa Lys Lys Gly Ser Gly
1               5                   10                  15

<210> SEQ ID NO 480
<211> LENGTH: 14
<212> TYPE: PRT
<213> ORGANISM: Artificial Sequence
<220> FEATURE:
<223> OTHER INFORMATION: CPP

<400> SEQUENCE: 480

Gly Ser Gly Lys Lys Gly Gly Lys Lys His Cys Gln Lys Tyr
1               5                   10

<210> SEQ ID NO 481
<211> LENGTH: 14
<212> TYPE: PRT
<213> ORGANISM: Artificial Sequence
<220> FEATURE:
<223> OTHER INFORMATION: CPP

<400> SEQUENCE: 481

Gly Ser Gly Lys Lys Gly Gly Lys Lys Ile Cys Gln Lys Tyr
1               5                   10

<210> SEQ ID NO 482
<211> LENGTH: 16
<212> TYPE: PRT
```

```
<213> ORGANISM: Artificial Sequence
<220> FEATURE:
<223> OTHER INFORMATION: CPP

<400> SEQUENCE: 482

Tyr Thr Ala Ile Ala Trp Val Lys Ala Phe Ile Arg Lys Leu Arg Lys
1               5                   10                  15

<210> SEQ ID NO 483
<211> LENGTH: 17
<212> TYPE: PRT
<213> ORGANISM: Artificial Sequence
<220> FEATURE:
<223> OTHER INFORMATION: CPP

<400> SEQUENCE: 483

Ile Ala Trp Val Lys Ala Phe Ile Arg Lys Leu Arg Lys Gly Pro Leu
1               5                   10                  15

Gly

<210> SEQ ID NO 484
<211> LENGTH: 23
<212> TYPE: PRT
<213> ORGANISM: Artificial Sequence
<220> FEATURE:
<223> OTHER INFORMATION: CPP

<400> SEQUENCE: 484

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 485
<211> LENGTH: 34
<212> TYPE: PRT
<213> ORGANISM: Artificial Sequence
<220> FEATURE:
<223> OTHER INFORMATION: CPP

<400> SEQUENCE: 485

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Ile Leu Lys
            20                  25                  30

Gly Lys

<210> SEQ ID NO 486
<211> LENGTH: 14
<212> TYPE: PRT
<213> ORGANISM: Artificial Sequence
<220> FEATURE:
<223> OTHER INFORMATION: CPP

<400> SEQUENCE: 486

Arg Leu Ser Gly Met Asn Glu Val Leu Ser Phe Arg Trp Leu
1               5                   10

<210> SEQ ID NO 487
<211> LENGTH: 13
<212> TYPE: PRT
<213> ORGANISM: Artificial Sequence
<220> FEATURE:
<223> OTHER INFORMATION: CPP
```

```
<400> SEQUENCE: 487

Gly Pro Phe His Phe Tyr Gln Phe Leu Phe Pro Pro Val
1               5                   10

<210> SEQ ID NO 488
<211> LENGTH: 13
<212> TYPE: PRT
<213> ORGANISM: Artificial Sequence
<220> FEATURE:
<223> OTHER INFORMATION: CPP

<400> SEQUENCE: 488

Gly Ser Pro Trp Gly Leu Gln His His Pro Pro Arg Thr
1               5                   10

<210> SEQ ID NO 489
<211> LENGTH: 41
<212> TYPE: PRT
<213> ORGANISM: Artificial Sequence
<220> FEATURE:
<223> OTHER INFORMATION: CPP

<400> SEQUENCE: 489

Ala Ala Val Ala Leu Leu Pro Ala Val Leu Leu Ala Leu Leu Ala Pro
1               5                   10                  15

Glu Ile Leu Leu Pro Asn Asn Tyr Asn Ala Tyr Glu Ser Tyr Lys Tyr
                20                  25                  30

Pro Gly Met Phe Ile Ala Leu Ser Lys
        35                  40

<210> SEQ ID NO 490
<211> LENGTH: 26
<212> TYPE: PRT
<213> ORGANISM: Artificial Sequence
<220> FEATURE:
<223> OTHER INFORMATION: CPP

<400> SEQUENCE: 490

Ala Ala Val Ala Leu Leu Pro Ala Val Leu Leu Ala Leu Leu Ala Pro
1               5                   10                  15

Val Gln Arg Lys Arg Gln Lys Leu Met Pro
                20                  25

<210> SEQ ID NO 491
<211> LENGTH: 23
<212> TYPE: PRT
<213> ORGANISM: Artificial Sequence
<220> FEATURE:
<223> OTHER INFORMATION: CPP

<400> SEQUENCE: 491

Met Gly Leu Gly Leu His Leu Leu Val Leu Ala Ala Ala Leu Gln Gly
1               5                   10                  15

Ala Lys Lys Lys Arg Lys Val
                20

<210> SEQ ID NO 492
<211> LENGTH: 30
<212> TYPE: PRT
<213> ORGANISM: Artificial Sequence
<220> FEATURE:
<223> OTHER INFORMATION: CPP

<400> SEQUENCE: 492
```

```
Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
                20                  25                  30

<210> SEQ ID NO 493
<211> LENGTH: 20
<212> TYPE: PRT
<213> ORGANISM: Artificial Sequence
<220> FEATURE:
<223> OTHER INFORMATION: CPP

<400> SEQUENCE: 493

Gly Leu Phe Glu Ala Leu Leu Glu Leu Leu Glu Ser Leu Trp Glu Leu
1               5                   10                  15

Leu Leu Glu Ala
                20

<210> SEQ ID NO 494
<211> LENGTH: 20
<212> TYPE: PRT
<213> ORGANISM: Artificial Sequence
<220> FEATURE:
<223> OTHER INFORMATION: CPP

<400> SEQUENCE: 494

Gly Leu Phe Lys Ala Leu Leu Lys Leu Leu Lys Ser Leu Trp Lys Leu
1               5                   10                  15

Leu Leu Lys Ala
                20

<210> SEQ ID NO 495
<211> LENGTH: 20
<212> TYPE: PRT
<213> ORGANISM: Artificial Sequence
<220> FEATURE:
<223> OTHER INFORMATION: CPP

<400> SEQUENCE: 495

Gly Leu Phe Arg Ala Leu Leu Arg Leu Leu Arg Ser Leu Trp Arg Leu
1               5                   10                  15

Leu Leu Arg Ala
                20

<210> SEQ ID NO 496
<211> LENGTH: 23
<212> TYPE: PRT
<213> ORGANISM: Artificial Sequence
<220> FEATURE:
<223> OTHER INFORMATION: CPP

<400> SEQUENCE: 496

Cys Gly Ala Tyr Asp Leu Arg Arg Arg Glu Arg Gln Ser Arg Leu Arg
1               5                   10                  15

Arg Arg Glu Arg Gln Ser Arg
                20

<210> SEQ ID NO 497
<211> LENGTH: 17
<212> TYPE: PRT
<213> ORGANISM: Artificial Sequence
<220> FEATURE:
<223> OTHER INFORMATION: CPP

<400> SEQUENCE: 497
```

-continued

```
Arg Lys Lys Arg Arg Arg Glu Ser Arg Lys Lys Arg Arg Arg Glu Ser
1               5                   10                  15

Cys

<210> SEQ ID NO 498
<211> LENGTH: 19
<212> TYPE: PRT
<213> ORGANISM: Artificial Sequence
<220> FEATURE:
<223> OTHER INFORMATION: CPP

<400> SEQUENCE: 498

Cys Val Lys Arg Gly Leu Lys Leu Arg His Val Arg Pro Arg Val Thr
1               5                   10                  15

Arg Asp Val

<210> SEQ ID NO 499
<211> LENGTH: 17
<212> TYPE: PRT
<213> ORGANISM: Artificial Sequence
<220> FEATURE:
<223> OTHER INFORMATION: CPP

<400> SEQUENCE: 499

Cys Arg Gln Ile Lys Ile Trp Phe Gln Asn Arg Arg Met Lys Trp Lys
1               5                   10                  15

Lys

<210> SEQ ID NO 500
<211> LENGTH: 15
<212> TYPE: PRT
<213> ORGANISM: Artificial Sequence
<220> FEATURE:
<223> OTHER INFORMATION: CPP

<400> SEQUENCE: 500

Pro Pro Lys Lys Ser Ala Gln Cys Leu Arg Tyr Lys Lys Pro Glu
1               5                   10                  15

<210> SEQ ID NO 501
<211> LENGTH: 15
<212> TYPE: PRT
<213> ORGANISM: Artificial Sequence
<220> FEATURE:
<223> OTHER INFORMATION: CPP

<400> SEQUENCE: 501

Asp Pro Val Asp Thr Pro Asn Pro Thr Arg Arg Lys Pro Gly Lys
1               5                   10                  15

<210> SEQ ID NO 502
<211> LENGTH: 13
<212> TYPE: PRT
<213> ORGANISM: Artificial Sequence
<220> FEATURE:
<223> OTHER INFORMATION: CPP

<400> SEQUENCE: 502

Lys Arg Val Ser Arg Asn Lys Ser Glu Lys Lys Arg Arg
1               5                   10

<210> SEQ ID NO 503
<211> LENGTH: 16
<212> TYPE: PRT
```

-continued

```
<213> ORGANISM: Artificial Sequence
<220> FEATURE:
<223> OTHER INFORMATION: CPP

<400> SEQUENCE: 503

Gly Arg Arg His His Cys Arg Ser Lys Ala Lys Arg Ser Arg His His
1               5                   10                  15

<210> SEQ ID NO 504
<211> LENGTH: 16
<212> TYPE: PRT
<213> ORGANISM: Artificial Sequence
<220> FEATURE:
<223> OTHER INFORMATION: CPP

<400> SEQUENCE: 504

Ser Ala Arg His His Cys Arg Ser Lys Ala Lys Arg Ser Arg His His
1               5                   10                  15

<210> SEQ ID NO 505
<211> LENGTH: 16
<212> TYPE: PRT
<213> ORGANISM: Artificial Sequence
<220> FEATURE:
<223> OTHER INFORMATION: CPP

<400> SEQUENCE: 505

Ser Arg Ala His His Cys Arg Ser Lys Ala Lys Arg Ser Arg His His
1               5                   10                  15

<210> SEQ ID NO 506
<211> LENGTH: 16
<212> TYPE: PRT
<213> ORGANISM: Artificial Sequence
<220> FEATURE:
<223> OTHER INFORMATION: CPP

<400> SEQUENCE: 506

Ser Arg Arg Ala His Cys Arg Ser Lys Ala Lys Arg Ser Arg His His
1               5                   10                  15

<210> SEQ ID NO 507
<211> LENGTH: 16
<212> TYPE: PRT
<213> ORGANISM: Artificial Sequence
<220> FEATURE:
<223> OTHER INFORMATION: CPP

<400> SEQUENCE: 507

Ser Arg Arg His Ala Cys Arg Ser Lys Ala Lys Arg Ser Arg His His
1               5                   10                  15

<210> SEQ ID NO 508
<211> LENGTH: 16
<212> TYPE: PRT
<213> ORGANISM: Artificial Sequence
<220> FEATURE:
<223> OTHER INFORMATION: CPP

<400> SEQUENCE: 508

Ser Arg Arg His His Ala Arg Ser Lys Ala Lys Arg Ser Arg His His
1               5                   10                  15

<210> SEQ ID NO 509
<211> LENGTH: 16
<212> TYPE: PRT
<213> ORGANISM: Artificial Sequence
```

<220> FEATURE:
<223> OTHER INFORMATION: CPP

<400> SEQUENCE: 509

Ser Arg Arg His His Cys Arg Ala Lys Ala Lys Arg Ser Arg His His
1               5                   10                  15

<210> SEQ ID NO 510
<211> LENGTH: 16
<212> TYPE: PRT
<213> ORGANISM: Artificial Sequence
<220> FEATURE:
<223> OTHER INFORMATION: CPP

<400> SEQUENCE: 510

Ser Arg Arg His His Cys Arg Ser Ala Ala Lys Arg Ser Arg His His
1               5                   10                  15

<210> SEQ ID NO 511
<211> LENGTH: 16
<212> TYPE: PRT
<213> ORGANISM: Artificial Sequence
<220> FEATURE:
<223> OTHER INFORMATION: CPP

<400> SEQUENCE: 511

Ser Arg Arg His His Cys Arg Ser Lys Ala Ala Arg Ser Arg His His
1               5                   10                  15

<210> SEQ ID NO 512
<211> LENGTH: 16
<212> TYPE: PRT
<213> ORGANISM: Artificial Sequence
<220> FEATURE:
<223> OTHER INFORMATION: CPP

<400> SEQUENCE: 512

Ser Arg Arg His His Cys Arg Ser Lys Ala Lys Ala Ser Arg His His
1               5                   10                  15

<210> SEQ ID NO 513
<211> LENGTH: 16
<212> TYPE: PRT
<213> ORGANISM: Artificial Sequence
<220> FEATURE:
<223> OTHER INFORMATION: CPP

<400> SEQUENCE: 513

Ser Arg Arg His His Cys Arg Ser Lys Ala Lys Arg Ala Arg His His
1               5                   10                  15

<210> SEQ ID NO 514
<211> LENGTH: 16
<212> TYPE: PRT
<213> ORGANISM: Artificial Sequence
<220> FEATURE:
<223> OTHER INFORMATION: CPP

<400> SEQUENCE: 514

Ser Arg Arg His His Cys Arg Ser Lys Ala Lys Arg Ser Ala His His
1               5                   10                  15

<210> SEQ ID NO 515
<211> LENGTH: 13
<212> TYPE: PRT
<213> ORGANISM: Artificial Sequence
<220> FEATURE:

```
<223> OTHER INFORMATION: CPP

<400> SEQUENCE: 515

Arg Arg His His Cys Arg Ser Lys Ala Lys Arg Ser Arg
1               5                   10

<210> SEQ ID NO 516
<211> LENGTH: 12
<212> TYPE: PRT
<213> ORGANISM: Artificial Sequence
<220> FEATURE:
<223> OTHER INFORMATION: CPP

<400> SEQUENCE: 516

Gly Arg Lys Gly Lys His Lys Arg Lys Lys Leu Pro
1               5                   10

<210> SEQ ID NO 517
<211> LENGTH: 10
<212> TYPE: PRT
<213> ORGANISM: Artificial Sequence
<220> FEATURE:
<223> OTHER INFORMATION: CPP

<400> SEQUENCE: 517

Gly Lys Lys Lys Lys Lys Lys Lys Lys
1               5                   10

<210> SEQ ID NO 518
<211> LENGTH: 18
<212> TYPE: PRT
<213> ORGANISM: Artificial Sequence
<220> FEATURE:
<223> OTHER INFORMATION: CPP

<400> SEQUENCE: 518

Gly Lys Arg Val Ala Lys Arg Lys Leu Ile Glu Gln Asn Arg Glu Arg
1               5                   10                  15

Arg Arg

<210> SEQ ID NO 519
<211> LENGTH: 18
<212> TYPE: PRT
<213> ORGANISM: Artificial Sequence
<220> FEATURE:
<223> OTHER INFORMATION: CPP

<400> SEQUENCE: 519

Gly Arg Lys Leu Lys Lys Lys Asn Glu Lys Glu Asp Lys Arg Pro
1               5                   10                  15

Arg Thr

<210> SEQ ID NO 520
<211> LENGTH: 17
<212> TYPE: PRT
<213> ORGANISM: Artificial Sequence
<220> FEATURE:
<223> OTHER INFORMATION: CPP

<400> SEQUENCE: 520

Gly Lys Lys Thr Asn Leu Phe Ser Ala Leu Ile Lys Lys Lys Thr
1               5                   10                  15

Ala
```

```
<210> SEQ ID NO 521
<211> LENGTH: 18
<212> TYPE: PRT
<213> ORGANISM: Artificial Sequence
<220> FEATURE:
<223> OTHER INFORMATION: CPP

<400> SEQUENCE: 521

Gly Arg Arg Glu Arg Asn Lys Met Ala Ala Lys Cys Arg Asn Arg
1               5                   10                  15

Arg Arg

<210> SEQ ID NO 522
<211> LENGTH: 18
<212> TYPE: PRT
<213> ORGANISM: Artificial Sequence
<220> FEATURE:
<223> OTHER INFORMATION: CPP

<400> SEQUENCE: 522

Gly Lys Arg Ala Arg Asn Thr Glu Ala Ala Arg Arg Ser Arg Ala Arg
1               5                   10                  15

Lys Leu

<210> SEQ ID NO 523
<211> LENGTH: 14
<212> TYPE: PRT
<213> ORGANISM: Artificial Sequence
<220> FEATURE:
<223> OTHER INFORMATION: CPP

<400> SEQUENCE: 523

Gly Arg Arg Arg Arg Ala Thr Ala Lys Tyr Arg Thr Ala His
1               5                   10

<210> SEQ ID NO 524
<211> LENGTH: 15
<212> TYPE: PRT
<213> ORGANISM: Artificial Sequence
<220> FEATURE:
<223> OTHER INFORMATION: CPP

<400> SEQUENCE: 524

Gly Lys Arg Arg Arg Arg Ala Thr Ala Lys Tyr Arg Ser Ala His
1               5                   10                  15

<210> SEQ ID NO 525
<211> LENGTH: 12
<212> TYPE: PRT
<213> ORGANISM: Artificial Sequence
<220> FEATURE:
<223> OTHER INFORMATION: CPP

<400> SEQUENCE: 525

Gly Arg Arg Arg Arg Lys Arg Leu Ser His Arg Thr
1               5                   10

<210> SEQ ID NO 526
<211> LENGTH: 10
<212> TYPE: PRT
<213> ORGANISM: Artificial Sequence
<220> FEATURE:
<223> OTHER INFORMATION: CPP

<400> SEQUENCE: 526

Gly Arg Arg Arg Arg Arg Glu Arg Asn Lys
```

<210> SEQ ID NO 527
<211> LENGTH: 16
<212> TYPE: PRT
<213> ORGANISM: Artificial Sequence
<220> FEATURE:
<223> OTHER INFORMATION: CPP

<400> SEQUENCE: 527

Gly Lys His Arg His Glu Arg Gly His His Arg Asp Arg Arg Glu Arg
1               5                   10                  15

<210> SEQ ID NO 528
<211> LENGTH: 17
<212> TYPE: PRT
<213> ORGANISM: Artificial Sequence
<220> FEATURE:
<223> OTHER INFORMATION: CPP

<400> SEQUENCE: 528

Gly Lys Lys Lys Arg Lys Leu Ser Asn Arg Glu Ser Ala Lys Arg Ser
1               5                   10                  15

Arg

<210> SEQ ID NO 529
<211> LENGTH: 10
<212> TYPE: PRT
<213> ORGANISM: Artificial Sequence
<220> FEATURE:
<223> OTHER INFORMATION: CPP

<400> SEQUENCE: 529

Met Ile Ile Tyr Arg Asp Leu Ile Ser His
1               5                   10

<210> SEQ ID NO 530
<211> LENGTH: 9
<212> TYPE: PRT
<213> ORGANISM: Artificial Sequence
<220> FEATURE:
<223> OTHER INFORMATION: CPP

<400> SEQUENCE: 530

Met Ile Ile Tyr Arg Asp Leu Ile Ser
1               5

<210> SEQ ID NO 531
<211> LENGTH: 8
<212> TYPE: PRT
<213> ORGANISM: Artificial Sequence
<220> FEATURE:
<223> OTHER INFORMATION: CPP

<400> SEQUENCE: 531

Met Ile Ile Tyr Arg Asp Leu Ile
1               5

<210> SEQ ID NO 532
<211> LENGTH: 9
<212> TYPE: PRT
<213> ORGANISM: Artificial Sequence
<220> FEATURE:
<223> OTHER INFORMATION: CPP

<400> SEQUENCE: 532

Ile Ile Tyr Arg Asp Leu Ile Ser His
1               5

<210> SEQ ID NO 533
<211> LENGTH: 7
<212> TYPE: PRT
<213> ORGANISM: Artificial Sequence
<220> FEATURE:
<223> OTHER INFORMATION: CPP

<400> SEQUENCE: 533

Met Ile Ile Tyr Arg Asp Leu
1               5

<210> SEQ ID NO 534
<211> LENGTH: 6
<212> TYPE: PRT
<213> ORGANISM: Artificial Sequence
<220> FEATURE:
<223> OTHER INFORMATION: CPP

<400> SEQUENCE: 534

Met Ile Ile Tyr Arg Asp
1               5

<210> SEQ ID NO 535
<211> LENGTH: 8
<212> TYPE: PRT
<213> ORGANISM: Artificial Sequence
<220> FEATURE:
<223> OTHER INFORMATION: CPP

<400> SEQUENCE: 535

Ile Tyr Arg Asp Leu Ile Ser His
1               5

<210> SEQ ID NO 536
<211> LENGTH: 9
<212> TYPE: PRT
<213> ORGANISM: Artificial Sequence
<220> FEATURE:
<223> OTHER INFORMATION: CPP

<400> SEQUENCE: 536

Ala Ile Ile Tyr Arg Asp Leu Ile Ser
1               5

<210> SEQ ID NO 537
<211> LENGTH: 9
<212> TYPE: PRT
<213> ORGANISM: Artificial Sequence
<220> FEATURE:
<223> OTHER INFORMATION: CPP

<400> SEQUENCE: 537

Met Ala Ile Tyr Arg Asp Leu Ile Ser
1               5

<210> SEQ ID NO 538
<211> LENGTH: 9
<212> TYPE: PRT
<213> ORGANISM: Artificial Sequence
<220> FEATURE:
<223> OTHER INFORMATION: CPP

<400> SEQUENCE: 538

Met Ile Ala Tyr Arg Asp Leu Ile Ser

```
1               5

<210> SEQ ID NO 539
<211> LENGTH: 9
<212> TYPE: PRT
<213> ORGANISM: Artificial Sequence
<220> FEATURE:
<223> OTHER INFORMATION: CPP

<400> SEQUENCE: 539

Met Ile Ile Ala Arg Asp Leu Ile Ser
1               5

<210> SEQ ID NO 540
<211> LENGTH: 9
<212> TYPE: PRT
<213> ORGANISM: Artificial Sequence
<220> FEATURE:
<223> OTHER INFORMATION: CPP

<400> SEQUENCE: 540

Met Ile Ile Tyr Ala Asp Leu Ile Ser
1               5

<210> SEQ ID NO 541
<211> LENGTH: 9
<212> TYPE: PRT
<213> ORGANISM: Artificial Sequence
<220> FEATURE:
<223> OTHER INFORMATION: CPP

<400> SEQUENCE: 541

Met Ile Ile Tyr Arg Ala Leu Ile Ser
1               5

<210> SEQ ID NO 542
<211> LENGTH: 9
<212> TYPE: PRT
<213> ORGANISM: Artificial Sequence
<220> FEATURE:
<223> OTHER INFORMATION: CPP

<400> SEQUENCE: 542

Met Ile Ile Tyr Arg Asp Ala Ile Ser
1               5

<210> SEQ ID NO 543
<211> LENGTH: 9
<212> TYPE: PRT
<213> ORGANISM: Artificial Sequence
<220> FEATURE:
<223> OTHER INFORMATION: CPP

<400> SEQUENCE: 543

Met Ile Ile Tyr Arg Asp Leu Ala Ser
1               5

<210> SEQ ID NO 544
<211> LENGTH: 9
<212> TYPE: PRT
<213> ORGANISM: Artificial Sequence
<220> FEATURE:
<223> OTHER INFORMATION: CPP

<400> SEQUENCE: 544

Met Ile Ile Tyr Arg Asp Leu Ile Ala
1               5
```

```
<210> SEQ ID NO 545
<211> LENGTH: 11
<212> TYPE: PRT
<213> ORGANISM: Artificial Sequence
<220> FEATURE:
<223> OTHER INFORMATION: CPP

<400> SEQUENCE: 545

Met Ile Ile Tyr Arg Asp Leu Ile Ser Lys Lys
1               5                   10

<210> SEQ ID NO 546
<211> LENGTH: 10
<212> TYPE: PRT
<213> ORGANISM: Artificial Sequence
<220> FEATURE:
<223> OTHER INFORMATION: CPP

<400> SEQUENCE: 546

Met Ile Ile Tyr Arg Asp Lys Lys Ser His
1               5                   10

<210> SEQ ID NO 547
<211> LENGTH: 10
<212> TYPE: PRT
<213> ORGANISM: Artificial Sequence
<220> FEATURE:
<223> OTHER INFORMATION: CPP

<400> SEQUENCE: 547

Met Ile Ile Phe Arg Asp Leu Ile Ser His
1               5                   10

<210> SEQ ID NO 548
<211> LENGTH: 10
<212> TYPE: PRT
<213> ORGANISM: Artificial Sequence
<220> FEATURE:
<223> OTHER INFORMATION: CPP

<400> SEQUENCE: 548

Met Ile Ile Ser Arg Asp Leu Ile Ser His
1               5                   10

<210> SEQ ID NO 549
<211> LENGTH: 10
<212> TYPE: PRT
<213> ORGANISM: Artificial Sequence
<220> FEATURE:
<223> OTHER INFORMATION: CPP

<400> SEQUENCE: 549

Gln Ile Ile Ser Arg Asp Leu Ile Ser His
1               5                   10

<210> SEQ ID NO 550
<211> LENGTH: 10
<212> TYPE: PRT
<213> ORGANISM: Artificial Sequence
<220> FEATURE:
<223> OTHER INFORMATION: CPP

<400> SEQUENCE: 550

Cys Ile Ile Ser Arg Asp Leu Ile Ser His
1               5                   10
```

```
<210> SEQ ID NO 551
<211> LENGTH: 12
<212> TYPE: PRT
<213> ORGANISM: Artificial Sequence
<220> FEATURE:
<223> OTHER INFORMATION: CPP

<400> SEQUENCE: 551

Met Ile Ile Tyr Arg Ala Leu Ile Ser His Lys Lys
1               5                   10

<210> SEQ ID NO 552
<211> LENGTH: 12
<212> TYPE: PRT
<213> ORGANISM: Artificial Sequence
<220> FEATURE:
<223> OTHER INFORMATION: CPP

<400> SEQUENCE: 552

Met Ile Ile Tyr Arg Ile Ala Ala Ser His Lys Lys
1               5                   10

<210> SEQ ID NO 553
<211> LENGTH: 10
<212> TYPE: PRT
<213> ORGANISM: Artificial Sequence
<220> FEATURE:
<223> OTHER INFORMATION: CPP

<400> SEQUENCE: 553

Met Ile Ile Arg Arg Asp Leu Ile Ser Glu
1               5                   10

<210> SEQ ID NO 554
<211> LENGTH: 10
<212> TYPE: PRT
<213> ORGANISM: Artificial Sequence
<220> FEATURE:
<223> OTHER INFORMATION: CPP

<400> SEQUENCE: 554

Met Ile Ile Tyr Arg Ala Glu Ile Ser His
1               5                   10

<210> SEQ ID NO 555
<211> LENGTH: 10
<212> TYPE: PRT
<213> ORGANISM: Artificial Sequence
<220> FEATURE:
<223> OTHER INFORMATION: CPP

<400> SEQUENCE: 555

Met Ile Ile Tyr Ala Arg Arg Ala Glu Glu
1               5                   10

<210> SEQ ID NO 556
<211> LENGTH: 12
<212> TYPE: PRT
<213> ORGANISM: Artificial Sequence
<220> FEATURE:
<223> OTHER INFORMATION: CPP

<400> SEQUENCE: 556

Met Ile Ile Phe Arg Ile Ala Ala Ser His Lys Lys
1               5                   10
```

```
<210> SEQ ID NO 557
<211> LENGTH: 12
<212> TYPE: PRT
<213> ORGANISM: Artificial Sequence
<220> FEATURE:
<223> OTHER INFORMATION: CPP

<400> SEQUENCE: 557

Met Ile Ile Phe Arg Ala Leu Ile Ser His Lys Lys
1               5                   10

<210> SEQ ID NO 558
<211> LENGTH: 12
<212> TYPE: PRT
<213> ORGANISM: Artificial Sequence
<220> FEATURE:
<223> OTHER INFORMATION: CPP

<400> SEQUENCE: 558

Met Ile Ile Phe Arg Ala Ala Ala Ser His Lys Lys
1               5                   10

<210> SEQ ID NO 559
<211> LENGTH: 12
<212> TYPE: PRT
<213> ORGANISM: Artificial Sequence
<220> FEATURE:
<223> OTHER INFORMATION: CPP

<400> SEQUENCE: 559

Phe Ile Ile Phe Arg Ile Ala Ala Ser His Lys Lys
1               5                   10

<210> SEQ ID NO 560
<211> LENGTH: 12
<212> TYPE: PRT
<213> ORGANISM: Artificial Sequence
<220> FEATURE:
<223> OTHER INFORMATION: CPP

<400> SEQUENCE: 560

Leu Ile Ile Phe Arg Ile Ala Ala Ser His Lys Lys
1               5                   10

<210> SEQ ID NO 561
<211> LENGTH: 12
<212> TYPE: PRT
<213> ORGANISM: Artificial Sequence
<220> FEATURE:
<223> OTHER INFORMATION: CPP

<400> SEQUENCE: 561

Trp Ile Ile Phe Arg Ile Ala Ala Ser His Lys Lys
1               5                   10

<210> SEQ ID NO 562
<211> LENGTH: 12
<212> TYPE: PRT
<213> ORGANISM: Artificial Sequence
<220> FEATURE:
<223> OTHER INFORMATION: CPP

<400> SEQUENCE: 562

Trp Ile Ile Phe Arg Ala Ala Ala Ser His Lys Lys
1               5                   10

<210> SEQ ID NO 563
```

```
<211> LENGTH: 12
<212> TYPE: PRT
<213> ORGANISM: Artificial Sequence
<220> FEATURE:
<223> OTHER INFORMATION: CPP

<400> SEQUENCE: 563

Trp Ile Ile Phe Arg Ala Leu Ile Ser His Lys Lys
1               5                   10

<210> SEQ ID NO 564
<211> LENGTH: 12
<212> TYPE: PRT
<213> ORGANISM: Artificial Sequence
<220> FEATURE:
<223> OTHER INFORMATION: CPP

<400> SEQUENCE: 564

Met Ile Ile Phe Arg Ile Ala Ala Tyr His Lys Lys
1               5                   10

<210> SEQ ID NO 565
<211> LENGTH: 12
<212> TYPE: PRT
<213> ORGANISM: Artificial Sequence
<220> FEATURE:
<223> OTHER INFORMATION: CPP

<400> SEQUENCE: 565

Trp Ile Ile Phe Arg Ile Ala Ala Tyr His Lys Lys
1               5                   10

<210> SEQ ID NO 566
<211> LENGTH: 12
<212> TYPE: PRT
<213> ORGANISM: Artificial Sequence
<220> FEATURE:
<223> OTHER INFORMATION: CPP

<400> SEQUENCE: 566

Met Ile Ile Phe Arg Ile Ala Ala Thr His Lys Lys
1               5                   10

<210> SEQ ID NO 567
<211> LENGTH: 12
<212> TYPE: PRT
<213> ORGANISM: Artificial Sequence
<220> FEATURE:
<223> OTHER INFORMATION: CPP

<400> SEQUENCE: 567

Trp Ile Ile Phe Arg Ile Ala Ala Thr His Lys Lys
1               5                   10

<210> SEQ ID NO 568
<211> LENGTH: 12
<212> TYPE: PRT
<213> ORGANISM: Artificial Sequence
<220> FEATURE:
<223> OTHER INFORMATION: CPP

<400> SEQUENCE: 568

Met Ile Ile Phe Lys Ile Ala Ala Ser His Lys Lys
1               5                   10

<210> SEQ ID NO 569
<211> LENGTH: 12
```

```
<212> TYPE: PRT
<213> ORGANISM: Artificial Sequence
<220> FEATURE:
<223> OTHER INFORMATION: CPP

<400> SEQUENCE: 569

Trp Ile Ile Phe Lys Ile Ala Ala Ser His Lys Lys
1               5                   10

<210> SEQ ID NO 570
<211> LENGTH: 12
<212> TYPE: PRT
<213> ORGANISM: Artificial Sequence
<220> FEATURE:
<223> OTHER INFORMATION: CPP

<400> SEQUENCE: 570

Met Ile Ile Phe Ala Ile Ala Ala Ser His Lys Lys
1               5                   10

<210> SEQ ID NO 571
<211> LENGTH: 12
<212> TYPE: PRT
<213> ORGANISM: Artificial Sequence
<220> FEATURE:
<223> OTHER INFORMATION: CPP

<400> SEQUENCE: 571

Leu Ile Ile Phe Arg Ile Leu Ile Ser His Lys Lys
1               5                   10

<210> SEQ ID NO 572
<211> LENGTH: 12
<212> TYPE: PRT
<213> ORGANISM: Artificial Sequence
<220> FEATURE:
<223> OTHER INFORMATION: CPP

<400> SEQUENCE: 572

Met Ile Ile Phe Arg Ile Leu Ile Ser His Lys Lys
1               5                   10

<210> SEQ ID NO 573
<211> LENGTH: 12
<212> TYPE: PRT
<213> ORGANISM: Artificial Sequence
<220> FEATURE:
<223> OTHER INFORMATION: CPP

<400> SEQUENCE: 573

Leu Ile Ile Phe Arg Ile Leu Ile Ser His Arg Arg
1               5                   10

<210> SEQ ID NO 574
<211> LENGTH: 12
<212> TYPE: PRT
<213> ORGANISM: Artificial Sequence
<220> FEATURE:
<223> OTHER INFORMATION: CPP

<400> SEQUENCE: 574

Leu Ile Ile Phe Arg Ile Leu Ile Ser His His His
1               5                   10

<210> SEQ ID NO 575
<211> LENGTH: 11
<212> TYPE: PRT
```

```
<213> ORGANISM: Artificial Sequence
<220> FEATURE:
<223> OTHER INFORMATION: CPP

<400> SEQUENCE: 575

Leu Ile Ile Phe Arg Ile Leu Ile Ser His Lys
1               5                   10

<210> SEQ ID NO 576
<211> LENGTH: 11
<212> TYPE: PRT
<213> ORGANISM: Artificial Sequence
<220> FEATURE:
<223> OTHER INFORMATION: CPP

<400> SEQUENCE: 576

Leu Ile Ile Phe Arg Ile Leu Ile Ser His Arg
1               5                   10

<210> SEQ ID NO 577
<211> LENGTH: 10
<212> TYPE: PRT
<213> ORGANISM: Artificial Sequence
<220> FEATURE:
<223> OTHER INFORMATION: CPP

<400> SEQUENCE: 577

Leu Ile Ile Phe Arg Ile Leu Ile Ser His
1               5                   10

<210> SEQ ID NO 578
<211> LENGTH: 12
<212> TYPE: PRT
<213> ORGANISM: Artificial Sequence
<220> FEATURE:
<223> OTHER INFORMATION: CPP

<400> SEQUENCE: 578

Leu Ile Ile Phe Ala Ile Ala Ala Ser His Lys Lys
1               5                   10

<210> SEQ ID NO 579
<211> LENGTH: 12
<212> TYPE: PRT
<213> ORGANISM: Artificial Sequence
<220> FEATURE:
<223> OTHER INFORMATION: CPP

<400> SEQUENCE: 579

Leu Ile Ile Phe Ala Ile Leu Ile Ser His Lys Lys
1               5                   10

<210> SEQ ID NO 580
<211> LENGTH: 20
<212> TYPE: PRT
<213> ORGANISM: Artificial Sequence
<220> FEATURE:
<223> OTHER INFORMATION: CPP

<400> SEQUENCE: 580

Arg Ile Leu Gln Gln Leu Leu Phe Ile His Phe Arg Ile Gly Cys Arg
1               5                   10                  15

His Ser Arg Ile
            20

<210> SEQ ID NO 581
```

```
<211> LENGTH: 17
<212> TYPE: PRT
<213> ORGANISM: Artificial Sequence
<220> FEATURE:
<223> OTHER INFORMATION: CPP

<400> SEQUENCE: 581

Arg Ile Leu Gln Gln Leu Leu Phe Ile His Phe Arg Ile Gly Cys Arg
1               5                   10                  15

His

<210> SEQ ID NO 582
<211> LENGTH: 15
<212> TYPE: PRT
<213> ORGANISM: Artificial Sequence
<220> FEATURE:
<223> OTHER INFORMATION: CPP

<400> SEQUENCE: 582

Arg Ile Leu Gln Gln Leu Leu Phe Ile His Phe Arg Ile Gly Cys
1               5                   10                  15

<210> SEQ ID NO 583
<211> LENGTH: 10
<212> TYPE: PRT
<213> ORGANISM: Artificial Sequence
<220> FEATURE:
<223> OTHER INFORMATION: CPP

<400> SEQUENCE: 583

Arg Ile Phe Ile His Phe Arg Ile Gly Cys
1               5                   10

<210> SEQ ID NO 584
<211> LENGTH: 8
<212> TYPE: PRT
<213> ORGANISM: Artificial Sequence
<220> FEATURE:
<223> OTHER INFORMATION: CPP

<400> SEQUENCE: 584

Arg Ile Phe Ile Arg Ile Gly Cys
1               5

<210> SEQ ID NO 585
<211> LENGTH: 11
<212> TYPE: PRT
<213> ORGANISM: Artificial Sequence
<220> FEATURE:
<223> OTHER INFORMATION: CPP

<400> SEQUENCE: 585

Arg Ile Leu Gln Gln Leu Leu Phe Ile His Phe
1               5                   10

<210> SEQ ID NO 586
<211> LENGTH: 6
<212> TYPE: PRT
<213> ORGANISM: Artificial Sequence
<220> FEATURE:
<223> OTHER INFORMATION: CPP

<400> SEQUENCE: 586

Arg Ile Phe Ile Gly Cys
1               5
```

```
<210> SEQ ID NO 587
<211> LENGTH: 6
<212> TYPE: PRT
<213> ORGANISM: Artificial Sequence
<220> FEATURE:
<223> OTHER INFORMATION: CPP

<400> SEQUENCE: 587

Phe Ile Arg Ile Gly Cys
1               5

<210> SEQ ID NO 588
<211> LENGTH: 22
<212> TYPE: PRT
<213> ORGANISM: Artificial Sequence
<220> FEATURE:
<223> OTHER INFORMATION: CPP

<400> SEQUENCE: 588

Asp Thr Trp Ala Gly Val Glu Ala Ile Ile Arg Ile Leu Gln Gln Leu
1               5                   10                  15

Leu Phe Ile His Phe Arg
            20

<210> SEQ ID NO 589
<211> LENGTH: 5
<212> TYPE: PRT
<213> ORGANISM: Artificial Sequence
<220> FEATURE:
<223> OTHER INFORMATION: CPP

<400> SEQUENCE: 589

Ile Gly Cys Arg His
1               5

<210> SEQ ID NO 590
<211> LENGTH: 23
<212> TYPE: PRT
<213> ORGANISM: Artificial Sequence
<220> FEATURE:
<223> OTHER INFORMATION: CPP

<400> SEQUENCE: 590

Gly Tyr Gly Arg Lys Lys Arg Arg Gly Arg Arg Thr His Arg Leu
1               5                   10                  15

Pro Arg Arg Arg Arg Arg Arg
            20

<210> SEQ ID NO 591
<211> LENGTH: 12
<212> TYPE: PRT
<213> ORGANISM: Artificial Sequence
<220> FEATURE:
<223> OTHER INFORMATION: CPP

<400> SEQUENCE: 591

Lys Arg Ile Ile Gln Arg Ile Leu Ser Arg Asn Ser
1               5                   10

<210> SEQ ID NO 592
<211> LENGTH: 12
<212> TYPE: PRT
<213> ORGANISM: Artificial Sequence
<220> FEATURE:
<223> OTHER INFORMATION: CPP

<400> SEQUENCE: 592
```

```
Lys Arg Ile His Pro Arg Leu Thr Arg Ser Ile Arg
1               5                   10
```

<210> SEQ ID NO 593
<211> LENGTH: 12
<212> TYPE: PRT
<213> ORGANISM: Artificial Sequence
<220> FEATURE:
<223> OTHER INFORMATION: CPP

<400> SEQUENCE: 593

```
Pro Pro Arg Leu Arg Lys Arg Arg Gln Leu Asn Met
1               5                   10
```

<210> SEQ ID NO 594
<211> LENGTH: 12
<212> TYPE: PRT
<213> ORGANISM: Artificial Sequence
<220> FEATURE:
<223> OTHER INFORMATION: CPP

<400> SEQUENCE: 594

```
Met His Lys Arg Pro Thr Thr Pro Ser Arg Lys Met
1               5                   10
```

<210> SEQ ID NO 595
<211> LENGTH: 12
<212> TYPE: PRT
<213> ORGANISM: Artificial Sequence
<220> FEATURE:
<223> OTHER INFORMATION: CPP

<400> SEQUENCE: 595

```
Arg Gln Arg Ser Arg Arg Arg Pro Leu Asn Ile Arg
1               5                   10
```

<210> SEQ ID NO 596
<211> LENGTH: 12
<212> TYPE: PRT
<213> ORGANISM: Artificial Sequence
<220> FEATURE:
<223> OTHER INFORMATION: CPP

<400> SEQUENCE: 596

```
Arg Ile Arg Met Ile Gln Asn Leu Ile Lys Lys Thr
1               5                   10
```

<210> SEQ ID NO 597
<211> LENGTH: 12
<212> TYPE: PRT
<213> ORGANISM: Artificial Sequence
<220> FEATURE:
<223> OTHER INFORMATION: CPP

<400> SEQUENCE: 597

```
Ser Arg Arg Lys Arg Gln Arg Ser Asn Met Arg Ile
1               5                   10
```

<210> SEQ ID NO 598
<211> LENGTH: 12
<212> TYPE: PRT
<213> ORGANISM: Artificial Sequence
<220> FEATURE:
<223> OTHER INFORMATION: CPP

<400> SEQUENCE: 598

```
Gln Arg Ile Arg Lys Ser Lys Ile Ser Arg Thr Leu
1               5                   10
```

<210> SEQ ID NO 599
<211> LENGTH: 12
<212> TYPE: PRT
<213> ORGANISM: Artificial Sequence
<220> FEATURE:
<223> OTHER INFORMATION: CPP

<400> SEQUENCE: 599

```
Pro Ser Lys Arg Leu Leu His Asn Asn Leu Arg Arg
1               5                   10
```

<210> SEQ ID NO 600
<211> LENGTH: 12
<212> TYPE: PRT
<213> ORGANISM: Artificial Sequence
<220> FEATURE:
<223> OTHER INFORMATION: CPP

<400> SEQUENCE: 600

```
His Arg His Ile Arg Arg Gln Ser Leu Ile Met Leu
1               5                   10
```

<210> SEQ ID NO 601
<211> LENGTH: 12
<212> TYPE: PRT
<213> ORGANISM: Artificial Sequence
<220> FEATURE:
<223> OTHER INFORMATION: CPP

<400> SEQUENCE: 601

```
Pro Gln Asn Arg Leu Gln Ile Arg Arg His Ser Lys
1               5                   10
```

<210> SEQ ID NO 602
<211> LENGTH: 12
<212> TYPE: PRT
<213> ORGANISM: Artificial Sequence
<220> FEATURE:
<223> OTHER INFORMATION: CPP

<400> SEQUENCE: 602

```
Pro Pro His Asn Arg Ile Gln Arg Arg Leu Asn Met
1               5                   10
```

<210> SEQ ID NO 603
<211> LENGTH: 12
<212> TYPE: PRT
<213> ORGANISM: Artificial Sequence
<220> FEATURE:
<223> OTHER INFORMATION: CPP

<400> SEQUENCE: 603

```
Ser Met Leu Lys Arg Asn His Ser Thr Ser Asn Arg
1               5                   10
```

<210> SEQ ID NO 604
<211> LENGTH: 12
<212> TYPE: PRT
<213> ORGANISM: Artificial Sequence
<220> FEATURE:
<223> OTHER INFORMATION: CPP

<400> SEQUENCE: 604

```
Gly Ser Arg His Pro Ser Leu Ile Ile Pro Arg Gln
```

```
1               5                  10

<210> SEQ ID NO 605
<211> LENGTH: 12
<212> TYPE: PRT
<213> ORGANISM: Artificial Sequence
<220> FEATURE:
<223> OTHER INFORMATION: CPP

<400> SEQUENCE: 605

Ser Pro Met Gln Lys Thr Met Asn Leu Pro Pro Met
1               5                  10

<210> SEQ ID NO 606
<211> LENGTH: 12
<212> TYPE: PRT
<213> ORGANISM: Artificial Sequence
<220> FEATURE:
<223> OTHER INFORMATION: CPP

<400> SEQUENCE: 606

Asn Lys Arg Ile Leu Ile Arg Ile Met Thr Arg Pro
1               5                  10

<210> SEQ ID NO 607
<211> LENGTH: 12
<212> TYPE: PRT
<213> ORGANISM: Artificial Sequence
<220> FEATURE:
<223> OTHER INFORMATION: CPP

<400> SEQUENCE: 607

His Gly Trp Glx Ile His Gly Leu Leu His Arg Ala
1               5                  10

<210> SEQ ID NO 608
<211> LENGTH: 11
<212> TYPE: PRT
<213> ORGANISM: Artificial Sequence
<220> FEATURE:
<223> OTHER INFORMATION: CPP

<400> SEQUENCE: 608

Ala Val Pro Ala Lys Lys Arg Glx Lys Ser Val
1               5                  10

<210> SEQ ID NO 609
<211> LENGTH: 11
<212> TYPE: PRT
<213> ORGANISM: Artificial Sequence
<220> FEATURE:
<223> OTHER INFORMATION: CPP

<400> SEQUENCE: 609

Pro Asn Thr Arg Val Arg Pro Asp Val Ser Phe
1               5                  10

<210> SEQ ID NO 610
<211> LENGTH: 12
<212> TYPE: PRT
<213> ORGANISM: Artificial Sequence
<220> FEATURE:
<223> OTHER INFORMATION: CPP

<400> SEQUENCE: 610

Leu Thr Arg Asn Tyr Glu Ala Trp Val Pro Thr Pro
1               5                  10
```

<210> SEQ ID NO 611
<211> LENGTH: 13
<212> TYPE: PRT
<213> ORGANISM: Artificial Sequence
<220> FEATURE:
<223> OTHER INFORMATION: CPP

<400> SEQUENCE: 611

Ser Ala Glu Thr Val Glu Ser Cys Leu Ala Lys Ser His
1               5                   10

<210> SEQ ID NO 612
<211> LENGTH: 12
<212> TYPE: PRT
<213> ORGANISM: Artificial Sequence
<220> FEATURE:
<223> OTHER INFORMATION: CPP

<400> SEQUENCE: 612

Tyr Ser His Ile Ala Thr Leu Pro Phe Thr Pro Thr
1               5                   10

<210> SEQ ID NO 613
<211> LENGTH: 12
<212> TYPE: PRT
<213> ORGANISM: Artificial Sequence
<220> FEATURE:
<223> OTHER INFORMATION: CPP

<400> SEQUENCE: 613

Ser Tyr Ile Gln Arg Thr Pro Ser Thr Thr Leu Pro
1               5                   10

<210> SEQ ID NO 614
<211> LENGTH: 12
<212> TYPE: PRT
<213> ORGANISM: Artificial Sequence
<220> FEATURE:
<223> OTHER INFORMATION: CPP

<400> SEQUENCE: 614

Ala Val Pro Ala Glu Asn Ala Leu Asn Asn Pro Phe
1               5                   10

<210> SEQ ID NO 615
<211> LENGTH: 12
<212> TYPE: PRT
<213> ORGANISM: Artificial Sequence
<220> FEATURE:
<223> OTHER INFORMATION: CPP

<400> SEQUENCE: 615

Ser Phe His Gln Phe Ala Arg Ala Thr Leu Ala Ser
1               5                   10

<210> SEQ ID NO 616
<211> LENGTH: 12
<212> TYPE: PRT
<213> ORGANISM: Artificial Sequence
<220> FEATURE:
<223> OTHER INFORMATION: CPP

<400> SEQUENCE: 616

Gln Ser Pro Thr Asp Phe Thr Phe Pro Asn Pro Leu
1               5                   10

```
<210> SEQ ID NO 617
<211> LENGTH: 12
<212> TYPE: PRT
<213> ORGANISM: Artificial Sequence
<220> FEATURE:
<223> OTHER INFORMATION: CPP

<400> SEQUENCE: 617

His Phe Ala Ala Trp Gly Gly Trp Ser Leu Val His
1               5                   10

<210> SEQ ID NO 618
<211> LENGTH: 12
<212> TYPE: PRT
<213> ORGANISM: Artificial Sequence
<220> FEATURE:
<223> OTHER INFORMATION: CPP

<400> SEQUENCE: 618

His Ile Gln Leu Ser Pro Phe Ser Gln Ser Trp Arg
1               5                   10

<210> SEQ ID NO 619
<211> LENGTH: 12
<212> TYPE: PRT
<213> ORGANISM: Artificial Sequence
<220> FEATURE:
<223> OTHER INFORMATION: CPP

<400> SEQUENCE: 619

Leu Thr Met Pro Ser Asp Leu Gln Pro Val Leu Trp
1               5                   10

<210> SEQ ID NO 620
<211> LENGTH: 12
<212> TYPE: PRT
<213> ORGANISM: Artificial Sequence
<220> FEATURE:
<223> OTHER INFORMATION: CPP

<400> SEQUENCE: 620

Phe Gln Pro Tyr Asp His Pro Ala Glu Val Ser Tyr
1               5                   10

<210> SEQ ID NO 621
<211> LENGTH: 12
<212> TYPE: PRT
<213> ORGANISM: Artificial Sequence
<220> FEATURE:
<223> OTHER INFORMATION: CPP

<400> SEQUENCE: 621

Phe Asp Pro Phe Phe Trp Lys Tyr Ser Pro Arg Asp
1               5                   10

<210> SEQ ID NO 622
<211> LENGTH: 12
<212> TYPE: PRT
<213> ORGANISM: Artificial Sequence
<220> FEATURE:
<223> OTHER INFORMATION: CPP

<400> SEQUENCE: 622

Phe Ala Pro Trp Asp Thr Ala Ser Phe Met Leu Gly
1               5                   10
```

```
<210> SEQ ID NO 623
<211> LENGTH: 12
<212> TYPE: PRT
<213> ORGANISM: Artificial Sequence
<220> FEATURE:
<223> OTHER INFORMATION: CPP

<400> SEQUENCE: 623

Phe Thr Tyr Lys Asn Phe Phe Trp Leu Pro Glu Leu
1               5                   10

<210> SEQ ID NO 624
<211> LENGTH: 12
<212> TYPE: PRT
<213> ORGANISM: Artificial Sequence
<220> FEATURE:
<223> OTHER INFORMATION: CPP

<400> SEQUENCE: 624

Ser Ala Thr Gly Ala Pro Trp Lys Met Trp Val Arg
1               5                   10

<210> SEQ ID NO 625
<211> LENGTH: 12
<212> TYPE: PRT
<213> ORGANISM: Artificial Sequence
<220> FEATURE:
<223> OTHER INFORMATION: CPP

<400> SEQUENCE: 625

Ser Leu Gly Trp Met Leu Pro Phe Ser Pro Pro Phe
1               5                   10

<210> SEQ ID NO 626
<211> LENGTH: 12
<212> TYPE: PRT
<213> ORGANISM: Artificial Sequence
<220> FEATURE:
<223> OTHER INFORMATION: CPP

<400> SEQUENCE: 626

Ser His Ala Phe Thr Trp Pro Thr Tyr Leu Gln Leu
1               5                   10

<210> SEQ ID NO 627
<211> LENGTH: 12
<212> TYPE: PRT
<213> ORGANISM: Artificial Sequence
<220> FEATURE:
<223> OTHER INFORMATION: CPP

<400> SEQUENCE: 627

Ser His Asn Trp Leu Pro Leu Trp Pro Leu Arg Pro
1               5                   10

<210> SEQ ID NO 628
<211> LENGTH: 12
<212> TYPE: PRT
<213> ORGANISM: Artificial Sequence
<220> FEATURE:
<223> OTHER INFORMATION: CPP

<400> SEQUENCE: 628

Ser Trp Leu Pro Tyr Pro Trp His Val Pro Ser Ser
1               5                   10

<210> SEQ ID NO 629
```

```
<211> LENGTH: 12
<212> TYPE: PRT
<213> ORGANISM: Artificial Sequence
<220> FEATURE:
<223> OTHER INFORMATION: CPP

<400> SEQUENCE: 629

Ser Trp Trp Thr Pro Trp His Val His Ser Glu Ser
1               5                   10

<210> SEQ ID NO 630
<211> LENGTH: 12
<212> TYPE: PRT
<213> ORGANISM: Artificial Sequence
<220> FEATURE:
<223> OTHER INFORMATION: CPP

<400> SEQUENCE: 630

Ser Trp Ala Gln His Leu Ser Leu Pro Pro Val Leu
1               5                   10

<210> SEQ ID NO 631
<211> LENGTH: 12
<212> TYPE: PRT
<213> ORGANISM: Artificial Sequence
<220> FEATURE:
<223> OTHER INFORMATION: CPP

<400> SEQUENCE: 631

Ser Ser Ser Ile Phe Pro Pro Trp Leu Ser Phe Phe
1               5                   10

<210> SEQ ID NO 632
<211> LENGTH: 12
<212> TYPE: PRT
<213> ORGANISM: Artificial Sequence
<220> FEATURE:
<223> OTHER INFORMATION: CPP

<400> SEQUENCE: 632

Leu Asn Val Pro Pro Ser Trp Phe Leu Ser Gln Arg
1               5                   10

<210> SEQ ID NO 633
<211> LENGTH: 12
<212> TYPE: PRT
<213> ORGANISM: Artificial Sequence
<220> FEATURE:
<223> OTHER INFORMATION: CPP

<400> SEQUENCE: 633

Leu Asp Ile Thr Pro Phe Leu Ser Leu Thr Leu Pro
1               5                   10

<210> SEQ ID NO 634
<211> LENGTH: 12
<212> TYPE: PRT
<213> ORGANISM: Artificial Sequence
<220> FEATURE:
<223> OTHER INFORMATION: CPP

<400> SEQUENCE: 634

Leu Pro His Pro Val Leu His Met Gly Pro Leu Arg
1               5                   10

<210> SEQ ID NO 635
<211> LENGTH: 12
```

```
<212> TYPE: PRT
<213> ORGANISM: Artificial Sequence
<220> FEATURE:
<223> OTHER INFORMATION: CPP

<400> SEQUENCE: 635

Val Ser Lys Gln Pro Tyr Tyr Met Trp Asn Gly Asn
1               5                   10

<210> SEQ ID NO 636
<211> LENGTH: 12
<212> TYPE: PRT
<213> ORGANISM: Artificial Sequence
<220> FEATURE:
<223> OTHER INFORMATION: CPP

<400> SEQUENCE: 636

Asn Tyr Thr Thr Tyr Lys Ser His Phe Gln Asp Arg
1               5                   10

<210> SEQ ID NO 637
<211> LENGTH: 12
<212> TYPE: PRT
<213> ORGANISM: Artificial Sequence
<220> FEATURE:
<223> OTHER INFORMATION: CPP

<400> SEQUENCE: 637

Ala Ile Pro Asn Asn Gln Leu Gly Phe Pro Phe Lys
1               5                   10

<210> SEQ ID NO 638
<211> LENGTH: 12
<212> TYPE: PRT
<213> ORGANISM: Artificial Sequence
<220> FEATURE:
<223> OTHER INFORMATION: CPP

<400> SEQUENCE: 638

Asn Ile Glu Asn Ser Thr Leu Ala Thr Pro Leu Ser
1               5                   10

<210> SEQ ID NO 639
<211> LENGTH: 12
<212> TYPE: PRT
<213> ORGANISM: Artificial Sequence
<220> FEATURE:
<223> OTHER INFORMATION: CPP

<400> SEQUENCE: 639

Tyr Pro Tyr Asp Ala Asn His Thr Arg Ser Pro Thr
1               5                   10

<210> SEQ ID NO 640
<211> LENGTH: 12
<212> TYPE: PRT
<213> ORGANISM: Artificial Sequence
<220> FEATURE:
<223> OTHER INFORMATION: CPP

<400> SEQUENCE: 640

Asp Pro Ala Thr Asn Pro Gly Pro His Phe Pro Arg
1               5                   10

<210> SEQ ID NO 641
<211> LENGTH: 12
<212> TYPE: PRT
```

<213> ORGANISM: Artificial Sequence
<220> FEATURE:
<223> OTHER INFORMATION: CPP

<400> SEQUENCE: 641

Thr Leu Pro Ser Pro Leu Ala Leu Leu Thr Val His
1               5                   10

<210> SEQ ID NO 642
<211> LENGTH: 12
<212> TYPE: PRT
<213> ORGANISM: Artificial Sequence
<220> FEATURE:
<223> OTHER INFORMATION: CPP

<400> SEQUENCE: 642

His Pro Gly Ser Pro Phe Pro Pro Glu His Arg Pro
1               5                   10

<210> SEQ ID NO 643
<211> LENGTH: 12
<212> TYPE: PRT
<213> ORGANISM: Artificial Sequence
<220> FEATURE:
<223> OTHER INFORMATION: CPP

<400> SEQUENCE: 643

Thr Ser His Thr Asp Ala Pro Pro Ala Arg Ser Pro
1               5                   10

<210> SEQ ID NO 644
<211> LENGTH: 12
<212> TYPE: PRT
<213> ORGANISM: Artificial Sequence
<220> FEATURE:
<223> OTHER INFORMATION: CPP

<400> SEQUENCE: 644

Met Thr Pro Ser Ser Leu Ser Thr Leu Pro Trp Pro
1               5                   10

<210> SEQ ID NO 645
<211> LENGTH: 12
<212> TYPE: PRT
<213> ORGANISM: Artificial Sequence
<220> FEATURE:
<223> OTHER INFORMATION: CPP

<400> SEQUENCE: 645

Val Leu Gly Gln Ser Gly Tyr Leu Met Pro Met Arg
1               5                   10

<210> SEQ ID NO 646
<211> LENGTH: 12
<212> TYPE: PRT
<213> ORGANISM: Artificial Sequence
<220> FEATURE:
<223> OTHER INFORMATION: CPP

<400> SEQUENCE: 646

Gln Pro Ile Ile Ile Thr Ser Pro Tyr Leu Pro Ser
1               5                   10

<210> SEQ ID NO 647
<211> LENGTH: 12
<212> TYPE: PRT
<213> ORGANISM: Artificial Sequence

```
<220> FEATURE:
<223> OTHER INFORMATION: CPP

<400> SEQUENCE: 647

Thr Pro Lys Thr Met Thr Gln Thr Tyr Asp Phe Ser
1               5                   10

<210> SEQ ID NO 648
<211> LENGTH: 12
<212> TYPE: PRT
<213> ORGANISM: Artificial Sequence
<220> FEATURE:
<223> OTHER INFORMATION: CPP

<400> SEQUENCE: 648

Asn Ser Gly Thr Met Gln Ser Ala Ser Arg Ala Thr
1               5                   10

<210> SEQ ID NO 649
<211> LENGTH: 12
<212> TYPE: PRT
<213> ORGANISM: Artificial Sequence
<220> FEATURE:
<223> OTHER INFORMATION: CPP

<400> SEQUENCE: 649

Gln Ala Ala Ser Arg Val Glu Asn Tyr Met His Arg
1               5                   10

<210> SEQ ID NO 650
<211> LENGTH: 12
<212> TYPE: PRT
<213> ORGANISM: Artificial Sequence
<220> FEATURE:
<223> OTHER INFORMATION: CPP

<400> SEQUENCE: 650

His Gln His Lys Pro Pro Pro Leu Thr Asn Asn Trp
1               5                   10

<210> SEQ ID NO 651
<211> LENGTH: 12
<212> TYPE: PRT
<213> ORGANISM: Artificial Sequence
<220> FEATURE:
<223> OTHER INFORMATION: CPP

<400> SEQUENCE: 651

Ser Asn Pro Trp Asp Ser Leu Leu Ser Val Ser Thr
1               5                   10

<210> SEQ ID NO 652
<211> LENGTH: 12
<212> TYPE: PRT
<213> ORGANISM: Artificial Sequence
<220> FEATURE:
<223> OTHER INFORMATION: CPP

<400> SEQUENCE: 652

Lys Thr Ile Glu Ala His Pro Pro Tyr Tyr Ala Ser
1               5                   10

<210> SEQ ID NO 653
<211> LENGTH: 12
<212> TYPE: PRT
<213> ORGANISM: Artificial Sequence
<220> FEATURE:
```

<223> OTHER INFORMATION: CPP

<400> SEQUENCE: 653

Glu Pro Asp Asn Trp Ser Leu Asp Phe Pro Arg Arg
1               5                   10

<210> SEQ ID NO 654
<211> LENGTH: 12
<212> TYPE: PRT
<213> ORGANISM: Artificial Sequence
<220> FEATURE:
<223> OTHER INFORMATION: CPP

<400> SEQUENCE: 654

His Gln His Lys Pro Pro Pro Leu Thr Asn Asn Trp
1               5                   10

<210> SEQ ID NO 655
<211> LENGTH: 20
<212> TYPE: PRT
<213> ORGANISM: Artificial Sequence
<220> FEATURE:
<223> OTHER INFORMATION: CPP

<400> SEQUENCE: 655

Gly Leu Trp Arg Ala Leu Trp Arg Leu Leu Arg Ser Leu Trp Arg Leu
1               5                   10                  15

Leu Trp Lys Ala
            20

<210> SEQ ID NO 656
<211> LENGTH: 21
<212> TYPE: PRT
<213> ORGANISM: Artificial Sequence
<220> FEATURE:
<223> OTHER INFORMATION: CPP

<400> SEQUENCE: 656

Gly Leu Trp Arg Ala Leu Trp Arg Ala Leu Trp Arg Ser Leu Trp Lys
1               5                   10                  15

Leu Lys Arg Lys Val
            20

<210> SEQ ID NO 657
<211> LENGTH: 20
<212> TYPE: PRT
<213> ORGANISM: Artificial Sequence
<220> FEATURE:
<223> OTHER INFORMATION: CPP

<400> SEQUENCE: 657

Gly Leu Trp Arg Ala Leu Trp Arg Ala Leu Arg Ser Leu Trp Lys Leu
1               5                   10                  15

Lys Arg Lys Val
            20

<210> SEQ ID NO 658
<211> LENGTH: 20
<212> TYPE: PRT
<213> ORGANISM: Artificial Sequence
<220> FEATURE:
<223> OTHER INFORMATION: CPP

<400> SEQUENCE: 658

Gly Leu Trp Arg Ala Leu Trp Arg Gly Leu Arg Ser Leu Trp Lys Leu

```
                1               5                  10                 15
Lys Arg Lys Val
            20

<210> SEQ ID NO 659
<211> LENGTH: 20
<212> TYPE: PRT
<213> ORGANISM: Artificial Sequence
<220> FEATURE:
<223> OTHER INFORMATION: CPP

<400> SEQUENCE: 659

Gly Leu Trp Arg Ala Leu Trp Arg Gly Leu Arg Ser Leu Trp Lys Lys
1               5                  10                 15

Lys Arg Lys Val
            20

<210> SEQ ID NO 660
<211> LENGTH: 21
<212> TYPE: PRT
<213> ORGANISM: Artificial Sequence
<220> FEATURE:
<223> OTHER INFORMATION: CPP

<400> SEQUENCE: 660

Gly Leu Trp Arg Ala Leu Trp Arg Ala Leu Trp Arg Ser Leu Trp Lys
1               5                  10                 15

Leu Lys Trp Lys Val
            20

<210> SEQ ID NO 661
<211> LENGTH: 21
<212> TYPE: PRT
<213> ORGANISM: Artificial Sequence
<220> FEATURE:
<223> OTHER INFORMATION: CPP

<400> SEQUENCE: 661

Gly Leu Trp Arg Ala Leu Trp Arg Ala Leu Trp Arg Ser Leu Trp Lys
1               5                  10                 15

Ser Lys Arg Lys Val
            20

<210> SEQ ID NO 662
<211> LENGTH: 21
<212> TYPE: PRT
<213> ORGANISM: Artificial Sequence
<220> FEATURE:
<223> OTHER INFORMATION: CPP

<400> SEQUENCE: 662

Gly Leu Trp Arg Ala Leu Trp Arg Ala Leu Trp Arg Ser Leu Trp Lys
1               5                  10                 15

Lys Lys Arg Lys Val
            20

<210> SEQ ID NO 663
<211> LENGTH: 21
<212> TYPE: PRT
<213> ORGANISM: Artificial Sequence
<220> FEATURE:
<223> OTHER INFORMATION: CPP

<400> SEQUENCE: 663
```

Gly Leu Trp Arg Ala Leu Trp Arg Ala Leu Trp Arg Ser Leu Trp Lys
1               5                   10                  15

Leu Lys Arg Lys Val
            20

<210> SEQ ID NO 664
<211> LENGTH: 27
<212> TYPE: PRT
<213> ORGANISM: Artificial Sequence
<220> FEATURE:
<223> OTHER INFORMATION: CPP

<400> SEQUENCE: 664

Gly Leu Trp Arg Ala Leu Trp Arg Leu Leu Arg Ser Leu Trp Arg Leu
1               5                   10                  15

Leu Trp Ser Gln Pro Lys Lys Lys Arg Lys Val
            20                  25

<210> SEQ ID NO 665
<211> LENGTH: 11
<212> TYPE: PRT
<213> ORGANISM: Artificial Sequence
<220> FEATURE:
<223> OTHER INFORMATION: CPP

<400> SEQUENCE: 665

Tyr Ala Arg Ala Ala Arg Arg Ala Ala Arg Arg
1               5                   10

<210> SEQ ID NO 666
<211> LENGTH: 11
<212> TYPE: PRT
<213> ORGANISM: Artificial Sequence
<220> FEATURE:
<223> OTHER INFORMATION: CPP

<400> SEQUENCE: 666

Pro Ala Arg Ala Ala Arg Arg Ala Ala Arg Arg
1               5                   10

<210> SEQ ID NO 667
<211> LENGTH: 11
<212> TYPE: PRT
<213> ORGANISM: Artificial Sequence
<220> FEATURE:
<223> OTHER INFORMATION: CPP

<400> SEQUENCE: 667

Tyr Pro Arg Ala Ala Arg Arg Ala Ala Arg Arg
1               5                   10

<210> SEQ ID NO 668
<211> LENGTH: 11
<212> TYPE: PRT
<213> ORGANISM: Artificial Sequence
<220> FEATURE:
<223> OTHER INFORMATION: CPP

<400> SEQUENCE: 668

Tyr Arg Arg Ala Ala Arg Arg Ala Ala Arg Ala
1               5                   10

<210> SEQ ID NO 669
<211> LENGTH: 11
<212> TYPE: PRT
<213> ORGANISM: Artificial Sequence

```
<220> FEATURE:
<223> OTHER INFORMATION: CPP

<400> SEQUENCE: 669

Tyr Gly Arg Ala Ala Arg Arg Ala Ala Arg Arg
1               5                   10

<210> SEQ ID NO 670
<211> LENGTH: 11
<212> TYPE: PRT
<213> ORGANISM: Artificial Sequence
<220> FEATURE:
<223> OTHER INFORMATION: CPP

<400> SEQUENCE: 670

Tyr Ala Arg Glu Ala Arg Arg Ala Ala Arg Arg
1               5                   10

<210> SEQ ID NO 671
<211> LENGTH: 11
<212> TYPE: PRT
<213> ORGANISM: Artificial Sequence
<220> FEATURE:
<223> OTHER INFORMATION: CPP

<400> SEQUENCE: 671

Tyr Glu Arg Glu Ala Arg Arg Ala Ala Arg Arg
1               5                   10

<210> SEQ ID NO 672
<211> LENGTH: 11
<212> TYPE: PRT
<213> ORGANISM: Artificial Sequence
<220> FEATURE:
<223> OTHER INFORMATION: CPP

<400> SEQUENCE: 672

Tyr Lys Arg Ala Ala Arg Arg Ala Ala Arg Arg
1               5                   10

<210> SEQ ID NO 673
<211> LENGTH: 11
<212> TYPE: PRT
<213> ORGANISM: Artificial Sequence
<220> FEATURE:
<223> OTHER INFORMATION: CPP

<400> SEQUENCE: 673

Tyr Ala Arg Lys Ala Arg Arg Ala Ala Arg Arg
1               5                   10

<210> SEQ ID NO 674
<211> LENGTH: 11
<212> TYPE: PRT
<213> ORGANISM: Artificial Sequence
<220> FEATURE:
<223> OTHER INFORMATION: CPP

<400> SEQUENCE: 674

Tyr Lys Arg Lys Ala Arg Arg Ala Ala Arg Arg
1               5                   10

<210> SEQ ID NO 675
<211> LENGTH: 11
<212> TYPE: PRT
<213> ORGANISM: Artificial Sequence
<220> FEATURE:
```

<223> OTHER INFORMATION: CPP

<400> SEQUENCE: 675

Tyr Gly Arg Arg Ala Arg Arg Ala Ala Arg Arg
1               5                   10

<210> SEQ ID NO 676
<211> LENGTH: 11
<212> TYPE: PRT
<213> ORGANISM: Artificial Sequence
<220> FEATURE:
<223> OTHER INFORMATION: CPP

<400> SEQUENCE: 676

Tyr Gly Arg Arg Ala Arg Arg Ala Arg Arg
1               5                   10

<210> SEQ ID NO 677
<211> LENGTH: 11
<212> TYPE: PRT
<213> ORGANISM: Artificial Sequence
<220> FEATURE:
<223> OTHER INFORMATION: CPP

<400> SEQUENCE: 677

Tyr Gly Arg Arg Arg Arg Arg Arg Arg Arg
1               5                   10

<210> SEQ ID NO 678
<211> LENGTH: 11
<212> TYPE: PRT
<213> ORGANISM: Artificial Sequence
<220> FEATURE:
<223> OTHER INFORMATION: CPP

<400> SEQUENCE: 678

Tyr Arg Arg Arg Arg Arg Arg Arg Arg Arg
1               5                   10

<210> SEQ ID NO 679
<211> LENGTH: 16
<212> TYPE: PRT
<213> ORGANISM: Artificial Sequence
<220> FEATURE:
<223> OTHER INFORMATION: CPP

<400> SEQUENCE: 679

Gly Lys Ile Asn Leu Lys Ala Leu Ala Ala Leu Ala Lys Lys Ile Leu
1               5                   10                  15

<210> SEQ ID NO 680
<211> LENGTH: 39
<212> TYPE: PRT
<213> ORGANISM: Artificial Sequence
<220> FEATURE:
<223> OTHER INFORMATION: CPP

<400> SEQUENCE: 680

Gly Arg Lys Lys Arg Gln Arg Arg Arg Pro Pro Gln Gly Arg Lys
1               5                   10                  15

Lys Arg Arg Gln Arg Arg Arg Pro Pro Gln Gly Arg Lys Lys Arg Arg
                20                  25                  30

Gln Arg Arg Arg Pro Pro Gln
35

-continued

```
<210> SEQ ID NO 681
<211> LENGTH: 22
<212> TYPE: PRT
<213> ORGANISM: Artificial Sequence
<220> FEATURE:
<223> OTHER INFORMATION: CPP

<400> SEQUENCE: 681

Gly Glu Gln Ile Ala Gln Leu Ile Ala Gly Tyr Ile Asp Ile Ile Leu
1               5                   10                  15

Lys Lys Lys Lys Ser Lys
            20

<210> SEQ ID NO 682
<211> LENGTH: 28
<212> TYPE: PRT
<213> ORGANISM: Artificial Sequence
<220> FEATURE:
<223> OTHER INFORMATION: CPP

<400> SEQUENCE: 682

Ala Ala Val Ala Leu Leu Pro Ala Val Leu Leu Ala Leu Leu Ala Pro
1               5                   10                  15

Arg Lys Lys Arg Arg Gln Arg Arg Pro Pro Gln
            20                  25

<210> SEQ ID NO 683
<211> LENGTH: 29
<212> TYPE: PRT
<213> ORGANISM: Artificial Sequence
<220> FEATURE:
<223> OTHER INFORMATION: CPP

<400> SEQUENCE: 683

Ala Ala Val Ala Leu Leu Pro Ala Val Leu Leu Ala Leu Leu Ala Pro
1               5                   10                  15

Arg Lys Lys Arg Arg Gln Arg Arg Pro Pro Gln Cys
            20                  25

<210> SEQ ID NO 684
<211> LENGTH: 29
<212> TYPE: PRT
<213> ORGANISM: Artificial Sequence
<220> FEATURE:
<223> OTHER INFORMATION: CPP

<400> SEQUENCE: 684

Arg Lys Lys Arg Arg Gln Arg Arg Pro Pro Gln Cys Ala Ala Val
1               5                   10                  15

Ala Leu Leu Pro Ala Val Leu Leu Ala Leu Leu Ala Pro
            20                  25

<210> SEQ ID NO 685
<211> LENGTH: 29
<212> TYPE: PRT
<213> ORGANISM: Artificial Sequence
<220> FEATURE:
<223> OTHER INFORMATION: CPP

<400> SEQUENCE: 685

Arg Arg Arg Gln Arg Arg Lys Arg Gly Gly Asp Ile Met Gly Glu Trp
1               5                   10                  15

Gly Asn Glu Ile Phe Gly Ala Ile Ala Gly Phe Leu Gly
            20                  25
```

<210> SEQ ID NO 686
<211> LENGTH: 29
<212> TYPE: PRT
<213> ORGANISM: Artificial Sequence
<220> FEATURE:
<223> OTHER INFORMATION: CPP

<400> SEQUENCE: 686

Arg Arg Arg Gln Arg Arg Lys Arg Gly Gly Asp Ile Met Gly Glu Trp
1               5                   10                  15

Gly Asn Glu Ile Phe Gly Ala Ile Ala Gly Phe Leu Gly
            20                  25

<210> SEQ ID NO 687
<211> LENGTH: 25
<212> TYPE: PRT
<213> ORGANISM: Artificial Sequence
<220> FEATURE:
<223> OTHER INFORMATION: CPP

<400> SEQUENCE: 687

Tyr Gly Arg Lys Lys Arg Arg Gln Arg Arg Gly Cys Tyr Gly Arg
1               5                   10                  15

Lys Lys Arg Arg Gln Arg Arg Arg Gly
            20                  25

<210> SEQ ID NO 688
<211> LENGTH: 22
<212> TYPE: PRT
<213> ORGANISM: Artificial Sequence
<220> FEATURE:
<223> OTHER INFORMATION: CPP

<400> SEQUENCE: 688

Ala Ala Val Ala Leu Leu Pro Ala Val Leu Leu Ala Leu Leu Ala Pro
1               5                   10                  15

Arg Arg Arg Arg Arg Arg
            20

<210> SEQ ID NO 689
<211> LENGTH: 16
<212> TYPE: PRT
<213> ORGANISM: Artificial Sequence
<220> FEATURE:
<223> OTHER INFORMATION: CPP

<400> SEQUENCE: 689

Arg Leu Trp Arg Ala Leu Pro Arg Val Leu Arg Arg Leu Leu Arg Pro
1               5                   10                  15

<210> SEQ ID NO 690
<211> LENGTH: 28
<212> TYPE: PRT
<213> ORGANISM: Artificial Sequence
<220> FEATURE:
<223> OTHER INFORMATION: CPP

<400> SEQUENCE: 690

Ala Ala Val Ala Leu Leu Pro Ala Val Leu Leu Ala Leu Leu Ala Pro
1               5                   10                  15

Ser Gly Ala Ser Gly Leu Asp Lys Arg Asp Tyr Val
            20                  25

<210> SEQ ID NO 691

<211> LENGTH: 33
<212> TYPE: PRT
<213> ORGANISM: Artificial Sequence
<220> FEATURE:
<223> OTHER INFORMATION: CPP

<400> SEQUENCE: 691

Leu Leu Glu Thr Leu Leu Lys Pro Phe Gln Cys Arg Ile Cys Met Arg
1               5                   10                  15

Asn Phe Ser Thr Arg Gln Ala Arg Arg Asn His Arg Arg His Arg
            20                  25                  30

Arg

<210> SEQ ID NO 692
<211> LENGTH: 27
<212> TYPE: PRT
<213> ORGANISM: Artificial Sequence
<220> FEATURE:
<223> OTHER INFORMATION: CPP

<400> SEQUENCE: 692

Ala Ala Val Ala Cys Arg Ile Cys Met Arg Asn Phe Ser Thr Arg Gln
1               5                   10                  15

Ala Arg Arg Asn His Arg Arg His Arg Arg
            20                  25

<210> SEQ ID NO 693
<211> LENGTH: 35
<212> TYPE: PRT
<213> ORGANISM: Artificial Sequence
<220> FEATURE:
<223> OTHER INFORMATION: CPP

<400> SEQUENCE: 693

Arg Gln Ile Lys Ile Trp Phe Gln Asn Arg Arg Met Lys Trp Lys Lys
1               5                   10                  15

Asp Ile Met Gly Glu Trp Gly Asn Glu Ile Phe Gly Ala Ile Ala Gly
            20                  25                  30

Phe Leu Gly
        35

<210> SEQ ID NO 694
<211> LENGTH: 37
<212> TYPE: PRT
<213> ORGANISM: Artificial Sequence
<220> FEATURE:
<223> OTHER INFORMATION: CPP

<400> SEQUENCE: 694

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly
        35

<210> SEQ ID NO 695
<211> LENGTH: 38
<212> TYPE: PRT
<213> ORGANISM: Artificial Sequence
<220> FEATURE:
<223> OTHER INFORMATION: CPP

<400> SEQUENCE: 695

-continued

Ser Gly Arg Gly Lys Gln Gly Lys Ala Arg Ala Lys Ala Lys Thr
1               5                   10                  15

Arg Ser Ser Arg Ala Gly Leu Gln Phe Pro Val Gly Arg Val His Arg
                20                  25                  30

Leu Leu Arg Lys Gly Cys
        35

<210> SEQ ID NO 696
<211> LENGTH: 25
<212> TYPE: PRT
<213> ORGANISM: Artificial Sequence
<220> FEATURE:
<223> OTHER INFORMATION: CPP

<400> SEQUENCE: 696

Lys Lys Asp Gly Lys Lys Arg Lys Arg Ser Arg Lys Glu Ser Tyr Ser
1               5                   10                  15

Val Tyr Val Tyr Lys Val Leu Lys Gln
            20                  25

<210> SEQ ID NO 697
<211> LENGTH: 36
<212> TYPE: PRT
<213> ORGANISM: Artificial Sequence
<220> FEATURE:
<223> OTHER INFORMATION: CPP

<400> SEQUENCE: 697

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
                20                  25                  30

Val Leu Lys Gln
        35

<210> SEQ ID NO 698
<211> LENGTH: 28
<212> TYPE: PRT
<213> ORGANISM: Artificial Sequence
<220> FEATURE:
<223> OTHER INFORMATION: CPP

<400> SEQUENCE: 698

Lys Glu Thr Trp Trp Glu Thr Trp Trp Thr Glu Trp Ser Gln Pro Gly
1               5                   10                  15

Arg Lys Lys Arg Arg Gln Arg Arg Pro Pro Gln
                20                  25

<210> SEQ ID NO 699
<211> LENGTH: 15
<212> TYPE: PRT
<213> ORGANISM: Artificial Sequence
<220> FEATURE:
<223> OTHER INFORMATION: CPP

<400> SEQUENCE: 699

Arg Val Ile Arg Trp Phe Gln Asn Lys Arg Cys Lys Asp Lys Lys
1               5                   10                  15

<210> SEQ ID NO 700
<211> LENGTH: 18
<212> TYPE: PRT
<213> ORGANISM: Artificial Sequence

```
<220> FEATURE:
<223> OTHER INFORMATION: CPP

<400> SEQUENCE: 700

Leu Gly Leu Leu Leu Arg His Leu Arg His His Ser Asn Leu Leu Ala
1               5                   10                  15

Asn Ile

<210> SEQ ID NO 701
<211> LENGTH: 16
<212> TYPE: PRT
<213> ORGANISM: Artificial Sequence
<220> FEATURE:
<223> OTHER INFORMATION: CPP

<400> SEQUENCE: 701

Lys Leu Trp Ser Ala Trp Pro Ser Leu Trp Ser Ser Leu Trp Lys Pro
1               5                   10                  15

<210> SEQ ID NO 702
<211> LENGTH: 22
<212> TYPE: PRT
<213> ORGANISM: Artificial Sequence
<220> FEATURE:
<223> OTHER INFORMATION: CPP

<400> SEQUENCE: 702

Gly Leu Gly Ser Leu Leu Lys Lys Ala Gly Lys Lys Leu Lys Gln Pro
1               5                   10                  15

Lys Ser Lys Arg Lys Val
            20

<210> SEQ ID NO 703
<211> LENGTH: 12
<212> TYPE: PRT
<213> ORGANISM: Artificial Sequence
<220> FEATURE:
<223> OTHER INFORMATION: CPP

<400> SEQUENCE: 703

Phe Lys Gln Gln Gln Gln Gln Gln Gln Gln Gln Gln
1               5                   10

<210> SEQ ID NO 704
<211> LENGTH: 4
<212> TYPE: PRT
<213> ORGANISM: Artificial Sequence
<220> FEATURE:
<223> OTHER INFORMATION: CPP

<400> SEQUENCE: 704

Tyr Arg Phe Lys
1

<210> SEQ ID NO 705
<211> LENGTH: 13
<212> TYPE: PRT
<213> ORGANISM: Artificial Sequence
<220> FEATURE:
<223> OTHER INFORMATION: CPP

<400> SEQUENCE: 705

Tyr Arg Phe Lys Tyr Arg Phe Lys Tyr Arg Leu Phe Lys
1               5                   10
```

```
<210> SEQ ID NO 706
<211> LENGTH: 10
<212> TYPE: PRT
<213> ORGANISM: Artificial Sequence
<220> FEATURE:
<223> OTHER INFORMATION: CPP

<400> SEQUENCE: 706

Trp Arg Phe Lys Lys Ser Lys Arg Lys Val
1               5                   10

<210> SEQ ID NO 707
<211> LENGTH: 20
<212> TYPE: PRT
<213> ORGANISM: Artificial Sequence
<220> FEATURE:
<223> OTHER INFORMATION: CPP

<400> SEQUENCE: 707

Trp Arg Phe Lys Ala Ala Val Ala Leu Leu Pro Ala Val Leu Leu Ala
1               5                   10                  15

Leu Leu Ala Pro
            20

<210> SEQ ID NO 708
<211> LENGTH: 8
<212> TYPE: PRT
<213> ORGANISM: Artificial Sequence
<220> FEATURE:
<223> OTHER INFORMATION: CPP

<400> SEQUENCE: 708

Trp Arg Phe Lys Trp Arg Phe Lys
1               5

<210> SEQ ID NO 709
<211> LENGTH: 12
<212> TYPE: PRT
<213> ORGANISM: Artificial Sequence
<220> FEATURE:
<223> OTHER INFORMATION: CPP

<400> SEQUENCE: 709

Trp Arg Phe Lys Trp Arg Phe Lys Trp Arg Phe Lys
1               5                   10

<210> SEQ ID NO 710
<211> LENGTH: 36
<212> TYPE: PRT
<213> ORGANISM: Artificial Sequence
<220> FEATURE:
<223> OTHER INFORMATION: CPP

<400> SEQUENCE: 710

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
                20                  25                  30

Val Leu Lys Gln
            35

<210> SEQ ID NO 711
<211> LENGTH: 36
<212> TYPE: PRT
<213> ORGANISM: Artificial Sequence
<220> FEATURE:
```

```
<223> OTHER INFORMATION: CPP

<400> SEQUENCE: 711

Arg Gly Ser Arg Arg Ala Val Thr Arg Ala Gln Arg Arg Asp Gly Arg
1               5                   10                  15

Arg Arg Arg Arg Ser Arg Arg Glu Ser Tyr Ser Val Tyr Val Tyr Arg
            20                  25                  30

Val Leu Arg Gln
        35

<210> SEQ ID NO 712
<211> LENGTH: 15
<212> TYPE: PRT
<213> ORGANISM: Artificial Sequence
<220> FEATURE:
<223> OTHER INFORMATION: CPP

<400> SEQUENCE: 712

Arg Val Ile Arg Trp Phe Gln Asn Lys Arg Ser Lys Asp Lys Lys
1               5                   10                  15

<210> SEQ ID NO 713
<211> LENGTH: 28
<212> TYPE: PRT
<213> ORGANISM: Artificial Sequence
<220> FEATURE:
<223> OTHER INFORMATION: CPP

<400> SEQUENCE: 713

Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln
            20                  25

<210> SEQ ID NO 714
<211> LENGTH: 5
<212> TYPE: PRT
<213> ORGANISM: Artificial Sequence
<220> FEATURE:
<223> OTHER INFORMATION: CPP

<400> SEQUENCE: 714

Cys Trp Lys Lys Lys
1               5

<210> SEQ ID NO 715
<211> LENGTH: 10
<212> TYPE: PRT
<213> ORGANISM: Artificial Sequence
<220> FEATURE:
<223> OTHER INFORMATION: CPP

<400> SEQUENCE: 715

Cys Trp Lys Lys Lys Lys Lys Lys Lys Lys
1               5                   10

<210> SEQ ID NO 716
<211> LENGTH: 15
<212> TYPE: PRT
<213> ORGANISM: Artificial Sequence
<220> FEATURE:
<223> OTHER INFORMATION: CPP

<400> SEQUENCE: 716

Cys Trp Lys Lys Lys Lys Lys Lys Lys Lys Lys Lys Lys Lys Lys
```

-continued

```
1               5                   10                  15

<210> SEQ ID NO 717
<211> LENGTH: 20
<212> TYPE: PRT
<213> ORGANISM: Artificial Sequence
<220> FEATURE:
<223> OTHER INFORMATION: CPP

<400> SEQUENCE: 717

Cys Trp Lys Lys Lys Lys Lys Lys Lys Lys Lys Lys Lys Lys Lys
1               5                   10                  15

Lys Lys Lys Lys
            20

<210> SEQ ID NO 718
<211> LENGTH: 19
<212> TYPE: PRT
<213> ORGANISM: Artificial Sequence
<220> FEATURE:
<223> OTHER INFORMATION: CPP

<400> SEQUENCE: 718

Lys Lys Lys Lys Lys Lys Lys Lys Lys Lys Lys Lys Lys Lys Lys
1               5                   10                  15

Lys Lys Lys Lys

<210> SEQ ID NO 719
<211> LENGTH: 19
<212> TYPE: PRT
<213> ORGANISM: Artificial Sequence
<220> FEATURE:
<223> OTHER INFORMATION: CPP

<400> SEQUENCE: 719

Lys Lys Trp Lys Met Arg Arg Gly Ala Gly Arg Arg Arg Arg Arg
1               5                   10                  15

Arg Arg Arg

<210> SEQ ID NO 720
<211> LENGTH: 12
<212> TYPE: PRT
<213> ORGANISM: Artificial Sequence
<220> FEATURE:
<223> OTHER INFORMATION: CPP

<400> SEQUENCE: 720

Ala Pro Trp His Leu Ser Ser Gln Tyr Ser Arg Thr
1               5                   10

<210> SEQ ID NO 721
<211> LENGTH: 26
<212> TYPE: PRT
<213> ORGANISM: Artificial Sequence
<220> FEATURE:
<223> OTHER INFORMATION: CPP

<400> SEQUENCE: 721

Ala Ala Val Ala Leu Leu Pro Ala Val Leu Leu Ala Leu Leu Ala Lys
1               5                   10                  15

Lys Asn Asn Leu Lys Asp Cys Gly Leu Phe
            20                  25

<210> SEQ ID NO 722
```

```
<211> LENGTH: 26
<212> TYPE: PRT
<213> ORGANISM: Artificial Sequence
<220> FEATURE:
<223> OTHER INFORMATION: CPP

<400> SEQUENCE: 722

Ala Ala Val Ala Leu Leu Pro Ala Val Leu Ala Leu Leu Ala Lys
1               5                   10                  15

Lys Asn Asn Leu Lys Glu Cys Gly Leu Tyr
            20                  25

<210> SEQ ID NO 723
<211> LENGTH: 26
<212> TYPE: PRT
<213> ORGANISM: Artificial Sequence
<220> FEATURE:
<223> OTHER INFORMATION: CPP

<400> SEQUENCE: 723

Ala His Ala Leu Cys Leu Thr Glu Arg Gln Ile Lys Ile Trp Phe Gln
1               5                   10                  15

Asn Arg Arg Met Lys Trp Lys Lys Glu Asn
            20                  25

<210> SEQ ID NO 724
<211> LENGTH: 26
<212> TYPE: PRT
<213> ORGANISM: Artificial Sequence
<220> FEATURE:
<223> OTHER INFORMATION: CPP

<400> SEQUENCE: 724

Ala His Ala Leu Cys Pro Pro Glu Arg Gln Ile Lys Ile Trp Phe Gln
1               5                   10                  15

Asn Arg Arg Met Lys Trp Lys Lys Glu Asn
            20                  25

<210> SEQ ID NO 725
<211> LENGTH: 26
<212> TYPE: PRT
<213> ORGANISM: Artificial Sequence
<220> FEATURE:
<223> OTHER INFORMATION: CPP

<400> SEQUENCE: 725

Ala Tyr Ala Leu Cys Leu Thr Glu Arg Gln Ile Lys Ile Trp Phe Ala
1               5                   10                  15

Asn Arg Arg Met Lys Trp Lys Lys Glu Asn
            20                  25

<210> SEQ ID NO 726
<211> LENGTH: 34
<212> TYPE: PRT
<213> ORGANISM: Artificial Sequence
<220> FEATURE:
<223> OTHER INFORMATION: CPP

<400> SEQUENCE: 726

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp
```

<210> SEQ ID NO 727
<211> LENGTH: 34
<212> TYPE: PRT
<213> ORGANISM: Artificial Sequence
<220> FEATURE:
<223> OTHER INFORMATION: CPP

<400> SEQUENCE: 727

Gly Gly Val Cys Pro Lys Ile Leu Ala Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 728
<211> LENGTH: 34
<212> TYPE: PRT
<213> ORGANISM: Artificial Sequence
<220> FEATURE:
<223> OTHER INFORMATION: CPP

<400> SEQUENCE: 728

Gly Gly Val Cys Pro Ala Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 729
<211> LENGTH: 34
<212> TYPE: PRT
<213> ORGANISM: Artificial Sequence
<220> FEATURE:
<223> OTHER INFORMATION: CPP

<400> SEQUENCE: 729

Gly Gly Val Cys Pro Lys Ile Leu Ala Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 730
<211> LENGTH: 34
<212> TYPE: PRT
<213> ORGANISM: Artificial Sequence
<220> FEATURE:
<223> OTHER INFORMATION: CPP

<400> SEQUENCE: 730

Gly Gly Val Cys Pro Lys Ile Leu Lys Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 731
<211> LENGTH: 29
<212> TYPE: PRT
<213> ORGANISM: Artificial Sequence
<220> FEATURE:

<223> OTHER INFORMATION: CPP

<400> SEQUENCE: 731

Gly Leu Pro Val Cys Gly Glu Thr Cys Val Gly Gly Thr Cys Asn Thr
1               5                   10                  15

Pro Gly Cys Lys Cys Ser Trp Pro Val Cys Thr Arg Asn
            20                  25

<210> SEQ ID NO 732
<211> LENGTH: 29
<212> TYPE: PRT
<213> ORGANISM: Artificial Sequence
<220> FEATURE:
<223> OTHER INFORMATION: CPP

<400> SEQUENCE: 732

Gly Leu Pro Val Cys Gly Glu Thr Cys Val Gly Gly Thr Cys Asn Thr
1               5                   10                  15

Pro Gly Cys Thr Cys Ser Trp Pro Lys Cys Thr Arg Asn
            20                  25

<210> SEQ ID NO 733
<211> LENGTH: 14
<212> TYPE: PRT
<213> ORGANISM: Artificial Sequence
<220> FEATURE:
<223> OTHER INFORMATION: CPP

<400> SEQUENCE: 733

Gly Arg Cys Thr Lys Ser Ile Pro Pro Ile Cys Phe Pro Asp
1               5                   10

<210> SEQ ID NO 734
<211> LENGTH: 33
<212> TYPE: PRT
<213> ORGANISM: Artificial Sequence
<220> FEATURE:
<223> OTHER INFORMATION: CPP

<400> SEQUENCE: 734

Arg Gln Ile Lys Ile Trp Phe Gln Asn Arg Arg Met Lys Trp Lys Lys
1               5                   10                  15

Thr Tyr Ala Asp Phe Ile Ala Ser Gly Arg Thr Gly Arg Arg Asn Ala
            20                  25                  30

Ile

<210> SEQ ID NO 735
<211> LENGTH: 30
<212> TYPE: PRT
<213> ORGANISM: Artificial Sequence
<220> FEATURE:
<223> OTHER INFORMATION: CPP

<400> SEQUENCE: 735

Gly Arg Lys Lys Arg Arg Gln Arg Arg Pro Pro Gln Thr Tyr Ala
1               5                   10                  15

Asp Phe Ile Ala Ser Gly Arg Thr Gly Arg Arg Asn Ala Ile
            20                  25                  30

<210> SEQ ID NO 736
<211> LENGTH: 21
<212> TYPE: PRT
<213> ORGANISM: Artificial Sequence
<220> FEATURE:

<223> OTHER INFORMATION: CPP

<400> SEQUENCE: 736

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 737
<211> LENGTH: 38
<212> TYPE: PRT
<213> ORGANISM: Artificial Sequence
<220> FEATURE:
<223> OTHER INFORMATION: CPP

<400> SEQUENCE: 737

Ala Gly Tyr Leu Leu Gly Lys Ile Asn Leu Lys Ala Leu Ala Ala Leu
1               5                   10                  15

Ala Lys Lys Ile Leu Thr Tyr Ala Asp Phe Ile Ala Ser Gly Arg Thr
            20                  25                  30

Gly Arg Arg Asn Ala Ile
        35

<210> SEQ ID NO 738
<211> LENGTH: 11
<212> TYPE: PRT
<213> ORGANISM: Artificial Sequence
<220> FEATURE:
<223> OTHER INFORMATION: CPP

<400> SEQUENCE: 738

Arg Arg Arg Arg Arg Arg Arg Arg Arg Arg Arg
1               5                   10

<210> SEQ ID NO 739
<211> LENGTH: 28
<212> TYPE: PRT
<213> ORGANISM: Artificial Sequence
<220> FEATURE:
<223> OTHER INFORMATION: CPP

<400> SEQUENCE: 739

Arg Arg Arg Arg Arg Arg Arg Arg Arg Arg Arg Thr Tyr Ala Asp Phe
1               5                   10                  15

Ile Ala Ser Gly Arg Thr Gly Arg Arg Asn Ala Ile
            20                  25

<210> SEQ ID NO 740
<211> LENGTH: 10
<212> TYPE: PRT
<213> ORGANISM: Artificial Sequence
<220> FEATURE:
<223> OTHER INFORMATION: CPP

<400> SEQUENCE: 740

Arg Arg Arg Arg Arg Arg Arg Arg Arg Lys
1               5                   10

<210> SEQ ID NO 741
<211> LENGTH: 9
<212> TYPE: PRT
<213> ORGANISM: Artificial Sequence
<220> FEATURE:
<223> OTHER INFORMATION: CPP

```
<400> SEQUENCE: 741

Arg Arg Arg Arg Arg Arg Arg Arg
1               5

<210> SEQ ID NO 742
<211> LENGTH: 9
<212> TYPE: PRT
<213> ORGANISM: Artificial Sequence
<220> FEATURE:
<223> OTHER INFORMATION: CPP

<400> SEQUENCE: 742

Arg Arg Arg Arg Arg Arg Arg Arg Arg
1               5

<210> SEQ ID NO 743
<211> LENGTH: 22
<212> TYPE: PRT
<213> ORGANISM: Artificial Sequence
<220> FEATURE:
<223> OTHER INFORMATION: CPP

<400> SEQUENCE: 743

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 744
<211> LENGTH: 22
<212> TYPE: PRT
<213> ORGANISM: Artificial Sequence
<220> FEATURE:
<223> OTHER INFORMATION: CPP

<400> SEQUENCE: 744

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 745
<211> LENGTH: 20
<212> TYPE: PRT
<213> ORGANISM: Artificial Sequence
<220> FEATURE:
<223> OTHER INFORMATION: CPP

<400> SEQUENCE: 745

Lys Leu Ala Leu Lys Leu Ala Leu Lys Ala Leu Lys Ala Ala Leu Lys
1               5                   10                  15

Leu Ala Gly Cys
            20

<210> SEQ ID NO 746
<211> LENGTH: 20
<212> TYPE: PRT
<213> ORGANISM: Artificial Sequence
<220> FEATURE:
<223> OTHER INFORMATION: CPP MAP (Aib), wherein each Xaa = Aib, U
      (alpha-amino isobutyric acid)
<220> FEATURE:
<221> NAME/KEY: misc_feature
<222> LOCATION: (3)..(3)
<223> OTHER INFORMATION: Xaa can be any naturally occurring amino acid
<220> FEATURE:
```

```
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 746

Lys Leu Xaa Leu Lys Leu Xaa Leu Lys Xaa Leu Lys Ala Xaa Leu Lys
1               5                   10                  15

Leu Xaa Gly Cys
            20

<210> SEQ ID NO 747
<211> LENGTH: 35
<212> TYPE: PRT
<213> ORGANISM: Artificial Sequence
<220> FEATURE:
<223> OTHER INFORMATION: CPP

<400> SEQUENCE: 747

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala
        35

<210> SEQ ID NO 748
<211> LENGTH: 14
<212> TYPE: PRT
<213> ORGANISM: Artificial Sequence
<220> FEATURE:
<223> OTHER INFORMATION: CPP

<400> SEQUENCE: 748

Gly Arg Lys Lys Arg Arg Gln Arg Arg Pro Pro Gln Cys
1               5                   10

<210> SEQ ID NO 749
<211> LENGTH: 19
<212> TYPE: PRT
<213> ORGANISM: Artificial Sequence
<220> FEATURE:
<223> OTHER INFORMATION: CPP

<400> SEQUENCE: 749

Thr Arg Gln Ala Arg Arg Asn Arg Arg Arg Trp Arg Glu Arg Gln
1               5                   10                  15

Arg Gly Cys

<210> SEQ ID NO 750
<211> LENGTH: 17
<212> TYPE: PRT
<213> ORGANISM: Artificial Sequence
<220> FEATURE:
<223> OTHER INFORMATION: CPP
```

```
<400> SEQUENCE: 750

Arg Arg Arg Arg Asn Arg Thr Arg Arg Asn Arg Arg Arg Val Arg Gly
1               5                   10                  15

Cys

<210> SEQ ID NO 751
<211> LENGTH: 21
<212> TYPE: PRT
<213> ORGANISM: Artificial Sequence
<220> FEATURE:
<223> OTHER INFORMATION: CPP

<400> SEQUENCE: 751

Lys Met Thr Arg Ala Gln Arg Arg Ala Ala Ala Arg Arg Asn Arg Trp
1               5                   10                  15

Thr Ala Arg Gly Cys
            20

<210> SEQ ID NO 752
<211> LENGTH: 15
<212> TYPE: PRT
<213> ORGANISM: Artificial Sequence
<220> FEATURE:
<223> OTHER INFORMATION: CPP

<400> SEQUENCE: 752

Thr Arg Arg Gln Arg Thr Arg Arg Ala Arg Arg Asn Arg Gly Cys
1               5                   10                  15

<210> SEQ ID NO 753
<211> LENGTH: 30
<212> TYPE: PRT
<213> ORGANISM: Artificial Sequence
<220> FEATURE:
<223> OTHER INFORMATION: CPP

<400> SEQUENCE: 753

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg Gly Cys
            20                  25                  30

<210> SEQ ID NO 754
<211> LENGTH: 28
<212> TYPE: PRT
<213> ORGANISM: Artificial Sequence
<220> FEATURE:
<223> OTHER INFORMATION: CPP

<400> SEQUENCE: 754

Lys Arg Arg Ile Arg Arg Glu Arg Asn Lys Met Ala Ala Ala Lys Ser
1               5                   10                  15

Arg Asn Arg Arg Arg Glu Leu Thr Asp Thr Gly Cys
            20                  25

<210> SEQ ID NO 755
<211> LENGTH: 23
<212> TYPE: PRT
<213> ORGANISM: Artificial Sequence
<220> FEATURE:
<223> OTHER INFORMATION: CPP

<400> SEQUENCE: 755

Trp Leu Arg Arg Ile Lys Ala Trp Leu Arg Arg Ile Lys Ala Leu Asn
1               5                   10                  15
```

```
1               5                   10                  15
Arg Gln Leu Gly Val Ala Ala
            20
```

<210> SEQ ID NO 756
<211> LENGTH: 10
<212> TYPE: PRT
<213> ORGANISM: Artificial Sequence
<220> FEATURE:
<223> OTHER INFORMATION: CPP

<400> SEQUENCE: 756

```
Cys Arg Lys Lys Arg Gln Arg Arg Arg
1               5                   10
```

<210> SEQ ID NO 757
<211> LENGTH: 10
<212> TYPE: PRT
<213> ORGANISM: Artificial Sequence
<220> FEATURE:
<223> OTHER INFORMATION: CPP

<400> SEQUENCE: 757

```
Cys Arg Arg Arg Arg Arg Arg Arg Arg
1               5                   10
```

<210> SEQ ID NO 758
<211> LENGTH: 10
<212> TYPE: PRT
<213> ORGANISM: Artificial Sequence
<220> FEATURE:
<223> OTHER INFORMATION: CPP

<400> SEQUENCE: 758

```
Cys Lys Lys Lys Lys Lys Lys Lys Lys
1               5                   10
```

<210> SEQ ID NO 759
<211> LENGTH: 12
<212> TYPE: PRT
<213> ORGANISM: Artificial Sequence
<220> FEATURE:
<223> OTHER INFORMATION: CPP

<400> SEQUENCE: 759

```
Gly Arg Lys Lys Arg Arg Gln Arg Arg Arg Pro Pro
1               5                   10
```

<210> SEQ ID NO 760
<211> LENGTH: 8
<212> TYPE: PRT
<213> ORGANISM: Artificial Sequence
<220> FEATURE:
<223> OTHER INFORMATION: CPP

<400> SEQUENCE: 760

```
Arg Arg Arg Arg Arg Arg Arg Arg
1               5
```

<210> SEQ ID NO 761
<211> LENGTH: 12
<212> TYPE: PRT
<213> ORGANISM: Artificial Sequence
<220> FEATURE:
<223> OTHER INFORMATION: CPP

<400> SEQUENCE: 761

```
Thr Pro Pro Lys Lys Lys Arg Lys Val Glu Asp Pro
1               5                   10
```

<210> SEQ ID NO 762
<211> LENGTH: 5
<212> TYPE: PRT
<213> ORGANISM: Artificial Sequence
<220> FEATURE:
<223> OTHER INFORMATION: CPP

<400> SEQUENCE: 762

```
Lys Lys Lys Lys Lys
1               5
```

<210> SEQ ID NO 763
<211> LENGTH: 17
<212> TYPE: PRT
<213> ORGANISM: Artificial Sequence
<220> FEATURE:
<223> OTHER INFORMATION: CPP

<400> SEQUENCE: 763

```
Thr Pro Pro Lys Lys Lys Arg Lys Val Glu Asp Pro Lys Lys Lys Lys
1               5                   10                  15

Lys
```

<210> SEQ ID NO 764
<211> LENGTH: 17
<212> TYPE: PRT
<213> ORGANISM: Artificial Sequence
<220> FEATURE:
<223> OTHER INFORMATION: CPP

<400> SEQUENCE: 764

```
Lys Lys Lys Lys Lys Thr Pro Pro Lys Lys Lys Arg Lys Val Glu Asp
1               5                   10                  15

Pro
```